US011607411B2

(12) United States Patent
Machado De Lacerda et al.

(10) Patent No.: US 11,607,411 B2
(45) Date of Patent: *Mar. 21, 2023

(54) METHODS OF TREATING CROHN'S DISEASE AND ULCERATIVE COLITIS

(71) Applicant: AbbVie Inc., North Chicago, IL (US)

(72) Inventors: Ana Paula Machado De Lacerda, Vernon Hills, IL (US); Jose Jeffrey V. Enejosa, Chicago, IL (US); Aileen L. Pangan, La Grange, IL (US); Mohamed-Eslam F. Mohamed, Gurnee, IL (US); Ahmed A. Othman, Libertyville, IL (US); Ben Klünder, Ludwigshafen (DE); Wen Zhou, Cambridge, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/712,008

(22) Filed: Apr. 1, 2022

(65) Prior Publication Data

US 2022/0233527 A1 Jul. 28, 2022

Related U.S. Application Data

(63) Continuation of application No. 17/667,748, filed on Feb. 9, 2022, now abandoned, which is a continuation-in-part of application No. 17/115,833, filed on Dec. 9, 2020, which is a continuation of application No. 15/917,013, filed on Mar. 9, 2018, now abandoned.

(60) Provisional application No. 63/285,916, filed on Dec. 3, 2021, provisional application No. 63/211,412, filed on Jun. 16, 2021, provisional application No. 63/151,429, filed on Feb. 19, 2021, provisional application No. 62/593,629, filed on Dec. 1, 2017, provisional application No. 62/483,289, filed on Apr. 7, 2017, provisional application No. 62/470,565, filed on Mar. 13, 2017, provisional application No. 62/469,337, filed on Mar. 9, 2017.

(51) Int. Cl.
*A61K 31/4985* (2006.01)
*A61K 31/495* (2006.01)
*A61P 1/00* (2006.01)
*A61K 9/00* (2006.01)
*A61K 9/48* (2006.01)

(52) U.S. Cl.
CPC ........ *A61K 31/4985* (2013.01); *A61K 9/0053* (2013.01); *A61K 9/48* (2013.01); *A61K 31/495* (2013.01); *A61P 1/00* (2018.01)

(58) Field of Classification Search
CPC .... A61K 31/4985; A61K 9/0053; A61K 9/48; A61K 31/495; A61P 1/00
See application file for complete search history.

(56) References Cited

U.S. PATENT DOCUMENTS

| 8,426,411 B2 | 4/2013 | Wishart et al. |
| 8,962,629 B2 | 2/2015 | Wishart et al. |
| 9,365,579 B2 | 6/2016 | Wishart et al. |
| 9,879,018 B2 | 1/2018 | Mulhern et al. |
| 9,879,019 B2 | 1/2018 | Nordstroem et al. |
| 9,951,080 B2 | 4/2018 | Allian et al. |
| 9,963,459 B1 | 5/2018 | Jayanth et al. |
| 10,017,517 B2 | 7/2018 | Borchardt et al. |
| RE47,221 E | 2/2019 | Wishart et al. |
| 10,202,393 B2 | 2/2019 | Jayanth et al. |
| 10,202,394 B2 | 2/2019 | Jayanth et al. |
| 10,344,036 B2 | 7/2019 | Jayanth et al. |
| 10,519,164 B2 | 12/2019 | Allian et al. |
| 10,550,126 B2 | 2/2020 | Pangan et al. |
| 10,597,400 B2 | 3/2020 | Othman et al. |
| 10,730,883 B2 | 8/2020 | Allian et al. |
| 10,981,923 B2 | 4/2021 | Allian et al. |
| 10,981,924 B2 | 4/2021 | Jayanth et al. |
| 10,995,095 B2 | 5/2021 | Pangan et al. |
| 11,186,584 B2 | 11/2021 | Allian et al. |
| 11,198,697 B1 | 12/2021 | Allian et al. |
| 2006/0183779 A1 | 8/2006 | Brauns et al. |
| 2013/0216497 A1 | 8/2013 | Wishart et al. |
| 2013/0295189 A1 | 11/2013 | Maier et al. |

(Continued)

FOREIGN PATENT DOCUMENTS

| CN | 1762333 A | 4/2006 |
| EA | 200400073 A1 | 8/2004 |

(Continued)

OTHER PUBLICATIONS

History of Changes for Study: NCT02365649 (Year: 2016).*
Barbeiro et al., "Efficacy of biological therapies and small molecules in induction and maintenance of remission in luminal Crohn's disease: systematic review and network meta-analysis" Gut 2022; doi:10 1136/gutjnl-2022-328052.
Burr et al. "Efficacy of biological therapies and small molecules in moderate to severe ulcerative colitis: systematic review and network meta-analysis" Gut. 2021; doi: 10.1136/gutjnl-2021-326390.

(Continued)

*Primary Examiner* — Kortney L. Klinkel
*Assistant Examiner* — Jason Deck
(74) *Attorney, Agent, or Firm* — Womble Bond Dickinson (US) LLP; Danielle L. Herritt; Scott R. Breining

(57) ABSTRACT

The present disclosure is directed to methods for treating Crohn's disease, and in particular, to methods for inducing clinical remission and/or endoscopic improvement of Crohn's disease, using a JAK1 inhibitor. In certain embodiments, the patient is administered an induction dose of the JAK1 inhibitor to induce clinical remission and/or endoscopic improvement of the Crohn's disease, followed by administration of at least one maintenance dose of the JAK1 inhibitor thereafter. In other embodiments, the present disclosure is directed to methods for treating ulcerative colitis using a JAK1 inhibitor.

4 Claims, 66 Drawing Sheets

(56) References Cited

U.S. PATENT DOCUMENTS

| | | | |
|---|---|---|---|
| 2014/0271842 | A1 | 9/2014 | Herbig et al. |
| 2015/0118229 | A1 | 4/2015 | Voss et al. |
| 2016/0222020 | A1 | 8/2016 | Wishart et al. |
| 2016/0326181 | A1 | 11/2016 | Wishart et al. |
| 2017/0129902 | A1 | 5/2017 | Allian et al. |
| 2017/0266289 | A1 | 9/2017 | Lipari et al. |
| 2018/0291029 | A1 | 10/2018 | Wishart et al. |
| 2019/0023714 | A1 | 1/2019 | Allian et al. |
| 2020/0197295 | A1* | 6/2020 | Jones .................... A61K 31/00 |
| 2021/0061813 | A1 | 3/2021 | Wishart et al. |
| 2021/0309667 | A1 | 10/2021 | Allian et al. |
| 2021/0361647 | A1 | 11/2021 | Thakkar et al. |
| 2021/0363149 | A1 | 11/2021 | Allian et al. |
| 2022/0073530 | A1 | 3/2022 | Allian et al. |

FOREIGN PATENT DOCUMENTS

| | | | | |
|---|---|---|---|---|
| EP | 2438909 | A1 | 4/2012 | |
| WO | WO-200015231 | A1 | 3/2000 | |
| WO | WO-2003000695 | A1 | 1/2003 | |
| WO | WO-2003/031606 | A2 | 4/2003 | |
| WO | WO-2005/110410 | A2 | 11/2005 | |
| WO | WO-2007/079164 | A2 | 7/2007 | |
| WO | WO-2008/063287 | A2 | 5/2008 | |
| WO | WO-2008135090 | A1 | 11/2008 | |
| WO | WO-2009/005675 | A1 | 1/2009 | |
| WO | WO-2009/152133 | A1 | 12/2009 | |
| WO | WO-201113082 | A1 | 2/2011 | |
| WO | WO-2011068881 | A1 | 6/2011 | |
| WO | WO-2013178752 | A1 | 12/2013 | |
| WO | WO-2015061665 | A1 * | 4/2015 | ........... A61K 31/167 |
| WO | WO-2016198983 | A1 | 12/2016 | |

OTHER PUBLICATIONS

Cholapranee et al. "Systematic review with meta-analysis: comparative efficacy of biologies for induction and maintenance of mucosal healing in Crohn's disease and ulcerative colitis controlled trials" Aliment Pharmacol Ther. 2017;45(10):1291-1302.

Hirten RP and Sands BE. "New Therapeutics for Ulcerative Colitis" Annu Rev Med. 2021;72:199-213.

Lasa et al. "Efficacy and safety of biologies and small molecule drugs for patients with moderate-to-severe ulcerative colitis: a systematic review and network meta-analysis" Lancet Gastroenterol Hepatol. 2021;7(12):161-170.

Lichtenstein et al. "ACG Clinical Guideline: Management of Crohn's Disease in Adults" Am J Gastroenterol. 2018;113(4):481-517.

Panaccione et al., "Efficacy and safety of advanced induction and maintenance therapies in patients with moderately to severely active ulcerative colitis: An indirect treatment comparison using Bayesian network meta-analysis" European Crohn's and Colitis Organisation 2022, Vienna, Austria.

U.S. Appl. No. 17/566,748, filed Dec. 31, 2021, Pending.
U.S. Appl. No. 17/575,731, filed Jan. 14, 2022, Pending.
U.S. Appl. No. 17/717,486, filed Apr. 11, 2022, Pending.
U.S. Appl. No. 17/115,833, filed Dec. 9, 2020, Published, US-2021-0361647-A1.
U.S. Appl. No. 17/732,070, filed Apr. 28, 2022, Pending.
U.S. Appl. No. 17/667,748, filed Feb. 9, 2022, Pending.
U.S. Appl. No. 17/712,008, filed Apr. 1, 2022, Pending.
U.S. Appl. No. 17/230,418, filed Apr. 14, 2021, Granted, U.S. Pat. No. 11,198,697-B1.
U.S. Appl. No. 17/507,885, filed Oct. 22, 2021, Pending, Not yet published.
U.S. Appl. No. 17/039,470, filed Sep. 30, 2020, Pending, Not yet published.
U.S. Appl. No. 17/508,451, filed Oct. 22, 2021, Pending, Not yet published.
U.S. Appl. No. 17/508,576, filed Oct. 22, 2021, Pending, Not yet published.
U.S. Appl. No. 17/205,066, filed Mar. 18, 2021, Abandoned, Not yet published.
U.S. Appl. No. 17/230,288, filed Apr. 14, 2021, Granted, U.S. Pat. No. 11,186,584-B2.
U.S. Appl. No. 17/184,194, filed Feb. 24, 2021, Published, US-2021-0363149-A1.
U.S. Appl. No. 16/983,703, filed Aug. 3, 2020, Granted, U.S. Pat. No. 10,981,924-B2.
U.S. Appl. No. 16/905,667, filed Jun. 18, 2020, Granted, U.S. Pat. No. 10,981,923-B2.
U.S. Appl. No. 16/787,251, filed Feb. 11, 2020, Granted, U.S. Pat. No. 10,730,883-B2.
U.S. Appl. No. 16/656,237, filed Oct. 17, 2019, Abandoned, US-2020-0291040-A1.
U.S. Appl. No. 16/458,622, filed Jul. 1, 2019, Granted, U.S. Pat. No. 10,597,400-B2.
U.S. Appl. No. 16/453,684, filed Jun. 26, 2019, Granted, U.S. Pat. No. 10,519,164-B2.
U.S. Appl. No. 15/945,231, filed Apr. 4, 2018, Granted, U.S. Pat. No. 10,202,394-B2.
U.S. Appl. No. 15/945,225, filed Apr. 4, 2018, Granted, U.S. Pat. No. 10,202,393-B2.
U.S. Appl. No. 15/908,347, filed Feb. 28, 2018, Granted, U.S. Pat. No. 10,344,036-B2.
U.S. Appl. No. 15/891,012, filed Feb. 7, 2018, Abandoned, US-20190023714-A1.
U.S. Appl. No. 15/954,039, filed Apr. 16, 2018, Granted, U.S. Pat. No. 10,550,126-B2.
U.S. Appl. No. 15/857,892, filed Dec. 29, 2017, Granted, U.S. Pat. No. 9,963,459-B1.
U.S. Appl. No. 15/803,538, filed Nov. 3, 2017, Granted, U.S. Pat. No. 9,951,080-B2.
U.S. Appl. No. 15/682,457, filed Aug. 21, 2017, Granted, U.S. Pat. No. 9,879,019-B2.
U.S. Appl. No. 15/682,451, filed Aug. 21, 2017, Granted, U.S. Pat No. 9,879,018-B2.
U.S. Appl. No. 15/891,306, filed Feb. 7, 2017, Granted U.S. Pat. No. 10,017,517-B2.
U.S. Appl. No. 15/295,561, filed Oct. 17, 2016, Abandoned, US-20170129902-A1.
U.S. Appl. No. 15/917,013, filed Mar. 9, 2018, Abandoned, US-20190046527-A1.
U.S. Appl. No. 16/440,442, filed Jun. 13, 2019, Abandoned, US-2021-0061813-A1.
U.S. Appl. No. 15/806,104, filed Nov. 7, 2017, Abandoned US-20180291029-A1.
U.S. Appl. No. 15/152,823, filed May 12, 2016, Abandoned US-20160326181-A1.
U.S. Appl. No. 15/017,802, filed Feb. 8, 2016, Abandoned, US-20160222020-A1.
U.S. Appl. No. 14/610,119, filed Jan. 30, 2015, Granted, U.S. Pat. No. 9,365,579-B2.
U.S. Appl. No. 13/761,501, filed Feb. 7, 2013, Abandoned, US-20130216497-A1.
U.S. Appl. No. 12/481,028, filed Jun. 9, 2009, Granted, U.S. Pat. No. 8,962,629-B2.
U.S. Appl. No. 15/446,102, filed Mar. 1, 2017, Granted, Re. 47,221-E1.
U.S. Appl. No. 12/958,115, filed Dec. 1, 2010, Granted, U.S. Pat. No. 8,426,411-B2.
U.S. Appl. No. 15/506,310, filed Feb. 24, 2017, Abandoned, US-20170266289-A1.
U.S. Appl. No. 14/523,052, filed Oct. 24, 2014, Abandoned, US-20150118229-A1.
U.S. Appl. No. 17/527,717, filed Nov. 16, 2021, Allowed, US-2022-0073530-A1.
History of Changes for Study: NCT02819635 (2017).
U.S. Appl. No. 17/338,322.
U.S. Appl. No. 17/566,748.
U.S. Appl. No. 17/575,731.
U.S. Appl. No. 17/508,451.
U.S. Appl. No. 17/507,885.
U.S. Appl. No. 17/508,576.

(56) References Cited

OTHER PUBLICATIONS

U.S. Appl. No. 17/668,249.
U.S. Appl. No. 17/717,486.
U.S. Appl. No. 17/667,748.
U.S. Appl. No. 17/712,008.
Aratari A., et al., "Colectomy Rate in Acute Severe Ulcerative Colitis in the Infliximab Era," Digestive and Liver Disease, Oct. 2008, vol. 40(10), pp. 821-826.
Beaugerie L., et al., "Lymphoproliferative Disorders in Patients Receiving Thiopurines for Inflammatory Bowel Disease: a Prospective Observational Cohort Study," Lancet (London, England), Nov. 2009, vol. 374(9701), pp. 1617-1625.
Colombel J.F., et al., "Adalimumab for Maintenance of Clinical Response and Remission in Patients with Crohn's Disease the CHARM Trial," Gastroenterology, 2007, vol. 132 (1), pp. 52-65.
Dignass A et al., "Second European Evidence-based Consensus on the Diagnosis and Management of Ulcerative Colitis Part 1: Definitions and Diagnosis," Journal of Crohn's & Colitis, Dec. 2012, vol. 6(10), pp. 965-990.
Dignass A., et al., "The Second European Evidence-based Consensus on the Diagnosis and Management of Crohn's Disease: Current Management," Journal of Crohn's & Colitis, Feb. 2010, vol. 4(1), pp. 28-62. Erratum in: J Crohn's Colitis, 2010, 4(3):353.
Feagan B.G., et al., "Treatment of Ulcerative Colitis with a Humanized Antibody to the Alpha4beta7 Integrin," The New England Journal of Medicine, Jun. 2005, vol. 352(24), pp. 2499-2507.
Guyatt G., et al., "A New Measure of Health Status for Clinical Trials in Inflammatory Bowel Disease," Gastroenterology, Mar. 1989, vol. 96(3), pp. 804-810.
Hanauer S.B., et al., "Human Anti-Tumor Necrosis Factor Monoclonal Antibody (Adalimumab) In Crohn's Disease: The Classic-I Trial," Gastroenterology, 2006, vol. 130 (2), pp. 323-333.
Hanauer S.B., et al., "Maintenance Infliximab for Crohn's Disease: The Accent I Randomised Trial," Lancet, 2002, vol. 359 (9317), pp. 1541-1549.
Hanauer S.B., "Update on the Etiology, Pathogenesis and Diagnosis of Ulcerative Colitis," Nature Clinical Practice. Gastroenterology & Hepatology, Nov. 2004, vol. 1(1), pp. 26-31.
Irving P.M., et al., "Review Article: Appropriate Use of Corticosteroids in Crohn's Disease," Alimentary Pharmacology & Therapeutics, Aug. 2007, vol. 26(3), pp. 313-329.
Jenkins R., et al., "Introduction to XRay Powder Diffractometry," John Wiley & Sons, 1996.
Kornbluth A., et al., "Ulcerative Colitis Practice Guidelines in Adults: American College of Gastroenterology, Practice Parameters Committee," The American Journal of Gastroenterology, Mar. 2010, vol. 105(3), pp. 501-523.
Lichtenstein G.R., et al., "Management of Crohn's Disease in Adults," The American Journal of Gastroenterology, Practice guideline, Feb. 2009, vol. 104(2), pp. 465-483.
Loftus EV J.R., "Clinical Epidemiology of Inflammatory Bowel Disease: Incidence, Prevalence, and Environmental Influences," Gastroenterology, May 2004, vol. 126(6), pp. 1504-1517.
Molodecky N.A., et al., "Increasing Incidence and Prevalence of the Inflammatory Bowel Diseases With Time, Based on Systematic Review," Gastroenterology, Jan. 2012, vol. 142(1), pp. 46-54.
Munkholm P., et al., "Intestinal Cancer Risk and Mortality in Patients With Crohn's Disease," Gastroenterology, Dec. 1993, vol. 105(6), pp. 1716-1723.
Probert C.S., et al., "Epidemiology of Inflammatory Bowel Disease in Different Ethnic and Religious Groups: Limitations and Aetiological Clues," International Journal of Colorectal Disease, 1996, vol. 11(1), pp. 25-28.
Rowe R.C., et al., "Handbook of Pharmaceutical Excipients," 7th Edition, Pharmaceutical Press, 2012.
Rubin D., et al., "The Effect of Vedolizumab on Extraintestinal Manifestations in Patients With Crohn's Disease in Gemini 2," Inflammatory Bowel Diseases, 2016, vol. 22 (Suppl1), pp. S42-S43.

Rutgeerts P., et al., "Infliximab for Induction and Maintenance Therapy for Ulcerative Colitis," The New England Journal of Medicine, 2005, vol. 353 (23), pp. 2462-2476.
Rutgeerts P., et al., "Review Article: The Limitations of Corticosteroid Therapy in Crohn's Disease," Alimentary Pharmacology & Therapeutics, Oct. 2001, vol. 15(10), pp. 1515-1525.
Rutter M et al., "Severity of Inflammation is a Risk Factor for Colorectal Neoplasia in Ulcerative Colitis," Gastroenterology, Feb. 2004, vol. 126(2), pp. 451-459.
Sandborn W.J., et al., "Adalimumab Induces and Maintains Clinical Remission in Patients With Moderate-to-severe Ulcerative Colitis," Gastroenterology, Feb. 2012, vol. 142(2), pp. 257-265.
Sandborn W.J., et al., "Certolizumab Pegol for the Treatment of Crohn's Disease," The New England Journal of Medicine, 2007, vol. 357(3), pp. 228-238.
Sandborn W.J., et al., "Natalizumab Induction and Maintenance Therapy for Crohn's Disease," The New England Journal of Medicine, 2005, vol. 353 (18), pp. 1912-1925.
Sandborn W.J., et al., "Subcutaneous Golimumab Induces Clinical Response and Remission in Patients With Moderate-to-severe Ulcerative Colitis," Gastroenterology, Jan. 2014, vol. 146(1), pp. 85-95.
Sandborn W.J., "State-of-the-art: Immunosuppression and Biologic Therapy," Digestive Diseases, 2010, vol. 28(3), pp. 536-542.
Sandler R.S., et al., "The Burden of Selected Digestive Diseases in the United States," Gastroenterology, 2002, vol. 122(5), pp. 1500-1511.
Sands B.E., et al., "Effects of Vedolizumab Induction Therapy for Patients With Crohn's Disease in Whom Tumor Necrosis Factor Antagonist Treatment Failed," Gastroenterology, Sep. 2014, vol. 147(3), pp. 618-627.
Schreiber S., et al., "Maintenance Therapy With Certolizumab Pegol for Crohn's Disease," The New England Journal of Medicine, Jul. 2007, pp. 239-250. Erratum in: N Engl. J Med., 2007, 357(13): 1357.
Schreiber S., et al., "Maintenance Therapy With Certolizumab Pegol for Crohn's Disease," The New England Journal of Medicine, Jul. 2007, pp. 239-250.
Siegel C.A. and Sands B.E., "Review Article: Practical Management of Inflammatory Bowel Disease Patients Taking Immunomodulators," Alimentary Pharmacology & Therapeutics, 2005, vol. 22(1), pp. 1-16.
Simon E.G., et al., "Ustekinumab for the Treatment of Crohn's Disease: Can It Find Its Niche ?," Therapeutic Advances in Gastroenterology, Jan. 2016, vol. 9(1), pp. 26-36.
Solberg I.C., et al., "Clinical Course in Crohn's Disease: Results of a Norwegian Population-based Ten-year Follow-up Study," Clinical Gastroenterology and Hepatology, Dec. 2007, vol. 5(12), pp. 1430-1438.
Stahl P.H., et al., eds., Handbook of Pharmaceutical Salts: Properties, Selection, and Use, Verlag Helvetica Chimica Acta, Wiley-VCH, 2002.
Truelove S.C. and Witts L.J., "Cortisone and Corticotrophin in Ulcerative Colitis," British Medical Journal, Feb. 1959, vol. 1(5119), pp. 387-394.
Turner D., et al., "Response to Corticosteroids in Severe Ulcerative Colitis: a Systematic Review of the Literature and a Meta-regression," Clinical Gastroenterology and Hepatology, Jan. 2007, vol. 5(1), pp. 103-110.
Van Assche G., et al., "Progressive Multifocal Leukoencephalopathy after Natalizumab Therapy for Crohn's Disease," The New England Journal of Medicine, 2005, vol. 353 (4), pp. 362-368.
Product Label: "SEPINEO P 600", XP002744402, accessed at http://gyermedhu/pdf/3664_Leaflet_Sepineo_P600_gb.pdf, accessed on Apr. 2008, pp. 1-2.
International Search Report and Written Opinion for International Application No. PCT/US2015/047152, European Patent Office, Iceland , dated Nov. 6, 2015, 20 pages.
AbbVie Announces Positive Phase 2 Study Results for Upadacitinib (ABT-494), an Investigational JAK 1—Selective Inhibitor, in Crohn's Disease (May 9, 2017), accessed at htt12s://newsabbive.com/news/12ress-release/abbive-announces-12ostive-12hase-2-study_-results-for-u12dateiting-abt-494-an-investigation-jak1-selective-inhibitor-in-crohns-disease.htm,accessed on Dec. 18, 2017, 3 pages.

(56) References Cited

OTHER PUBLICATIONS

Genovese, M.C., et al., "Efficacy and Safety of ABT-494, a Selective JAK-1 Inhibitor, in a Phase IIb Study in Patients With Rheumatoid Arthritis and an Inadequate Response to Methotrexate," Arthritis & Rheumatology (2016) 68(12):2857-2866.

International Search Report and Written Opinion for International Application No. PCT/US2016/057372, European Patent office, Netherlands, dated Feb. 13, 2017, 13 pages.

Klunder, B., et al., "Exposure-Response Analyses of the Effect of Upadacitinib on ACR Responses in th Phase 2b Rheumatoid Arthritis Trials in Patients with Inadequate Response to Methotrexate or to Anti-Tumor Necrosis Factor Therapy," 2017 AGRI ARHP Annual Meeting, Abstract No. 505, 4 pages (2017).

Kremer, J.M., et al., "A Phase IIb Study of ABT-494, a Selective JAK-1 Inhibitor, in Patients with Rheumatoid Arthritis and an Inadequate Response to Anti-Tumor Necrosis Factor Therapy," Arthritis & Rheumatology (2016) 68(12):2867-2877.

Mohamed, M.F., et al., "Pharmacokinetics, Safety and Tolerability of ABT-494, a Novel Selective JAK 1 Inhibitor, in Healthy Volunteers and Subjects with Rheumatoid Arthritis," Clinical Pharmacokinetics (2016) 55(12):1547-1558.

Nayana, M.R.S., et al., "CoMFA and Docking Studies on Triazolopyridine Oxazole Derivatives as P38 MAP Kinase Inhibitors," European Journal of Medicinal Chemistry (2008) 43(6):1261-1269.

Notice of Opposition for European Patent Application No. EP2506716, dated Feb. 16, 2018, 5 pages.

Opposition Brief for European Patent Application No. EP2506716, dated Feb. 16, 2018, 16 pages.

International Search Report and Written Opinion for International Application No. PCT/US2014/062145, European Patent Office, Netherlands, dated Jan. 22, 2015, 13 pages.

SEPPIC: "How to use Sepineo P600 in a formulation", XP054976186, accessed at https://www.youtube.com/watch?v=SHiwvwnx1tA, access on Aug. 30, 2012, 1 page.

Statement of Case in Opposition for Israel Patent Application 248466, mailed on Nov. 23, 2017, 4 pages.

Van Epps S., et al., "Design and Synthesis of Tricyclic Cores for Kinase Inhibition," Bioorganic & Medicinal Chemistry Letters((2013)) 23(3): 693-698.

International Search Report and Written Opinion for International Application No. PCT/US2018/021800, European Patent Office, Netherlands, dated May 23, 2018, 23 pages.

International Search Report and Written Opinion for International Application No. PCT/US2009/046714, European Patent Office, Netherlands, dated Aug. 13, 2009, 10 pages.

International Search Report and Written Opinion for International Application No. PCT/US2010/058572, European Patent office, Netherlands, dated Feb. 2, 2011, 10 pages.

AbbVie Announces New Phase 2 Data for Upadacitinib Showing Clinical and Endoscopic Outcomes in Crohn's Disease at 52 Weeks, accessed at https://news.abbvie.com/news/abbvie-announces-new-phase-2-data-for-upadacitinib-showing-clinical-and-endoscopic-outcomes-in-crohns-disease-at-52-weeks.htm, accessed on Feb. 16, 2018, 8 pages.

AbbVie Demonstrates Leadership in Gastroenterology and Hepatology with New Data and Late—Breaking Studies to be Presented at Digestive Disease Week, accessed at https://news.abbvie.com/news/abbvie-demonstrates-leadership-in-gastroenterology-and-hepatology-with-new-data-and-late-breaking-studies-to-be-presented-at-digestive-disease-week.him, accessed on May 4, 2017.

Aguilar, D., et al., "P843 Upadacitinib-induced Endoscopic Improvement Is Associated With Modulation of Pathways Involved in Crohn's Disease Pathogenesis," Abstracts of the 13th Congress of ECCO—European Crohn's and Colitis Organisation, pp. S542-S543 (2018).

Klunder, B ., et al., "Population Pharmacokinetics of Upadacitinib in Healthy Subjects and Subjects with Rheumatoid Arthritis: Analyses of Phase I and II Clinical Trials," Clinical Pharmacokinetics (2018) 57(8):977-988.

Minocha, M., et al., "Exposure—Response Analyses of Upadacitinib (ABT-494) Efficacy in Subjects with Moderately to Severely Active Ulcerative Colitis—Analyses of a Phase 2 Dose Ranging Induction Study, IBD," United European Gastroenterology Week, Presentation #P0347, Oct. 20-24, 2018 , Vienna, Austria, 3 pages.

Mohamed, M.E.F., et al., "Sa1764 Upadacitinib Exposure—response Relationships for Efficacy in Subjects With Moderately to Severely Active Crohn's Disease—Analysis of Celest Study," Digestive Disease Week p. S-386, May 2018.

Mohamed, M.F., et al., "Exposure—response Relationships for the Effect of Upadacitinib on Clinical and Endoscopic Efficacy Endpoints in Subjects With Moderately to Severely Active Crohn's Disease—Analysis of Celest Study,"United European Gastroenterology Week Abstract No. OP010, pp. A5-A6 (2017).

Mohamed, M.F., et al., "Pharmacokinetics of Upadacitinib With the Clinical Regimens of the Extended-Release Formulation Utilized in Rheumatoid Arthritis Phase 3 Trials," Clinical Pharmacology in Drug Development, (2019) 8(2):208-216.

Panaccione, R., et al., "Correlation between clinical and endoscopic endpoints and remission per Inflammatory Bowel Disease Questionnaire score in patients with Crohn's disease: data from CELEST.," United European Gastroenterology Journal (2018) 6(8S):A120-A121.

Panaccione, R., et al., "Upadacitinib improves steroid-free clinical and endoscopic endpoints in patients with Crohn's disease: Data from the CELEST study," Gastroenterology (2018) 154(6):S384.

Panaccione, R., et al., "Upadacitinib Improves Steroid-Free Clinical and Endoscopic Endpoints in Patients with Crohn's disease: Data from the CELEST study," Poster P601, Congress of the European Crohn's and Colitis Organisation, pp. S412-S413 (2018).

Panes, J., et al., "Efficacy and Safety of Upadacitinib Maintenance Treatment for Moderate to Severe Crohn's Disease: Results From the CELEST Study," Digestive Disease Week Poster P273, pp. S238-S239 (2008).

Peyrin-Biroulet, L., et al., "Patient-reported Outcomes With Upadacitinib in Subjects With Moderately to Severely Active Crohn's Disease: Phase 2 Results From Celest Study," United European Gastroenterology Week, Abstract No. OP263, p. A112 (2017).

Panes, J., et al., "Efficacy and safety of upadacitinib maintenance treatment for moderate to severe Crohn's disease: Results from the CELEST study," Journal of Crohn's and Colitis (2018) 12(1):S-178-179.

Sandborn, W.J., et al., "Correlation of endoscopic and clinical endpoints during induction therapy in patients with moderate-to-severe Crohn's disease: Analysis from CELEST study." Gastroenterology (2018) 154(6):S-590.

Sandborn, W.J., et al., "Safety and Efficacy of ABT-494 (Upadacitinib), an Oral Jak1 Inhibitor, as Induction Therapy in Patients with Crohn's Disease: Results from Celest," Digestive Disease Week Abstracts 8474h, pp. S1308-S1309 (2017).

Sandborn, W.J., et al., "Safety and Efficacy of Upadacitinib (Abt-494), an Oral Jak1 Inhibitor, as Induction Therapy in Patients With Crohn's Disease: Results From Celest," United European Gastroenterology Week, Abstract No. OP007, pp. A3-A4 (2017).

Sandborn, W.J., et al., "OP195-Efficacy and Safety of Upadacitinib as an Induction Therapy for Patients With Moderately-To-Severely Active Ulcerative Colitis: Data From The Phase 2b Study U-Achieve," United European Gastroenterology Week Oct. 20-24, 2018, Vienna, Austria, 3 pages.

Sandborn, W.J., et al., "P533 Correlation of Endoscopic and Clinical Endpoints During Induction Therapy in Patients With Moderate-to-severe Crohn's Disease: Analysis From CELEST Study," Abstracts of the 13th Congress of ECCO—European Crohn's and Colitis Organisation, pp. S375-S376 (2018).

Schreiber, S., et al., "OP022 Rapidity of Clinical and Laboratory Improvements Following Upadacitinib Induction Treatment: Data From the CELEST Study," Abstracts of the 13th Congress of ECCO—European Crohn's and Colitis Organisation, p. S015 (2018).

Schreiber, S., et al., "Rapidity of clinical and laboratory improvements following upadacitinib induction treatment: data from the CELEST study," Gastroenterology (2018) 154(6); S382- S383.

Colombel, J.F., et al., "Correlation of biomarkers of inflammation with clinical and endoscopic endpoints in patients with moderate-

(56) References Cited

OTHER PUBLICATIONS to-severe Crohn's disease: data from CELEST," United European Gastroenterology Journal (2018) 6(8s):A242-A243.
Mohamed, M.E.F., et al., "Upadacitinib Exposure—Response Relationships for Efficacy in Subjects with Moderately to Severely Active Crohn's Disease—Analysis of Celest Study," Gastroenterology (2018) 154(6):S-386.
Peyrin-Biroulet, L., et al., "Improvement in patient-reported outcomes with upadacitinib in patients with moderately to severely active Crohn's disease: 52-week data from the CELEST study," United European Gastroenterology Journal (2018) 6(8S): A91-A92.
Targan, S.R., et al., "A Short-Term Study of Chimeric Monoclonal Antibody cA2 to Tumor Necrosis Factor Alpha for Crohn's Disease. Crohn's Disease cA2 Study Group," The New England Journal of Medicine (1997) 337(15):1029-1035.
Dignass, A., et al., "Second European Evidence-Based Consensus on the Diagnosis and Management of Ulcerative Colitis Part 1: Definitions and Diagnosis," Journal of Crohn's & Colitis (2012) 6(10):965-990.
Amended Pleadings on Behalf of the Opponent in Opposition to Israel Patent Application 248466, dated Mar. 26, 2018, 136 pages.
D'amico F., et al., "Janus Kinase Inhibitors for the Treatment of Inflammatory Bowel Diseases: Developments from Phase I and Phase II Clinical Trials," Expert Opinion on Investigational Drugs, (2018) 27(7):595-599.

\* cited by examiner

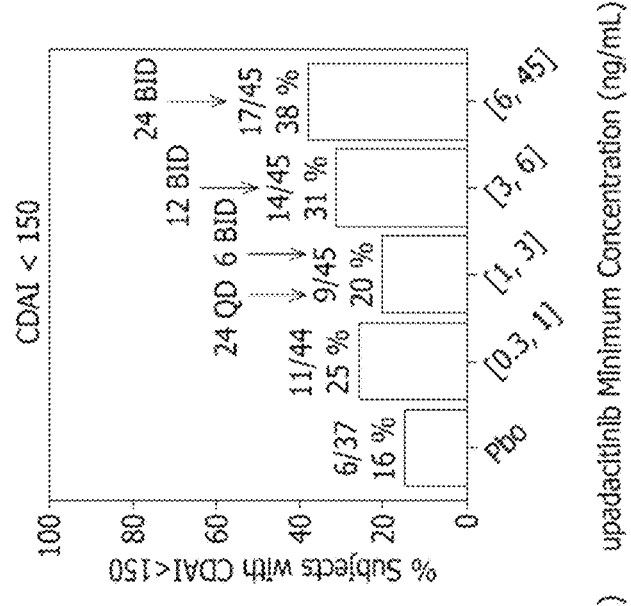
Figure 3D   Figure 3E   Figure 3F

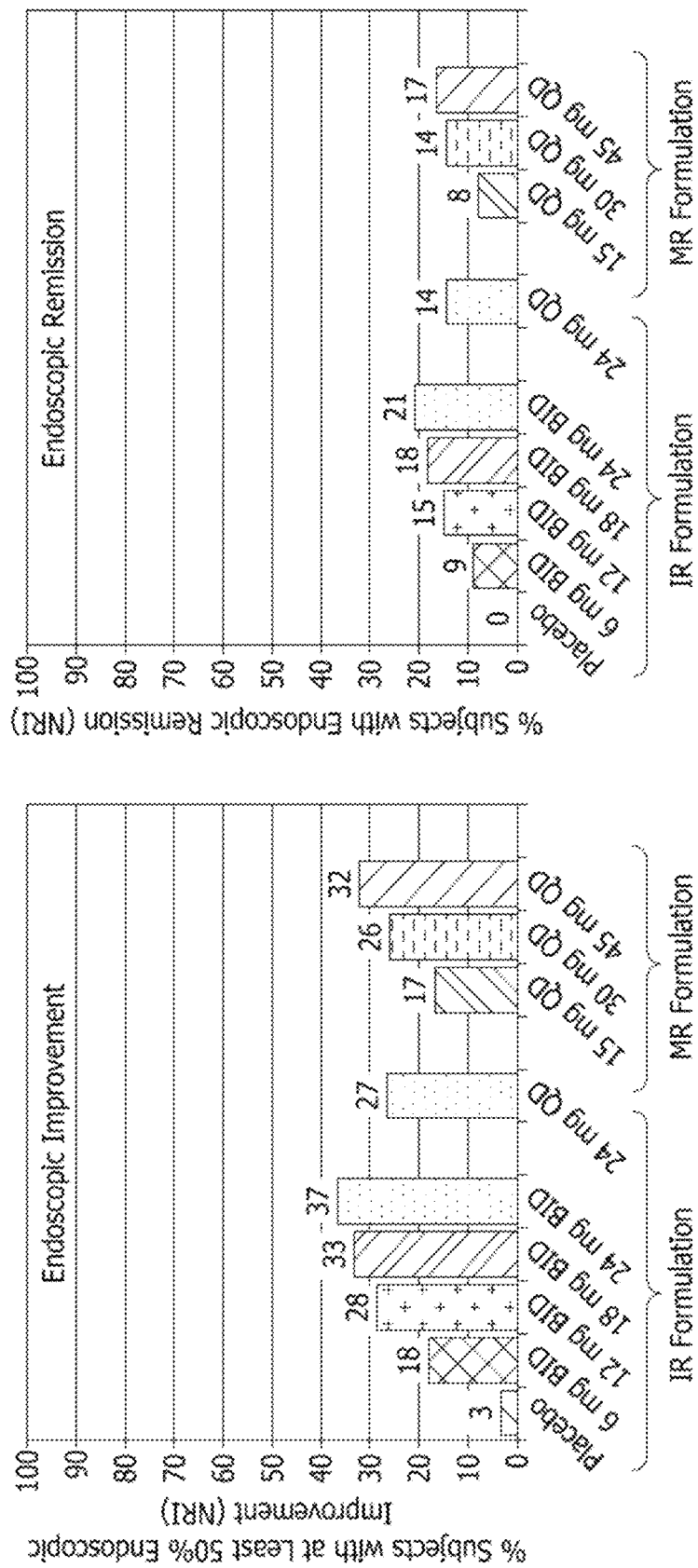

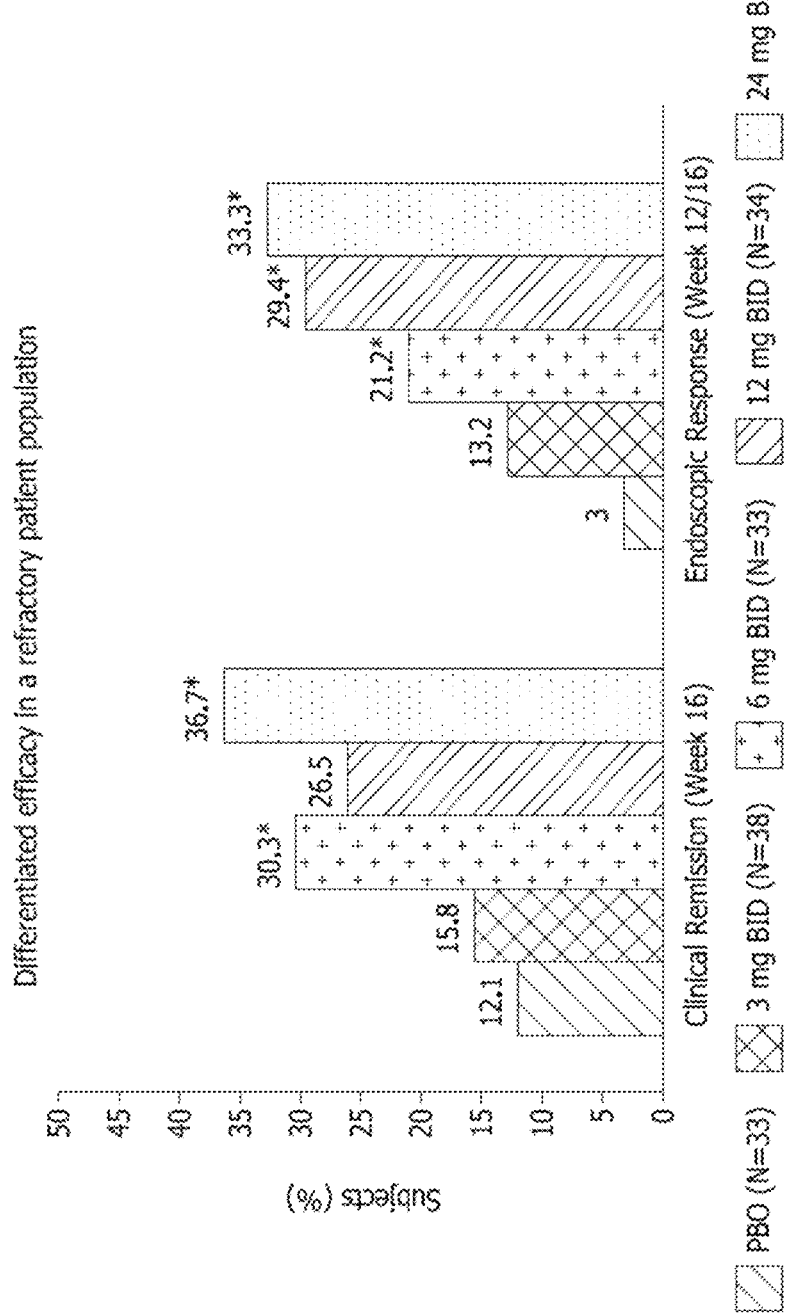

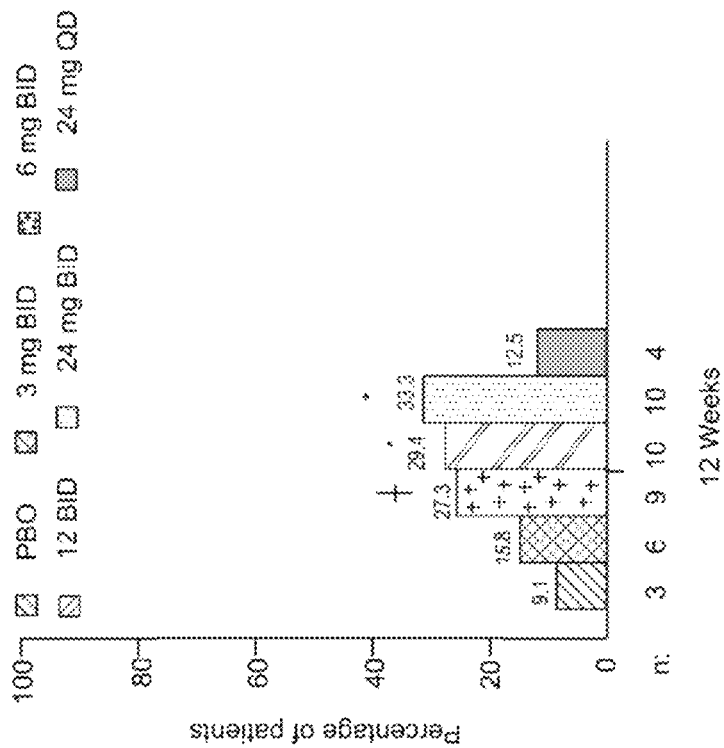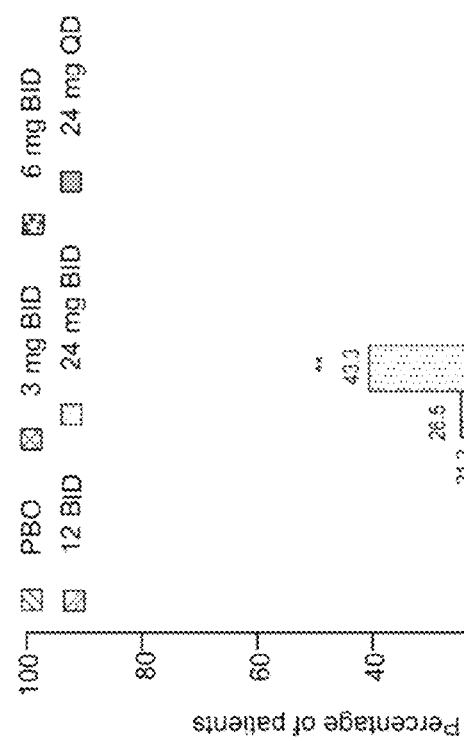

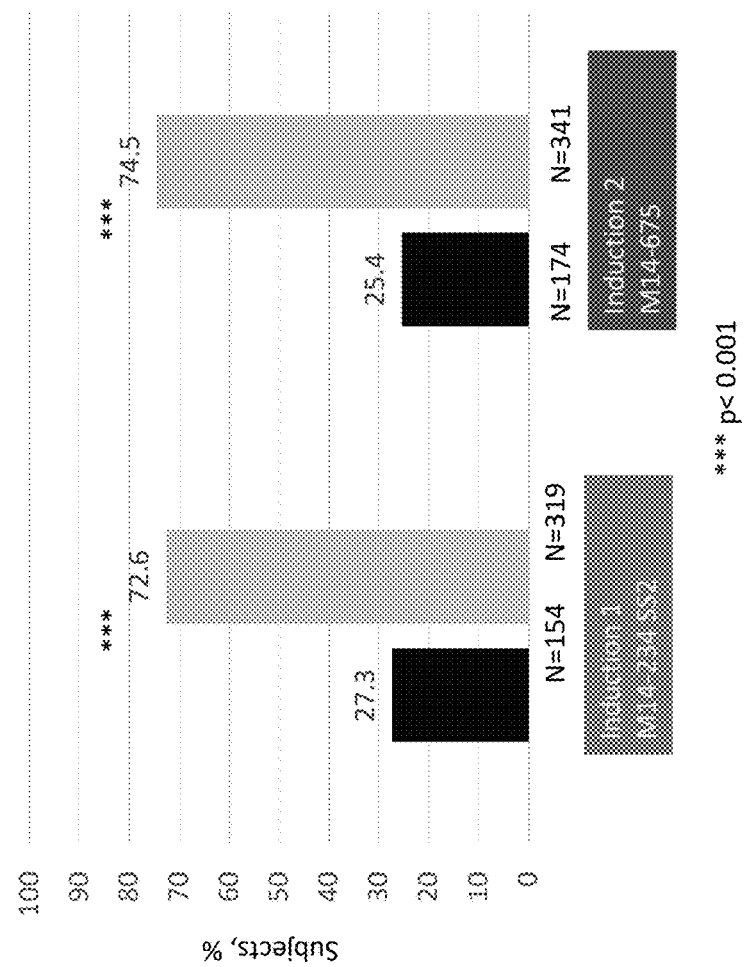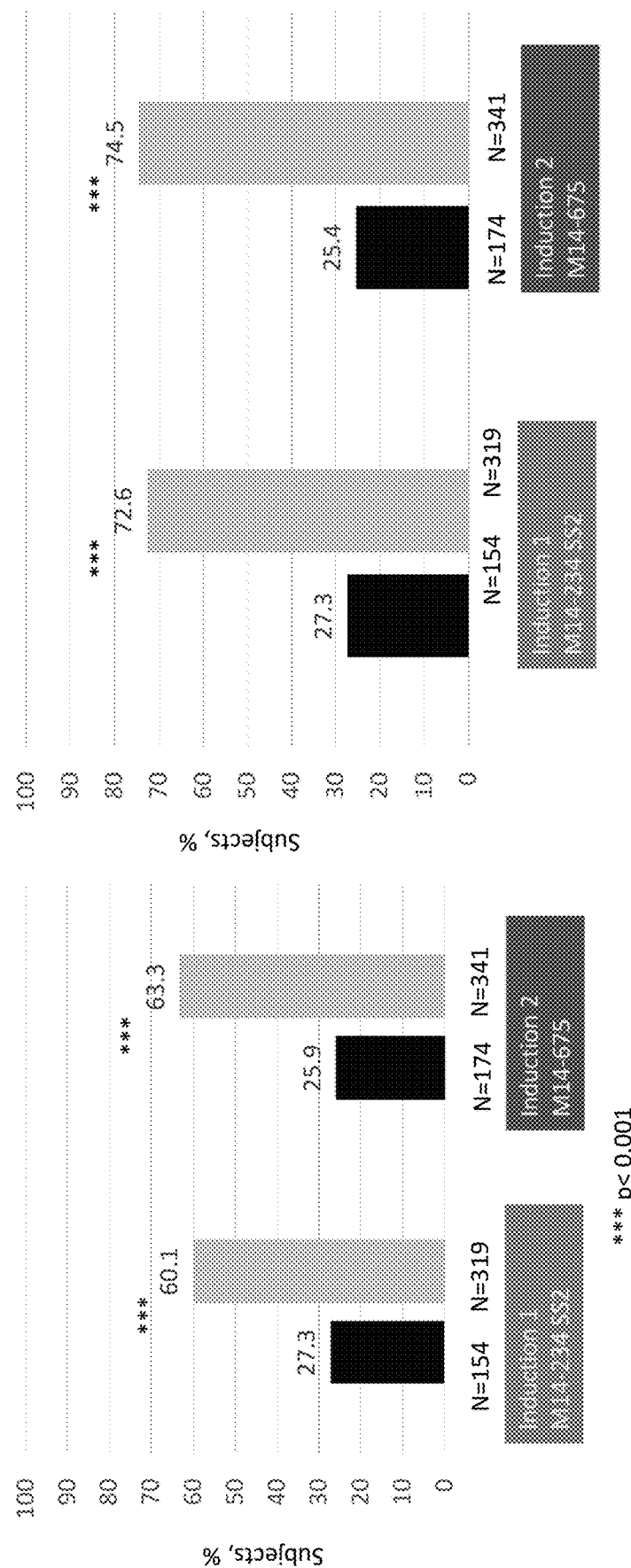
Figure 26A
Figure 26B

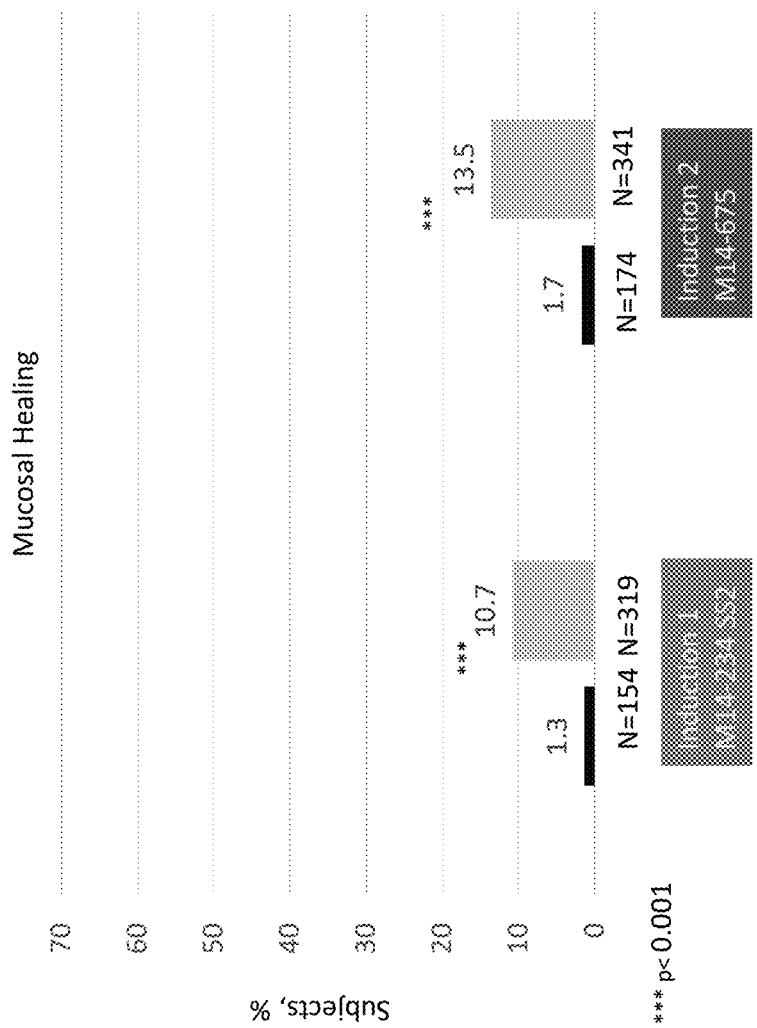
Figure 28C Mucosal Healing

Figure 29

| Endpoints (Week 52) | Placebo (N = 149) % (n⁶) or LSMEAN (SE) | UPA 15 mg (N = 148) % (n⁶) or LSMEAN (SE) | UPA 30 mg (N = 154) % (n⁶) or LSMEAN (SE) | p-Value UPA vs. Placebo UPA 15 mg | p-Value UPA vs. Placebo UPA 30 mg |
|---|---|---|---|---|---|
| Clinical remission per Adapted Mayo score - Primary | 12.1% (18) | 42.3% (63) | 51.7% (80) | <0.001ˢ | <0.001ˢ |
| 1. Endoscopic improvement | 14.5% (22) | 48.7% (72) | 61.6% (95) | <0.001ˢ | <0.001ˢ |
| 2. Clinical remission per Adapted Mayo score among Induction remitters | N=54 22.2% (12) | N=47 59.2% (28) | N=58 69.7% (40) | <0.001ˢ | <0.001ˢ |
| 3. Clinical remission per Adapted Mayo score and corticosteroid free for ≥ 90 days immediately preceding Week 52 among Induction remitters | N=54 22.2% (12) | N=47 57.1% (27) | N=58 68.0% (39) | p<0.001ˢ | <0.001ˢ |
| 4. Endoscopic improvement among subjects with endoscopic improvement at the end of the Induction Studies | N=74 18.9% (14) | N=63 61.6% (39) | N=79 69.5% (55) | <0.001ˢ | <0.001ˢ |
| 5. Endoscopic remission | 5.6% (8) | 24.2% (36) | 25.9% (40) | <0.001ˢ | <0.001ˢ |
| 6. Clinical response per Adapted Mayo score among Induction responders | N=134 18.8% (25) | N=135 63.0% (85) | N=144 76.6% (110) | <0.001ˢ | <0.001ˢ |
| 7. Histologic-endoscopic mucosal improvement | 11.8% (18) | 34.8% (51) | 49.3% (76) | <0.001ˢ | <0.001ˢ |
| 8. Change from Baseline in IBDQ total score | 17.9 (3.62) | 49.2 (3.39) | 58.9 (3.43) | <0.001ˢ | <0.001ˢ |
| 9. Mucosal healing | 4.7% (7) | 17.6% (26) | 19.0% (29) | <0.001ˢ | <0.001ˢ |
| 10. No bowel urgency | 17.4% (26) | 56.1% (83) | 63.6% (98) | <0.001ˢ | <0.001ˢ |
| 11. No abdominal pain | 20.8% (31) | 45.9% (68) | 55.3% (85) | <0.001ˢ | <0.001ˢ |
| 12. Change from Baseline in FACIT-F score | 3.7 (0.90) | 8.7 (0.89) | 9.5 (0.87) | <0.001ˢ | <0.001ˢ |

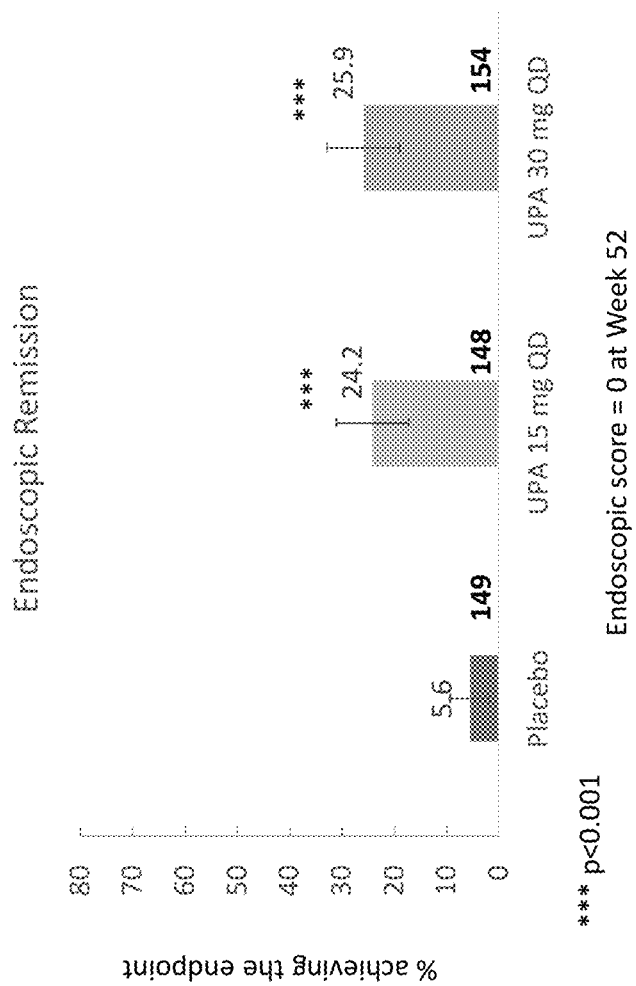

Figure 44

| | Endpoint | Definition | Ranking |
|---|---|---|---|
| Clinical Endpoints | Clinical Remission (PRO) | Average daily stool frequency (SF) ≤ 2.8 and not worse than baseline AND Average daily abdominal pain (AP) score ≤ 1 and not worse than baseline | EU Co-Primary<br>US Ranked Secondary |
| | Clinical Remission (CDAI) | CDAI < 150 | US Co-Primary<br>EU Ranked Secondary |
| | CDAI Clinical Response (CR-100) | Reduction of CDAI ≥ 100 points from baseline | US Ranked Secondary |
| | Steroid-free Clinical Remission | Discontinuation of steroid and achievement of clinical remission (CDAI or PRO) among patients on steroid at Baseline | EU/US Ranked Secondary |
| Endoscopic Endpoints | Endoscopic Response | Decrease in SES-CD > 50% from baseline (or for subjects with isolated ileal disease and a baseline SES-CD of 4, at least a 2-point reduction from baseline), as scored by central reviewer | US/EU Co-Primary |
| | Endoscopic Remission | SES-CD ≤ 4 and at least a 2-point reduction versus baseline and no subscore greater than 1 in any individual variable, as scored by a central reviewer | US/EU Ranked Secondary |

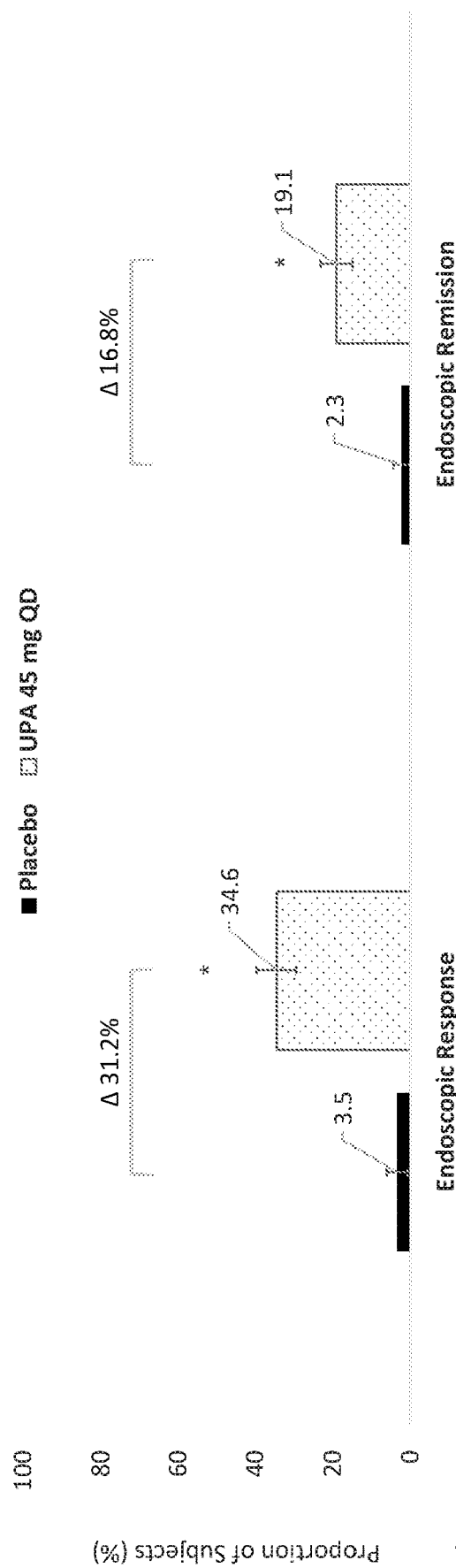

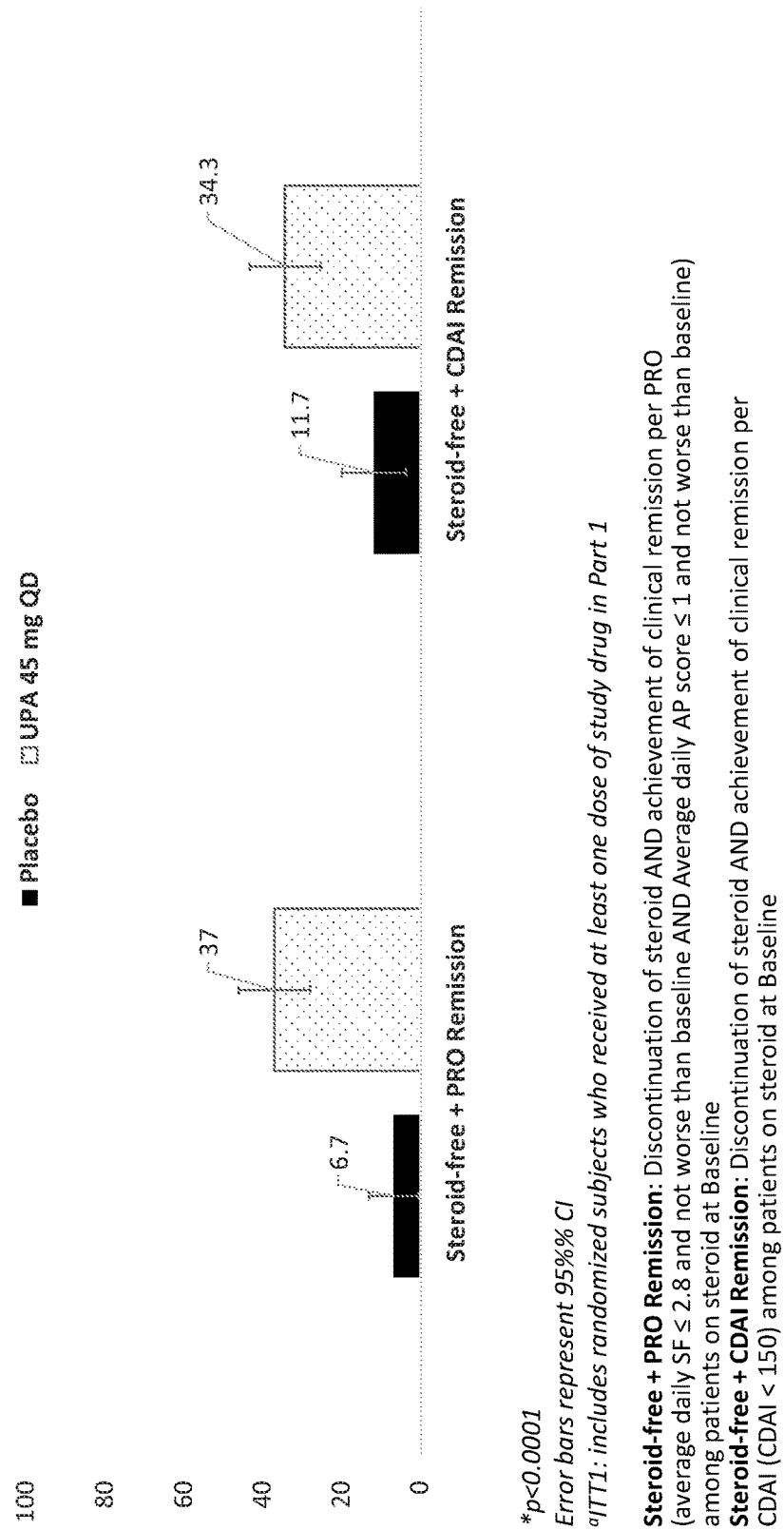

METHODS OF TREATING CROHN'S DISEASE AND ULCERATIVE COLITIS

RELATED APPLICATIONS

This application is a continuation of U.S. patent application Ser. No. 17/667,748, filed Feb. 9, 2022, which is a continuation in part of U.S. patent application Ser. No. 17/115,833, filed Dec. 9, 2020, which is a continuation of U.S. patent application Ser. No. 15/917,013, filed Mar. 9, 2018, and which claims priority to U.S. Provisional Application No. 62/469,337, filed Mar. 9, 2017, U.S. Provisional Application No. 62/470,565, filed Mar. 13, 2017, U.S. Provisional Application 62/483,289, filed Apr. 7, 2017 and U.S. Provisional Application No. 62/593,629, filed Dec. 1, 2017; and this application also claims priority to U.S. Provisional Application No. 63/151,429, filed Feb. 19, 2021, U.S. Provisional Application No. 63/211,412, filed Jun. 16, 2021, and U.S. Provisional Application No. 63/285,916, filed Dec. 3, 2021, each of which is incorporated by reference in its entirety.

FIELD OF THE DISCLOSURE

The present disclosure is directed to methods for treating inflammatory bowel diseases, such as Crohn's disease and ulcerative colitis, and in particular, to methods for inducing clinical remission and endoscopic improvement of Crohn's disease or a clinical remission and endoscopic improvement of ulcerative colitis, using a JAK1 inhibitor. In certain embodiments, the patient is administered an induction dose of the JAK1 inhibitor to induce clinical remission and/or endoscopic improvement of the Crohn's disease or a clinical remission of ulcerative colitis, followed by administration of at least one maintenance dose of the JAK1 inhibitor thereafter.

BACKGROUND OF THE DISCLOSURE

Inflammatory bowel disease (IBD) involves chronic inflammation of a patient's digestive tract. IBD includes both Crohn's disease and ulcerative colitis. The exact cause of IBD is not known. The IBD can be idiopathic IBD.

Crohn's Disease (CD) encompasses a spectrum of clinical and pathological processes manifested by focal asymmetric, transmural, and occasionally granulomatous inflammation that can affect any segment of the gastrointestinal tract (Lichtenstein G R, Hanauer S B, Sandborn W J; Practice Parameters Committee of American College of Gastroenterology, Management of Crohn's disease in adults, *Am J Gastroenterol.* 2009; 104(2):465-83). The disease can affect persons of any age, and its onset is most common in the second and third decades. Females are affected slightly more than males, and the risk for disease is higher in some ethnic groups (Loftus E V Jr., "Clinical epidemiology of inflammatory bowel disease: incidence, prevalence, and environmental influences," *Gastroenterology,* 2004; 126(6):1504-17; Probert C S, Jayanthi V, Rampton D S, et al., "Epidemiology of inflammatory bowel disease in different ethnic and religious groups: limitations and aetiological clues," *Int. J Colorectal Dis.,* 1996; 11(1):25-28). In North America, the incidence of CD is estimated to be 3.1 to 14.6 cases per 100,000 persons. Prevalence rates range from 26 to 99 cases per 100,000 persons. In Europe, CD has an incidence of 0.7 to 9.8 cases per 100,000 persons and a prevalence of 8.3 to 214 cases per 100,000 persons (Loftus E V Jr. Clinical epidemiology of inflammatory bowel disease: incidence, prevalence, and environmental influences. *Gastroenterology.* 2004; 126(6):1504-17).

CD has been characterized by significant morbidity including abdominal pain, diarrhea, weight loss/malnutrition, fatigue and a progressive nature that leads to complications such as fistulas, strictures and abscesses. In a population based study from southeastern Norway, a substantial number of patients demonstrated a stricturing or penetrating phenotype at 10 years after diagnosis (Solberg I C, Vatn M H, Hoie O, et al; IBSEN Study Group. Clinical course in Crohn's disease: results of a Norwegian population-based ten-year follow-up study. *Clin Gastroenterol Heptaol.* 2007; 5(12):1430-8). Moreover, approximately 80% of patients diagnosed with CD will require at least 1 surgery related to the disease at some point in time (Munkholm P, Langholz E, Davidsen M, et al. Intestinal cancer risk and mortality in patients with Crohn's disease. *Gastroenterology.* 1993:105 (6):1716-23).

Ulcerative colitis (UC) is one of the two primary forms of idiopathic inflammatory bowel disease (IBD). It is postulated that UC is caused by unregulated and exaggerated local immune response to environmental triggers in genetically susceptible individuals (Hanauer S B. Update on the etiology, pathogenesis and diagnosis of ulcerative colitis. *Nat Clin Pract Gastroenterol Hepatol.* 2004; 1(1):26-31). UC is a chronic, relapsing inflammatory disease of the large intestine characterized by inflammation and ulceration of mainly the mucosal and occasionally submucosal intestinal layers. The highest annual incidence of UC was 24.3 per 100,000 person-years in Europe, 6.3 per 100,000 person-years in Asia and the Middle East, and 19.2 per 100,000 person-years in North America, with a prevalence of 505 cases per 100,000 persons in Europe and 249 cases per 100,000 persons in North America. (Molodecky N A, Soon I S, Rabi D M, et al. Increasing incidence and prevalence of the inflammatory bowel diseases with time, based on systematic review. *Gastroenterology.* 2012:142(1):46-54). There is increasing incidence and prevalence of the inflammatory bowel diseases with time, based on systematic review. (*Gastroenterology.* 2012; 142(1):46-54.e42; quiz e30.) The burden of UC on the healthcare system is profound, accounting for nearly 500,000 physician visits and more than 46,000 hospitalizations per year in the United States (US) alone. (Sandler R S, Everhart J E, Donowitz M, et al., *Gastroenterology,* 2002; 122(5):1500-11).

The hallmark clinical symptoms of UC include bloody diarrhea associated with rectal urgency and tenesmus. The clinical course is marked by exacerbation and remission. The diagnosis of UC is suspected on clinical grounds and supported by diagnostic testing, and elimination of infectious causes. (Dignass A, Eliakim R, Magro F, et al. Second European evidence-based consensus on the diagnosis and management of ulcerative colitis part 1: definitions and diagnosis. *J Crohn's Colitis.* 2012; 6(10):965-90)

The most severe intestinal manifestations of UC are toxic megacolon and perforation. Extraintestinal complications include arthritis (peripheral or axial involvement), dermatological conditions (erythema nodosum, aphthous stomatitis, and pyoderma gangrenosum), inflammation of the eye (uveitis), and liver dysfunction (primary sclerosing cholangitis). Patients with UC are at an increased risk for colon cancer, and the risk increases with the duration of disease as well as extent of colon affected by the disease. (Rutter M, Saunders B, Wilkinson K, et al. Severity of inflammation is a risk factor for colorectal neoplasia in ulcerative colitis. (*Gastroenterology,* 2004; 126(2):451-9).

The aim of medical treatment in UC is to control inflammation and reduce symptoms. Available pharmaceutical therapies are limited, do not always completely abate the inflammatory process, and may have significant adverse effects. Therapies for mild to moderate active UC include 5-aminosalicylic acid derivatives and immunosuppressants.

Corticosteroids are used in patients with more severe UC symptoms but are not useful for longer term therapy. (Truelove S C, Witts Li. Cortisone and corticotrophin in ulcerative colitis. *Br Med J.* 1959; 1(5119):387-94). The frequency and severity of corticosteroid toxicities are significant, including infections, emotional and psychiatric disturbances, skin injury, and metabolic bone disease. Corticosteroids are not effective for the maintenance of remission and the UC practice guidelines from the American College of Gastroenterology recommend against chronic steroid treatment. (Kornbluth A, Sachar D B; Practice Parameters Committee of the American College of Gastroenterology. Ulcerative colitis practice guidelines in adults: American College of Gastroenterology, Practice Parameters Committee. *Am J Gastroenterol.* 2010; 105(3):501-23; quiz 524). Patients with moderate to severe symptoms may derive some benefits from immunosuppressant agents (azathioprine [AZA], 6-mercaptopurine [6-MP], or methotrexate [MTX]); however, the use of these agents is limited as induction treatment due to a slow onset of action (3 to 6 months) and as maintenance therapy due to adverse events (AEs), including bone marrow suppression, infections, hepatotoxicity, pancreatitis, and malignancies. (Kornbluth A, Sachar D B; Practice Parameters Committee of the American College of Gastroenterology. Ulcerative colitis practice guidelines in adults: American College of Gastroenterology, Practice Parameters Committee. *Am J Gastroenterol.,* 2010; 105(3): 501-23; quiz 524; Beaugerie L, Brousse N, Bouvier A M, et al. Lymphoproliferative disorders in patients receiving thiopurines for inflammatory bowel disease: a prospective observational cohort study. *Lancet.* 2009; 374(9701):1617-25). Despite these therapies, approximately 15% of ulcerative colitis patients experience a severe clinical course, and 30% of these patients require removal of the colon/rectum, to eliminate the source of the inflammatory process, although accompanied by significant morbidity (Aratari A, Papi C, Clemente V, et al. Colectomy rate in acute severe ulcerative colitis in the infliximab era. *Dig Liver Dis.* 2008; 40(10):821-6; Turner D, Walsh C M, Steinhart A H, et al. Response to corticosteroids in severe ulcerative colitis: a systematic review of the literature and a meta-regression. *Clin Gastroenterol Hepatol.* 2007; 5(1):103-10).

Biological agents targeting specific immunological pathways have been evaluated for their therapeutic effect in treating patients with UC. Anti-tumor necrosis factor (TNF) agents were the first biologics to be used for IBD. Infliximab, adalimumab, and golimumab are successfully being used for the treatment of UC. Recently, vedolizumab, an anti-adhesion therapy, has been approved for the treatment of UC by the US Food and Drug Administration (FDA) and the European Medicines Agency (EMA), and clinical development is ongoing in Japan.

Anti-TNF therapies are an effective treatment for patients who are steroid refractory or steroid dependent, who had inadequate response to a thiopurine, or who are intolerant to these medications. Potential risks with anti-TNF therapies include infusion or injection site reactions, serious infections, lymphoma, heart failure, lupus-like syndromes, and demyelinating conditions (Sandborn W J. State-of-the-art: immunosuppression and biologic therapy. *Dig Dis.* 2010; 28(3):536-42). Despite the beneficial results achieved with the available biologic agents, only 17% to 45% of patients who receive them are able to achieve clinical remission. (Rutgeerts P, Sandborn W, Feagan B, et al., Infliximab for induction and maintenance therapy for ulcerative colitis. *N Engl J Med.* 2005, 353(23):2462-76; Sandborn W J, van Assche G, Reinisch W, et al. Adalimumab induces and maintains clinical remission in patients with moderate-to-severe ulcerative colitis. *Gastroenterology,* 2012, 142(2): 257-65; Feagan B, Greenberg G, Wild G, et al., Treatment of ulcerative colitis with a humanized antibody to the alpha4beta7 integrin, *N. Engl. J. Med.* 2005, 352(24):2499-507; Sandborn W, Feagan B, Marano C, et al. Subcutaneous golimumab induces clinical response and remission in patients with moderate-to-severe ulcerative colitis, Gastroenterology, 2014, 146(1):85-95; quiz e14-5), Thus, there remains a clear medical need for additional therapeutic options in UC for patients with inadequate response to or intolerance to conventional therapies and biologic therapies.

Given that no known medical or surgical cure currently exists for CD, the therapeutic strategy is to reduce symptoms, improve quality of life, reduce endoscopic evidence of inflammation, and minimize short- and long term toxicity and complications (Lichtenstein G R, Hanauer S B, Sandborn W J; Practice Parameters Committee of American College of Gastroenterology, Management of Crohn's disease in adults, *Am J Gastroenterol.,* 2009, 104(2):465-83). Currently, patients with moderate to severe disease are usually treated with conventional pharmacologic interventions, which include corticosteroids and immunosuppressant agents such as azathioprine, 6-mercaptopurine, or methotrexate (MTX) (Lichtenstein G R, Hanauer S B, Sandborn W J, Practice Parameters Committee of American College of Gastroenterology, Management of Crohn's disease in adults, *Am J Gastroenterol,* 2009, 104(2):465-83; Dignass A, Van Assche G, Lindsay J O, et al., European Crohn's and Colitis Oganisation (ECCO), The second European evidence-based Consensus on the diagnosis and management of Crohn's disease: current management, *J Crohn's Colitis,* 2010, 4(1): 28-62, Erratum in: *J Crohn's Colitis,* 2010, 4(3):353).

The potential risks from long term use of corticosteroids are well-known. Adverse events (AEs) associated with short-term use of corticosteroids include acne, moon face, edema, skin striae, glucose intolerance, and sleep/mood disturbances, while potential AEs observed with longer term use (usually 12 weeks or longer but sometimes shorter durations) include posterior subcapsular cataracts, osteoporosis, osteonecrosis of the femoral head, myopathy, and susceptibility to infection (Irving P M, Gearry R B, Sparrow M P, et al., Review article: appropriate use of corticosteroids in Crohn's disease, *Aliment Pharmacol Ther.,* 2007, 26(3): 313-29; Rutgeerts P J, Review article: the limitations of corticosteroid therapy in Crohn's disease, *Aliment Pharmacol Ther.,* 2001, 15(10):1515-25). The safety risks for azathioprine and 6-mercaptopurine include pancreatitis, bone marrow depression, infectious complications, and malignant neoplasms (Sandborn, W J, State-of-the-art: immunosuppression and biologic therapy, *Dig Dis.,* 2010, 28(3):536-42). MTX may be associated with nausea, bone marrow depression and liver and pulmonary toxicity (Siegel, et al., Review article: Practical Management of Inflammatory Bowel Disease Patients Taking Immunosuppressants, *Aliment Pharmacol Ther.,* 2005, 22:1-16). Patients who do not respond to conventional therapies are treated with anti-TNF-α therapies (i.e., biologics) (Lichtenstein G R, Hanauer S B, Sandborn W J, Practice Parameters Committee of American College of Gastroenterology, Management of Crohn's disease in adults, *Am J Gastroenterol.,* 2009, 104

(2):465-83; Dignass A, Van Assche G, Lindsay J O, et al., European Crohn's and Colitis Oganisation (ECCO), The second European evidence-based Consensus on the diagnosis and management of Crohn's disease: current management, *J Crohn's Colitis*, 2010, 4(1):28-62, Erratum in: *J. Crohn's Colitis*, 2010, 4(3):353). Potential risks with biologics include infusion or injection site reactions, serious infections, lymphoma and other malignancies, heart failure, cytopenias, lupus-like syndromes, and demyelinating conditions (Sandborn W J, State-of-the-art: immunosuppression and biologic therapy, *Dig. Dis.*, 2010, 28(3):536-42).

Despite the beneficial results achieved with the available anti-TNF-α agents, approximately 40% of patients who receive them for the first time do not have a clinically meaningful response (primary nonresponders) (Targan S R, Hanauer S B, van Deventer S J, et al., A short-term study of chimeric monoclonal antibody cA2 to tumor necrosis factor alpha for Crohn's disease, *N. Engl. J. Med.*, 1997, 337(15): 1029-35; Hanauer S B, Feagan B G, Lichtenstein G R, et al., ACCENT I Study Group, Maintenance infliximab for Crohn's disease: the ACCENT I randomized trial, *Lancet*, 2002, 359(9317):1541-9; Hanauer S B, Sandborn W J, Rutgeerts P, et al., Human anti-tumor necrosis factor monoclonal antibody (adalimumab) in Crohn's disease: the CLASSIC-I trial, *Gastroenterology*, 2007, 132(1):52-65; Colombel J F, Sandborn W J, Rutgeerts P, et al., Adalimumab for maintenance of clinical response and remission in patients with Crohn's disease: the CHARM trial, *Gastroenterology*, 2007, 132(1):52-65; Sandborn W J, Feagan B G, Stoinov S, et al., PRECISE I Study Investigators, Certolizumab pegol for the treatment of Crohn's disease, *N. Engl. J. Med.*, 2007, 357(3):228-38). Among patients who initially respond and continue to receive maintenance treatment for longer durations, approximately 38% become nonresponders after 6 months (Schribeinger S, Khaliq-Kareemi M, Lawrance I C, et al; PRECISE 2 Study Investigators, Maintenance therapy with certolizumab pegol for Crohn's disease, *N. Engl. J. Med.*, 2007, 357(3):239-50, Erratum in: *N. Engl. J. Med.*, 2007, 357(13):1357) and approximately 50% become nonresponders at 1 year lose response (secondary nonresponders) (Hanauer S B, Feagan B G, Lichtenstein G R, et al., ACCENT I Study Group, Maintenance infliximab for Crohn's disease: the ACCENT I randomized trial, *Lancet*, 2002, 359(9317):1541-9; Colombel J F, Sandborn W J, Rutgeerts P, et al., Adalimumab for maintenance of clinical response and remission in patients with Crohn's disease: the CHARM trial, *Gastroenterology*, 2007, 132(1): 52-65). Patients who initially respond to a first anti-TNF agent but then lose response tend to have lower response and remission rates to the second anti-TNF agent (Colombel J F, Sandborn W J, Rutgeerts P, et al., Adalimumab for maintenance of clinical response and remission in patients with Crohn's disease: the CHARM trial, *Gastroenterology*, 2007, 132(1):52-65; Sandborn, et al., "Natalizumab induction and maintenance therapy for Crohn's disease," *N. Engl. J. Med.*, 2005, 353(18):1912-25).

New classes of biologics have been studied in patients with prior anti-TNF use. Natalizumab, a humanized monoclonal antibody to α4β1 and α4β7 integrins, showed promise for patients with prior exposure to anti-TNF-α therapy; more than half of the patients had a response to the induction regimen (Sandborn, et al., "Natalizumab induction and maintenance therapy for Crohn's disease," *N. Engl. J. Med.*, 2005, 353(18):1912-25). However, natalizumab's use after approval in 2008 has been severely limited due to the serious risk for progressive multifocal leukoencephalopathy (PML) attributed to activation of the latent JC virus (Van Assche G, Van Ranst M, Sciot R, et al., "Progressive multifocal leukoencephalopathy after natalizumab therapy for Crohn's disease," *N. Engl. J. Med.*, 2005, 353(4):362-8). Vedolizumab is specific to the α4β7 integrin, which does not affect lymphocyte trafficking to the brain. Therefore, it is presumed to not have the PML risk associated with natalizumab. However, it does not fulfill many of the unmet needs of patients who have failed treatment with anti-TNFs, such as the improvement of extra-intestinal manifestations (Rubin, et al., *Inflammatory Bowel Diseases*, 2016, 22 Supp.1:S42-S43). In the induction study with vedolizumab, the primary endpoint of clinical remission in patients who had previously failed treatment with an anti TNF was not statistically significant nor was it clinically meaningful since there was only a 3% difference from placebo (Sands, et al., "Effects of Vedolizumab Induction Therapy for Patients with Crohn's Disease in Whom Tumor Necrosis Factor Antagonist Treatment Failed," *Gastroenterology*, 2014, 147:618-627). Ustekinumab, a human monoclonal antibody that selectively targets IL-12 and IL-23, has efficacy in both patients who have responded to and patients who have not responded to prior anti-TNFα therapy. The efficacy of ustekinumab, however, is broadly similar to that of anti-TNF agents, and therefore subject to similar drawbacks (*Ther. Adv. Gastroenterology*, 2016, Vol. 9(1), pp. 26-36). Clearly, the need for additional therapeutic options in CD for patients who fail or are intolerant to conventional therapies, and anti-TNF-α agents or other biologic therapies remains.

SUMMARY OF THE DISCLOSURE

The present disclosure addresses the above needs and provides methods for treating Crohn's disease and ulcerative colitis. In some aspects, the present disclosure provides methods for treating Crohn's disease in patients that have moderately to severely active Crohn's disease. In some aspects, the present disclosure provides methods for treating ulcerative colitis in patients that have moderately to severely active ulcerative colitis. The patient may have had an inadequate response to or experienced intolerance to conventional treatment, such as aminosalicylates, corticosteroids or immunosuppressants, or to a previous treatment with an anti-TNF therapy or another biologic agent. In one embodiment, the patient is an adult with moderately to severely active Crohn's disease and has had an inadequate response to, or were intolerant to, corticosteroid, immunomodulator, or biologic therapy.

In one embodiment, the present disclosure is directed to a method of inducing clinical remission of Crohn's disease in a patient, said method comprising: a) administering to the patient at least one induction dose of (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (upadacitinib), or a pharmaceutically acceptable salt or solid state form thereof, wherein said induction dose comprises 30 to 45 mg of upadacitinib, or a pharmaceutically acceptable salt or solid state form thereof. In one embodiment, the method further comprises maintaining the clinical remission of Crohn's disease, wherein the method further comprises b) administering a first maintenance dose of upadacitinib, or a pharmaceutically acceptable salt or solid state form thereof to the patient after the last induction dose is administered; and c) administering at least one additional maintenance dose once daily thereafter.

In another embodiment, the present disclosure is directed to a method of inducing endoscopic improvement of Crohn's disease in a patient, said method comprising: a)

administering to the patient at least one induction dose of upadacitinib, or a pharmaceutically acceptable salt or solid state form thereof, wherein said induction dose comprises 30 to 45 mg of upadacitinib, or a pharmaceutically acceptable salt or solid state form thereof. In one embodiment, the method further comprises maintaining the endoscopic improvement of Crohn's disease, wherein the method further comprises b) administering a first maintenance dose of upadacitinib, or a pharmaceutically acceptable salt or solid state form thereof to the patient after the last induction dose is administered; and c) administering at least one additional maintenance dose once daily thereafter.

In another embodiment, the present disclosure is directed to a method of inducing clinical remission of Crohn's disease in a patient, said method comprising: a) administering to the patient at least one induction dose of upadacitinib, or a pharmaceutically acceptable salt or solid state form thereof, wherein said induction dose comprises 45 mg of upadacitinib, or a pharmaceutically acceptable or solid state form salt thereof. In one embodiment, the method further comprises maintaining the clinical remission of Crohn's disease, wherein the method further comprises b) administering a first maintenance dose of upadacitinib, or a pharmaceutically acceptable salt or solid state form thereof to the patient after the last induction dose is administered; and c) administering at least one additional maintenance dose once daily thereafter.

In another embodiment, the present disclosure is directed to a method of inducing endoscopic remission of Crohn's disease in a patient, said method comprising: a) administering to the patient at least one induction dose of upadacitinib, or a pharmaceutically acceptable salt or solid state form thereof, wherein said induction dose comprises 45 mg of upadacitinib, or a pharmaceutically acceptable salt or solid state form thereof. In one embodiment, the method further comprises maintaining the endoscopic remission of Crohn's disease, wherein the method further comprises b) administering a first maintenance dose of upadacitinib, or a pharmaceutically acceptable salt or solid state form thereof to the patient after the last induction dose is administered; and c) administering at least one additional maintenance dose once daily thereafter.

In one embodiment, the induction dose comprises 45 mg of upadacitinib, or a pharmaceutically acceptable salt or solid state form thereof.

In one embodiment, the patient had an inadequate response to or experienced intolerance to a previous treatment with a corticosteroid, an immunosuppressant, or a biologic agent. In one embodiment, the patient had an inadequate response to or experienced intolerance to a previous treatment with an anti-TNF agent. In one embodiment, the patient had moderately to severely active Crohn's disease prior to administration of the induction dose.

In one embodiment, the induction dose is administered orally to the patient. In one embodiment, the induction dose is administered once daily to the patient.

In one embodiment, clinical remission is achieved within 16 weeks of initiating administration of upadacitinib, or a pharmaceutically acceptable salt or solid state form thereof. In one embodiment, clinical remission is achieved within 12 weeks of initiating administration of upadacitinib, or a pharmaceutically acceptable salt or solid state form thereof.

In one embodiment, endoscopic improvement is achieved within 16 weeks of initiating administration of upadacitinib, or a pharmaceutically acceptable salt or solid state form thereof. In one embodiment, endoscopic improvement is achieved within 12 weeks of initiating administration of upadacitinib, or a pharmaceutically acceptable salt or solid state form thereof.

In one embodiment, clinical remission is achieved within 16 weeks of initiating administration of upadacitinib, or a pharmaceutically acceptable salt or solid state form thereof. In one embodiment, clinical remission is achieved within 12 weeks of initiating administration of upadacitinib, or a pharmaceutically acceptable salt or solid state form thereof.

In one embodiment, endoscopic remission is achieved within 16 weeks of initiating administration of upadacitinib, or a pharmaceutically acceptable salt or solid state form thereof. In one embodiment, endoscopic remission is achieved within 12 weeks of initiating administration of upadacitinib, or a pharmaceutically acceptable salt or solid state form thereof.

In one embodiment, after administration of at least one induction dose, the patient's Simplified Endoscopic Score for Crohn's Disease (SES-CD) is greater than a 50% decrease or endoscopic remission versus the patient's baseline SES-CD. In one embodiment, after administration of at least one induction dose, the patient's Simplified Endoscopic Score for Crohn's Disease (SES-CD) is at least a 2 point reduction versus the patient's baseline SES-CD. In one embodiment, after administration of at least one induction dose, the patient achieves an endoscopic remission. In one embodiment, after administration of at least one induction dose, the patient achieves a clinical response. In one embodiment, the patient achieves a clinical response as early as two weeks from the first induction dose. In one embodiment, after administration of at least one induction dose, the patient achieves a CDAI score of less than 150.

In one embodiment, the first maintenance dose comprises 15 mg of upadacitinib, or a pharmaceutically acceptable salt or solid state form thereof. In one embodiment, the first maintenance dose comprises 30 mg of upadacitinib, or a pharmaceutically acceptable salt or solid state form thereof.

In one embodiment, the at least one additional maintenance dose comprises 15 mg of upadacitinib, or a pharmaceutically acceptable salt or solid state form thereof. In one embodiment, the at least one additional maintenance dose comprises 30 mg of upadacitinib, or a pharmaceutically acceptable salt or solid state form thereof.

In one embodiment, the first maintenance dose and said at least one additional maintenance dose are administered orally. In one embodiment, the first maintenance dose and said at least one additional maintenance dose are administered once daily.

In one embodiment, the patient maintains clinical remission. In one embodiment, the patient maintains endoscopic improvement. In one embodiment, the patient maintains endoscopic remission.

In one embodiment, the patient maintains a Simplified Endoscopic Score for Crohn's Disease (SES-CD) that is greater than a 50% decrease or endoscopic remission versus the patient's baseline SES-CD. In one embodiment, the said patient maintains a Simplified Endoscopic Score for Crohn's Disease (SES-CD) that is at least a 2 point reduction versus the patient's baseline SES-CD. In one embodiment, the patient maintains an endoscopic remission. In one embodiment, the patient maintains a CDAI score of less than 150. In one embodiment, the patient maintains a clinical response.

In one embodiment, the patient achieves a CDAI score of less than 150 before administration of the first maintenance dose. In one embodiment, the patient achieves a clinical response before administration of the first maintenance dose.

In one embodiment, the induction dose comprises 45 mg of upadacitinib, or a pharmaceutically acceptable salt or solid state form thereof, administered orally once daily, the first maintenance dose comprises 30 mg of upadacitinib, or a pharmaceutically acceptable salt or solid state form thereof, administered orally once daily, and the at least one additional maintenance dose comprises 30 mg of upadacitinib, or a pharmaceutically acceptable salt or solid state form thereof, administered orally once daily.

In one embodiment, the induction dose comprises 45 mg of upadacitinib, or a pharmaceutically acceptable salt or solid state form thereof, administered orally once daily, the first maintenance dose comprises 15 mg of upadacitinib, or a pharmaceutically acceptable salt or solid state form thereof, administered orally once daily, and the at least one additional maintenance dose comprises 15 mg of upadacitinib, or a pharmaceutically acceptable salt or solid state form thereof, administered orally once daily.

In one embodiment, the induction dose is in a once-daily, modified release formulation. In one embodiment, the first maintenance dose and the at least one additional maintenance dose are each in a once-daily, modified release formulation.

In one embodiment, the present disclosure is directed to a method for treating Crohn's disease comprising administering to a patient 15 mg to 45 mg of upadacitinib, or a pharmaceutically acceptable salt or solid state form thereof. In one embodiment, the method comprising administering 15 mg of upadacitinib, or a pharmaceutically acceptable salt or solid state form thereof. In one embodiment, the method comprising administering 30 mg of upadacitinib, or a pharmaceutically acceptable salt or solid state form thereof. In one embodiment, the method comprising administering 45 mg of upadacitinib, or a pharmaceutically acceptable salt or solid state form thereof. In one embodiment, upadacitinib, or a pharmaceutically acceptable salt or solid state form thereof is administered orally to the patient. In one embodiment, upadacitinib, or a pharmaceutically acceptable salt or solid state form thereof is administered once daily to the patient.

In one embodiment, the present disclosure is directed to a method for treating Crohn's disease comprising: a) administering to a patient at least one induction dose of upadacitinib, or a pharmaceutically acceptable salt or solid state form thereof, wherein said induction dose comprises 45 mg of upadacitinib, or a pharmaceutically acceptable salt or solid state form thereof. In one embodiment, the method further comprises b) administering a first maintenance dose of upadacitinib, or a pharmaceutically acceptable salt or solid state form thereof to the patient after the last induction dose is administered; and c) administering at least one additional maintenance dose to the patient once daily thereafter.

In one such embodiment, the first maintenance dose comprises 15 mg of upadacitinib, or a pharmaceutically acceptable salt or solid state form thereof. In one embodiment, the first maintenance dose comprises 30 mg of upadacitinib, or a pharmaceutically acceptable salt or solid state form thereof. In one embodiment, the first maintenance dose is administered orally.

In one embodiment, the at least one additional maintenance dose comprises 15 mg of upadacitinib, or a pharmaceutically acceptable salt or solid state form thereof. In one embodiment, the at least one additional maintenance dose comprises 30 mg of upadacitinib, or a pharmaceutically acceptable salt or solid state form thereof. In one embodiment, the at least one additional maintenance dose is administered orally.

In one embodiment, the patient maintains a CDAI score of less than 150.

In one embodiment, the patient had an inadequate response to or experienced intolerance to a previous treatment with a corticosteroid, an immunosuppressant, or a biologic agent. In one embodiment, the patient had an inadequate response to or experienced intolerance to a previous treatment with an anti-TNF agent.

In one embodiment, the patient achieves a clinical remission after administration of at least one induction dose. In one embodiment, the patient achieves an endoscopic improvement after administration of at least one induction dose. In one embodiment, the patient achieves an endoscopic remission after administration of at least one induction dose. In one embodiment, the patient achieves a clinical response after administration of at least one induction dose.

In one embodiment, the induction dose comprises 45 mg of upadacitinib, or a pharmaceutically acceptable salt or solid state form thereof, administered orally once daily, said first maintenance dose comprises 30 mg of upadacitinib, or a pharmaceutically acceptable salt or solid state form thereof, administered orally once daily, and said at least one additional maintenance dose comprises 30 mg of upadacitinib, or a pharmaceutically acceptable salt or solid state form thereof, administered orally once daily.

In one embodiment, the induction dose comprises 45 mg of upadacitinib, or a pharmaceutically acceptable salt or solid state form thereof, administered orally once daily, said first maintenance dose comprises 15 mg of upadacitinib, or a pharmaceutically acceptable salt or solid state form thereof, administered orally once daily, and said at least one additional maintenance dose comprises 15 mg of upadacitinib, or a pharmaceutically acceptable salt or solid state form thereof, administered orally once daily.

In one embodiment, the induction dose is in a once-daily, modified release formulation. In one embodiment, the first maintenance dose and the at least one additional maintenance dose are each in a once-daily, modified release formulation. In one embodiment, the patient had moderately to severely active Crohn's disease prior to administration of the induction dose.

In one embodiment, the present disclosure is directed to a method of inducing remission in a patient having moderately to severely active Crohn's disease, the method comprising administering 45 mg of upadacitinib or a pharmaceutically acceptable salt or solid state form thereof, to the patient. In one such embodiment, the patient had an inadequate response to or was intolerant to aminosalicylates, corticosteroids, immunosuppressants, biologic agents, anti-TNF agents, or combinations thereof.

In one embodiment, the present disclosure is directed to a method of inducing clinical remission in a patient having moderately to severely active Crohn's disease the method comprising administering 45 mg of upadacitinib or a pharmaceutically acceptable salt or solid state form thereof, to the patient. In one such embodiment, the patient had an inadequate response to or was intolerant to aminosalicylates, corticosteroids, immunosuppressants, biologic agents, anti-TNF agents, or combinations thereof.

In one embodiment, the present disclosure is directed to a method of inducing endoscopic improvement in a patient having moderately to severely active Crohn's disease the method comprising administering 45 mg of upadacitinib or a pharmaceutically acceptable salt or solid state form thereof to the patient. In one such embodiment, the patient had an inadequate response to or was intolerant to aminosalicylates, corticosteroids, immunosuppressants, biologic agents, anti-TNF agents, or combinations thereof.

In one embodiment, the present disclosure is directed to a method of treating a refractory patient having moderately to severely active Crohn's disease the method comprising administering 45 mg of upadacitinib, or a pharmaceutically acceptable salt or solid state form thereof, to the patient. In one such embodiment, clinical remission is induced within 16 weeks of administering the initial dose of upadacitinib or a pharmaceutically acceptable salt or solid state form thereof. In one such embodiment, endoscopic improvement is induced within 12 weeks or within 16 weeks of administering the initial dose of upadacitinib or a pharmaceutically acceptable salt or solid state form thereof.

In one embodiment, the induction dose comprises 45 mg of upadacitinib or a pharmaceutically acceptable salt or solid state form thereof. In another embodiment, the first maintenance dose and/or the at least one additional maintenance doses comprise 15 mg to 30 mg of upadacitinib, or a pharmaceutically acceptable salt or solid state form thereof.

In another embodiment, the method of the present disclosure is a method of inducing clinical remission of Crohn's disease in a patient, the method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; and b) wherein said patient achieves clinical remission within 12 weeks of administration of the first induction dose.

In one embodiment, clinical remission of Crohn's disease is induced within 4 weeks of the first induction dose of upadacitinib, or a pharmaceutically acceptable salt thereof.

In another embodiment, the method is a method of inducing clinical response of Crohn's disease in a patient, said method comprising: a) administering to the patient an induction dose of upadacitinib, or a pharmaceutically acceptable salt thereof, wherein said induction dose is administered orally once a day for at least 2 weeks and comprises 45 mg of upadacitinib or a 45 mg free base equivalent amount of a pharmaceutically acceptable salt thereof; and b) wherein said patient achieves clinical response.

In one embodiment, the clinical response of Crohn's disease is induced within 4 weeks of the first induction dose of upadacitinib, or a pharmaceutically acceptable salt thereof. In one embodiment, the clinical response of Crohn's disease is induced within 12 weeks of the first induction dose of upadacitinib, or a pharmaceutically acceptable salt thereof.

In another embodiment, the method is a method of inducing endoscopic remission of Crohn's disease in a patient, said method comprising: a) administering to the patient an induction dose of upadacitinib, or a pharmaceutically acceptable salt thereof, wherein said induction dose is administered orally once a day for at least 12 weeks and comprises 45 mg of upadacitinib, or a 45 mg free base equivalent amount of a pharmaceutically acceptable salt thereof; and b) wherein said patient achieves endoscopic remission within 12 weeks of administration of the first induction dose.

In one embodiment, the endoscopic remission of Crohn's disease is induced within 4 weeks of the first induction dose of upadacitinib, or a pharmaceutically acceptable salt thereof.

In one embodiment, the endoscopic remission of Crohn's disease is induced within 12 weeks of the first induction dose of upadacitinib, or a pharmaceutically acceptable salt thereof.

In another embodiment, the method is a method of inducing endoscopic response of Crohn's disease in a patient, said method comprising: a) administering to the patient an induction dose of upadacitinib, or a pharmaceutically acceptable salt thereof, wherein said induction dose is administered orally once a day for at least 12 weeks and comprises 45 mg of upadacitinib, or a 45 mg free base equivalent amount of a pharmaceutically acceptable salt thereof; and b) wherein said patient achieves endoscopic response within 12 weeks of administration of the first induction dose.

In one embodiment, the endoscopic response of Crohn's disease is induced within 12 weeks of the first induction dose of upadacitinib, or a pharmaceutically acceptable salt thereof.

In another embodiment, the method is a method of inducing corticosteroid-free remission of Crohn's disease in a patient, said method comprising: a) administering to the patient an induction dose of upadacitinib, or a pharmaceutically acceptable salt thereof, wherein said induction dose is administered orally once a day for at least 12 weeks and comprises 45 mg of upadacitinib, or a 45 mg free base equivalent amount of a pharmaceutically acceptable salt thereof; and b) wherein said patient achieves steroid-free remission within 4 weeks of administration of the first induction dose.

In one embodiment, the patient is an adult with moderately to severely active Crohn's disease.

In one embodiment, the patient experiences a CDAI reduction of greater than 150 within 12 weeks of administration of the first induction dose.

In one embodiment, the patient had an inadequate response to or experienced intolerance to a previous treatment with a corticosteroid, an immunosuppressant, or a biologic agent.

In one embodiment, the patient had an inadequate response to or experienced intolerance to a previous treatment with an anti-TNF agent.

In one embodiment, the patient had an inadequate response to or experienced intolerance to an infliximab, adalimumab or certolizumab pegol.

In one embodiment, the patient had an inadequate response to or experienced intolerance to an anti-integrin or an anti-IL12/23. In one embodiment, the patient had an inadequate response to or experienced intolerance to vedolizumab, natalizumab, or ustekinumab.

In one embodiment, the patient has had a diagnosis of Crohn's disease for more than ten years and has had an inadequate response to or experienced intolerance to one or more previous treatments. In one embodiment, the previous treatments are selected from the group consisting of corticosteroids, immunosuppressants, antibiotics and biologic therapies.

In one embodiment, the method comprises a method of inducing and maintaining clinical remission of Crohn's disease in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; b) wherein said patient achieves clinical remission within 12 weeks of administration of the first induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method comprises a method of inducing and maintaining clinical response of Crohn's disease in a patient, said method comprising: a) administering to the patient an induction dose of upadacitinib, or a pharmaceutically acceptable salt thereof, wherein said induction dose is administered orally once a day for at least 2 weeks and comprises 45 mg of upadacitinib, or a 45 mg free base equivalent amount of a pharmaceutically acceptable salt thereof; and b) wherein said patient achieves clinical response within 2 weeks of administration of the first induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical response for 52 weeks after administration of the first induction dose.

In one embodiment, the clinical response of Crohn's disease is induced within 4 weeks of the first induction dose of upadacitinib, or a pharmaceutically acceptable salt thereof.

In one embodiment, the clinical response of Crohn's disease is induced within 12 weeks of the first induction dose of upadacitinib, or a pharmaceutically acceptable salt thereof.

In one embodiment, the method comprises a method of inducing and maintaining endoscopic remission of Crohn's disease in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; and b) wherein said patient achieves endoscopic remission within 12 weeks of administration of the first induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains endoscopic remission for 52 weeks after administration of the first induction dose.

In one embodiment, the endoscopic remission of Crohn's disease is induced within 12 weeks of the first induction dose of upadacitinib, or a pharmaceutically acceptable salt thereof.

In one embodiment, the method is a method of inducing and maintaining endoscopic response of Crohn's disease in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; and b) wherein said patient achieves endoscopic response within 4 weeks of administration of the first induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains endoscopic response for 52 weeks after administration of the first induction dose.

In one embodiment, the endoscopic response of Crohn's disease is induced within 12 weeks of the first induction dose of upadacitinib, or a pharmaceutically acceptable salt thereof.

In one embodiment, the method is a method of inducing and maintaining corticosteroid-free remission of Crohn's disease in a patient, said method comprising: a) administering to the patient an induction dose of upadacitinib, or a pharmaceutically acceptable salt thereof, wherein said induction dose is administered orally once a day for at least 12 weeks and comprises 45 mg of upadacitinib, or a 45 mg free base equivalent amount of a pharmaceutically acceptable salt thereof; b) wherein said patient achieves steroid-free remission within 4 weeks of administration of the first induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered and; d) administering at least one additional maintenance dose to the patient of upadacitinib, or a pharmaceutically acceptable salt thereof; and e) wherein said patient maintains corticosteroid-free remission for 52 weeks after administration of the first induction dose.

In one embodiment, the patient is an adult with moderately to severely active Crohn's disease.

In one embodiment, the patient experiences improvement in stool frequency one week after the first induction dose. In one embodiment the patient experiences improvement in abdominal pain at 8 weeks after the first induction dose.

In one embodiment, the patient experiences a CDAI reduction of greater than 150 within 12 weeks of administration of the first induction dose.

In one embodiment, the patient had an inadequate response to or experienced intolerance to a previous treatment with a corticosteroid, an immunosuppressant, or a biologic agent.

In one embodiment, the patient had an inadequate response to or experienced intolerance to a previous treatment with an anti-TNF agent.

In one embodiment, the anti-TNF agent is infliximab, adalimumab or certolizumab pegol.

In one embodiment, the patient had an inadequate response to or experienced intolerance to an anti-integrin or an anti-IL12/23. In one embodiment, the patient had an inadequate response to or experienced intolerance to vedolizumab, natalizumab, or ustekinumab.

In one embodiment, the patient has had a diagnosis of Crohn's disease for more than ten years and has had an inadequate response to or experienced intolerance to a previous treatment.

In one embodiment, the previous treatments are selected from corticosteroids, immunosuppressants, antibiotics and biologic therapies.

In one embodiment, the method is a method of inducing and maintaining clinical remission of Crohn's disease in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; b) wherein said patient achieves clinical remission within 4 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining clinical response of Crohn's disease in a patient, said method comprising: a) administering to the patient an induction dose of upadacitinib, or a pharmaceutically acceptable salt thereof, wherein said induction dose is administered orally once a day for at least 2 weeks and comprises 45 mg of upadacitinib, or a 45 mg free base equivalent amount of a pharmaceutically acceptable salt thereof; and b) wherein said patient achieves clinical response within 2 weeks of administration of the first induction dose; c) administering to the patient a first maintenance dose of upadacitinib, or a pharmaceutically acceptable salt thereof, wherein said maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof, and e) wherein said patient maintains clinical response for 52 weeks after administration of the first induction dose.

In one embodiment, the clinical response of Crohn's disease is induced within 4 weeks of the first induction dose of upadacitinib, or a pharmaceutically acceptable salt thereof.

In one embodiment, the clinical response of Crohn's disease is induced within 12 weeks of the first induction dose of upadacitinib, or a pharmaceutically acceptable salt thereof.

In one embodiment, the method is a method of inducing and maintaining endoscopic remission of Crohn's disease in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; and b) wherein said patient achieves endoscopic remission within 4 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains endoscopic remission for 52 weeks after administration of the first induction dose.

In one embodiment, the method is a method of inducing and maintaining endoscopic remission of Crohn's disease in a patient, said method comprising: a) administering to the patient an induction dose of upadacitinib, or a pharmaceutically acceptable salt thereof, wherein said induction dose is administered orally once a day for at least 12 weeks and comprises 45 mg of upadacitinib, or a 45 mg free base equivalent amount of a pharmaceutically acceptable salt thereof; and b) wherein said patient achieves endoscopic remission within 4 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains endoscopic remission for 52 weeks after administration of the first induction dose.

In one embodiment, the endoscopic remission of Crohn's disease is induced within 12 weeks of the first induction dose of upadacitinib, or a pharmaceutically acceptable salt thereof.

In one embodiment, the method is a method of inducing and maintaining endoscopic response of Crohn's disease in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; and b) wherein said patient achieves endoscopic response within 4 weeks of administration of the first induction dose; c) administering to the patient a first maintenance dose of upadacitinib, or a pharmaceutically acceptable salt thereof, wherein said maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains endoscopic response for 52 weeks after administration of the first induction dose.

In one embodiment, the endoscopic response of Crohn's disease is induced within 12 weeks of the first induction dose of upadacitinib, or a pharmaceutically acceptable salt thereof.

In one embodiment, the method is a method of inducing and maintaining corticosteroid-free remission of Crohn's disease in a patient, said method comprising: a) administering to the patient an induction dose of upadacitinib, or a pharmaceutically acceptable salt thereof, wherein said induction dose is administered orally once a day for at least 12 weeks and comprises 45 mg of upadacitinib, or a 45 mg free base equivalent amount of a pharmaceutically acceptable salt thereof; b) wherein said patient achieves steroid-free remission within 12 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered and; d) administering at least one additional maintenance dose to the patient of upadacitinib, or a pharmaceutically acceptable salt thereof; and e) wherein said patient maintains corticosteroid-free remission for 52 weeks after administration of the first induction dose.

In one embodiment, the patient is an adult with moderately to severely active Crohn's disease.

In one embodiment, the patient experiences a CDAI reduction of >150 within 12 weeks of administration of the first induction dose.

In one embodiment, the patient had an inadequate response to or experienced intolerance to a previous treatment with a corticosteroid, an immunosuppressant, or a biologic agent.

In one embodiment, the patient had an inadequate response to or experienced intolerance to a previous treatment with an anti-TNF agent.

In one embodiment, the patient had an inadequate response to or experienced intolerance to a previous treatment anti-TNF agent is infliximab, adalimumab or certolizumab pegol.

In one embodiment, the patient had an inadequate response to or experienced intolerance to an anti-integrin or an anti-IL12/23. In one embodiment, the patient had an inadequate response to or experienced intolerance to vedolizumab, natalizumab, or ustekinumab.

In one embodiment, the patient has had a diagnosis of Crohn's disease for more than ten years and has had an inadequate response to or experienced intolerance to one or more previous treatment.

In one embodiment, the method comprises a method wherein the previous treatments are selected from corticosteroids, immunodulators, antibiotics and biologic therapies.

In one embodiment, the method is a method of inducing clinical remission of Crohn's disease in an adult patient having moderately to severely active Crohn's disease, the method comprising orally administering once daily to the patient a 45 mg dose of upadacitinib, wherein the patient achieves clinical remission per Crohn's Disease Activity Index (CDAI) at 12 weeks after the first daily administration.

In one embodiment, the patient has had an inadequate response or intolerance to biologic therapy prior to the first daily administration.

In one embodiment, the biologic therapy comprises an anti-TNF agent.

In one embodiment, the biologic therapy comprises an anti-integrin or an anti-IL12/23.

In one embodiment, the biologic therapy comprises vedolizumab, natalizumab, or ustekinumab.

In one embodiment, the method is a method of inducing clinical remission of Crohn's disease in an adult patient having moderately to severely active Crohn's disease, the method comprising orally administering once daily to the patient a 45 mg dose of upadacitinib, wherein the patient achieves clinical remission patient reported outcomes (PROs) at 12 weeks after the first daily administration.

In one embodiment, the patient has had an inadequate response or intolerance to biologic therapy prior to the first daily administration.

In one embodiment, the biologic therapy comprises an anti-TNF agent.

In one embodiment, the biologic therapy comprises an anti-integrin or an anti-IL12/23.

In one embodiment, the biologic therapy comprises vedolizumab, natalizumab, or ustekinumab.

In one embodiment, the method is a method of inducing clinical remission of Crohn's disease in an adult patient having moderately to severely active Crohn's disease, the method comprising orally administering once daily to the patient a 45 mg dose of upadacitinib, wherein the patient achieves clinical remission per patient reported outcomes (PROs) at 4 weeks after the first daily administration.

In one embodiment, the patient has had an inadequate response or intolerance to biologic therapy prior to the first daily administration.

In one embodiment, the biologic therapy comprises an anti-TNF agent.

In one embodiment, the biologic therapy comprises an anti-integrin or an anti-IL12/23.

In one embodiment, the biologic therapy comprises vedolizumab, natalizumab, or ustekinumab.

In one embodiment, the method is a method of inducing endoscopic response of Crohn's disease in an adult patient having moderately to severely active Crohn's disease, the method comprising orally administering once daily to the patient a 45 mg dose of upadacitinib, wherein the patient achieves endoscopic response at 12 weeks after the first daily administration.

In one embodiment, the patient has had an inadequate response or intolerance to biologic therapy prior to the first daily administration.

In one embodiment, the biologic therapy comprises an anti-TNF agent.

In one embodiment, the biologic therapy comprises an anti-integrin or an anti-IL12/23.

In one embodiment, the biologic therapy comprises vedolizumab, natalizumab, or ustekinumab.

In one embodiment, the method is a method of inducing endoscopic remission of Crohn's disease in an adult patient having moderately to severely active Crohn's disease, the method comprising orally administering once daily to the patient a 45 mg dose of upadacitinib, wherein the patient achieves endoscopic remission at 12 weeks after the first daily administration.

In one embodiment, the patient has had an inadequate response or intolerance to biologic therapy prior to the first daily administration.

In one embodiment, the biologic therapy comprises an anti-TNF agent.

In one embodiment, the biologic therapy comprises an anti-integrin or an anti-IL12/23.

In one embodiment, the biologic therapy comprises vedolizumab, natalizumab, or ustekinumab.

In one embodiment, the method comprises inducing clinical remission of ulcerative colitis in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; and b) wherein said patient achieves clinical remission within 4 weeks of administration of the first induction dose.

In one embodiment, the method comprises inducing clinical remission of ulcerative colitis in a patient, said method comprising: a) administering to the patient an induction dose of upadacitinib, or a pharmaceutically acceptable salt thereof, wherein said induction dose is administered orally once a day for at least 6 weeks and comprises 45 mg of upadacitinib, or a 45 mg free base equivalent amount of a pharmaceutically acceptable salt thereof; and b) wherein said patient achieves clinical remission within 6 weeks of administration of the first 45 mg induction dose.

In one embodiment, the method comprises inducing clinical remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves clinical remission within 8 weeks of administration of the first 45 mg induction dose.

In one embodiment, the method comprises a method of inducing endoscopic improvement of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic improvement within 8 weeks of administration of the first induction dose.

In one embodiment, the method comprises a method of inducing endoscopic remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic remission within 8 weeks of administration of the first 45 mg induction dose.

In one embodiment, the patient has moderately to severely active ulcerative colitis.

In one embodiment, the patient is taking corticosteroids at the time of the first induction dose.

In one embodiment, the clinical remission, endoscopic improvement or endoscopic remission is corticosteroid free.

In one embodiment, the patient demonstrated an inadequate response to, loss of response to or intolerance to one or more corticosteroids, immunosuppressants or biologic therapies.

In one embodiment, the immunosuppressants are selected form oral azathioprine, 6-mercaptopurine, injectable methotrexate and tacrolimus.

In one embodiment, the biologic therapy is selected from infliximab, adalimumab, golimumab and vedolizumab.

In one embodiment, the inadequate response in said patient taking corticosteroids is defined as said patient experiencing signs and symptoms of persistently active disease despite a history of at least one induction regimen that included a dose equivalent to prednisone ≥40 mg/day orally for 3 to 4 weeks or intravenously for one week.

In one embodiment, the patient is unable to taper corticosteroid below a dose equivalent to prednisone 10 mg daily orally without recurrent active disease.

In one embodiment, the intolerance of said patient to corticocosteroids leads to Cushing's syndrome, osteopenia, osteoporosis, hyperglycemia, insomnia or infection.

In one embodiment, the patient experiencing the inadequate response to immunosuppressants experienced signs and symptoms of persistently active disease despite a history of at least one 90-day regimen of oral azathioprine, 6-mercaptopurine, injectable methotrexate or tacrolimus.

In one embodiment, the patient experiencing the inadequate response to immunosuppressants experienced nausea, vomiting, abdominal pain, pancreatitis, liver enzyme abnormalities, lymphopenia or infection.

In one embodiment, the patient experiencing the inadequate response to biologic therapies experienced signs and symptoms of persistently active disease despite a history of a) at least one 6-week induction regimen of infliximab comprising a ≥5 mg/kg intravenous dose at 0, 2 and 6 weeks; b) at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; c) at least one 2-week induction regimen of golimumab comprising one 200 mg subcutaneous dose followed by one 100 mg subcutaneous dose at least 2 weeks apart); d) at least one 6-week induction regimen of vedolizumab comprising a 300 mg intravenous dose at 0, 2 and 6 weeks.

In one embodiment, the patient experiencing inadequate response to biologic therapies experienced recurrence of symptoms during scheduled maintenance dosing following prior clinical benefit.

In one embodiment, the patient experiencing intolerance to biologic therapies experienced infusion-related reaction, demyelination, congestive heart failure or infection.

In one embodiment, the method is a method of inducing clinical remission of ulcerative colitis in a patient, said method comprising: (a) administering to the patient an induction dose of upadacitinib, or a pharmaceutically acceptable salt thereof, wherein said induction dose is administered orally once a day for up to 16 weeks and comprises 45 mg of upadacitinib, or a 45 mg free base equivalent amount of a pharmaceutically acceptable salt thereof; and (b) wherein said patient achieves clinical remission within 16 weeks of administration of the first induction dose.

In one embodiment, the method is a method of inducing clinical remission of ulcerative colitis in a patient, said method comprising: (a) administering to the patient an induction dose of upadacitinib, or a pharmaceutically acceptable salt thereof, wherein said induction dose is administered orally once a day and comprises 45 mg of upadacitinib, or a 45 mg free base equivalent amount of a pharmaceutically acceptable salt thereof; and (b) continuing the administering until said patient achieves clinical remission.

In one embodiment, the clinical remission is defined by an Adapted Mayo score ≤2.

In one embodiment, the method comprises an SFS≤1 and not greater than baseline, a RBS of 0, and an endoscopic subscore ≤1.

In one embodiment, the clinical remission is achieved after more than 8 weeks, but within 16 weeks of administration of the first 45 mg induction dose.

In one embodiment, the method is a method of inducing clinical remission of ulcerative colitis, said method comprising: (a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and (b) wherein the patient achieves clinical response within 8 weeks of administration of the first 45 mg induction dose, wherein the patient was previously treated with 45 mg of upadacitinib for at least 8 weeks and did not exhibit a clinical response.

In one embodiment, the method is a method of inducing clinical response in a patient having ulcerative colitis, said method comprising: (a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and (b) wherein the patient achieves clinical response within 8 weeks of administration of the first 45 mg induction dose, wherein the patient was previously treated with 45 mg of upadacitinib for at least 8 weeks and did not exhibit a clinical response.

In one embodiment, the present disclosure is directed to a method of inducing a clinical response in a patient with moderately to severely active ulcerative colitis, said method comprising: a) administering to the patient at least one induction dose of upadacitinib, or a pharmaceutically acceptable salt or solid state form thereof, wherein said induction dose comprises 45 mg of upadacitinib, or a pharmaceutically acceptable salt or solid state form thereof.

In one such embodiment, the clinical response is a clinical response is wherein the patient has a decrease from a baseline Adapted Mayo score greater than or equal to 2 points and greater than or equal to 30% accompanied by a decrease in rectal bleeding subscore of greater than or equal to 1 or an absolute rectal bleeding subscore of 0 or 1.

In another such embodiment, the clinical response is a clinical response is wherein the patient has a decrease from a baseline Full Mayo score greater than or equal to 3 points and greater than or equal to 30% accompanied by a decrease in rectal bleeding subscore from baseline of greater than or equal to 1 or an absolute rectal bleeding subscore of 0 or 1.

In yet another embodiment, the method further comprising maintaining the clinical response, said method further comprising: b) administering a first maintenance dose of upadacitinib, or a pharmaceutically acceptable salt or solid state form thereof to the patient after the last induction dose is administered; and c) administering at least one additional maintenance dose once daily thereafter.

In another embodiment, the induction dose comprises 45 mg of upadacitinib, or a pharmaceutically acceptable salt or solid state form thereof. In another embodiment, the first maintenance dose and/or the at least one additional maintenance dose comprises 15 mg to 30 mg of upadacitinib, or a pharmaceutically acceptable salt or solid state form thereof.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; b) wherein said patient achieves clinical remission within 4 weeks of administration of the first induction dose) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 6 weeks and comprises 45 mg of upadacitinib, or a 45 mg free base equivalent amount of a pharmaceutically acceptable salt thereof; b) wherein said patient achieves clinical remission within 6 weeks of administration of the first 45 mg induction dose; and c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves clinical remission within 8 weeks of administration of the first 45 mg induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is inducing and maintaining endoscopic improvement of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic improvement within 8 weeks of administration of the first induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method comprises inducing and maintaining endoscopic remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic remission within 8 weeks of administration of the first 45 mg induction dose; c) administering to the patient a first maintenance dose of upadacitinib, or a pharmaceutically acceptable salt thereof, wherein said first maintenance dose is administered orally once a day and comprises 30 mg of upadacitinib, or a 30 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method comprises inducing and maintaining endoscopic remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic remission within 8 weeks of administration of the first 45 mg induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the patient has moderately to severely active ulcerative colitis. In one embodiment the patient is an adult. In one embodiment, the patient has had an inadequate response corticosteroid, immunomodulatory or biologic therapy. In one embodiment, the patient has had loss of response to aminosalicylate, corticosteroid, immunomodulatory or biologic therapy. In one embodiment, the patient was intolerant to corticosteroid, immunomodulatory or biologic therapy. In one embodiment, the patient is an adult and has moderately to severely active ulcerative colitis and has had an inadequate response to, loss of response to, or was intolerant to aminosalicylate, corticosteroid, immunomodulatory (IMM), or biologic therapy.

In one embodiment, the patient is taking corticosteroids at the time of the first induction dose.

In one embodiment, the clinical remission, endoscopic improvement or endoscopic remission is corticosteroid free.

In one embodiment, the patient demonstrated an inadequate response to, loss of response to or intolerance to one or more corticosteroids, immunosuppressants or biologic therapies.

In one embodiment, the immunosuppressants are selected form oral azathioprine, 6-mercaptopurine, injectable methotrexate and tacrolimus.

In one embodiment, the biologic therapy is selected from infliximab, adalimumab, golimumab and vedolizumab.

In one embodiment, the inadequate response in said patient taking corticosteroids is defined as said patient experiencing signs and symptoms of persistently active disease despite a history of at least one induction regimen that included a dose equivalent to prednisone ≥40 mg/day orally for 3 to 4 weeks or intravenously for one week.

In one embodiment, the patient is unable to taper corticosteroid below a dose equivalent to prednisone 10 mg daily orally without recurrent active disease.

In one embodiment, the intolerance of said patient to corticocosteroids leads to Cushing's syndrome, osteopenia, osteoporosis, hyperglycemia, insomnia or infection.

In one embodiment, the patient experiencing the inadequate response to immunosuppressants experienced signs and symptoms of persistently active disease despite a history of at least one 90-day regimen of oral azathioprine, 6-mercaptopurine, injectable methotrexate or tacrolimus.

In one embodiment, the patient experiencing the inadequate response to immunosuppressants experienced nausea, vomiting, abdominal pain, pancreatitis, liver enzyme abnormalities, lymphopenia or infection.

In one embodiment, the ulcerative colitis patient experiencing the inadequate response to biologic therapies experienced signs and symptoms of persistently active disease despite a history of a) at least one 6-week induction regimen of infliximab comprising a ≥5 mg/kg intravenous dose at 0, 2 and 6 weeks; b) at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; c) at least one 2-week induction regimen of golimumab comprising one 200 mg subcutaneous dose followed by one 100 mg subcutaneous dose at least 2 weeks apart; d) at least one 6-week induction regimen of vedolizumab comprising a 300 mg intravenous dose at 0, 2 and 6 weeks.

In one embodiment, the patient experiencing inadequate response to biologic therapies experienced recurrence of symptoms during scheduled maintenance dosing following prior clinical benefit.

In one embodiment, the patient experiencing intolerance to biologic therapies experienced infusion-related reaction, demyelination, congestive heart failure or infection.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; b) wherein said patient achieves clinical remission within 4 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 6 weeks and comprises 45 mg of upadacitinib, or a 45 mg free base equivalent amount of a pharmaceutically acceptable salt thereof; b) wherein said patient achieves clinical remission within 6 weeks of administration of the first 45 mg induction dose; and c) administering to the patient a first maintenance dose of upadacitinib, or a pharmaceutically acceptable salt thereof, wherein said maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves clinical remission within 8 weeks of administration of the first 45 mg induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining endoscopic improvement of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic improvement within 8 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains endoscopic improvement for 52 weeks after administration of the first induction dose.

In one embodiment, the method is a method of inducing and maintaining endoscopic remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic remission within 8 weeks of administration of the first 45 mg induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains endoscopic remission for 52 weeks after administration of the first induction dose.

In one embodiment, the patient has moderately to severely active ulcerative colitis.

In one embodiment, the patient is taking corticosteroids at the time of the first induction dose.

In one embodiment, the clinical remission, endoscopic improvement or endoscopic remission is corticosteroid free.

In one embodiment, the patient demonstrated an inadequate response to, loss of response to or intolerance to one or more corticosteroids, immunosuppressants or biologic therapies.

In one embodiment, the immunosuppressants are selected form oral azathioprine, 6-mercaptopurine, injectable methotrexate and tacrolimus.

In one embodiment, the biologic therapy is selected from infliximab, adalimumab, golimumab and vedolizumab.

In one embodiment, the inadequate response in said patient taking corticosteroids is defined as said patient experiencing signs and symptoms of persistently active disease despite a history of at least one induction regimen that included a dose equivalent to prednisone ≥40 mg/day orally for 3 to 4 weeks or intravenously for one week.

In one embodiment, the patient is unable to taper corticosteroid below a dose equivalent to prednisone 10 mg daily orally without recurrent active disease.

In one embodiment, the intolerance of said patient to corticocosteroids leads to Cushing's syndrome, osteopenia, osteoporosis, hyperglycemia, insomnia or infection.

In one embodiment, the patient experiencing the inadequate response to immunosuppressants experienced signs and symptoms of persistently active disease despite a history of at least one 90-day regimen of oral azathioprine, 6-mercaptopurine, injectable methotrexate or tacrolimus.

In one embodiment, the patient experiencing the intolerance to immunosuppressants experienced nausea, vomiting, abdominal pain, pancreatitis, liver enzyme abnormalities, lymphopenia or infection.

In one embodiment, the patient experiencing the inadequate response to biologic therapies experienced signs and symptoms of persistently active disease despite a history of a) at least one 6-week induction regimen of infliximab comprising a ≥5 mg/kg intravenous dose at 0, 2 and 6 weeks; b) at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; c) at least one 2-week induction regimen of golimumab comprising one 200 mg subcutaneous dose followed by one 100 mg subcutaneous dose at least 2 weeks apart; d) at least one 6-week induction regimen of vedolizumab comprising a 300 mg intravenous dose at 0, 2 and 6 weeks.

In one embodiment, the patient experiencing inadequate response to biologic therapies experienced recurrence of symptoms during scheduled maintenance dosing following prior clinical benefit.

In one embodiment, the patient experiencing intolerance to biologic therapies experienced infusion-related reaction, demyelination, congestive heart failure or infection.

In one embodiment, the method is a method of maintaining clinical remission of ulcerative colitis in a patient, said method comprising: administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains clinical remission.

In one embodiment, the method is a method of maintaining endoscopic improvement of ulcerative colitis in a patient, said method comprising: administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains endoscopic improvement.

In one embodiment, the method is a method of maintaining endoscopic remission of ulcerative colitis in a patient, said method comprising: administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains endoscopic remission.

In one embodiment, the method is a method of maintaining clinical remission of ulcerative colitis in a patient, said method comprising: administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains clinical remission.

In one embodiment, the method is a method of maintaining endoscopic improvement of ulcerative colitis in a patient, said method comprising administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains endoscopic improvement.

In one embodiment, the method is a method of maintaining endoscopic remission of ulcerative colitis in a patient, said method comprising: administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains endoscopic remission.

In one embodiment, the patient has moderately to severely active ulcerative colitis.

In one embodiment, the clinical remission, endoscopic improvement or endoscopic remission is corticosteroid free.

In one embodiment, the clinical remission, endoscopic improvement or endoscopic remission is maintained for at least 52 weeks.

In one embodiment, the patient demonstrated an inadequate response to, loss of response to or intolerance to one or more corticosteroids, immunosuppressants, or biologic therapies.

In one embodiment, the immunosuppressants are selected form oral azathioprine, 6-mercaptopurine, injectable methotrexate and tacrolimus.

In one embodiment, the biologic therapy is selected from infliximab, adalimumab, golimumab and vedolizumab.

In one embodiment, the inadequate response in said patient taking corticosteroids is defined as said patient experiencing signs and symptoms of persistently active disease despite a history of at least one induction regimen that included a dose equivalent to prednisone ≥40 mg/day orally for 3 to 4 weeks or intravenously for one week.

In one embodiment, the said patient is unable to taper corticosteroid below a dose equivalent to prednisone 10 mg daily orally without recurrent active disease.

In one embodiment, the intolerance of said patient to corticocosteroids leads to Cushing's syndrome, osteopenia, osteoporosis, hyperglycemia, insomnia or infection.

In one embodiment, the said patient experiencing the inadequate response to immunosuppressants experienced signs and symptoms of persistently active disease despite a history of at least one 90-day regimen of oral azathioprine, 6-mercaptopurine, injectable methotrexate or tacrolimus.

In one embodiment, the patient experiencing intolerance to immunosuppressants experienced nausea, vomiting, abdominal pain, pancreatitis, liver enzyme abnormalities, lymphopenia or infection.

In one embodiment, the patient experiencing the inadequate response to biologic therapies experienced signs and symptoms of persistently active disease despite a history of: at least one 6-week induction regimen of infliximab comprising a greater than or equal to 5 mg/kg intravenous dose at 0, 2 and 6 weeks; at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; at least one 2-week induction regimen of golimumab comprising one 200 mg subcutaneous dose followed by one 100 mg subcutaneous dose at least 2 weeks apart; or at least one 6-week induction regimen of vedolizumab comprising a 300 mg intravenous dose at 0, 2 and 6 weeks.

In one embodiment, the patient experiencing inadequate response to biologic therapies experienced recurrence of symptoms during scheduled maintenance dosing following prior clinical benefit.

In one embodiment, the patient experiencing intolerance to biologic therapies experienced infusion-related reaction, demyelination, congestive heart failure of infection.

In one embodiment, the clinical remission is defined by an Adapted Mayo score ≤2.

In one embodiment, the method comprises an SFS≤1 and not greater than baseline, a RBS of 0, and an endoscopic subscore ≤1.

In one embodiment, the clinical remission is defined by an Adapted Mayo score ≤2, and is corticosteroid free.

In one embodiment, the patient has been corticosteroid free for 90 days or more immediately preceding week 52 of daily maintenance dose administration.

In one embodiment, the patient exhibits a Histologic Endoscopic Mucosal Improvement (HEMI) comprising an endoscopic score ≤1 and a Geboes score ≤3.1 at week 52.

In one embodiment, the patient exhibits mucosal healing comprising an endoscopic score of 0 and a Geboes score <2 at week 52.

In one embodiment, the patient does not exhibit bowel urgency at week 52.

In one embodiment, the patient does not exhibit abdominal pain at week 52.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 4 weeks and comprises 45 mg of upadacitinib, or a 45 mg free base equivalent amount of a pharmaceutically acceptable salt thereof; b) wherein said patient achieves clinical remission within 4 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 6 weeks and comprises 45 mg of upadacitinib, or a 45 mg free base equivalent amount of a pharmaceutically acceptable salt thereof; b) wherein said patient achieves clinical remission within 6 weeks of administration of the first 45 mg induction dose; and c) administering to the patient a first maintenance dose of upadacitinib, or a pharmaceutically acceptable salt thereof, wherein said maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining clinical remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves clinical remission within 8 weeks of administration of the first 45 mg induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining endoscopic improvement of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic improvement within 8 weeks of administration of the first induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the method is a method of inducing and maintaining endoscopic remission of ulcerative colitis in a patient, said method comprising: a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and b) wherein said patient achieves endoscopic remission within 8 weeks of administration of the first 45 mg induction dose; c) administering to the patient a first maintenance dose of upadacitinib, or a pharmaceutically acceptable salt thereof, wherein said first maintenance dose is administered orally once a day and comprises 15 mg of upadacitinib, or a 15 mg free base equivalent amount of a pharmaceutically acceptable salt thereof after the last induction dose is administered; d) administering at least one additional maintenance dose to the patient of upadacitinib, or a pharmaceutically acceptable salt thereof; and e) wherein said patient maintains clinical remission for 52 weeks after administration of the first induction dose.

In one embodiment, the patient has moderately to severely active ulcerative colitis.

In one embodiment, the patient is taking corticosteroids at the time of the first induction dose.

In one embodiment, the clinical remission, endoscopic improvement or endoscopic remission is corticosteroid free.

In one embodiment, the patient demonstrated an inadequate response to, loss of response to or intolerance to one or more corticosteroids, immunosuppressants or biologic therapies.

In one embodiment, the immunosuppressants are selected form oral azathioprine, 6-mercaptopurine, injectable methotrexate and tacrolimus.

In one embodiment, the biologic therapy is selected from infliximab, adalimumab, golimumab and vedolizumab.

In one embodiment, the inadequate response in said patient taking corticosteroids is defined as said patient experiencing signs and symptoms of persistently active disease despite a history of at least one induction regimen that included a dose equivalent to prednisone ≥40 mg/day orally for 3 to 4 weeks or intravenously for one week.

In one embodiment, the patient is unable to taper corticosteroid below a dose equivalent to prednisone 10 mg daily orally without recurrent active disease.

In one embodiment, the intolerance of said patient to corticocosteroids leads to Cushing's syndrome, osteopenia, osteoporosis, hyperglycemia, insomnia or infection.

In one embodiment, the patient experiencing the inadequate response to immunosuppressants experienced signs and symptoms of persistently active disease despite a history of at least one 90-day regimen of oral azathioprine, 6-mercaptopurine, injectable methotrexate or tacrolimus.

In one embodiment, the patient experiencing the intolerance to immunosuppressants experienced nausea, vomiting, abdominal pain, pancreatitis, liver enzyme abnormalities, lymphopenia or infection.

In one embodiment, the patient experiencing the inadequate response to biologic therapies experienced signs and symptoms of persistently active disease despite a history of a) at least one 6-week induction regimen of infliximab comprising a ≥5 mg/kg intravenous dose at 0, 2 and 6 weeks; b) at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; c) at least one 2-week induction regimen of golimumab comprising one 200 mg subcutaneous dose followed by one 100 mg subcutaneous dose at least 2 weeks apart; d) at least one 6-week induction regimen of vedolizumab comprising a 300 mg intravenous dose at 0, 2 and 6 weeks.

In one embodiment, the patient experiencing inadequate response to biologic therapies experienced recurrence of symptoms during scheduled maintenance dosing following prior clinical benefit.

In one embodiment, the patient experiencing intolerance to biologic therapies experienced infusion-related reaction, demyelination, congestive heart failure or infection. In some embodiments, the method is a method of inducing Histologic Endoscopic Mucosal Improvement (HEMI) in a patient with ulcerative colitis, said method comprising: administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and wherein said patient achieves Histologic Endoscopic Mucosal Improvement (HEMI) comprising an endoscopic score ≤1 and a Geboes score ≤3.1 within 8 weeks of administration of the induction dose.

In some embodiments, the method is a method of inducing and maintaining Histologic Endoscopic Mucosal Improvement (HEMI) in a patient with ulcerative colitis, said method comprising: administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; wherein said patient achieves Histologic Endoscopic Mucosal Improvement (HEMI) comprising an endoscopic score ≤1 and a Geboes score ≤3.1 within 8 weeks of administration of the first induction dose; administering to the patient a maintenance dose of upadacitinib, or a pharmaceutically acceptable salt thereof, wherein said first maintenance dose is administered orally once a day for at least 52 weeks and comprises 15 mg of upadacitinib or 30 mg of upadacitinib, or a 15 mg or 30 mg free base equivalent amount of a pharmaceutically acceptable salt thereof after the last induction dose is administered; wherein said patient maintains Histologic Endoscopic Mucosal Improvement (HEMI) comprising an endoscopic score ≤1 and a Geboes score ≤3.1 for 52 weeks after administration of the first maintenance dose.

In some embodiments, the method is a method of maintaining Histologic Endoscopic Mucosal Improvement (HEMI) in a patient with ulcerative colitis, said method comprising: administering to the patient a maintenance dose of upadacitinib, or a pharmaceutically acceptable salt thereof, wherein said first maintenance dose is administered orally once a day for at least 52 weeks and comprises 15 mg of upadacitinib or 30 mg of upadacitinib, or a 15 mg or 30 mg free base equivalent amount of a pharmaceutically acceptable salt thereof; wherein said patient maintains Histologic Endoscopic Mucosal Improvement (HEMI) comprising an endoscopic score ≤1 and a Geboes score ≤3.1 for 52 weeks after administration of the first maintenance dose.

In one embodiment, the ulcerative colitis or Crohn's disease patient experiencing the inadequate response to biologic therapies experienced signs and symptoms of persistently active disease despite a history of a) at least one 6-week induction regimen of infliximab comprising a ≥5 mg/kg intravenous dose at 0, 2 and 6 weeks; b) at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; c) at least one 2-week induction regimen of golimumab comprising one 200 mg subcutaneous dose followed by one 100 mg subcutaneous dose at least 2 weeks apart; d) at least one 6-week induction regimen of vedolizumab comprising a 300 mg intravenous dose at 0, 2 and 6 weeks.

In one embodiment, the patient experiencing inadequate response to biologic therapies experienced recurrence of symptoms during scheduled maintenance dosing following prior clinical benefit. In one embodiment, the patient experiencing intolerance to biologic therapies experienced infusion-related reaction, demyelination, congestive heart failure or infection.

BRIEF DESCRIPTION OF THE DRAWINGS

FIGS. 3A-3I are graphs depicting the relationship between upadacitinib plasma concentration and clinical response (Week 16; FIG. 3A), (NRI) clinical remission (Week 16; FIG. 3B), modified clinical remission (Week 16; FIG. 3C); decrease in CDAI≥70 (Week 16; FIG. 3D); decrease in CDAI≥100 (Week 16; FIG. 3E); CDAI<150 (Week 16; FIG. 3F); endoscopic response (Week 12 or Week 16; FIG. 3G); endoscopic improvement (Week 16; FIG. 3H);

and endoscopic remission (Week 12 or Week 16; FIG. 3I) as determined in the Example 8 clinical study. Arrows indicate the median exposure (in mg) for each immediate release dose. The maximum and minimum plasma concentrations for each exposure bin are indicated in brackets.

FIGS. 4A-4F are graphs depicting the model-predicted efficacy (NRI) for different upadacitinib doses for immediate-release (IR) BID formulations or modified-release (MR) QD formulations (simulating for 200 patients/arm) at Weeks 12 or 16. The predicted results are based on the exposure-response relationships as determined in the Example 8 study.

FIG. 6A shows results for subjects who were not on steroids at baseline, and FIG. 6B shows results for subjects who were on steroids at baseline, and who underwent mandatory taper of steroid dose, starting at week 2 of the Example 8 clinical study.

FIG. 9 shows the clinical remission and endoscopic response in a refractory patient population administered upadacitinib or placebo in the Example 8 Crohn's disease clinical study.

FIGS. 10A-10E are graphs depicting the percentage of subjects who achieved modified clinical remission at week 2 (FIG. 10A), week 4 (FIG. 10B), week 8 (FIG. 10C), week 12 (FIG. 10D) and week 16 (FIG. 10E) of the Example 8 study.

FIG. 23A is the percentage of subjects predicted to achieve clinical response at week 12; FIG. 23B is the percentage of subjects predicted to achieve modified clinical remission at week 12; FIG. 23C is the percentage of subjects expected to achieve CDAI remission at week 12; FIG. 23D is the percentage of subjects predicted to achieve endoscopic response at week 12/16; FIG. 23E is the percentage of patients predicted to achieve endoscopic improvement at week 12/16; FIG. 23F is the percentage of patients predicted to achieve endoscopic remission at week 12/16.

FIG. 26A shows the clinical response rate at week 2 in a patient population administered upadacitinib or placebo in the Example 19 ulcerative colitis clinical study, based on achieving a decrease in Partial Adapted Mayo score ≥1 point and ≥30% from Baseline, PLUS a decrease in RBS≥1 or an absolute RBS≤1.

FIG. 26B shows the clinical response rate at week 8 in a patient population administered upadacitinib or placebo in the Example 19 ulcerative colitis clinical study, based on achieving a decrease in Partial Adapted Mayo score ≥1 point and ≥30% from Baseline, PLUS a decrease in RBS≥1 or an absolute RBS≤1.

Figure 28A:
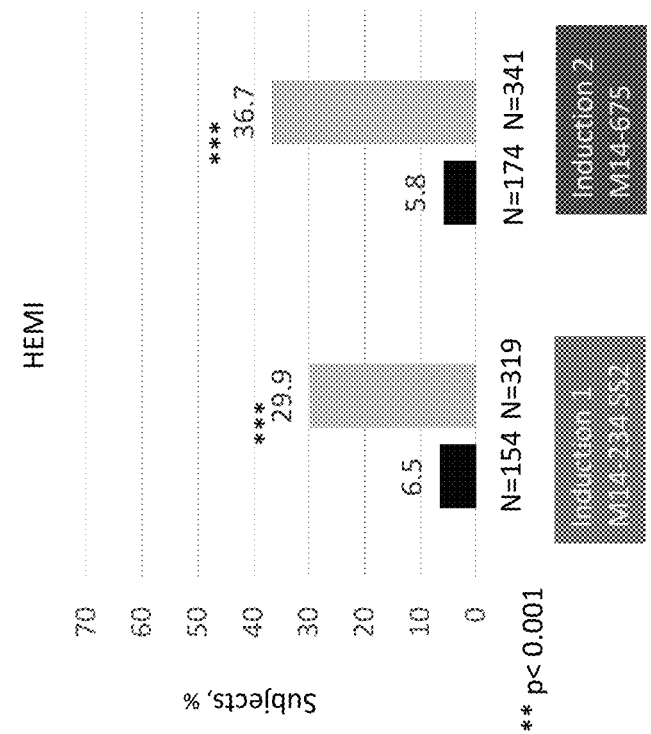
FIG. 28A shows the histologic improvement rate at week 8 in a patient population administered upadacitinib or placebo in the Example 19 ulcerative colitis clinical study, based on achieving any decrease from baseline in the Geboes score.
Figure 28B:
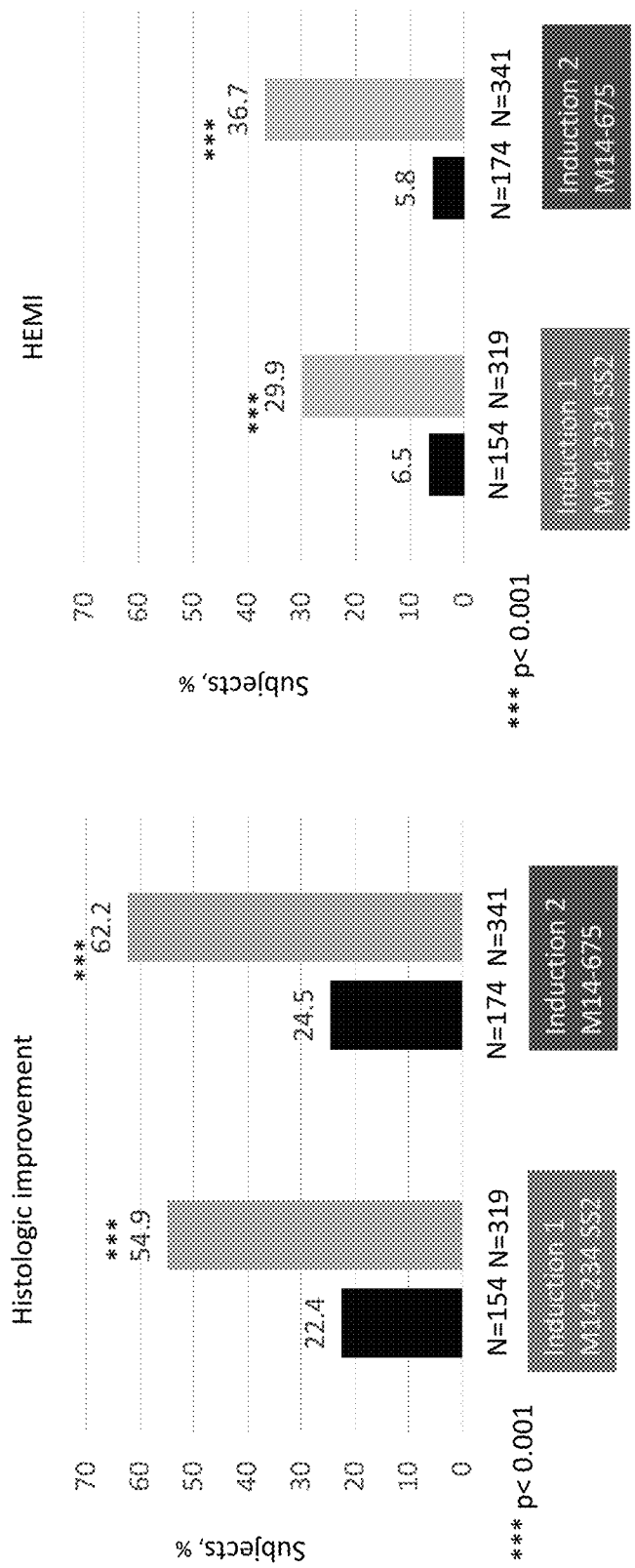
FIG. 28B shows the Histologic Endoscopic Mucosal Improvement (HEMI) rate at week 8 in a patient population administered upadacitinib or placebo in the Example 19 ulcerative colitis clinical study, based on achieving an Endoscopic subscore of 0 or 1 and a Geboes score ≤3.1.

FIG. 28C shows the Mucosal Healing rate at week 8 in a patient population administered upadicitinib or placebo in the Example 19 ulcerative colitis clinical study, based on achieving an Endoscopic score of 0 and a Geboes score less than 2.

FIG. 29 is a table summarizing the study endpoints at week 52 and percentage of subjects achieving each endpoint in the Example 20 UC maintenance study.

Figure 30:
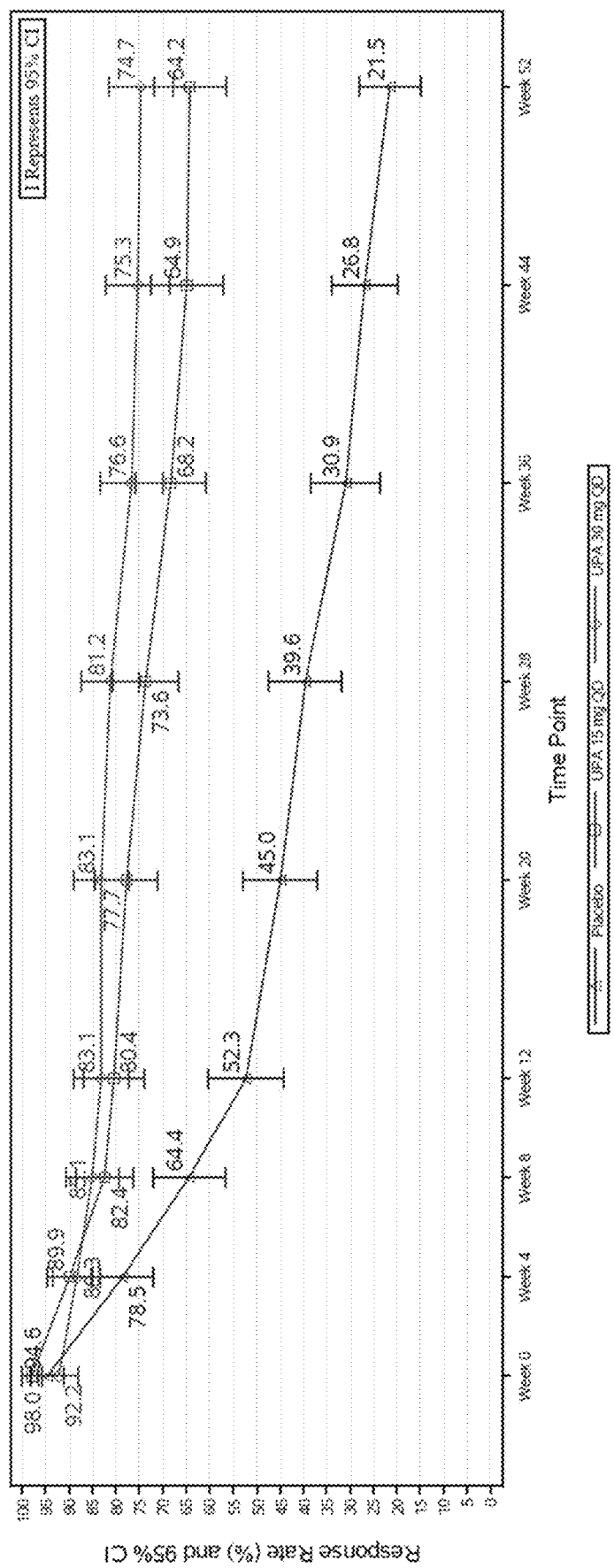

FIG. 30 shows the proportion of subjects with clinical response per Partial Adapted Mayo Score over time in the Example 20 UC maintenance study.

Figure 31:
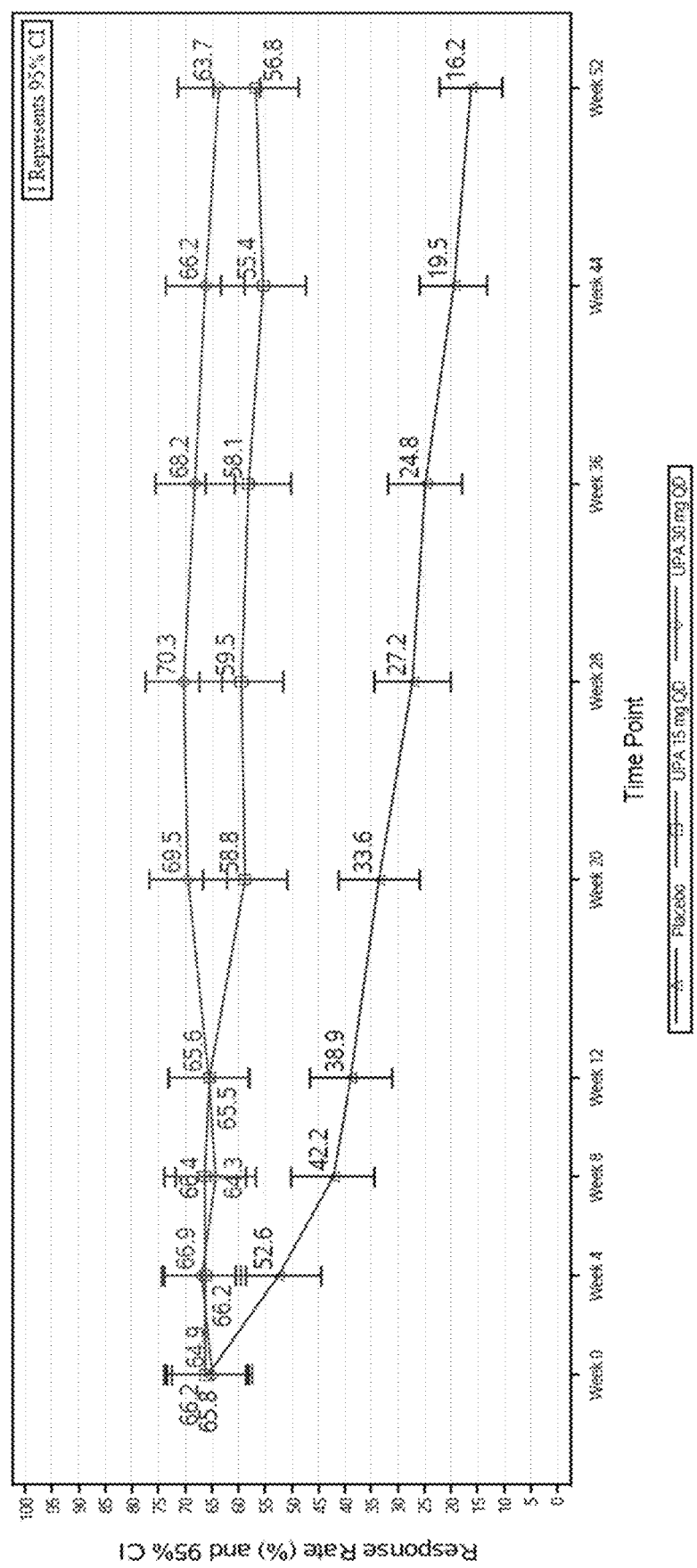

FIG. 31 shows the proportion of subjects with clinical remission per Partial Mayo Score over time in the Example 20 UC maintenance study.

Figure 32:
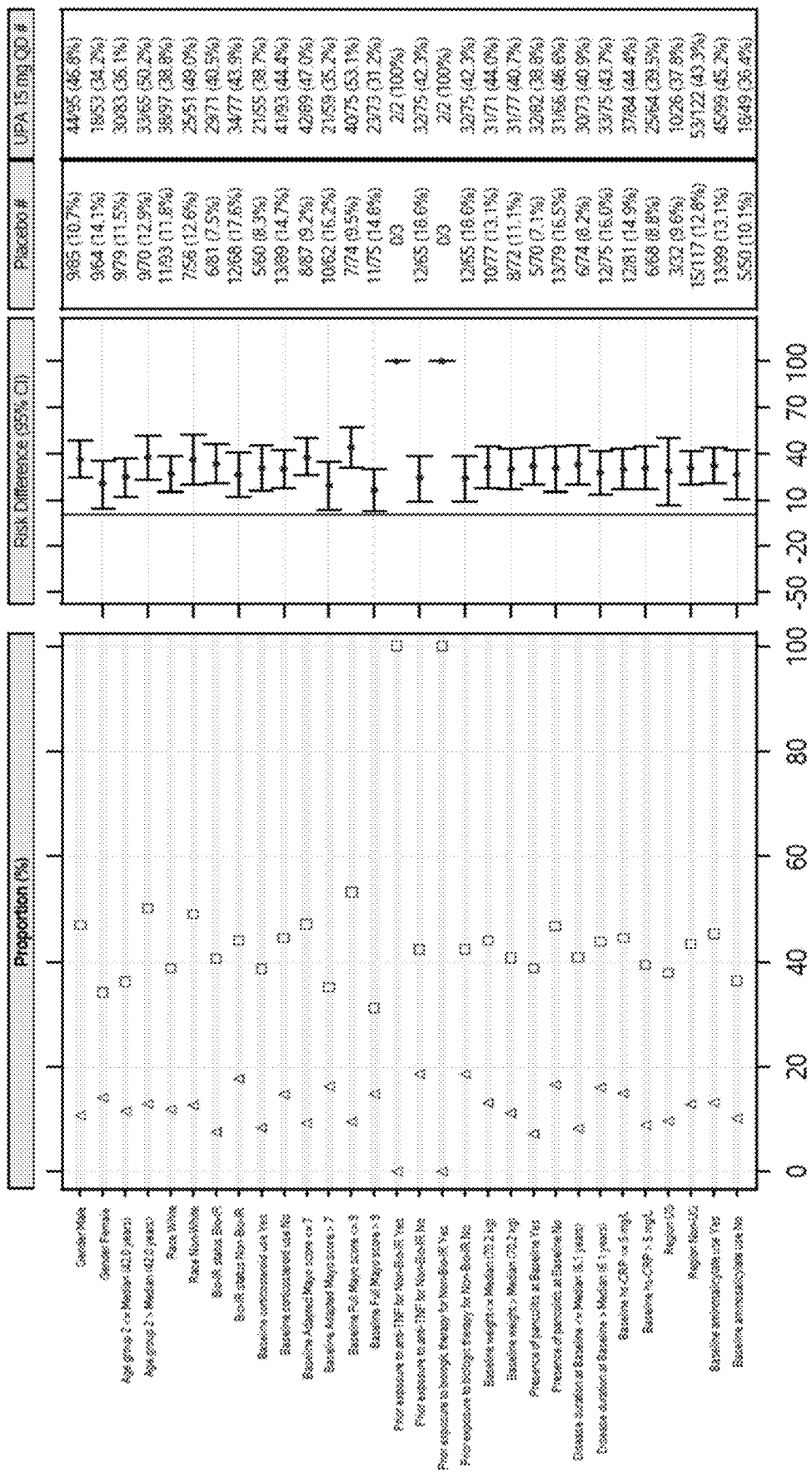

FIG. 32 is a Forest plot for the subgroup analysis of clinical remission per Adapted Mayo score at week 52 for the 15 mg dose of upadacitinib vs. placebo in the Example 20 study.

Figure 33:
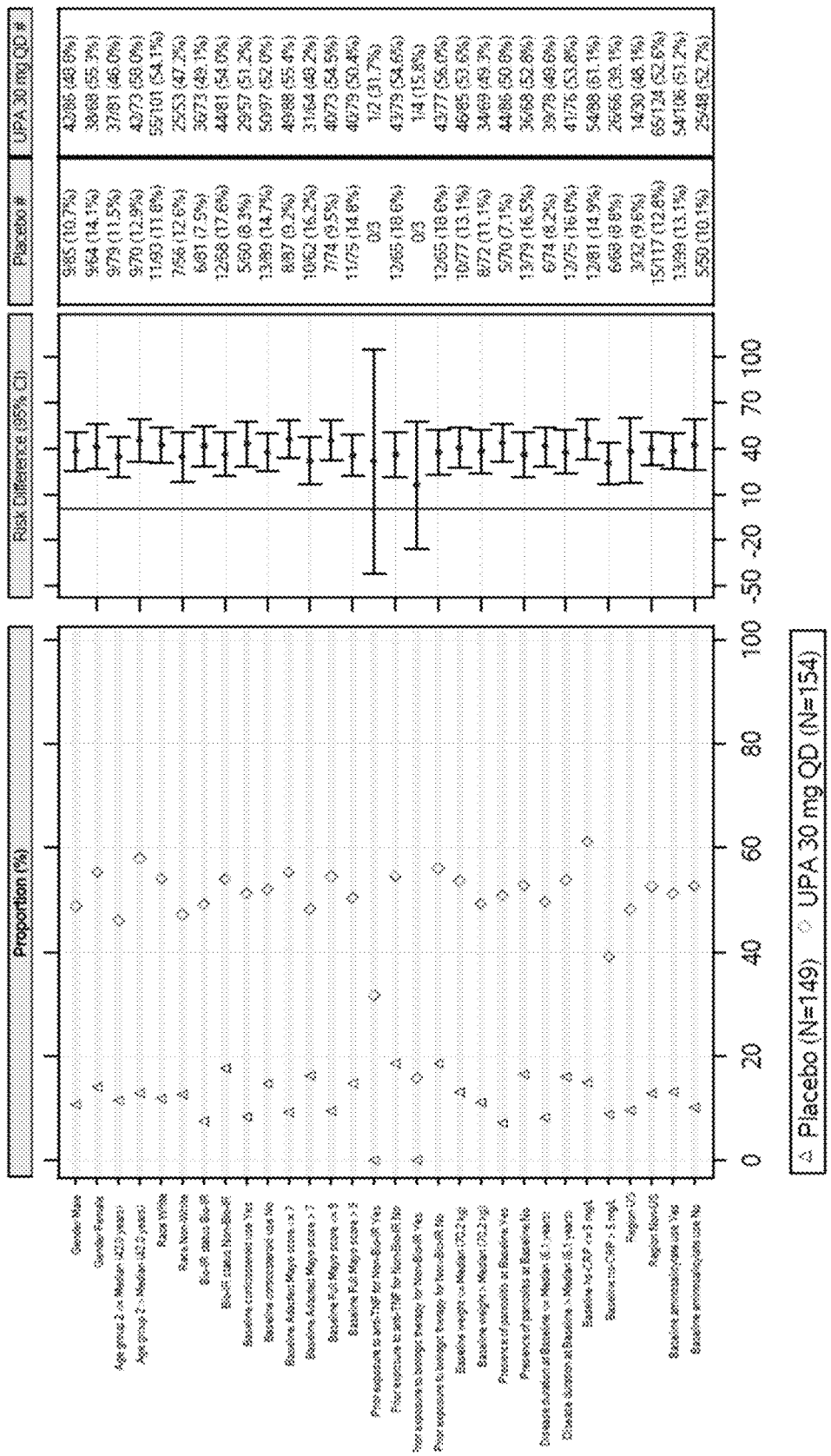

FIG. 33 is a Forest plot for the subgroup analysis of clinical remission per Adapted Mayo score at week 52 for the 30 mg dose of upadacitinib vs. placebo in the Example 20 study.

Figure 34:
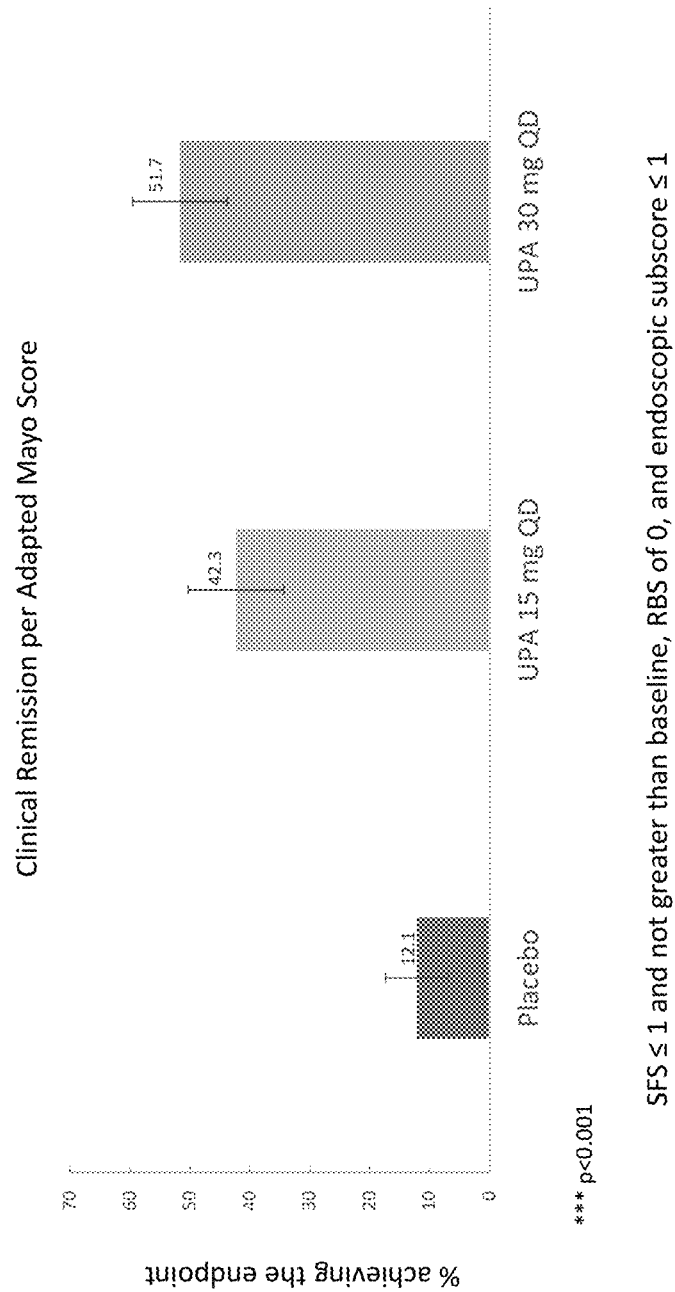

FIG. 34 shows the results for the primary endpoint of clinical remission at week 52 per Adapted Mayo Score for both doses of upadacitinib vs. placebo in the Example 20 study.

Figure 35A:
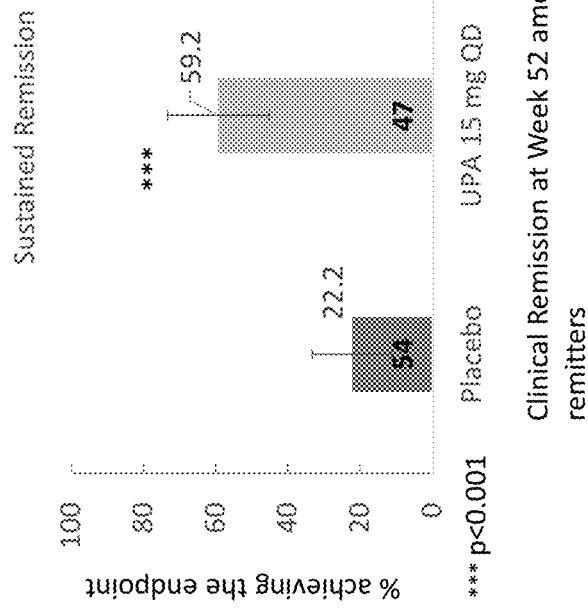
Figure 35B:
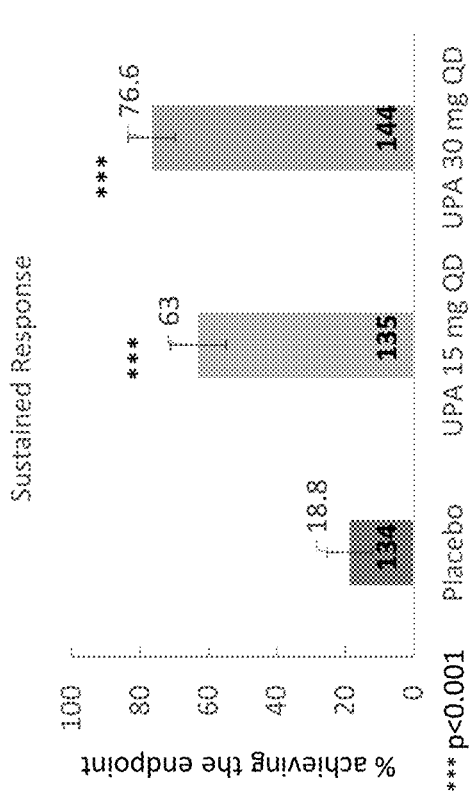
Figure 35C:
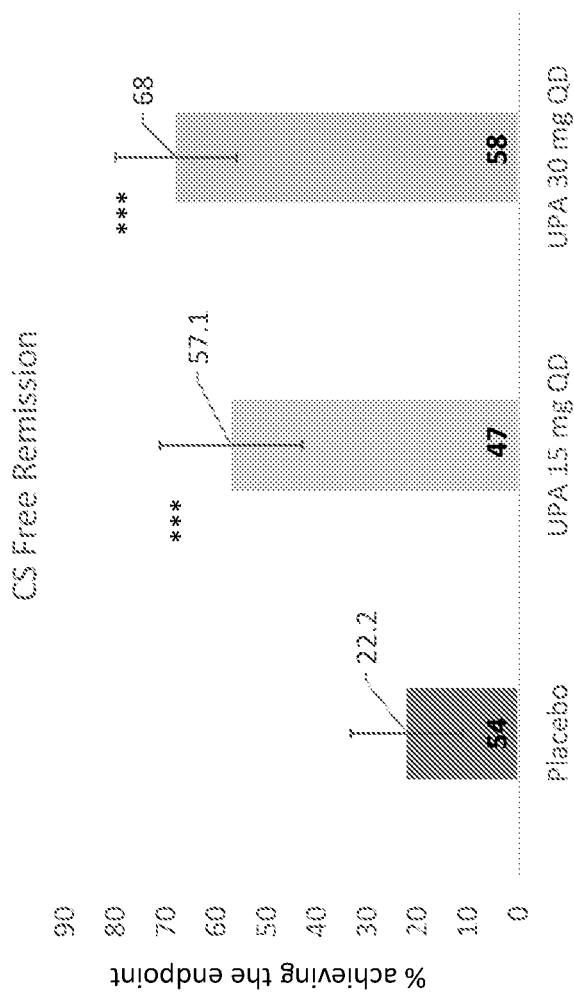

FIGS. 35A-35C show the percentage of subjects achieving the endpoints of sustained response (FIG. 35A), sustained remission (FIG. 35B), and corticosteroid free remission (FIG. 35C) for both doses of upadacitinib vs. placebo in the Example 20 study.

Figure 36A:
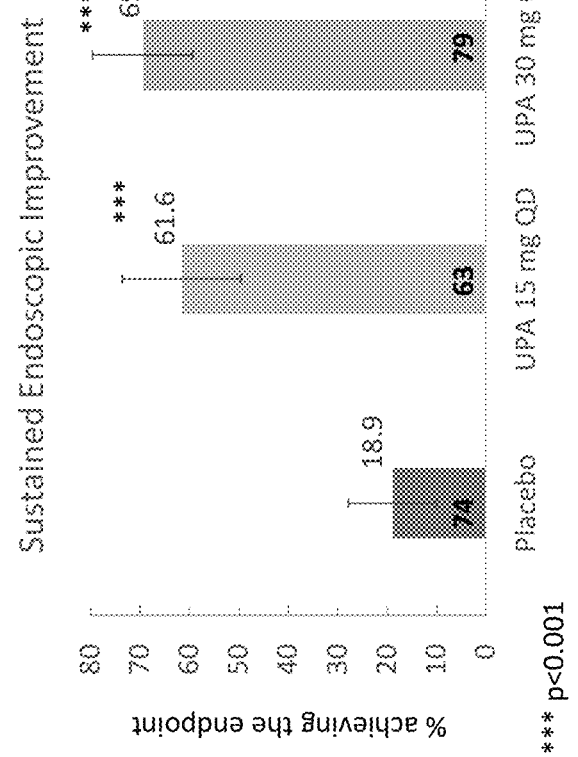
Figure 36B:
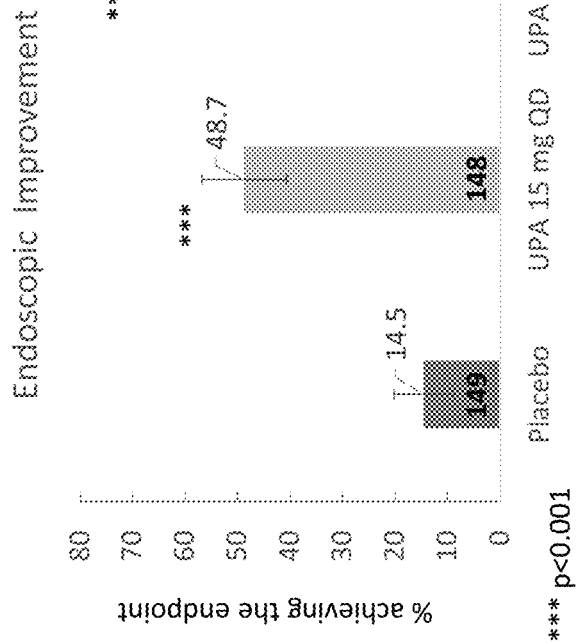

FIGS. 36A-36C show the percentage of subjects achieving the endpoints of endoscopic improvement (FIG. 36A), sustained endoscopic improvement (FIG. 36B), and endoscopic remission (FIG. 36C) for both doses of upadacitinib vs. placebo in the Example 20 study.

Figure 37A:
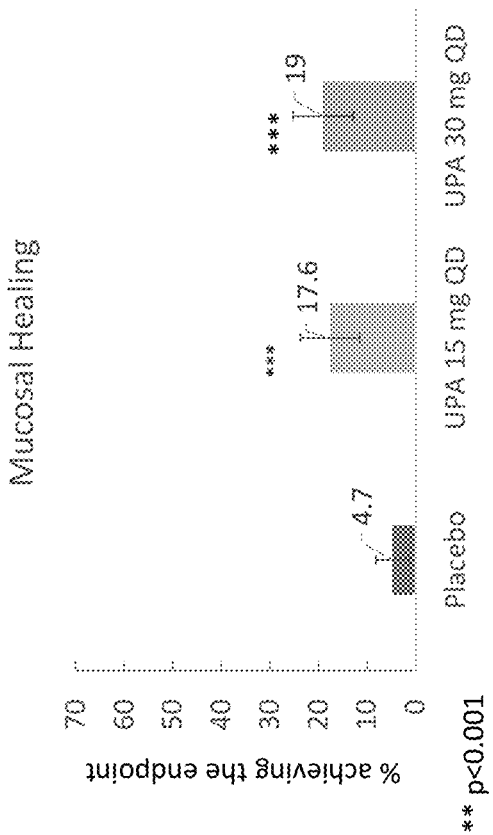
Figure 37B:
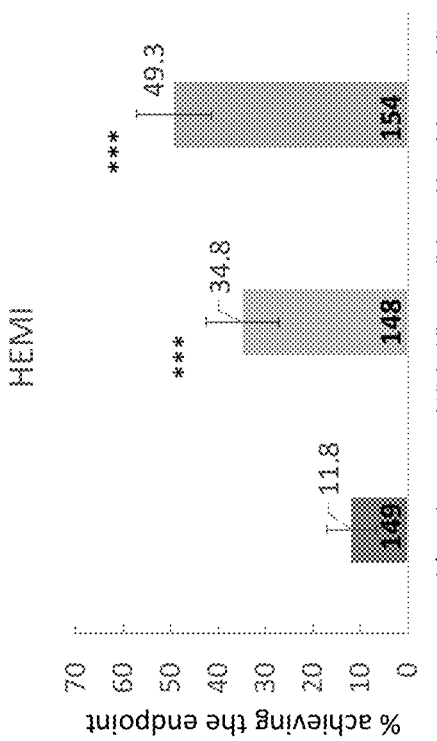

FIGS. 37A-37B show the percentage of subjects achieving the endpoints of Histologic-Endoscopic Improvement (HEMI) (FIG. 37A) and Mucosal Healing-Endoscopic and Histologic Assessment (FIG. 37B) in the Example 20 study.

Figure 38A:
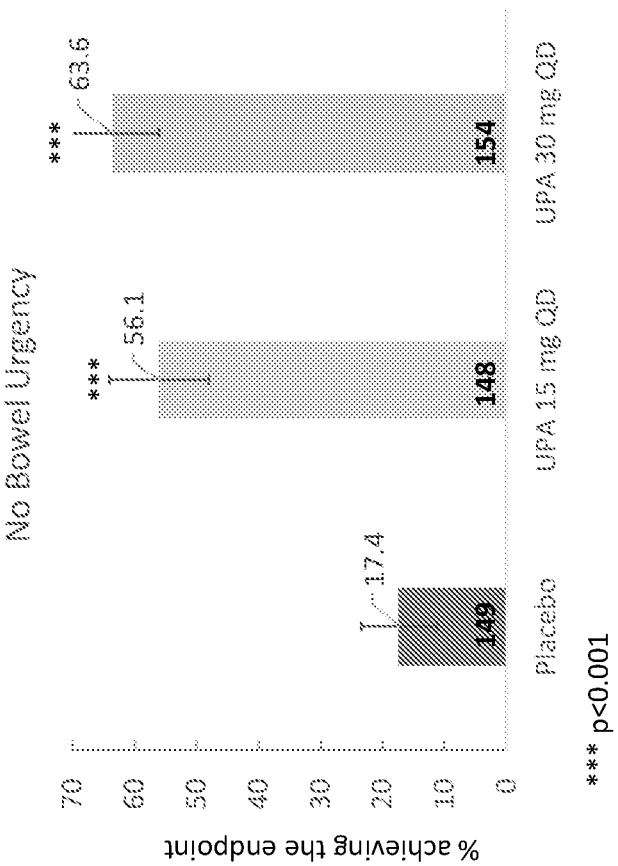
Figure 38B:
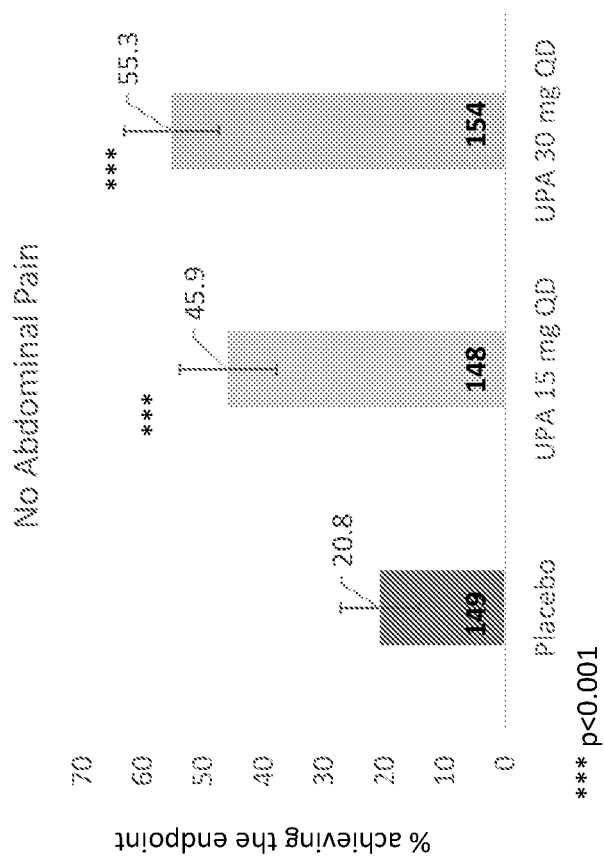

FIG. 38A-38B show the percentage of subjects achieving the endpoints of symptom improvement (no abdominal pain (FIG. 38A) and no bowel urgency (FIG. 38B)) in the Example 20 study.

Figure 39A:
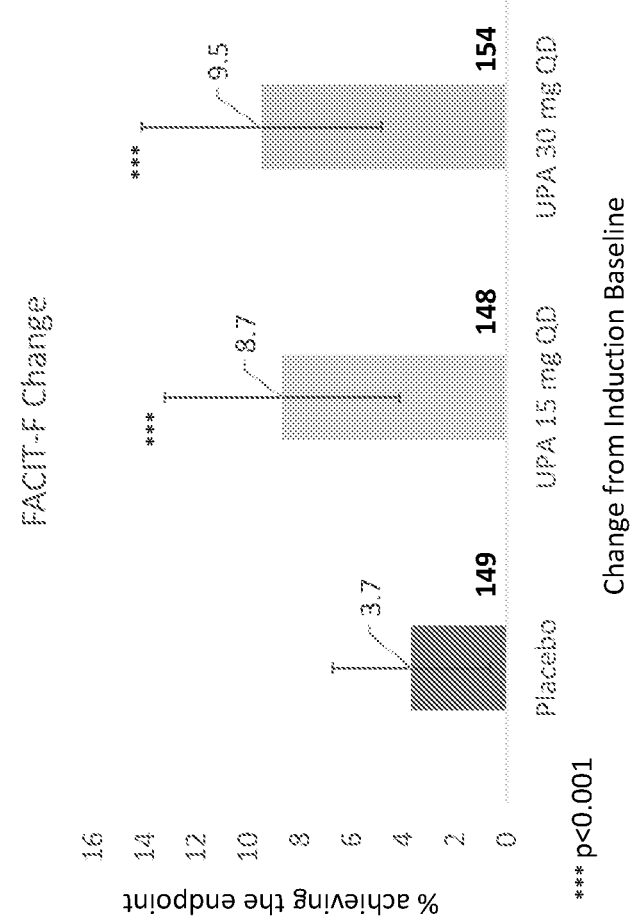
Figure 39B:
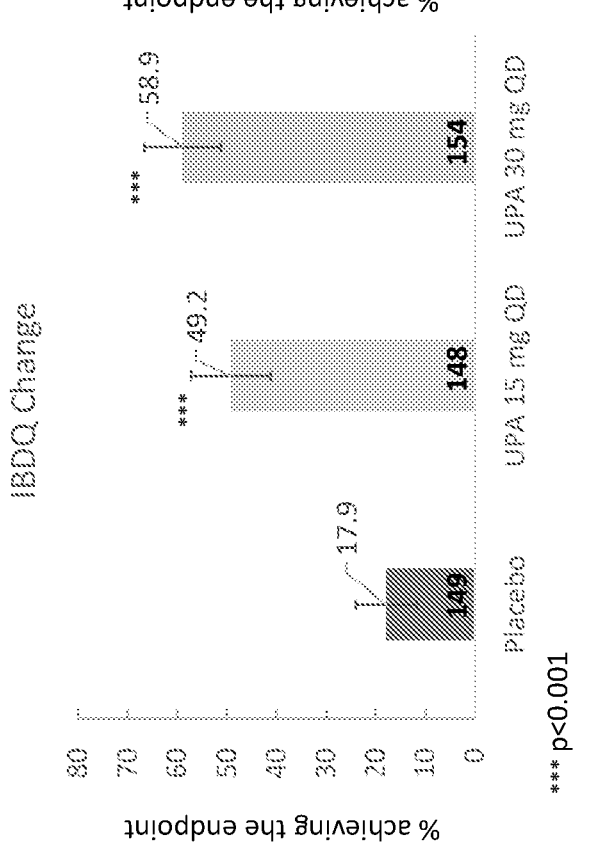
Figures 40A, 40B, 40C:
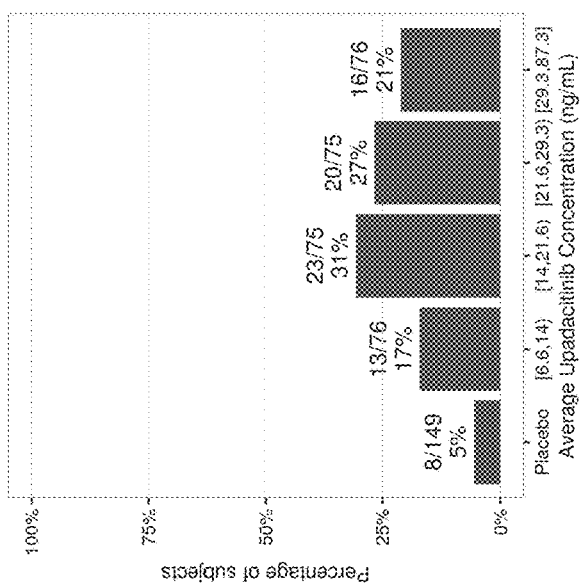
Figure 40D:
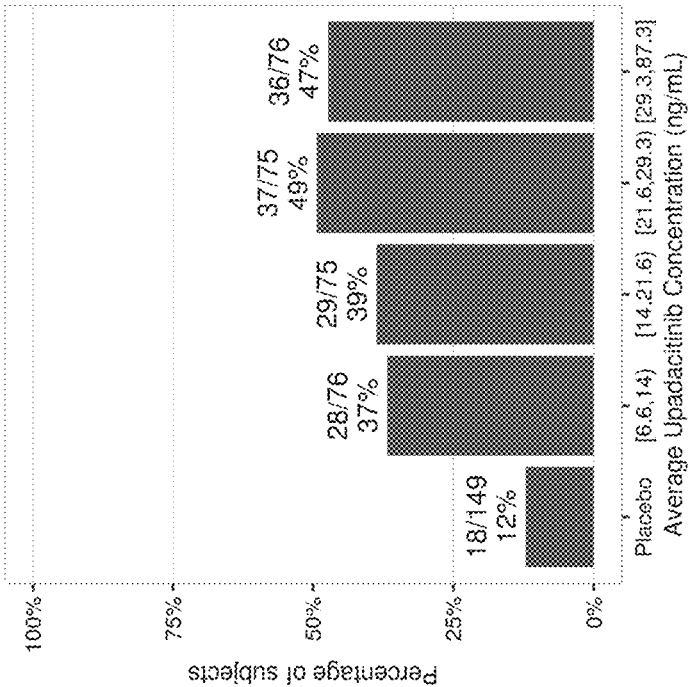
Figure 40E:
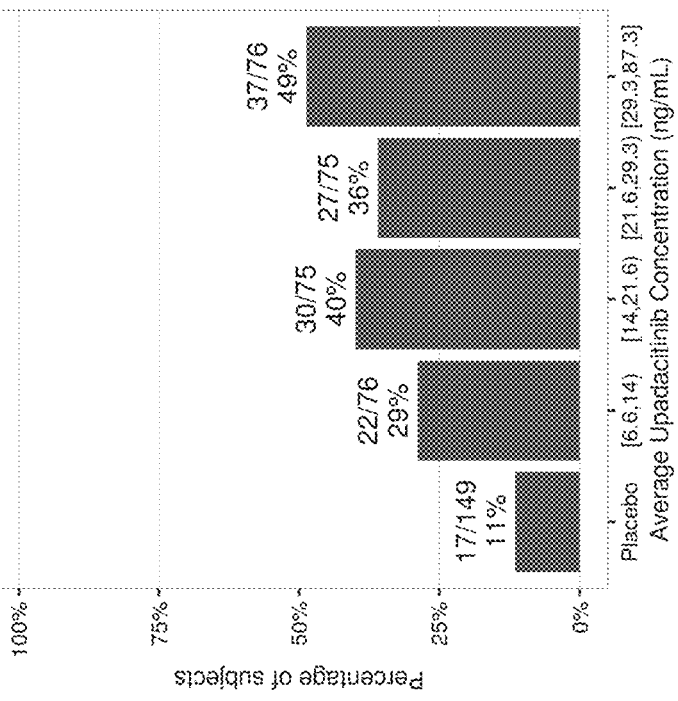
Figure 41A:
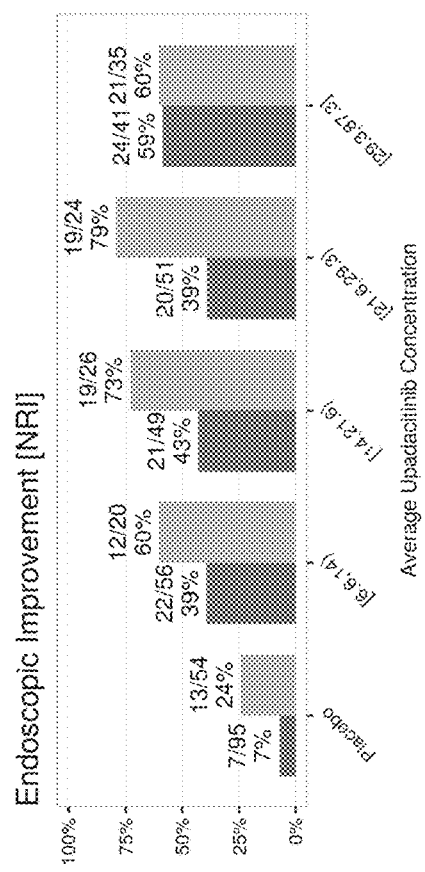
Figure 41B:
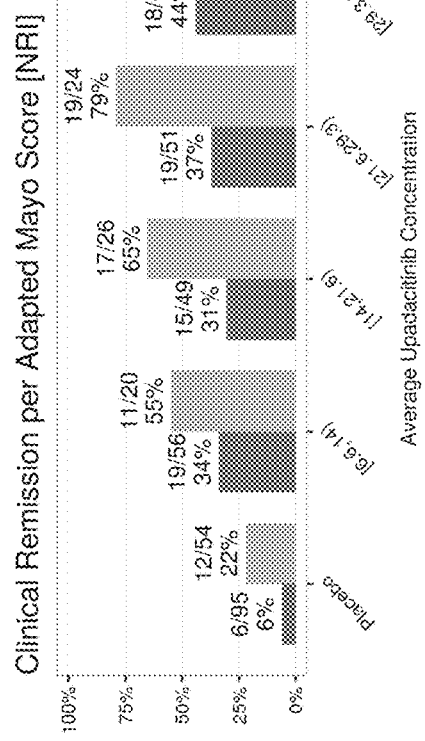
Figure 41C:
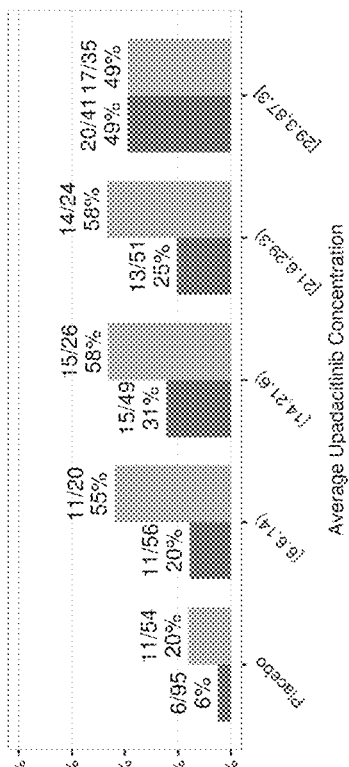
Figure 41D:
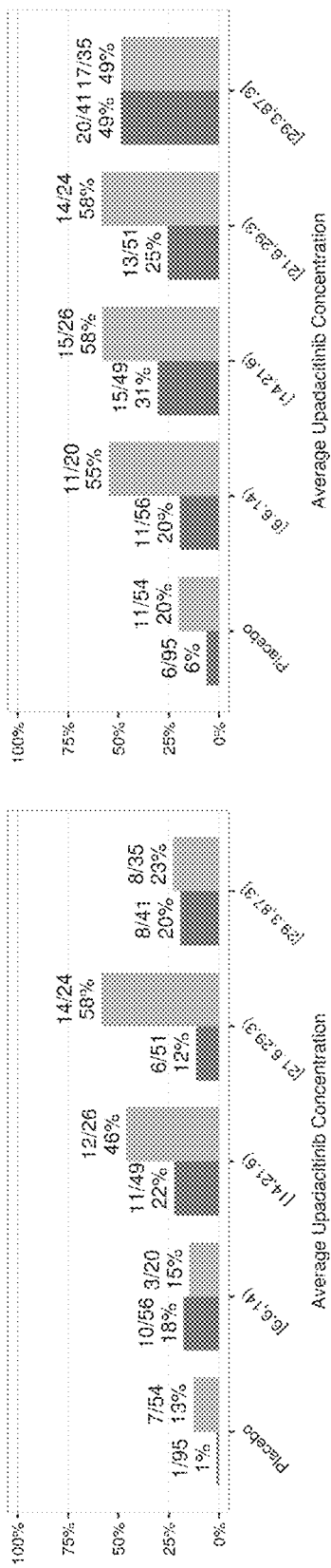
Figure 41E:
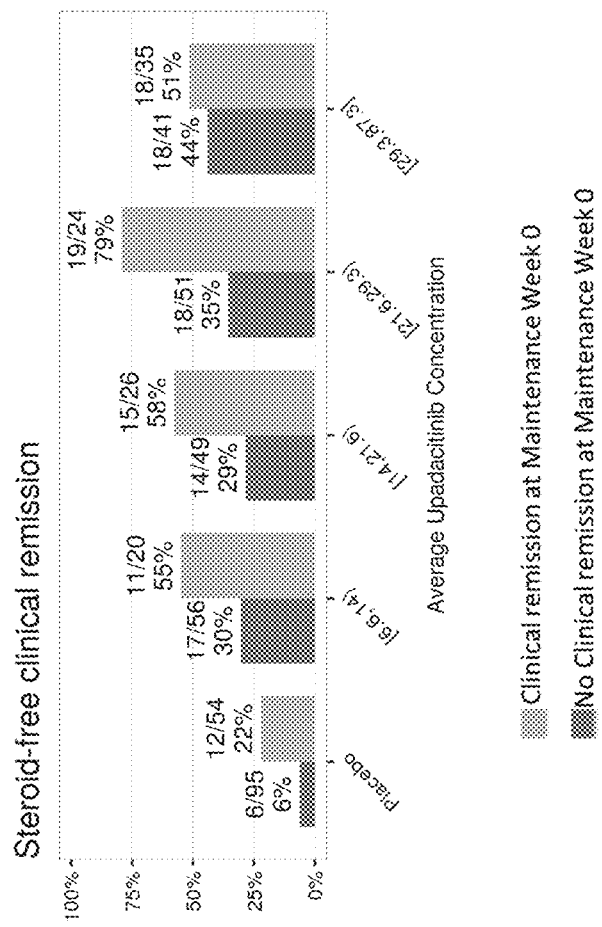

FIGS. 39A-39B show the change from induction baseline in quality of life measures using the IBDQ change scale (FIG. 39A) and FACIT-F change scale (FIG. 39B) in the Example 20 study.

FIGS. 40A-40E are a series of graphs demonstrating the observed exposure-response relationship between upadacitinib efficacy at week 52 in UC and average plasma concentration ($C_{avg}$) quartiles in the overall study population across various endpoints in the Example 20 study.

FIGS. 41A-41E are a series of graphs demonstrating the observed exposure-response relationship between upadacitinib efficacy at week 52 in UC and average plasma concentration ($C_{avg}$) quartiles stratified by clinical remission status at end of induction across various endpoints in the Example 20 study.

Figure 42:
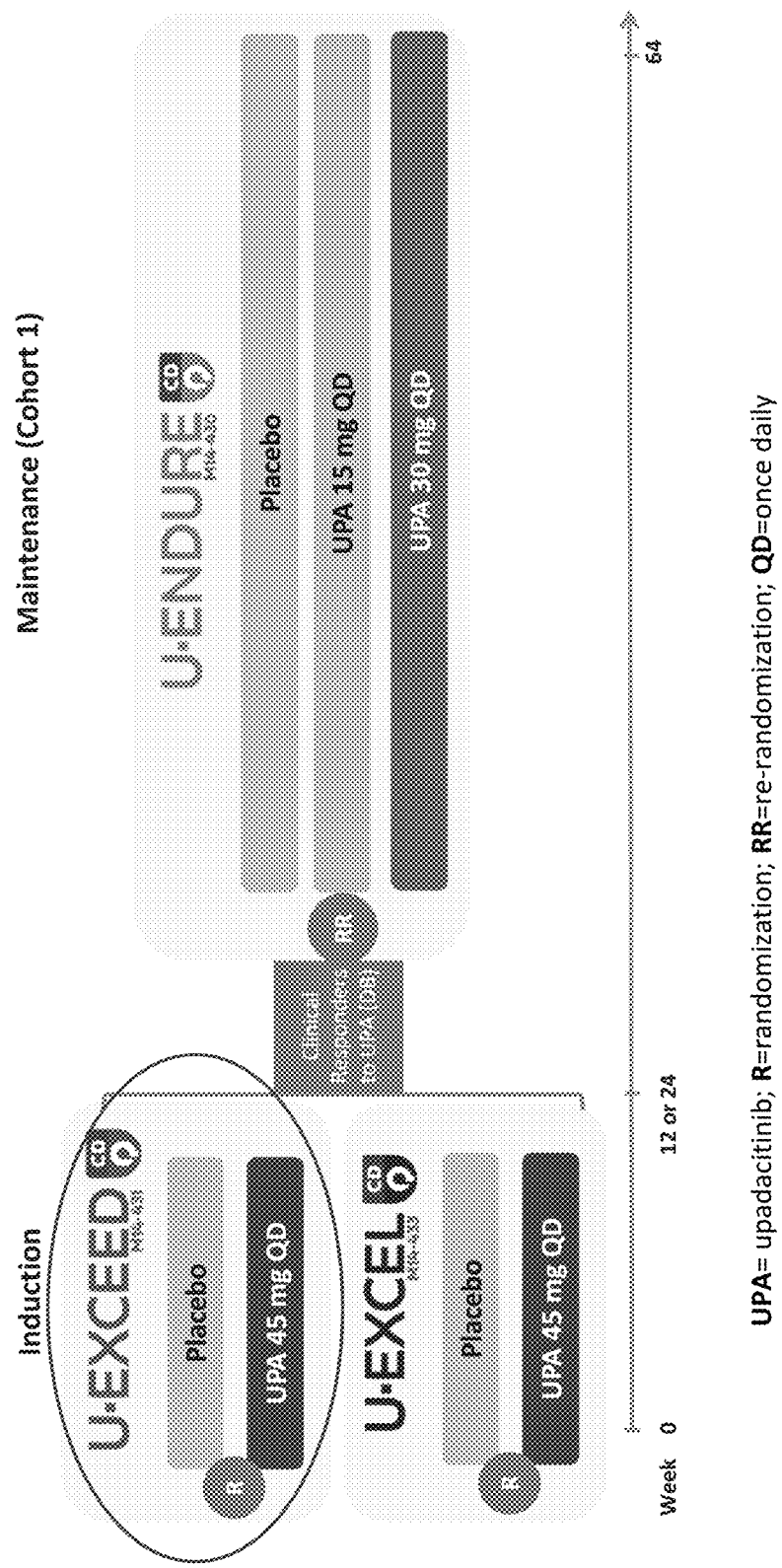

FIG. 42 is a schematic representation of a study design for Crohn's disease phase 3 clinical studies.

Figure 43:
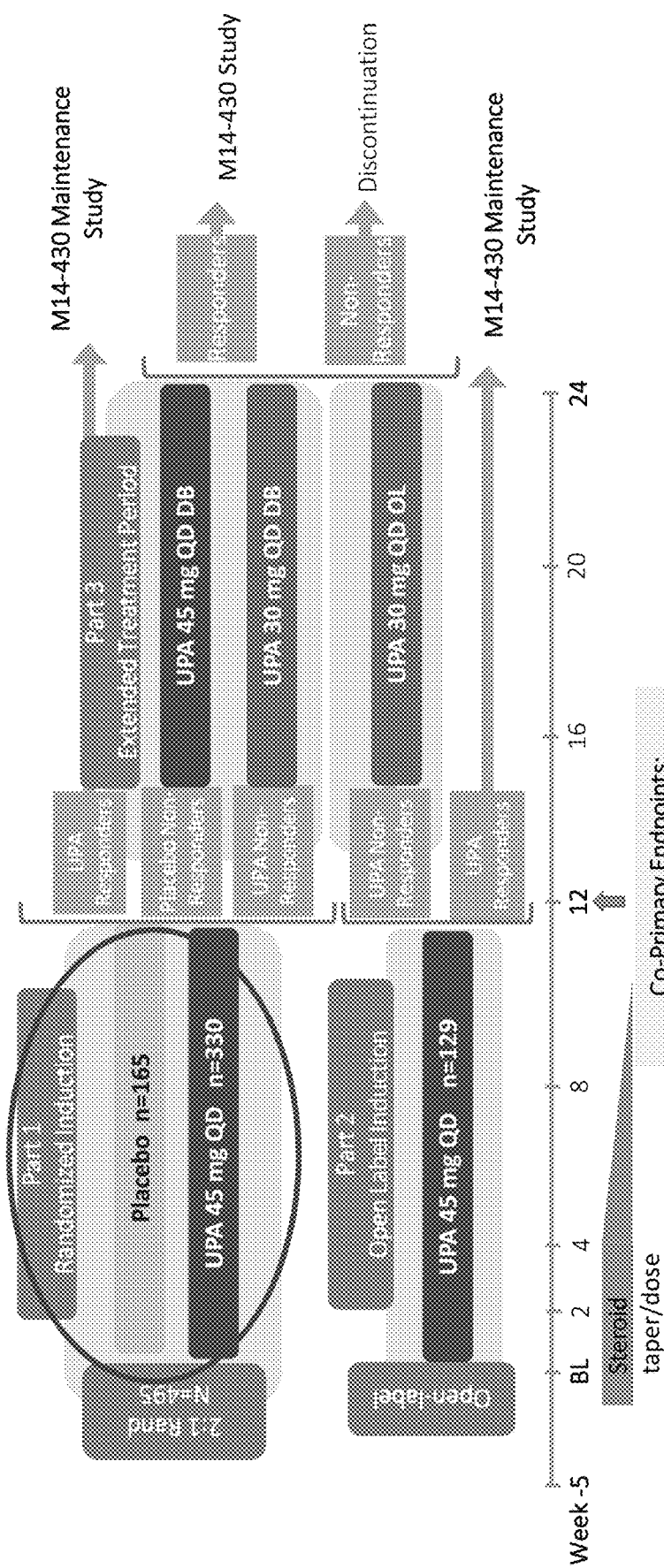

FIG. 43 is a more detailed schematic representation of the study design of FIG. 42.

FIG. 44 is a table providing endpoints, definitions, and rankings for the clinical study described in Example 21.

Figure 45:
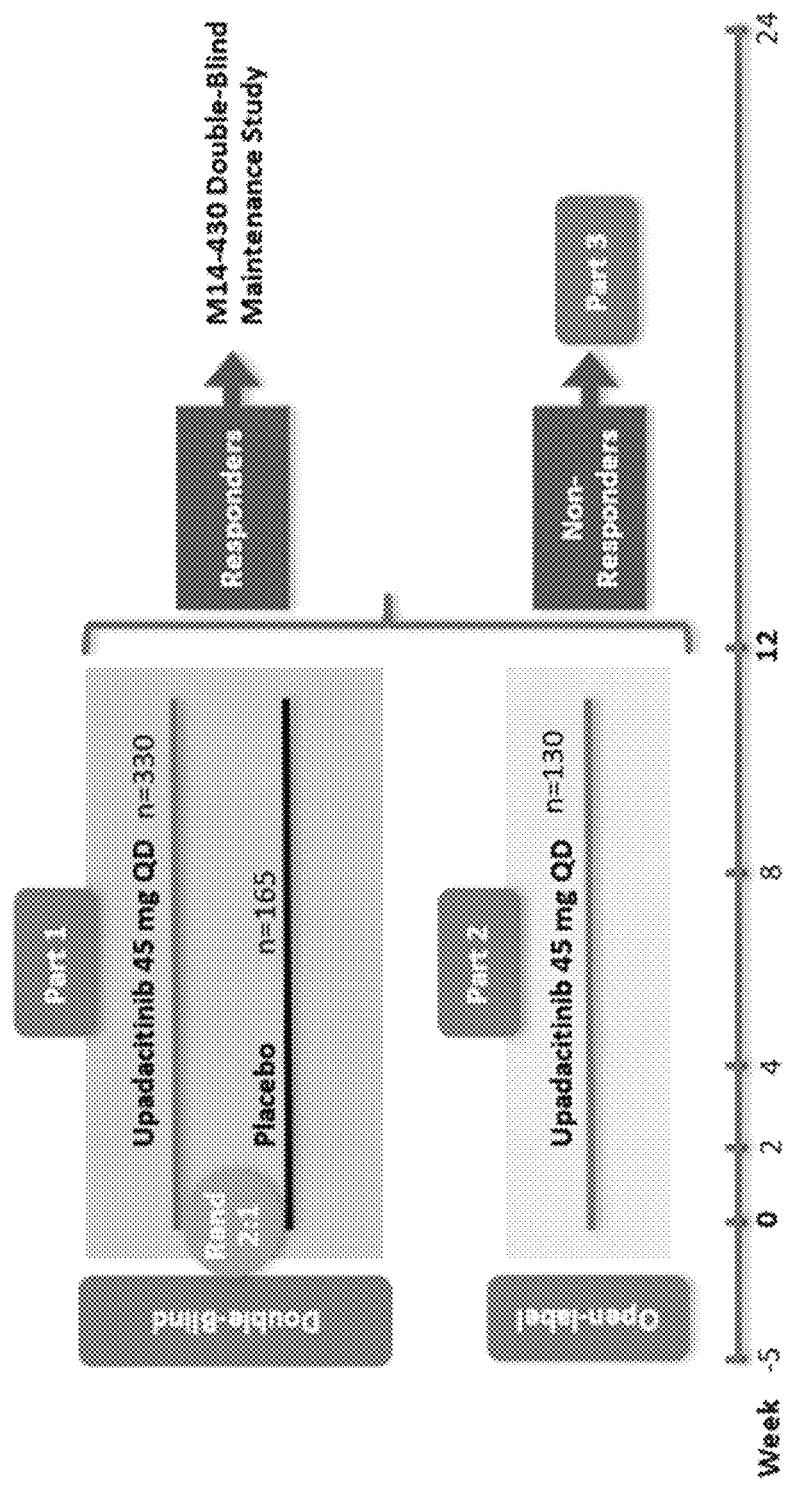

FIG. 45 is a schematic representation of the design of Parts 1 and 2 for the Crohn's disease clinical study described in Example 21.

Figure 46:
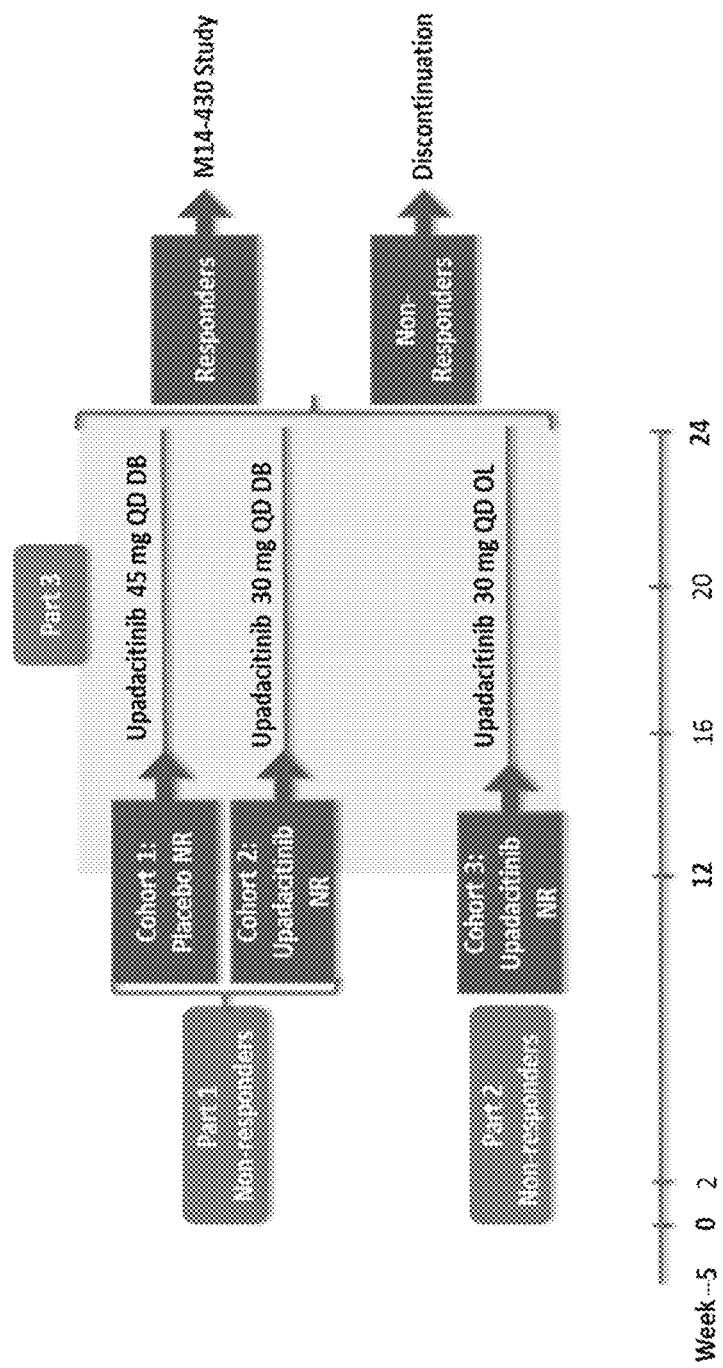

FIG. 46 is a schematic representation of the design for Part 3 of the Crohn's disease clinical study described in Example 21.

Figure 47:
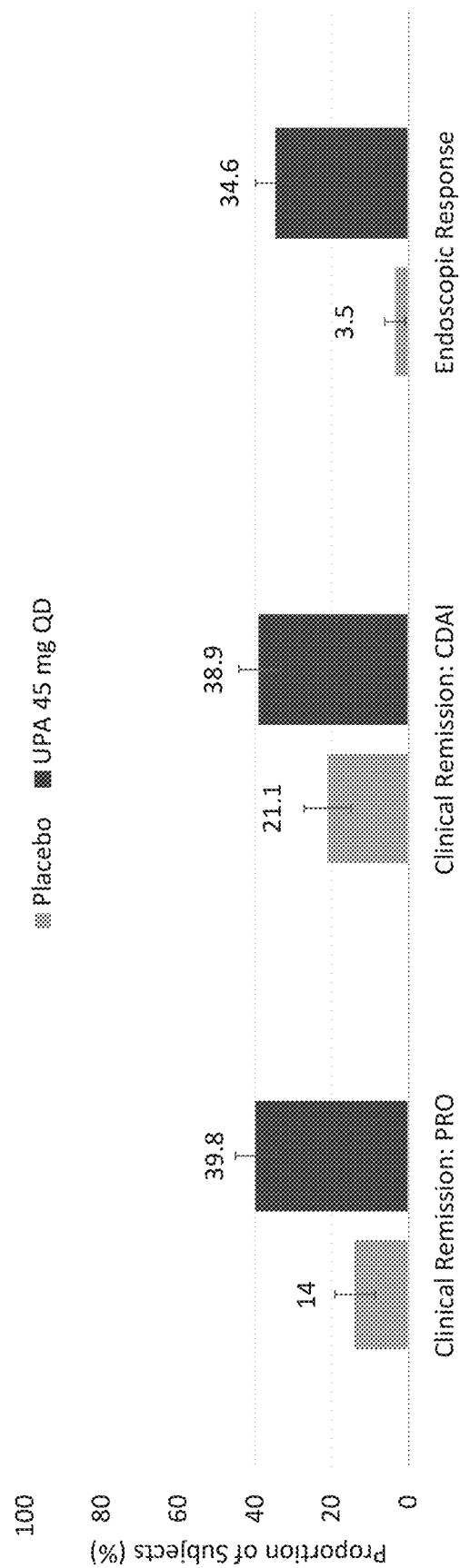

FIG. 47 is a graph showing the proportions of subjects achieving clinical remission and endoscopic response at week 12 for upadicitinib 45 mg QD versus placebo in the Example 21 study.

Figure 48:
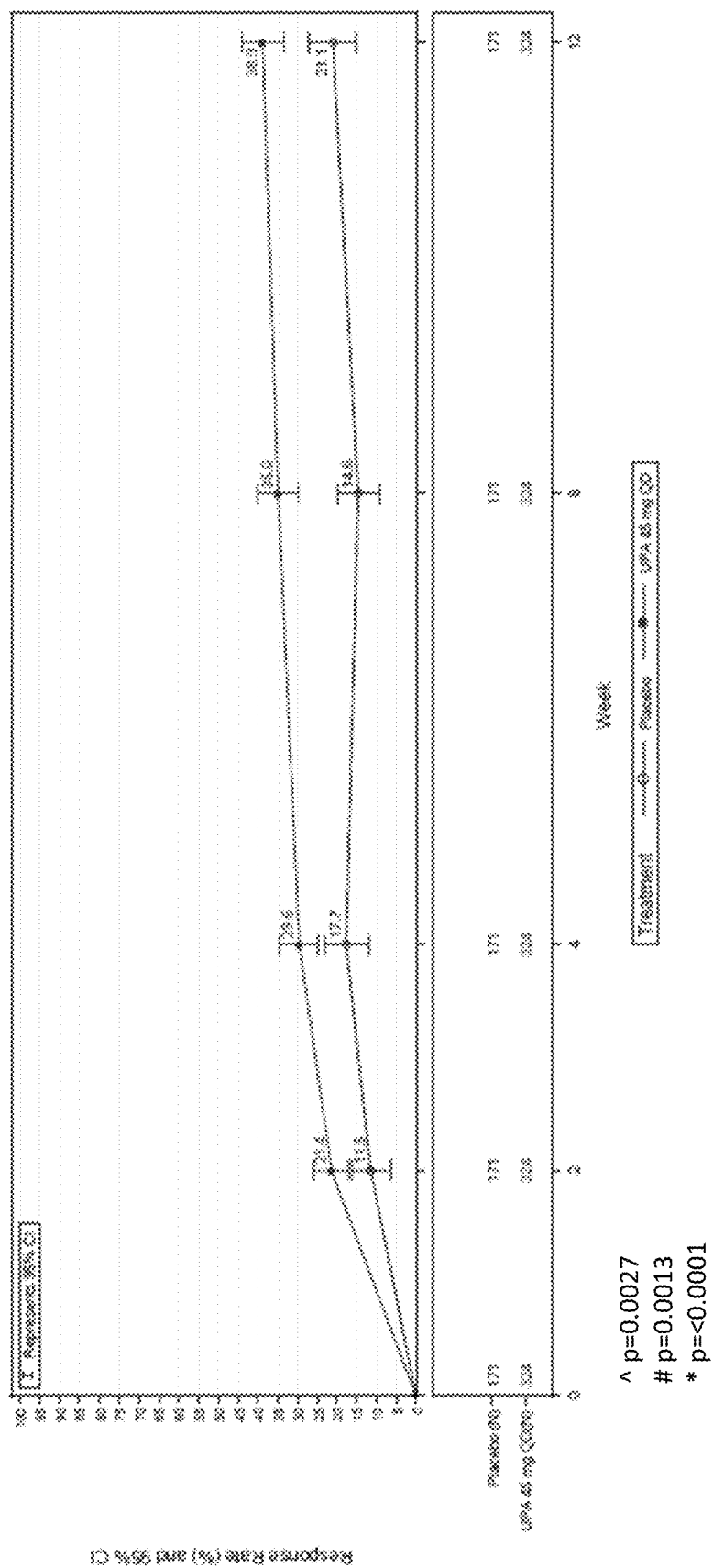

FIG. 48 is a graph showing the clinical remission rates per CDAI over time for subjects on upadicitinib 45 mg QD or placebo in the Example 21 study.

Figure 49:
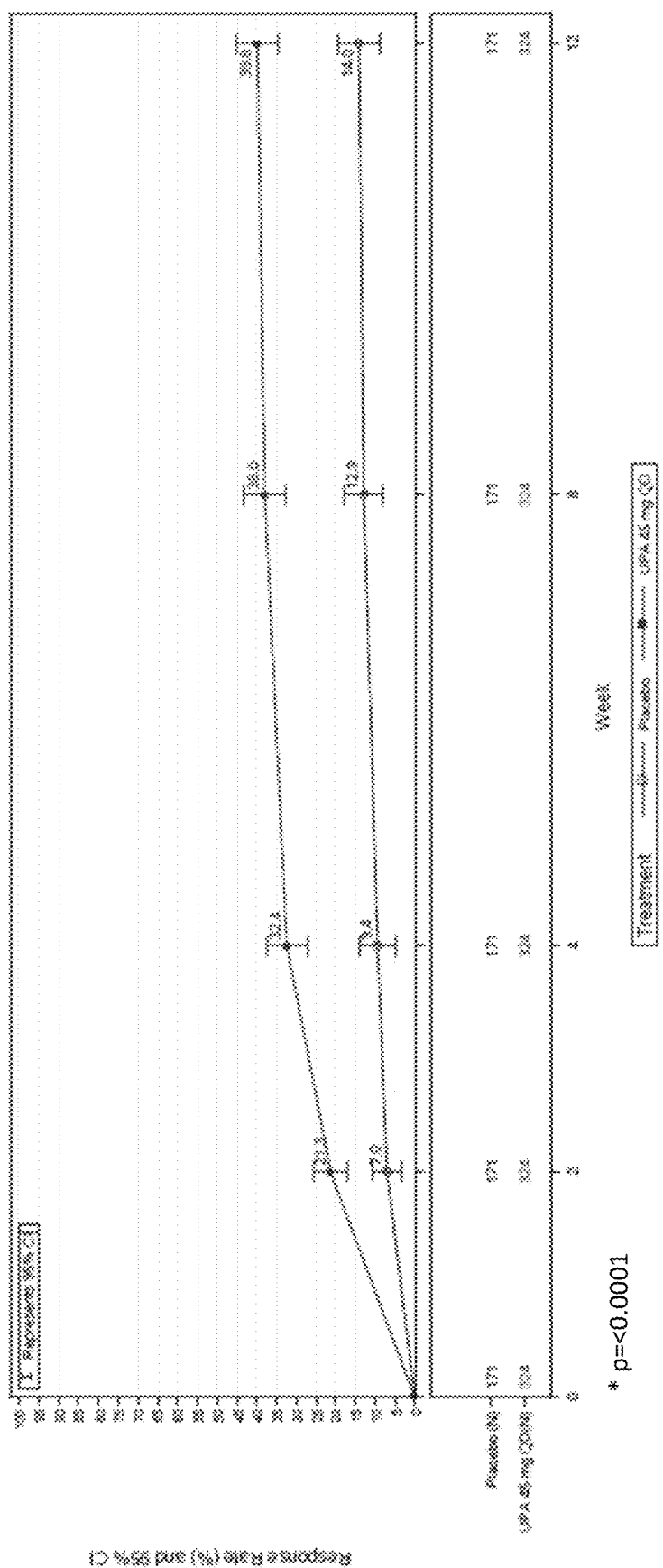

FIG. 49 is a graph showing the clinical remission rates per PRO over time for subjects on upadicitinib 45 mg QD or placebo in the Example 21 study.

FIG. 50 is a graph showing the proportion of subjects achieving endoscopic response and endoscopic remission at week 12 for upadicitinib 45 mg QD versus placebo in the Example 21 study.

FIG. 51 is a graph showing the proportions of subjects achieving steroid-free clinical remission at week 12 for upadicitinib 45 mg QD versus placebo in the Example 21 study.

DETAILED DESCRIPTION OF THE DISCLOSURE

This written description uses examples to disclose the invention and also to enable any person skilled in the art to practice the invention, including making and using any of the disclosed compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements.

I. DEFINITIONS

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0 to 7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The singular forms "a," "an" and "the" include plural referents unless the context clearly dictates otherwise.

The term "about" generally refers to a range of numbers that one of skill in the art would consider equivalent to the recited value (i.e., having the same function or result). In many instances, the term "about" may include numbers that are rounded to the nearest significant figure.

The term "abdominal pain" refers to pain originating from organs within the abdominal cavity including the stomach, small intestine, and colon. Abdominal pain can range in intensity from a mild to severe acute pain, and may be acute or chronic. Abdominal pain symptoms were collected by the patient and recorded daily in an electronic diary (e-diary) using an electronic handheld device, and scored as 0 (no pain), 1 (mild pain), 2 (moderate pain), or 3 (severe pain).

The term "Adapted Mayo" or "Adapted Mayo score" when used in connection with ulcerative colitis refers to the Mayo Scoring System for Assessment of Ulcerative Colitis Activity, excluding the Physician's Global Assessment subscore.

The term "adult" refers to a person 16 years of age or older.

The abbreviation "AE" refers to adverse event.

The term "alkyl" refers to straight chained or branched hydrocarbons which are completely saturated. For purposes of exemplification, which should not be construed as limiting the scope of this invention, examples of alkyls include methyl, ethyl, propyl, isopropyl, butyl, pentyl, hexyl, and isomers thereof.

The term "alkenyl" refers to a hydrocarbon moiety containing two to eight carbons, including straight chained or branched hydrocarbons which contain one or more double bonds. Non-limiting examples of alkenyls are ethenyl, propenyl, and butenyl.

The term "amorphous" as applied to a compound refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ("glass transition").

The term "anhydrate" as applied to a compound refers to a solid state wherein the compound contains no structural water within the crystal lattice.

The abbreviation "AP" refers to abdominal pain score. Unless otherwise indicated, the AP measurement discussed herein is an unweighted average of daily AP scores for seven days. The AP measurements are calculated by averaging the daily AP score used in calculating the CDAI (discussed below), without the weighting factor applied.

The term "aryl" refers to a mono-, bi-, or tricyclic aromatic hydrocarbon radical. Examples include phenyl, naphthyl, biphenyl, and 1,2,3,4-tetrahydronaphthyl.

As used herein, the term "$AUC_{24}$" refers to the area under the plasma concentration time curve from time zero to twenty-four hours after administration of the referent drug following a single dose.

The term "baseline" refers to the day of first dosing with the JAK1 inhibitor, and is also referred to herein as "Day 1" or "Week 0".

The abbreviation "BID" means twice a day.

The abbreviation "BL" means baseline.

As used herein, the term "bowel urgency" refers to a sudden, nearly uncontrollable need to defecate. Bowel urgency data were collected by the patient and recorded daily in an electronic diary (e-diary) using an electronic handheld device as a yes/no response with regard to symptom presence.

As used herein, the term "$C_{12}$" is the plasma concentration of the referent drug observed 12 hours after administration of a single dose, or the indicated number of doses, of the referent drug.

As used herein, the term "$C_{24}$" is the plasma concentration of the referent drug observed 24 hours after administration of a single dose, or the indicated number of doses, of the referent drug.

The term "$C_{ave}$" refers to the average plasma concentration of a drug during a dosage interval at steady-state (multiple-dosing).

The abbreviation "Cbz" refers to carboxybenzyl.

The abbreviation "CDI" refers to carbonyldiimidazole.

The abbreviation "CI" means confidence interval.

The abbreviation "CDAI" means Crohn's Disease Activity Index.

The term "clinical remission" when used in connection with Crohn's disease means average daily liquid/very soft stool frequency ≤2.8 and not greater than baseline and average daily abdominal pain ≤1.0 and not greater than baseline. As used in connection with clinical remission of Crohn's disease, the phrase "not greater than baseline" means the average daily SF or average daily AP score is not higher than the average daily SF score or average daily AP score, respectively, at baseline (i.e., prior to treatment).

The term "clinical remission" when used in connection with ulcerative colitis means a stool frequency (SF) subscore ≤1, a rectal bleeding subscore (RBS) of 0, and an endoscopic subscore of ≤0. The SF subscore, rectal bleeding subscore, and endoscopic subscore refer to the subscores used in the Mayo Scoring System for Assessment of Ulcerative Colitis Activity. This is also referred to as "clinical remission per Adapted Mayo Score".

The term "clinical response" when used in connection with Crohn's disease is defined as an average daily liquid/very soft SF score reduction of at least 30% from BL (i.e., ≥30% decrease from BL) and an average daily AP not greater than BL and/or "clinical response" is defined as an average daily AP score reduction of at least 30% from BL (i.e., ≥30% decrease from BL), and an average daily liquid/very soft SF score not greater than at BL (i.e., prior to treatment).

The term "clinical response" when used in connection with ulcerative colitis is defined as a decrease from baseline in the Adapted Mayo score ≥2 points and ≥30% from baseline accompanied by a decrease in RBS≥1 or an absolute RBS≤1.

The term "enhanced clinical response" when used in connection with Crohn's disease is defined as ≥60% decrease in average daily SF and/or ≥35% decrease in average daily AP and both not greater than baseline, and/or clinical remission.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

The term "$C_{max}$" refers to the plasma concentration of the referent drug at $T_{max}$, expressed herein as ng/mL, produced by the oral ingestion of a single dose, or indicated number of doses, of the dosage form or pharmaceutical composition, such as the dosage forms and compositions of the present disclosure. Unless specifically indicated, $C_{max}$ refers to the overall maximum observed concentration.

The term "$C_{min}$" refers to the minimum concentration of drug in blood plasma.

The term "corticosteroid-free" means a patient who was taking corticosteroids at the time of the first induction dose of upadacitinib and has completely discontinued use of corticosteroids.

The term "$C_p$" refers to plasma drug concentration at any time t.

The term "crystalline" as applied to a compound refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

The term "crystallization" as used throughout this application can refer to crystallization and/or recrystallization depending upon the applicable circumstances relating to the preparation of the compound.

The abbreviation "% CV" refers to the coefficient of variation, expressed as a percent. % CV is calculated according to the following equation: % CV=(SD/x)*100, wherein x is the mean value and SD is the standard deviation.

A "disorder", as used herein, is any condition that would benefit from treatment with a JAK1 inhibitor described herein. This includes chronic and acute disorders or diseases including those pathological conditions that predispose a mammal to the disorder in questions.

The term "endoscopic healing" means an SES-CD ulcerated surface subscore of 0 in subjects with SES-CD ulcerated surface subscore $\geq 1$ at baseline.

The term "endoscopic improvement" (also known as "endoscopic response by 50%") when used in connection with Crohn's disease means decrease in SES-CD>50% from baseline (or for subjects with an SES-CD of 4 at baseline of the induction study, at least a 2 point reduction from baseline).

The term "endoscopic improvement" when used in connection with ulcerative colitis means an endoscopic subscore ≤1 at week 8 during the induction phase and an endoscopic subscore of 0 at week 8 during the maintenance phase. The endoscopic subscore refers to the subscore used in the Mayo Scoring System for Assessment of Ulcerative Colitis Activity.

The term "endoscopic remission", when used in connection with Crohn's disease, unless otherwise indicated, means an SES-CD of ≤4 (≤2 for patients with isolated ileal CD) and at least a two point reduction in SES-CD versus BL and no subscore >1 in any individual variable used to calculate the SES-CD.

The term "endoscopic remission (by IOIBD (International Organization for the Study of Inflammatory Bowel Diseases) definition), when used in connection with Crohn's disease, means SDS≤2.

The term "endoscopic remission" when used in connection with ulcerative colitis means an endoscopic subscore of 0. The endoscopic subscore refer to the endoscopic subscore used in the Mayo Scoring System for Assessment of Ulcerative Colitis Activity.

The term "endoscopic response" when used in connection with Crohn's disease means at least a 50% reduction in SES-CD score from BL.

The abbreviation "EtOAc" refers to ethyl acetate.

The abbreviation "EtOH" refers to ethanol.

The term "Geboes score" means a histological score based on measurement of fecal calprotein and high-sensitivity C-reactive protein.

The term "histologic improvement" when used in connection with ulcerative colitis means a decrease from baseline in Geboes score.

The abbreviation "HDL" refers to high density lipoprotein.

The abbreviation "Hgb" refers to hemoglobin.

The abbreviation "HOAc" refers to acetic acid.

The abbreviation "HPMC" refers to hydroxypropyl methylcellulose.

As used herein, the term "inducing" or "induced", when used in connection with a particular therapeutic effect, means the therapeutic effect has been achieved. Typically, the therapeutic effect is induced in a patient previously suffering from a disease condition, such as in a patient having moderately to severely active Crohn's disease or moderately to severely active ulcerative colitis. For instance, in one embodiment, inducing a particular therapeutic effect, when used in connection with Crohn's disease, means the patient is brought from a state where the patient has 1) an average daily liquid/very soft stool frequency score ≥2.5 or average daily abdominal pain score ≥2, 2) CDAI≥220 and ≤450 or 3) Simplified Endoscopic Score for Crohn's disease (SES-CD)≥6 (or ≥4 for subjects with disease limited to the ileum) and bringing the patient to a state where the patient achieve the parameters for the specified therapeutic effect (e.g., endoscopic remission, clinical remission, endoscopic response, clinical response).

The abbreviation "IPAc" refers to isopropyl acetate.

The abbreviation "IR" means immediate release, unless otherwise indicated.

As used herein, the term "JAK1 inhibitor" or "upadacitinib" refers to the compound (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide.

The abbreviation "LDL" refers to low density lipoprotein.

The abbreviation "LOCF" means last observation carried forward method.

The abbreviation "Mayo" means the Mayo Scoring System for Assessment of Ulcerative Colitis Activity.

The term "moderately to severely active Crohn's disease", unless otherwise indicated, is defined as average daily very soft or liquid/soft stool frequency ≥4 and/or average daily abdominal pain score ≥2.0 and evidence of mucosal inflammation, defined as Simplified Endoscopic Score of or CD (SES-CD)≥6 (≥4 for subjects with isolated ileal disease), excluding the presence of narrowing component.

The term "moderately to severely active ulcerative colitis", unless otherwise indicated, is defined as having an Adapted Mayo score of 5 to 9, with an endoscopy subscore of 2 or 3.

The term "modified clinical remission" when used in connection with Crohn's disease is defined as an average daily liquid/very soft SF score of ≤2.8 and not greater than BL and an average daily AP score of ≤1.0 and not greater than BL. As used in connection with clinical remission, the phrase "not greater than baseline" means that average daily liquid/very soft SF score or average daily AP score is not higher than the average daily liquid/very soft SF score or average daily AP score, respectively, at baseline (i.e., prior to treatment).

The abbreviation "MR" means modified release.

The abbreviation "MTX" refers to methotrexate.

The term "Mucosal Healing" when used in connection with ulcerative colitis means an endoscopic subscore of 0 and a Geboes score of ≤2.0.

The term "patient" or "subject", used interchangeably herein, refers to a human patient or subject.

The term "NK cells" refers to natural killer cells.

The abbreviation "NRI" means non-responder imputation method.

The abbreviation "PBO" means placebo.

The abbreviation "Pd/C" refers to palladium on carbon.

The abbreviation "Pd(OH$_2$)/C" refers to palladium hydroxide on carbon.

The term "pharmaceutically acceptable" (such as in the recitation of a "pharmaceutically acceptable salt" or a "pharmaceutically acceptable diluent") refers to a material that is compatible with administration to a human subject, e.g., the material does not cause an undesirable biological effect. Examples of pharmaceutically acceptable salts are described in "Handbook of Pharmaceutical Salts: Properties, Selection, and Use" by Stahl and Wermuth (Wiley-VCH, Weinheim, Germany, 2002). Examples of pharmaceutically acceptable excipients are described in the "Handbook of Pharmaceutical Excipients," Rowe et al., Ed. (Pharmaceutical Press, 7th Ed., 2012).

The abbreviation "pTsOH" refers to p-toluene sulfonic acid.

The abbreviation "PVA" refers to polyvinyl acetate.

The abbreviation "PXRD" means powder X-ray diffraction.

The abbreviation "QD" means once daily.

The abbreviation "RBC" means red blood cells.

The abbreviation "RBS" means rectal bleeding subscore. The rectal bleeding subscore refers to the subscore used in the Mayo Scoring System for Assessment of Ulcerative Colitis Activity.

The term "refractory patient" means a patient with moderately to severely active Crohn's disease, who has had Crohn's disease for more than ten years and who has failed several treatments, including biologic treatments.

The term "remission" when used in connection with Crohn's disease is defined as both endoscopic remission and clinical remission.

The term "response" when used in connection with Crohn's disease is defined as both endoscopic response and clinical response.

The abbreviation "SC" means subcutaneous.

The abbreviation "(S)-Segphos Ru(OAc)$_2$" refers to diacetato[(S)-(−)5,5'-bis(diphenylphosphino)-4,4'-bi-1,3-benzodioxole]ruthenium(II).

The term "SES-CD" refers to the Simplified Endoscopic Score for Crohn's disease, which is calculated using the parameters listed in Table 2 below.

The abbreviation "SF" refers to stool frequency. Unless otherwise indicated, the SF measurement discussed herein when used in connection with Crohn's disease is an unweighted average of daily liquid/very soft SF scores for seven days. The SF measurements are calculated by averaging the daily liquid/very soft SF scores used in calculating the CDAI (discussed below), without the weighting factor applied. Unless otherwise indicated, the SF measurement discussed herein when used in connection with ulcerative colitis refers to the stool frequency subscore used in the Mayo Scoring System for Assessment of Ulcerative Colitis Activity.

The term "therapeutically effective amount" is used to refer to an amount of an active agent that relieves or ameliorates one or more of the symptoms of the disorder being treated. In another aspect, the therapeutically effective amount refers to a target serum concentration that has been shown to be effective in, for example, slowing disease progression. Efficacy can be measured in conventional ways, depending on the condition to be treated.

The abbreviation "6-TGN" refers to 6-tioguanine (thioguanine) nucleotides.

The abbreviation "THF" refers to tetrahydrofuran.

As used herein, the term "$T_{max}$" refers to the time to peak plasma concentration of the referent drug after oral ingestion of a single dose, or indicated number of doses, of the referent drug.

The terms "treating", "treatment", and "therapy" and the like, as used herein, are meant to include therapeutic as well as prophylactic, or suppressive measures for a disease or disorder leading to any clinical desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the disclosure either alone or in combination with another therapeutic agent alleviate or ameliorate at least one symptom of a disorder being treated as compared to that symptom in the absence of use of the JAK1 inhibitor composition, the result should be considered an effective treatment of the underlying disorder regardless of whether all the symptoms of the disorder are alleviated or not.

The abbreviation "TNF" means tumor necrosis factor.

As used herein, the term "$t_{1/2}$" refers to the terminal half-life of the referent drug after oral ingestion of a single dose, or indicated number of doses, of the referent drug.

The abbreviation "UC" refers to ulcerative colitis.

The abbreviation "w/w" refers to weight/weight.

II. JAK1-ASSOCIATED DISORDERS AND JAK1 INHIBITORS

In one aspect, the present disclosure provides methods for treating and/or inducing clinical remission, endoscopic improvement, and/or endoscopic remission of Crohn's disease. In another aspect, the present disclosure provides methods for treating ulcerative colitis and/or for inducing a clinical remission of ulcerative colitis. In one aspect, the methods comprise administering a JAK1 inhibitor to the patient.

Targeting the JAK (Janus activated kinase) signaling pathway for autoimmune diseases, such as rheumatoid arthritis (RA) and CD, is well-supported by the involvement of various pro-inflammatory cytokines that signal via JAK pathways in the pathogenesis of these immune-related disorders. The activation of the JAK signaling initiates expression of survival factors, cytokines, chemokines, and other molecules that facilitate leukocyte cellular trafficking and cell proliferation, which contribute to inflammatory and autoimmune disorders.

Although the pathogenesis of CD is not completely understood, the imbalance between anti-inflammatory and pro-inflammatory cytokines in the mucosal immune system is thought to play an important role in CD. Cells from the innate mucosal immune system, i.e. TH1 or TH17, are over-activated and secrete various pro-inflammatory cytokines such as interferon (INF)-g, TNFα, interleukin IL-6, IL1b, IL-12, IL23. These cytokines signal via JAK pathways.

The JAK comprises four family members: JAK1, 2, 3, and Tyrosine kinase 2 (Tyk2). These cytoplasmic tyrosine kinases transduce cytokine-mediated signals, and are associated with membrane cytokine receptors such as common gamma-chain (CGC) receptors and the glycoprotein 130 (gp130) trans-membrane proteins.

JAK3 and JAK1 are components of the CGC cytokine receptor complexes and blockade of either inhibits signaling by the inflammatory cytokines IL-2, -4, -7, -9, -15 and -21. Cytokines such as IL-6 bind to gp130 and transduce its signal predominantly via JAK1. Targeting the IL-6 receptor (IL-6R) is a promising approach given the fact that expression of IL-6 and soluble IL-6 receptors is elevated in patients with active CD. Further, a proof of concept study in patients with active CD with tocilizumab, a humanized monoclonal antibody against IL-6R, showed an encouraging clinical response. Thus, inhibition of JAK1 is expected to attenuate the signaling of IL-6 and other pro-inflammatory cytokines (i.e. IFN-g), that are involved in development of CD.

Thus, in one aspect, the present disclosure provides a compound useful in the treatment of Crohn's Disease and ulcerative colitis. In one aspect, the JAK1 inhibitor used in the methods of the present disclosure is the compound (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide ($C_{17}H_{19}F_3N_6O$), or a pharmaceutically acceptable salt or solid state form thereof. The compound (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide is also referred to herein as "upadacitinib", and has the structure shown below:

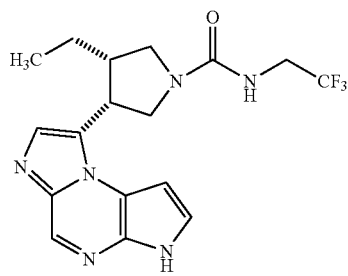

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, monomalic acid, mono oxalic acid, tartaric acid such as mono tartaric acid (e.g., (+) or (−)-tartaric acid or mixtures thereof), amino acids (e.g., (+) or (−)-amino acids or mixtures thereof), and the like. These salts can be prepared by methods known to those skilled in the art.

III. METHODS OF TREATMENT OF CROHN'S DISEASE

In one aspect, the present disclosure is directed to methods for the treatment of Crohn's disease. In one aspect, the present disclosure provides methods for treating Crohn's disease, in particular methods comprising administering a JAK1 inhibitor to a patient in certain amounts and/or at certain intervals. In one aspect, the JAK1 inhibitor is upadacitinib or a pharmaceutically acceptable salt or solid state form thereof.

In one aspect, the present disclosure provides a JAK1 inhibitor for use in the treatment of Crohn's disease, by administration in certain amounts and/or at certain intervals as described herein. In one aspect, the JAK1 inhibitor is upadacitinib or a pharmaceutically acceptable salt or solid state form thereof.

In one aspect, the present disclosure provides for the use of a JAK1 inhibitor for the preparation of a medicament for the treatment of Crohn's disease, by administration in certain amounts and/or at certain intervals as described herein. In one aspect, the JAK1 inhibitor is upadacitinib or a pharmaceutically acceptable salt or solid state form thereof.

In one aspect, the present disclosure is directed to methods for inducing clinical remission and/or endoscopic remission of Crohn's disease. In one aspect, the present disclosure provides methods for inducing clinical remission and/or endoscopic remission of Crohn's disease, in particular methods comprising administering a JAK1 inhibitor to a patient in certain amounts and/or at certain intervals. In one aspect, the JAK1 inhibitor is upadacitinib or a pharmaceutically acceptable salt or solid state form thereof.

In one aspect, the present disclosure provides a JAK1 inhibitor for use in inducing clinical remission and/or endoscopic remission of Crohn's disease by administration in certain amounts and/or at certain intervals as described herein. In one aspect, the JAK1 inhibitor is upadacitinib or a pharmaceutically acceptable salt or solid state form thereof.

In one aspect, the present disclosure provides for the use of a JAK1 inhibitor for the preparation of a medicament for inducing clinical remission and/or endoscopic remission of Crohn's Disease by administration in certain amounts and/or at certain intervals as described herein. In one aspect, the JAK1 inhibitor is upadacitinib or a pharmaceutically acceptable salt or solid state form thereof.

In one aspect, the present disclosure is directed to methods for inducing clinical remission and/or endoscopic improvement of Crohn's disease, in particular, methods comprising administering a JAK1 inhibitor to a patient in certain amounts and/or at certain intervals. In one aspect, the JAK1 inhibitor is upadacitinib or a pharmaceutically acceptable salt or solid state form thereof.

In one aspect, the present disclosure provides a JAK1 inhibitor for use in inducing clinical remission and/or endoscopic improvement of Crohn's disease by administration in certain amounts and/or at certain intervals as described herein. In one aspect, the JAK1 inhibitor is upadacitinib or a pharmaceutically acceptable salt or solid state form thereof.

In one aspect, the present disclosure provides for the use of a JAK1 inhibitor for the preparation of a medicament for inducing clinical remission and/or endoscopic improvement of Crohn's disease, by administration in certain amounts and/or at certain intervals as described herein. In one aspect, the JAK1 inhibitor is upadacitinib or a pharmaceutically acceptable salt or solid state form thereof.

In one particular aspect, the disease is moderately to severely active Crohn's disease. In one aspect, in the context of the present disclosure, a patient is naïve to, or was previously treated with immunosuppressants (e.g., methotrexate), aminosalicylates, corticosteroids, and/or a biologic agent (e.g., vedolizumab, ustekinumab, natalizumab, etc.). In one aspect, the patient is naïve to, or was previously treated with an anti-TNF therapy (e.g., infliximab, adalimumab, certolizumab pegol, golimumab, etc.). In one aspect, in the context of a method of the present disclosure a patient was previously treated with one, two, three or more TNF antagonist(s) (also referred to herein as anti-TNF agents). In one embodiment, the patient is a patient who had an inadequate response with, lost response, or was intolerant to a TNF antagonist. In one aspect, in the context of a method of the present disclosure a patient was previously treated with one, two, three or more biologic(s). In one embodiment, the patient is a patient who had an inadequate response with, lost response, or was intolerant to a biologic agent. In one embodiment, the patient is a patient who had an inadequate response with, lost response, or was intolerant to a TNF antagonist, aminosalicylates, corticosteroids, immunosuppressants, and/or a biologic agent. In one embodiment, the patient is a refractory patient who has moderately to severely active Crohn's disease. In one embodiment, the patient is either naïve to or has stopped using corticosteroids prior to treatment with the JAK1 inhibitor.

Biologic agents for Crohn's Disease:
1) Demonstrated an inadequate response to, loss of response to, recurrence of signs and symptoms or intolerance to any biologic therapy as defined below:
    a. at least one 6-week induction regimen of infliximab (≥5 mg/kg intravenous [IV] at 0, 2 and 6 weeks),
    b. at least one 4-week induction regimen of adalimumab (one 160 mg subcutaneous (SC) dose at Week 0, followed by one 80 mg SC dose at Week 2 [or one 80 mg SC dose at Week 0, followed by one 40 mg SC dose at Week 2, in countries where this dosing regimen is approved]),
    c. at least one 4-week induction regimen of certolizumab pegol (400 mg SC at Weeks 0, 2 and 4),
    d. at least one 6-week induction regimen of vedolizumab (300 mg IV at 0, 2 and 6 weeks),
    e. at least one 12-week induction regimen of natalizumab (300 mg IV every 4 weeks),
    f. at least on 8-week induction regimen of ustekinumab [260 mg (<55 kg) or 390 mg (56-85 kg) or 520 mg (>86 kg), followed by 90 mg SC at week 8] or
2) Recurrence of symptoms during scheduled maintenance dosing following prior clinical benefit (discontinuation despite clinical benefit does not qualify), or
3) History of intolerance to at least one biologic agent (including, but not limited to infusion-related reaction, demyelination, congestive heart failure (CHF), infection).

Disease severity for Crohn's disease may be measured using a variety of indexes, including the Crohn's Disease Activity Index (CDAI), the Simplified Endoscopic Score for CD (SES-CD), average daily liquid/very soft stool frequency (SF) (patient reported); and/or average daily abdominal pain (AP) score (patient reported). Unless otherwise indicated, the SF and AP scores discussed herein refer to their respective unweighted average of the daily scores that are used in calculation of the CDAI (discussed below). Measures for assessing health-related quality of life include the Inflammatory Bowel Disease Questionnaire (IBDQ). The IBDQ is a well-known 32 item validated questionnaire that assesses a patient's inflammatory bowel disease symptoms, general well-being, and mood, and may be used as a tool to evaluate a patient's quality of life (Guyatt, et al., Gastroenterology, 1989, 96:804-810). The IBDQ questionnaire is described in further detail below.

CDAI is a composite score used to quantify symptoms of patients with Crohn's disease. In one aspect, the index consists of eight factors added together after adjusting for a predefined weighting factor (see Table 1 below). CDAI scores range from 0 to 600. Index values of 150 and below are associated with quiescent disease; values above 150 are associated with active disease, and values above 450 are seen with extremely severe disease. In one aspect, a patient to be treated by a method according to the present disclosure has a CDAI score of 220 to 450 prior to treatment, which may be indicative of moderately to severely active CD.

TABLE 1

Format for Calculation of the CDAI

| Clinical or laboratory variable | Weighting factor |
|---|---|
| Number of liquid or very soft stools in the previous 7 days (sum of daily scores) | x2 |
| AP (graded from 0 (mild) to 3 (severe) on severity) each day for 7 days (sum of daily score) | x5 |
| General wellbeing, subjectively assessed from 0 (generally well) to 4 (terrible) each day for 7 days (sum of daily score) | x7 |
| Number of complications patient now has: (record 0 if none) Arthritis/arthralgia Iritis/uveitis Erythema nodosum/pyoderma gangrenosum/aphthous stomatitis Fissure, abscess and/or anal fistula (draining/non-draining) Other cutaneous fistula (draining/non-draining) Fever over 100° F. (37.8° C.) during past week | x20 |
| Taking lomotil/imodium/loperamide or opiates for diarrhea (0 = no, 1 = yes) | x30 |
| Presence of an abdominal mass (0 as none, 2 as questionable, 5 as defined) | x10 |
| Hematocrit (Male: 47-hematocrit; Female: 42-hematocrit; if hematocrit > normal, enter 0 | x6 |
| Percentage under standard weight | x1 |

SES-CD is calculated using the following parameters listed in Table 2:

TABLE 2

Parameters for Calculating SES-CD

| | Rectum | Sigmoid and left colon | Transverse Colon | Right colon | Ileum | Total |
|---|---|---|---|---|---|---|
| Size of Ulcers Enter: 0 if none 1 if aphthous ulcer (Ø 0.01 to 0.5 cm) 2 if large ulcers (Ø 0.05 to 2 cm) 3 if very large ulcer (Ø >2 cm) Ulcerated Surface | | | | | | |

TABLE 2-continued

Parameters for Calculating SES-CD

|  | Rectum | Sigmoid and left colon | Transverse Colon | Right colon | Ileum | Total |
|---|---|---|---|---|---|---|

Enter:
0 if none
1 if <10%
2 if 10%-30%
3 if >30%
Affected Surface
Enter:
0 if unaffected segments
1 if <50%
2 if 50%-75%
3 if >75%
Presence of Narrowing
Enter:
0 if none
1 if single, can be passed
2 if multiple, can be passed
3 if cannot be passed Total=

In one aspect, the patient to be treated has moderately to severely active Crohn's disease. Moderately to severely active Crohn's disease is characterized by a SES-CD of greater than or equal to 6 (or a SES-CD of greater than or equal to 4 for patients with disease limited to the ileum).

In one embodiment, the patient is a patient who had an inadequate response with, lost response, or was intolerant to a conventional therapy (e.g., aminosalicylates, corticosteroids, immunosuppressants), or to a biologic agent. In one embodiment, the patient is a patient who had an inadequate response with, lost response, or was intolerant to a TNF antagonist. Examples of such anti-TNF agents include infliximab, adalimumab, and certolizumab pegol. Criteria for determining if a patient has had an inadequate response to or experienced intolerance to previous treatment with an anti-TNF agent is defined as:
1) Signs and symptoms of persistently active disease despite a history of at least one 4-week induction regimen of one of the following agents:
   Infliximab: 5 mg/kg IV, 2 doses at least 2 weeks apart,
   Adalimumab: one 160 mg subcutaneous dose followed by one 80 mg subcutaneous dose (or one 80 mg subcutaneous dose) followed by one 40 mg dose at least 2 weeks apart,
   Certolizumab pegol: 400 mg subcutaneous, two doses at least two doses apart; or 2) Recurrence of symptoms during scheduled maintenance dosing following prior clinical benefit (discontinuation despite clinical benefit does not qualify); or
2) Recurrence of symptoms during scheduled maintenance dosing following prior clinical benefit (discontinuation despite clinical benefit does not qualify); or
3) History of intolerance of at least one TNF antagonist (including, but not limited to infusion related reaction, demyelination, congestive heart failure and infection).

In one aspect, the patient is one who has previously been treated with, or is currently being treated with aminosalicylates, immunosuppressants, corticosteroids, and/or a biologic agent.

In one aspect, CDAI or any of the evaluations described in the Examples herein below is/are used to assess the efficacy of upadacitinib in the treatment of Crohn's disease, for example moderately to severely active Crohn's disease.

In one embodiment, in the context of the present disclosure, the treatment of a patient, or the induction of clinical remission and/or endoscopic remission in a patient, or the induction of clinical remission and/or endoscopic improvement in a patient comprises an induction phase and a maintenance phase. In the induction phase, one or more doses of the JAK1 inhibitor, for example referred to herein as induction doses, are administered to the patient, for example, orally. In the maintenance phase, a first dose of the JAK1 inhibitor, for example referred to herein as the maintenance dose, is administered to the patient followed by at least one additional dose of the JAK1 inhibitor, for example, also referred to herein as a maintenance dose. The maintenance doses are, for example, administered orally. The JAK1 inhibitor may be, for example, upadacitinib, or a pharmaceutically acceptable salt or solid state form thereof. Examples of induction phases and maintenance phases are described herein.

In one aspect, a certain therapeutic result is achieved by the patient during or at the end of the induction phase, for example clinical remission, endoscopic remission, or both clinical remission and endoscopic remission (referred to herein as "remission"). In one aspect, the patient achieves clinical remission during or by the end of the induction phase. In one aspect, the patient achieves endoscopic remission during or by the end of the induction phase.

In another aspect, a certain therapeutic result is achieved by the patient during or at the end of the induction phase, for example clinical remission, endoscopic improvement, or both clinical remission and endoscopic improvement. In one aspect, the patient achieves clinical remission during or by the end of the induction phase. In one aspect, the patient achieves endoscopic improvement during or by the end of the induction phase.

In one embodiment, the induction phase lasts for up to 16 weeks (e.g., for up to 16 weeks following initiation of administration of upadacitinib, or a pharmaceutically acceptable salt or solid state form thereof). Thus, in one embodiment, the induction phase is 16 weeks. In another embodiment, the induction phase optionally lasts for less than 16 weeks, for instance, for 2 weeks, for 4 weeks, for 5 weeks, for 6 weeks, for 7 weeks, for 8 weeks, for 9 weeks, for 10 weeks, for 11 weeks, for 12 weeks, for 13 weeks, for 14 weeks, or for 15 weeks. In one aspect, the patient achieves an endoscopic remission within 12 weeks, or within 16 weeks of initiating administration of upadacitinib, or a pharmaceutically acceptable salt or solid state form thereof. In one aspect, the patient achieves a clinical remission within 16 weeks of initiating administration of upadacitinib, or a pharmaceutically acceptable salt or solid state form thereof. In one aspect, the patient achieves an endoscopic improvement within 12 weeks, or within 16 weeks of initiating administration of upadacitinib, or a pharmaceutically acceptable salt or solid state form thereof. In one aspect, the patient achieves a clinical remission within 12 weeks, or within 16 weeks of initiating administration of upadacitinib, or a pharmaceutically acceptable salt or solid state form thereof.

In one embodiment, the patient achieves clinical remission within 2 weeks of initiating administration of upadacitinib, or a pharmaceutically acceptable salt or solid state form thereof. In one embodiment, the patient achieves clinical remission within 4 weeks of initiating administration of upadacitinib, or a pharmaceutically acceptable salt or solid state form thereof.

In one embodiment, the patient achieves both 1) average daily liquid/very soft SF score of ≤1.5 and not worse than BL, and 2) average daily AP score of ≤1.0 and not worse than baseline within 2 weeks of initiating administration of upadacitinib, or a pharmaceutically acceptable salt or solid state form thereof. As used in connection with clinical remission, the phrase "not worse than baseline" means that the average daily liquid/very soft SF score or average daily AP score is not higher than the average daily liquid/very soft SF score or average daily AP score, respectively, at baseline (i.e., prior to treatment).

In one embodiment, the patient achieves both 1) average daily liquid/very soft SF score of ≤1.5 and not worse than BL, and 2) average daily AP score of ≤1.0 and not worse than baseline within 4 weeks of initiating administration of upadacitinib, or a pharmaceutically acceptable salt or solid state form thereof. As used in connection with clinical remission, the phrase "not worse than baseline" means that the average daily liquid/very soft SF score or average daily AP score is not higher than the average daily liquid/very soft SF score or average daily AP score, respectively, at baseline (i.e., prior to treatment).

In one embodiment, the patient achieves endoscopic remission and/or endoscopic improvement within 2 weeks of initiating administration of upadacitinib, or a pharmaceutically acceptable salt or solid state form thereof. In one embodiment, the patient achieves endoscopic remission and/or endoscopic improvement within 12 weeks of initiating administration of upadacitinib, or a pharmaceutically acceptable salt or solid state form thereof.

In one embodiment, the patient achieves corticosteroid-free remission within 12 weeks of initiating administration of upadacitinib, or a pharmaceutically acceptable salt or solid state form thereof.

In some embodiments, during or by the end of the induction phase (e.g., lasting for up to 16 weeks, including for 2 weeks, 4 weeks, 6 weeks, 8 weeks, 10 weeks, 12 weeks or for 16 weeks), the patient achieves at least one therapeutic result selected from the group consisting of:

1) a CDAI of less than 150 within 16 weeks of initiating administration of upadacitinib, or a pharmaceutically acceptable salt or solid state form thereof,
2) a CDAI of less than 150 within 12 weeks of initiating administration of upadacitinib, or a pharmaceutically acceptable salt or solid state form thereof,
3) a CDAI of less than 150 within 4 weeks of initiating administration of upadacitinib, or a pharmaceutically acceptable salt or solid state form thereof,
4) a decrease in CDAI of greater than or equal to 70 points from baseline within 16 weeks of initiating administration of upadacitinib, or a pharmaceutically acceptable salt or solid state form thereof,
5) a decrease in CDAI of greater than or equal to 70 points from baseline within 12 weeks of initiating administration of upadacitinib, or a pharmaceutically acceptable salt or solid state form thereof,
6) a decrease in CDAI of greater than or equal to 70 points from baseline within 4 weeks of initiating administration of upadacitinib, or a pharmaceutically acceptable salt or solid state form thereof,
7) a clinical remission within 12 weeks of initiating administration of upadacitinib, or a pharmaceutically acceptable salt or solid state form thereof,
8) a clinical remission within 4 weeks of initiating administration of upadacitinib, or a pharmaceutically acceptable salt or solid state form thereof,
9) remission within 16 weeks of initiating administration of upadacitinib, or a pharmaceutically acceptable salt or solid state form thereof (i.e., both endoscopic remission within 12 weeks or within 16 weeks and clinical remission within 16 weeks of initiating administration of upadacitinib, or a pharmaceutically acceptable salt or solid state form thereof),
10) remission within 12 weeks of initiating administration of upadacitinib, or a pharmaceutically acceptable salt or solid state form thereof (i.e., both endoscopic remission within 12 weeks and clinical remission within 12 weeks of initiating administration of upadacitinib, or a pharmaceutically acceptable salt or solid state form thereof),
11) remission within 4 weeks of initiating administration of upadacitinib, or a pharmaceutically acceptable salt or solid state form thereof (i.e., both endoscopic remission within 4 weeks and clinical remission within 4 weeks of initiating administration of upadacitinib, or a pharmaceutically acceptable salt or solid state form thereof),
12) response within 16 weeks of initiating administration of upadacitinib, or a pharmaceutically acceptable salt or solid state form thereof (i.e., both endoscopic response within 12 weeks or within 16 weeks and clinical response within 16 weeks of initiating administration of upadacitinib, or a pharmaceutically acceptable salt or solid state form thereof),
13) response within 12 weeks of initiating administration of upadacitinib, or a pharmaceutically acceptable salt or solid state form thereof (i.e., both endoscopic response within 12 weeks and clinical response within 12 weeks of initiating administration of upadacitinib, or a pharmaceutically acceptable salt or solid state form thereof),
14) response within 4 weeks of initiating administration of upadacitinib, or a pharmaceutically acceptable salt or solid state form thereof (i.e., both endoscopic response within 4 weeks and clinical response within 4 weeks of initiating administration of upadacitinib, or a pharmaceutically acceptable salt or solid state form thereof),
15) endoscopic response within 12 weeks or within 16 weeks of initiating administration of upadacitinib, or a pharmaceutically acceptable salt or solid state form thereof,
16) endoscopic response within 4 weeks of initiating administration of upadacitinib, or a pharmaceutically acceptable salt or solid state form thereof, 17) clinical response within 16 weeks of initiating administration of upadacitinib, or a pharmaceutically acceptable salt or solid state form thereof,
18) clinical response within 12 weeks of initiating administration of upadacitinib, or a pharmaceutically acceptable salt or solid state form thereof,
19) clinical response within 4 weeks of initiating administration of upadacitinib, or a pharmaceutically acceptable salt or solid state form thereof,
20) clinical response within 2 weeks of initiating administration of upadacitinib, or a pharmaceutically acceptable salt or solid state form thereof
21) a change from baseline in fecal calprotectin level within 16 weeks of initiating administration of upadacitinib, or a pharmaceutically acceptable salt or solid state form thereof,
22) a change from baseline in fecal calprotectin level within 12 weeks of initiating administration of upadacitinib, or a pharmaceutically acceptable salt or solid state form thereof,
23) a change from baseline in fecal calprotectin level within 4 weeks of initiating administration of upadacitinib, or a pharmaceutically acceptable salt or solid state form thereof,
24) a change from baseline in hs-CRP (high sensitivity C-reactive protein) within 16 weeks of initiating administration of upadacitinib, or a pharmaceutically acceptable salt or solid state form thereof,
25) a change from baseline in hs-CRP (high sensitivity C-reactive protein) within 12 weeks of initiating administration of upadacitinib, or a pharmaceutically acceptable salt or solid state form thereof,
26) a change from baseline in hs-CRP (high sensitivity C-reactive protein) within 8 weeks of initiating administration of upadacitinib, or a pharmaceutically acceptable salt or solid state form thereof,
27) a change from baseline in hs-CRP (high sensitivity C-reactive protein) within 4 weeks of initiating administration of upadacitinib, or a pharmaceutically acceptable salt or solid state form thereof,
28) a change from baseline in hs-CRP (high sensitivity C-reactive protein) within 2 weeks of initiating administration of upadacitinib, or a pharmaceutically acceptable salt or solid state form thereof,
29) a change in Inflammatory Bowel Disease Questionnaire (IBDQ) score from baseline within 16 weeks of initiating administration of upadacitinib, or a pharmaceutically acceptable salt or solid state form thereof,
30) a change in Inflammatory Bowel Disease Questionnaire (IBDQ) score from baseline within 12 weeks of initiating administration of upadacitinib, or a pharmaceutically acceptable salt or solid state form thereof,
31) a change in Inflammatory Bowel Disease Questionnaire (IBDQ) score from baseline within 8 weeks of initiating administration of upadacitinib, or a pharmaceutically acceptable salt or solid state form thereof,
32) modified clinical remission within 4 weeks of initiating administration of upadacitinib, or a pharmaceutically acceptable salt or solid state form thereof,
33) enhanced clinical response within 8 weeks of initiating administration of upadacitinib, or a pharmaceutically acceptable salt or solid state form thereof and combinations thereof,
34) steroid-free endoscopic improvement within 4 weeks of administration of upadacitinib, or a pharmaceutically acceptable salt or solid state form thereof,
35) steroid-free endoscopic improvement within 8 weeks of administration of upadacitinib, or a pharmaceutically acceptable salt or solid state form thereof,
36) steroid-free endoscopic improvement within 16 weeks of administration of upadacitinib, or a pharmaceutically acceptable salt or solid state form thereof,
37) steroid-free endoscopic response within 4 weeks of administration of upadacitinib, or a pharmaceutically acceptable salt or solid state form thereof,
38) steroid-free endoscopic response within 8 weeks of administration of upadacitinib, or a pharmaceutically acceptable salt or solid state form thereof,
39) steroid-free endoscopic response within 16 weeks of administration of upadacitinib, or a pharmaceutically acceptable salt or solid state form thereof,
40) steroid-free endoscopic remission within 4 weeks of administration of upadacitinib, or a pharmaceutically acceptable salt or solid state form thereof,
41) steroid-free endoscopic remission within 8 weeks of administration of upadacitinib, or a pharmaceutically acceptable salt or solid state form thereof,
42) steroid-free endoscopic remission within 16 weeks of administration of upadacitinib, or a pharmaceutically acceptable salt or solid state form thereof.

In some embodiments, the patient achieves either a clinical remission within 16 weeks of initiating administration of upadacitinib, or a pharmaceutically acceptable salt or solid state form thereof, or an endoscopic remission within 12 weeks or within 16 weeks of initiating administration of upadacitinib, or a pharmaceutically acceptable salt or solid state form thereof, and further achieves any combination of additional therapeutic results selected from the group consisting of therapeutic results 1), 2), 3), 4), 5), 6), 7), 8), 9), 10), 11), 12), 13), 14), 15), 16), 17), 18), 19), 20), 21), 22), 23), 24), 25), 26), 27), 28), 29), and combinations thereof. In one such embodiment, the induction phase is 16 weeks.

In one embodiment, the induction phase is 12 weeks, and the patient achieves either a clinical remission within 12 weeks of initiating administration of upadacitinib, or a pharmaceutically acceptable salt or solid state form thereof, or an endoscopic remission within 12 weeks of initiating administration of upadacitinib, or a pharmaceutically acceptable salt or solid state form thereof, and further achieves any combination of additional therapeutic results selected from the group consisting of therapeutic results 2), 3), 5), 6), 7), 8), 10), 11), 13), 14), 15), 16), 18), 19), 20), 22), 23), 25), 26), 28), 29), and combinations thereof, wherein the therapeutic result is achieved within 12 weeks of initiating administration of upadacitinib, or a pharmaceutically acceptable salt or solid state form thereof.

In one embodiment, the induction phase is 4 weeks, and the patient achieves either a clinical remission within 4 weeks of initiating administration of upadacitinib, or a pharmaceutically acceptable salt or solid state form thereof, or an endoscopic remission within 4 weeks of initiating administration of upadacitinib, or a pharmaceutically acceptable salt or solid state form thereof, and further achieves any combination of additional therapeutic results selected from the group consisting of therapeutic results 3), 6), 8), 11), 14), 16), 19), 20), 23), 26), 29), and combinations thereof, wherein the therapeutic result is achieved within 4 weeks of initiating administration of upadacitinib, or a pharmaceutically acceptable salt or solid state form thereof.

In one embodiment, the patient achieves a clinical remission within 12 weeks, or within 16 weeks of initiating administration of upadacitinib, or a pharmaceutically acceptable salt or solid state form thereof, and/or achieves an endoscopic improvement within 12 weeks or within 16 weeks of initiating administration of upadacitinib, or a pharmaceutically acceptable salt or solid state form thereof, and further achieves any combination of additional therapeutic results selected from the group consisting of therapeutic results 1), 2), 3), 4), 5), 6), 7), 8), 9), 10), 11), 12), 13), 14), 15), 16), 17), 18), 19), 20), 21), 22), 23), 24), 25), 26), 27), 28), 29), and combinations thereof. In one such embodiment, the induction phase is 16 weeks.

In one embodiment, the induction phase is 12 weeks, and the patient achieves a clinical remission within 12 weeks of initiating administration of upadacitinib, or a pharmaceutically acceptable salt or solid state form thereof, and/or achieves an endoscopic improvement within 12 weeks of initiating administration of upadacitinib, or a pharmaceutically acceptable salt or solid state form thereof, and further achieves any combination of additional therapeutic results selected from the group consisting of therapeutic results 2), 3), 5), 6), 7), 8), 10), 11), 13), 14), 15), 16), 18), 19), 20), 22), 23), 25), 26), 28), 29), and combinations thereof, wherein the therapeutic result is achieved within 12 weeks of initiating administration of upadacitinib, or a pharmaceutically acceptable salt or solid state form thereof.

In one embodiment, the induction phase is 16 weeks, and the patient achieves a clinical remission within 16 weeks of initiating administration of upadacitinib, or a pharmaceutically acceptable salt or solid state form thereof, and/or achieves an endoscopic improvement within 16 weeks of initiating administration of upadacitinib, or a pharmaceutically acceptable salt or solid state form thereof, and further achieves any combination of additional therapeutic results selected from the group consisting of therapeutic results 1), 2), 3), 4), 5), 6), 7), 8), 9), 10), 11), 12), 13), 14), 15), 16), 17), 18), 19), 20), 21), 22), 23), 24), 25), 26), 27), 28), 29), and combinations thereof, wherein the therapeutic result is achieved within 16 weeks of initiating administration of upadacitinib, or a pharmaceutically acceptable salt or solid state form thereof.

In one embodiment, the induction phase is 4 weeks, and the patient achieves a clinical remission within 4 weeks of initiating administration of upadacitinib, or a pharmaceutically acceptable salt or solid state form thereof, and/or achieves an endoscopic improvement within 4 weeks of initiating administration of upadacitinib, or a pharmaceutically acceptable salt or solid state form thereof, and further achieves any combination of additional therapeutic results selected from the group consisting of therapeutic results 3), 6), 8), 11), 14), 16), 19), 20), 23), 26), 29), and combinations thereof, wherein the therapeutic result is achieved within 4 weeks of initiating administration of upadacitinib, or a pharmaceutically acceptable salt or solid state form thereof.

In one embodiment, the patient achieves a clinical remission within 4 weeks, 12 weeks, or within 16 weeks of initiating administration of upadacitinib, or a pharmaceutically acceptable salt or solid state form thereof, and/or achieves an endoscopic improvement within 4 weeks, 12 weeks or within 16 weeks of initiating administration of upadacitinib, or a pharmaceutically acceptable salt or solid state form thereof, and further achieves an additional therapeutic result selected from the group consisting of a CDAI of less than 150 within 16 weeks of initiating administration of upadacitinib, or a pharmaceutically acceptable salt or solid state form thereof; a CDAI of less than 150 within 12 weeks of initiating administration of upadacitinib, or a pharmaceutically acceptable salt or solid state form thereof; a CDAI of less than 150 within 4 weeks of initiating administration of upadacitinib, or a pharmaceutically acceptable salt or solid state form thereof; an endoscopic remission within 16 weeks of initiating administration of upadacitinib, or a pharmaceutically acceptable salt or solid state form thereof; an endoscopic remission within 12 weeks of initiating administration of upadacitinib, or a pharmaceutically acceptable salt or solid state form thereof; an endoscopic remission within 4 weeks of initiating administration of upadacitinib, or a pharmaceutically acceptable salt or solid state form thereof; a clinical response within 16 weeks of initiating administration of upadacitinib, or a pharmaceutically acceptable salt or solid state form thereof; a clinical response within 12 weeks of initiating administration of upadacitinib, or a pharmaceutically acceptable salt or solid state form thereof; a clinical response within 4 weeks of initiating administration of upadacitinib, or a pharmaceutically acceptable salt or solid state form thereof; a clinical response within 2 weeks of initiating administration of upadacitinib, or a pharmaceutically acceptable salt or solid state form thereof; and combinations thereof. In one such embodiment, the induction phase is 16 weeks, and the additional therapeutic result is selected from the group consisting of a CDAI of less than 150 within 16 weeks, or within 12 weeks, or within 4 weeks, or within 2 weeks of initiating administration of upadacitinib, or a pharmaceutically acceptable salt or solid state form thereof, an endoscopic remission within 16 weeks or within 12 weeks or within 4 weeks of initiating administration of upadacitinib, or a pharmaceutically acceptable salt or solid state form thereof; a clinical response within 16 weeks or within 12 weeks or within 4 weeks, or within 2 weeks of initiating administration of upadacitinib, or a pharmaceutically acceptable salt or solid state form thereof; and combinations thereof. In one such embodiment, the induction phase is 12 weeks, and the additional therapeutic result is selected from the group consisting of a CDAI of less than 150 within 12 weeks of initiating administration of upadacitinib, or a pharmaceutically acceptable salt or solid state form thereof; an endoscopic remission within 12 weeks of initiating administration of upadacitinib, or a pharmaceutically acceptable salt or solid state form thereof; a clinical response within 12 weeks of initiating administration of upadacitinib, or a pharmaceutically acceptable salt or solid state form thereof; and combinations thereof.

In one embodiment, the additional therapeutic result may further be a clinical remission within 16 weeks of initiating administration of upadacitinib, or a pharmaceutically acceptable salt or solid state form thereof, wherein the patient has an average daily liquid/very soft SF score of greater than or equal to 2.5 and an average daily AP score of greater than or equal to 2.0 at baseline. In one embodiment, when the patient is one who was taking corticosteroids at baseline but who discontinued corticosteroid use during treatment with the JAK1 inhibitor, the additional therapeutic result may be selected from the group consisting of a CDAI score of less than 150 within 16 weeks of initiating administration of upadacitinib, or a pharmaceutically acceptable salt or solid state form thereof; an endoscopic remission within 12 weeks or within 16 weeks of initiating administration of upadacitinib, or a pharmaceutically acceptable salt or solid state form thereof and a clinical remission within 16 weeks of initiating administration of upadacitinib, or a pharmaceutically acceptable salt or solid state form thereof; a clinical remission within 16 weeks of initiating administration of upadacitinib, or a pharmaceutically acceptable salt or solid state form thereof; and an endoscopic remission within 12 weeks or within 16 weeks of initiating administration of upadacitinib, or a pharmaceutically acceptable salt or solid state form thereof; and combinations thereof. In one embodiment, when the patient has isolated ileal Crohn's disease, the additional therapeutic result may further be remission within 16 weeks of initiating administration of upadacitinib, or a pharmaceutically acceptable salt or solid state form thereof. In one aspect, a patient achieves a CDAI score of less than 150 during or by the end of the induction phase.

In one aspect, the patient may achieve an additional therapeutic result selected from the group consisting of a clinical remission (i.e., average daily SF score ≤2.8 and not greater than baseline and average daily AP score ≤1.0 and not greater than baseline) within 16 weeks of initiating administration of upadacitinib, or a pharmaceutically acceptable salt or solid state form thereof; an endoscopic improvement (i.e., SES-CD score that is greater than a 50% decrease from baseline or at least a 2 point reduction in SES-CD score from baseline or endoscopic remission) within 4 weeks, within 6 weeks, within 12 weeks, or within 16 weeks of initiating administration of upadacitinib, or a pharmaceutically acceptable salt or solid state form thereof; and combinations thereof.

In one aspect, the patient may achieve an additional therapeutic result selected from the group consisting of a decrease in CDAI score from baseline of greater than or equal to 70, and a decrease in CDAI score from baseline of greater than or equal to 100. In one embodiment, the induction phase is 16 weeks and the decrease in CDAI occurs within 16 weeks or within 12 weeks of initiating administration of upadacitinib, or a pharmaceutically acceptable salt or solid state form thereof. In one embodiment, the induction phase is 12 weeks and the decrease in CDAI occurs within 12 weeks of initiating administration of upadacitinib, or a pharmaceutically acceptable salt or solid state form thereof.

In one particular embodiment, the induction phase is 16 weeks, and the patient achieves a clinical remission within 16 weeks of initiating administration of upadacitinib, or a pharmaceutically acceptable salt or solid state form thereof; an endoscopic improvement (i.e., SES-CD score that is greater than a 50% decrease from baseline or at least a 2 point reduction in SES-CD score from baseline, or endoscopic remission) within 4 weeks, within 6 weeks, within 12 weeks or within 16 weeks of initiating administration of upadacitinib, or a pharmaceutically acceptable salt or solid state form thereof; and combinations thereof. In another embodiment, the induction phase is 12 weeks, and the patient achieves a clinical remission within 12 weeks of initiating administration of upadacitinib, or a pharmaceutically acceptable salt or solid state form thereof; an endoscopic improvement within 12 weeks of initiating administration of upadacitinib, or a pharmaceutically acceptable salt or solid state form thereof; or combinations thereof.

In one embodiment, the patient is administered upadacitinib, or a pharmaceutically acceptable salt or solid state form thereof, for at least 52 weeks. The administration of upadacitinib, or a pharmaceutically acceptable salt or solid state form thereof, may include an induction phase (e.g., an induction phase of up to 16 weeks), and additional weeks (e.g., 36 weeks or longer) of a maintenance phase (discussed hereinafter). In other embodiments, the administration of upadacitinib, or a pharmaceutically acceptable salt or solid state form thereof, may include a shorter induction phase (e.g., up to 2 weeks, up to 4 weeks, 6 weeks, 8 weeks, 10 weeks, 12 weeks, etc.), and a longer maintenance phase (e.g., a 12 week induction phase and a 40 week or longer maintenance phase). In some such embodiments, the patient may achieve at least one therapeutic result selected from the group consisting of: remission within 52 weeks of initiating administration of upadacitinib, or a pharmaceutically acceptable salt or solid state form thereof; endoscopic remission within 52 weeks of initiating administration of upadacitinib, or a pharmaceutically acceptable salt or solid state form thereof; clinical remission within 52 weeks of initiating administration of upadacitinib, or a pharmaceutically acceptable salt or solid state form thereof; endoscopic improvement within 52 weeks of initiating administration of upadacitinib, or a pharmaceutically acceptable salt or solid state form thereof; response within 52 weeks of initiating administration of upadacitinib, or a pharmaceutically acceptable salt or solid state form thereof; endoscopic response within 52 weeks of initiating administration of upadacitinib, or a pharmaceutically acceptable salt or solid state form thereof pharm; clinical response within 52 weeks of initiating administration of upadacitinib, or a pharmaceutically acceptable salt or solid state form thereof; CDAI of less than 150 within 52 weeks of initiating administration of upadacitinib, or a pharmaceutically acceptable salt or solid state form thereof; a decrease in CDAI of greater than or equal to 70 points from baseline within 52 weeks of initiating administration of upadacitinib, or a pharmaceutically acceptable salt or solid state form thereof; a change from baseline in fecal calprotectin level within 52 weeks of initiating administration of upadacitinib, or a pharmaceutically acceptable salt or solid state form thereof; a change from baseline in hs-CRP within 52 weeks of initiating administration of upadacitinib, or a pharmaceutically acceptable salt or solid state form thereof; a change in IBDQ score from baseline within 52 weeks of initiating administration of upadacitinib, or a pharmaceutically acceptable salt or solid state form thereof; a change in extra-intestinal manifestations (EIMS) from baseline within 52 weeks of initiating administration of upadacitinib, or a pharmaceutically acceptable salt or solid state form thereof; and combinations thereof.

In some embodiment when the patient is administered upadacitinib, or a pharmaceutically acceptable salt or solid state form thereof, for at least 52 weeks, when the patient is one who was taking corticosteroids at baseline but who discontinued corticosteroid use during treatment with the JAK1 inhibitor, the additional therapeutic result may be selected from the group consisting of a CDAI of less than 150 within 52 weeks of initiating administration of upadacitinib, or a pharmaceutically acceptable salt or solid state form thereof; a remission within 52 weeks of initiating administration of upadacitinib, or a pharmaceutically acceptable salt or solid state form thereof; a clinical remission within 52 weeks of initiating administration of upadacitinib, or a pharmaceutically acceptable salt or solid state form thereof; and an endoscopic remission within 52 weeks of initiating administration of upadacitinib, or a pharmaceutically acceptable salt or solid state form thereof; and combinations thereof. In one embodiment, when the patient has isolated ileal Crohn's disease, the additional therapeutic result may further be remission within 52 weeks of initiating administration of upadacitinib, or a pharmaceutically acceptable salt or solid state form thereof.

In one embodiment, in a method of the present disclosure, a patient is evaluated during or at the end of the induction phase for a therapeutic result selected from the group consisting of clinical remission, endoscopic improvement, endoscopic remission, endoscopic response, clinical response, CDAI, average daily liquid/very soft SF score, average daily AP score, fecal calprotectin level, hs-CRP, IBDQ score, and combinations thereof. In one embodiment, in a method of the present disclosure, a patient is evaluated for clinical remission during or at the end of the induction phase. In one embodiment, in a method of the present disclosure, a patient is evaluated for endoscopic improvement during or at the end of the induction phase. In one embodiment, in a method of the present disclosure, a patient is evaluated for endoscopic remission during or at the end of the induction phase.

In one embodiment, the patient is administered at least 14 doses, at least 28 doses, at least 42 doses, at least 70 doses, or at least 84 doses, or at least 112 doses, or at least 140 doses, or at least 168 doses, or at least 224 doses, or 70 doses, or 84 doses, or 112 doses, or 140 doses, or 168 doses, or 224 doses of upadacitinib, or a pharmaceutically acceptable salt or solid state form thereof, during the induction phase.

In one aspect, a certain therapeutic result is maintained by the patient during the maintenance phase. The maintenance phase may last for an indefinite period of time. In one embodiment, the maintenance phase is at least 36 weeks, including at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment, the maintenance phase is at least 40 additional weeks. In one embodiment, the therapeutic result maintained by the patient during the maintenance phase is selected from the group consisting of clinical remission, endoscopic remission, and combinations thereof. In one embodiment, the therapeutic result maintained by the patient during the maintenance phase is selected from the group consisting of clinical response, endoscopic improvement, and combinations thereof. In one aspect, a patient maintains a CDAI score of less than 150 during the maintenance phase. In one aspect, a patient maintains a SES-CD that is greater than a 50% decrease versus the patient's baseline SES-CD. In one embodiment, the patient maintains a SES-CD that is at least a 2 point reduction versus the patient's baseline SES-CD. In one embodiment, the therapeutic result maintained by the patient during the maintenance phase is clinical response. In one embodiment, the therapeutic result maintained by the patient during the maintenance phase is endoscopic remission.

In one embodiment, in a method of the present disclosure, a patient is evaluated for clinical remission during the maintenance phase. In one embodiment, a patient is evaluated for endoscopic improvement during the maintenance phase. In one embodiment, in a method of the present disclosure, a patient is evaluated for endoscopic remission during the maintenance phase.

In one embodiment, the present disclosure provides a method for treating an inflammatory disease, in one aspect for treating Crohn's Disease, comprising (a) administering to a patient a dose of a JAK1 inhibitor (e.g., upadacitinib or a pharmaceutically acceptable salt or solid state form thereof) at week 0 and once daily (QD) thereafter for 16 weeks, wherein the dose is 45 mg QD. In one embodiment, the method further comprises (b) administering to the patient additional doses once daily thereafter for at least 36 additional weeks, wherein the dose is 15 mg or 30 mg QD. In one embodiment the dose is administered orally.

In one embodiment, at week 12 (i.e., 12 weeks after initiating administration of upadacitinib, or a pharmaceutically acceptable salt or solid state form thereof), a patient is evaluated for clinical remission (average daily liquid/very soft SF score ≤2.8 and not worse than baseline and average daily AP score ≤1.0 and not worse than baseline) and/or for endoscopic remission (SES-CD≤4 (or SES-CD≤2 for patients with isolated ileal CD) and at least a two point reduction in SES-CD versus BL and no subscore >1 in any individual variable used to calculate SES-CD). In one embodiment, at week 16 (i.e., 16 weeks after initiating administration of upadacitinib, or a pharmaceutically acceptable salt or solid state form thereof), a patient is evaluated for clinical remission and/or for endoscopic remission.

In one embodiment, at week 4 (i.e., 4 weeks after initiating administration of upadacitinib, or a pharmaceutically acceptable salt or solid state form thereof), a patient is evaluated for clinical remission (average daily liquid/very soft SF score ≤2.8 and not worse than baseline and average daily AP score ≤1.0 and not worse than baseline) and/or for endoscopic remission (SES-CD≤4 (or SES-CD≤2 for patients with isolated ileal CD) and at least a two point reduction in SES-CD versus BL and no subscore >1 in any individual variable used to calculate SES-CD).

In one embodiment, at week 16 (i.e., 16 weeks after initiating administration of upadacitinib, or a pharmaceutically acceptable salt or solid state form thereof), a patient is evaluated for remission, for example defined as reaching clinical remission (average daily liquid/very soft SF score ≤2.8 and not worse than baseline and average daily AP score ≤1.0 and not worse than baseline) and endoscopic remission (SES-CD≤4 (or SES-CD≤2 for patients with isolated ileal CD) and at least a two point reduction in SES-CD versus BL and no subscore >1 in any individual variable used to calculate SES-CD).

In one embodiment, at week 12 (i.e., 12 weeks after initiating administration of upadacitinib, or a pharmaceutically acceptable salt or solid state form thereof), a patient is evaluated for clinical remission and/or for endoscopic improvement. In one embodiment, at week 16 (i.e., 16 weeks after initiating administration of upadacitinib, or a pharmaceutically acceptable salt or solid state form thereof), a patient is evaluated for clinical remission and/or for endoscopic improvement.

In one embodiment, at week 4 (i.e., 4 weeks after initiating administration of upadacitinib, or a pharmaceutically acceptable salt or solid state form thereof), a patient is evaluated for clinical remission and/or for endoscopic improvement. In one embodiment, at week 2 (i.e., 2 weeks after initiating administration of upadacitinib, or a pharmaceutically acceptable salt or solid state form thereof), a patient is evaluated for clinical remission and/or for endoscopic improvement.

In one embodiment, the present disclosure provides a method for treating Crohn's disease, comprising (a) administering to a patient a dose of a JAK1 inhibitor (e.g., upadacitinib or a pharmaceutically acceptable salt or solid state form thereof) at week 0 and once daily thereafter via an oral route, wherein the doses of the JAK1 inhibitor comprise 15 mg, 30 mg, or 45 mg QD, or any combination thereof.

In one embodiment, the present disclosure provides a method for treating Crohn's disease, comprising administering to a patient 15 mg to 45 mg of a JAK1 inhibitor. In one embodiment, the present disclosure provides a method for treating Crohn's disease, comprising administering to a patient orally 15 mg of a JAK1 inhibitor QD. In one embodiment, the present disclosure provides a method for treating Crohn's disease, comprising administering to a patient orally 30 mg of a JAK1 inhibitor QD. In one embodiment, the present disclosure provides a method for treating Crohn's disease, comprising administering to a patient orally 45 mg of a JAK1 inhibitor QD. In any such embodiments, the JAK1 inhibitor may be upadacitinib or a pharmaceutically acceptable salt or solid state form thereof. In any such embodiment, the JAK1 inhibitor may be in a once daily modified release formulation. In any such embodiment, the patient may have moderately to severely active Crohn's disease prior to treatment.

In one embodiment, the administration of a JAK1 inhibitor according to the present disclosure is further described in the Examples herein below or in FIG. 1.

In one embodiment, the present disclosure provides a method for treating Crohn's disease, said method comprising a) administering at least one induction dose of a JAK1 inhibitor (e.g., upadacitinib or a pharmaceutically acceptable salt or solid state form thereof) to a patient, wherein said induction dose comprises 45 mg of the JAK 1 inhibitor. In one aspect, the induction dose is administered orally. In one aspect, the induction dose is administered QD. In one aspect, the induction dose is administered for 12 weeks. In one aspect the induction dose is administered for 16 weeks. In one embodiment, the induction dose is administered for up to 16 weeks, including for 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks.

In one embodiment, the induction dose comprises 45 mg of the JAK1 inhibitor administered QD.

In one embodiment, the JAK1 inhibitor is upadacitinib or a pharmaceutically acceptable salt or solid state form thereof.

In one embodiment, the induction dose is in a once daily modified release formulation.

In one embodiment, the method further comprises b) administering a first maintenance dose of a JAK1 inhibitor (e.g., upadacitinib, or pharmaceutically acceptable salt or solid state form thereof), to the patient after the last induction dose is administered; and c) administering at least one additional maintenance dose to the patient once daily thereafter.

In one embodiment, the first maintenance dose comprises 15 mg to 30 mg of the JAK1 inhibitor. In one aspect, the first maintenance dose comprises 15 mg or 30 mg of the JAK1 inhibitor. In one aspect, the first maintenance dose is smaller than the induction dose. In one aspect, the first maintenance dose is administered QD. In one aspect the first maintenance dose is 15 mg. In one aspect the first maintenance dose is 30 mg. In one aspect, the first maintenance dose is administered orally. In one aspect, the first maintenance dose is in a once daily modified release formulation.

In one aspect, the at least one additional maintenance dose comprises 15 mg to 30 mg of the JAK 1 inhibitor. In one aspect, the at least one additional maintenance dose comprises 15 mg or 30 mg. In one aspect, the at least one additional maintenance dose is administered orally. In one aspect, the at least one additional maintenance dose is administered QD. In one embodiment, the at least one additional maintenance dose comprises 15 mg of the JAK1 inhibitor administered QD. In one embodiment, the at least one additional maintenance dose comprises 30 mg of the JAK1 inhibitor administered QD. In one aspect, the at least one additional maintenance dose is in a once daily modified release formulation.

In any of the foregoing embodiments, the JAK1 inhibitor may be upadacitinib or a pharmaceutically acceptable salt or solid state form thereof.

In one aspect, in any of the foregoing embodiments, the patient maintains a CDAI score of less than 150.

In one aspect, in any of the foregoing embodiments, the patient is one who had an inadequate response to or experienced intolerance to conventional treatment (e.g., aminosalicylates, corticosteroids, immunosuppressants) or to a previous treatment with a biologic agent. In one aspect, in any of the foregoing embodiments, the patient is one who had an inadequate response to or experienced intolerance to a previous treatment with an anti-TNF agent. In one aspect, in any of the foregoing embodiments, the patient is a refractory patient.

In one aspect, in any of the foregoing embodiments, the patient is one who is naïve to previous treatment with aminosalicylates, a corticosteroid, an immunosuppressant, a biologic agent or an anti-TNF agent.

In one aspect, in any of the foregoing embodiments, the patient is one who had moderately to severely active Crohn's disease prior to treatment or administration of the induction dose.

In one embodiment, the present disclosure further provides a method for inducing clinical remission of Crohn's Disease in a patient, said method comprising a) administering to the patient at least one induction dose of a JAK1 inhibitor as described above or herein (e.g., upadacitinib or a pharmaceutically acceptable salt or solid state form thereof). In one embodiment, the induction dose comprises 45 mg of upadacitinib, or a pharmaceutically acceptable salt or solid state form thereof. In one embodiment, an induction dose is administered at week 0 and once daily (QD) thereafter for up to 16 weeks (e.g., for 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks), wherein the dose is 45 mg QD. In one embodiment, the method further comprises maintaining clinical remission of Crohn's disease, said method further comprising b) administering a first maintenance dose of said JAK1 inhibitor to the patient after the last induction dose is administered and c) administering at least one additional maintenance dose to the patient as described above or herein. In one embodiment, the at least one additional maintenance dose is administered once daily. In one embodiment, the additional maintenance doses are administered once daily for at least 36 additional weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment, the additional maintenance doses are administered once daily for at least 40 additional weeks. In one embodiment, the maintenance dose is 15 mg or 30 mg QD. In one embodiment the induction and maintenance doses are administered orally. In one embodiment, the patient has a CDAI score of 220 to 450 before administration of the first induction dose. In one embodiment, the patient has moderately to severely active Crohn's disease prior to administration of the first induction dose. In one embodiment, the patient has had an inadequate response to or experienced intolerance to conventional treatment (e.g., aminosalicylates, corticosteroids, immunosuppressants) or to a previous treatment with a biologic agent and/or an anti-TNF agent. In one embodiment, the patient is naïve to previous treatment with a corticosteroid, an immunosuppressant, a biologic agent, and/or an anti-TNF agent. In one embodiment, the clinical remission is achieved within 16 weeks of initiating administration of upadacitinib, or a pharmaceutically acceptable salt or solid state form thereof. In one embodiment, the clinical remission is achieved within 12 weeks of initiating administration of upadacitinib, or a pharmaceutically acceptable salt or solid state form thereof.

In one embodiment, the clinical remission is achieved within 4 weeks of initiating administration of upadacitinib, or a pharmaceutically acceptable salt or solid state form thereof. In one embodiment, the patient achieves a CDAI score of less than 150 before administration of the first maintenance dose. In one embodiment, the induction and maintenance doses are in once-daily, modified release formulations.

In one embodiment, the present disclosure provides a method for inducing endoscopic remission of Crohn's disease, the method comprising (a) administering to a patient at least one induction dose of a JAK1 inhibitor (e.g., upadacitinib or a pharmaceutically acceptable salt or solid state form thereof), wherein the induction dose comprises 45 mg of upadacitinib, or a pharmaceutically acceptable salt or solid state form thereof. In one embodiment, an induction dose is administered at week 0 and once daily (QD) thereafter for up to 16 weeks (e.g., for 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks), wherein the dose is 45 mg QD. In one embodiment, the method further comprises maintaining endoscopic remission of Crohn's disease, said method further comprising (b) administering to the patient a first maintenance dose of upadacitinib, or a pharmaceutically acceptable salt or solid state form thereof, after the last induction dose is administered, and (c) administering at least one additional maintenance dose once daily thereafter. In one embodiment, the additional maintenance doses are administered once daily for at least 36 additional weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment, the additional maintenance doses are administered once daily for at least 40 additional weeks. In one embodiment, the maintenance dose is 15 mg or 30 mg QD. In one embodiment the induction and maintenance doses are administered orally. In one embodiment, the patient has a CDAI score of 220 to 450 before administration of the first induction dose. In one embodiment, the patient has moderately to severely active Crohn's disease prior to administration of the first induction dose. In one embodiment, the patient has had an inadequate response to or experienced intolerance to conventional treatment (e.g., aminosalicylates, corticosteroids, immunosuppressants) or to a previous treatment with a biologic and/or an anti-TNF agent. In one embodiment, the patient is naïve to previous treatment with a corticosteroid, an immunosuppressant, an anti-TNF agent and/or a biologic agent. In one embodiment, the endoscopic remission is achieved within 12 weeks or within 16 weeks of initiating administration of upadacitinib, or a pharmaceutically acceptable salt or solid state form thereof. In one embodiment, the endoscopic remission is achieved within 4 weeks of initiating administration of upadacitinib, or a pharmaceutically acceptable salt or solid state form thereof. In one embodiment, the patient achieves a CDAI score of less than 150 before administration of the first maintenance dose. In one embodiment, the induction and maintenance doses are in once-daily, modified release formulations.

In one embodiment, the present disclosure further provides a method for inducing endoscopic improvement of Crohn's Disease in a patient, said method comprising a) administering to the patient at least one induction dose of a JAK1 inhibitor as described above or herein (e.g., upadacitinib or a pharmaceutically acceptable salt or solid state form thereof). In one embodiment, the induction dose comprises 45 mg of upadacitinib, or a pharmaceutically acceptable salt or solid state form thereof. In one embodiment, an induction dose is administered at week 0 and once daily (QD) thereafter for up to 16 weeks (e.g., for 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks), wherein the dose is 45 mg QD. In one embodiment, the method further comprises maintaining endoscopic improvement of Crohn's disease, said method further comprising b) administering a first maintenance dose of said JAK1 inhibitor to the patient after the last induction dose is administered and c) administering at least one additional maintenance dose to the patient as described above or herein. In one embodiment, the at least one additional maintenance dose is administered once daily. In one embodiment, the additional maintenance doses are administered once daily for at least 36 additional weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment, the additional maintenance doses are administered once daily for at least 40 additional weeks. In one embodiment, the maintenance dose is 15 mg or 30 mg QD. In one embodiment the induction and maintenance doses are administered orally. In one embodiment, the patient has a CDAI score of 220 to 450 before administration of the first induction dose. In one embodiment, the patient has moderately to severely active Crohn's disease prior to administration of the first induction dose. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with a corticosteroid, an immunosuppressant, a biologic agent and/or an anti-TNF agent. In one embodiment, the endoscopic improvement is achieved within 16 weeks of initiating administration of upadacitinib, or a pharmaceutically acceptable salt or solid state form thereof. In one embodiment, the endoscopic improvement is achieved within 12 weeks of initiating administration of upadacitinib, or a pharmaceutically acceptable salt or solid state form thereof. In one embodiment, the endoscopic improvement is achieved within 4 weeks of initiating administration of upadacitinib, or a pharmaceutically acceptable salt or solid state form thereof. In one embodiment, the patient achieves a CDAI score of less than 150 before administration of the first maintenance dose. In one embodiment, the induction and maintenance doses are in once-daily, modified release formulations.

In one embodiment, the present disclosure further provides a method of maintaining clinical remission of Crohn's Disease in a patient, said method comprising administering 15 mg or 30 mg of upadacitinib or a pharmaceutically acceptable salt form thereof to the patient. In one embodiment, the upadacitinib or a pharmaceutically acceptable salt form thereof is administered once daily for at least 36 weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment the upadacitinib or a pharmaceutically acceptable salt form thereof is administered orally. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with a corticosteroid, an immunosuppressant, a biologic agent and/or an anti-TNF agent. In one embodiment, the patient is a refractory patient. In one embodiment, the upadacitinib or a pharmaceutically acceptable salt form thereof is a once-daily, modified release formulation.

In one embodiment, the present disclosure further provides a method of maintaining endoscopic improvement of Crohn's Disease in a patient, said method comprising administering 15 mg or 30 mg of upadacitinib or a pharmaceutically acceptable salt form thereof to the patient. In one embodiment, the upadacitinib or a pharmaceutically acceptable salt form thereof is administered once daily for at least 36 weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment the upadacitinib or a pharmaceutically acceptable salt form thereof is administered orally. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with a corticosteroid, an immunosuppressant, a biologic agent and/or an anti-TNF agent. In one embodiment, the patient is a refractory patient. In one embodiment, the upadacitinib or a pharmaceutically acceptable salt form thereof is a once-daily, modified release formulation.

In one embodiment, the present disclosure further provides a method of maintaining endoscopic remission of Crohn's Disease in a patient, said method comprising administering 15 mg or 30 mg of upadacitinib or a pharmaceutically acceptable salt form thereof to the patient. In one embodiment, the upadacitinib or a pharmaceutically acceptable salt form thereof is administered once daily for at least 36 weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment the upadacitinib or a pharmaceutically acceptable salt form thereof is administered orally. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with a corticosteroid, an immunosuppressant, a biologic agent and/or an anti-TNF agent. In one embodiment, the patient is a refractory patient. In one embodiment, the upadacitinib or a pharmaceutically acceptable salt form thereof is a once-daily, modified release formulation.

In one embodiment, the present disclosure further provides a method of maintaining remission of Crohn's Disease in a patient, said method comprising administering 15 mg or 30 mg of upadacitinib or a pharmaceutically acceptable salt form thereof to the patient. In one embodiment, the upadacitinib or a pharmaceutically acceptable salt form thereof is administered once daily for at least 36 weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment the upadacitinib or a pharmaceutically acceptable salt form thereof is administered orally. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with a corticosteroid, an immunosuppressant, a biologic agent and/or an anti-TNF agent. In one embodiment, the patient is a refractory patient. In one embodiment, the upadacitinib or a pharmaceutically acceptable salt form thereof is in a once-daily, modified release formulation.

In one aspect, induction doses for the methods disclosed herein are administered for 12 weeks in a dose regimen described in Table 3. In one aspect, induction doses are administered for 16 weeks in a dose regimen described in Table 3. In one aspect, maintenance doses are administered for 36 weeks or more in a dose regimen described in Table 3. In one aspect, induction doses for the methods disclosed herein are administered for 16 weeks and the maintenance doses are administered for 36 weeks in a dosing regimen as described in Table 3.

TABLE 3

Doses and Dosing Regimens (BID)

| Induction Dose (mg) | Frequency of induction doses | Maintenance dose (mg) | Frequency of maintenance dose |
|---|---|---|---|
| 3 | BID | 3 | BID |
| 6 | BID | 3 | BID |
| 6 | BID | 6 | BID |
| 12 | BID | 3 | BID |
| 12 | BID | 6 | BID |
| 12 | BID | 12 | BID |
| 24 | BID | 3 | BID |
| 24 | BID | 6 | BID |
| 24 | BID | 12 | BID |
| 24 | QD[1] | 3 | BID |
| 24 | QD[1] | 6 | BID |
| 24 | QD[1] | 12 | BID |

[1]The 24 mg QD dose is two 12 mg tablets administered simultaneously.

In one aspect, the induction doses for the methods disclosed herein are administered for 2 weeks in a dose regimen described in Table 4. In one aspect, the induction doses for the methods disclosed herein are administered for 4 weeks in a dose regimen described in Table 4. In one aspect, induction doses for the methods disclosed herein are administered for 12 weeks in a dose regimen described in Table 4. In one aspect, induction doses are administered for 16 weeks in a dose regimen described in Table 4. In one aspect, maintenance doses are administered for 36 weeks or more in a dose regimen described in Table 4. In one aspect, induction doses for the methods disclosed herein are administered for 2 weeks and the maintenance doses are administered for 36 or 40 weeks in a dosing regimen as described in Table 4. In one aspect, induction doses for the methods disclosed herein are administered for 4 weeks and the maintenance doses are administered for 36 or 40 weeks in a dosing regimen as described in Table 4. In one aspect, induction doses for the methods disclosed herein are administered for 12 weeks and the maintenance doses are administered for 36 or 40 weeks in a dosing regimen as described in Table 4. In one aspect, induction doses for the methods disclosed herein are administered for 16 weeks and the maintenance doses are administered for 36 or 40 weeks in a dosing regimen as described in Table 4.

TABLE 4

Doses and Dose Regimens (QD)

| Induction Dose (mg) | Frequency of induction doses | Maintenance dose (mg) | Frequency of maintenance dose |
|---|---|---|---|
| 45 | QD | 15 | QD |
| 45 | QD | 30 | QD |

In one particular embodiment, the induction dose is 45 mg of upadacitinib or a pharmaceutically acceptable salt or solid state form thereof administered QD, and the maintenance dose, and any additional maintenance dose administered thereafter, is 30 mg of upadacitinib or a pharmaceutically acceptable salt or solid state form thereof administered QD. In another embodiment, the induction dose is 45 mg of upadacitinib or a pharmaceutically acceptable salt or solid state form thereof administered QD, and the maintenance dose, and any additional maintenance dose administered thereafter, is 15 mg of upadacitinib or a pharmaceutically acceptable salt or solid state form thereof administered QD. In one embodiment, the maintenance and induction doses are in once-daily, modified release formulations.

In one embodiment, the present disclosure further provides a method of inducing clinical remission of Crohn's disease in an adult patient having moderately to severely active Crohn's disease, the method comprising orally administering once daily to the patient a 45 mg dose of upadacitinib, wherein the patient achieves clinical remission per Crohn's Disease Activity Index (CDAI) at 12 weeks after the first daily administration.

In one embodiment, the patient has had an inadequate response or intolerance to biologic therapy prior to the first daily administration. In one embodiment, the biologic therapy comprises an anti-TNF agent. In one embodiment, the biologic therapy comprises an anti-integrin or an anti-IL12/23. In one embodiment, the biologic therapy comprises vedolizumab, natalizumab, or ustekinumab.

In one embodiment, the present disclosure further provides a method of inducing clinical remission of Crohn's disease in an adult patient having moderately to severely active Crohn's disease, the method comprising orally administering once daily to the patient a 45 mg dose of upadacitinib, wherein the patient achieves clinical remission patient reported outcomes (PROs) at 12 weeks after the first daily administration.

In one embodiment, the patient has had an inadequate response or intolerance to biologic therapy prior to the first daily administration. In one embodiment, the biologic therapy comprises an anti-TNF agent. In one embodiment, the biologic therapy comprises an anti-integrin or an anti-IL12/23. In one embodiment, the biologic therapy comprises vedolizumab, natalizumab, or ustekinumab.

In one embodiment, the present disclosure further provides a method of inducing clinical remission of Crohn's disease in an adult patient having moderately to severely active Crohn's disease, the method comprising orally administering once daily to the patient a 45 mg dose of upadacitinib, wherein the patient achieves clinical remission per patient reported outcomes (PROs) at 4 weeks after the first daily administration.

In one embodiment, the patient has had an inadequate response or intolerance to biologic therapy prior to the first daily administration. In one embodiment, the biologic therapy comprises an anti-TNF agent. In one embodiment, the biologic therapy comprises an anti-integrin or an anti-IL12/23. In one embodiment, the biologic therapy comprises vedolizumab, natalizumab, or ustekinumab.

In one embodiment, the present disclosure further provides a method of inducing endoscopic response of Crohn's disease in an adult patient having moderately to severely active Crohn's disease, the method comprising orally administering once daily to the patient a 45 mg dose of upadacitinib, wherein the patient achieves endoscopic response at 12 weeks after the first daily administration.

In one embodiment, the patient has had an inadequate response or intolerance to biologic therapy prior to the first daily administration. In one embodiment, the biologic therapy comprises an anti-TNF agent. In one embodiment, the biologic therapy comprises an anti-integrin or an anti-IL12/23. In one embodiment, the biologic therapy comprises vedolizumab, natalizumab, or ustekinumab.

In one embodiment, the present disclosure further provides a method of inducing endoscopic remission of Crohn's disease in an adult patient having moderately to severely active Crohn's disease, the method comprising orally administering once daily to the patient a 45 mg dose of upadacitinib, wherein the patient achieves endoscopic remission at 12 weeks after the first daily administration.

In one embodiment, the patient has had an inadequate response or intolerance to biologic therapy prior to the first daily administration. In one embodiment, the biologic therapy comprises an anti-TNF agent. In one embodiment, the biologic therapy comprises an anti-integrin or an anti-IL12/23. In one embodiment, the biologic therapy comprises vedolizumab, natalizumab, or ustekinumab.

IV. METHODS OF TREATMENT OF ULCERATIVE COLITIS

In one aspect, the present disclosure is directed to methods for the treatment of ulcerative colitis. In one aspect, the present disclosure provides methods for treating ulcerative colitis, in particular methods comprising administering a JAK1 inhibitor to a patient in certain amounts and/or at certain intervals. In one aspect, the JAK1 inhibitor is upadacitinib or a pharmaceutically acceptable salt or solid state form thereof.

In one aspect, the present disclosure provides a JAK1 inhibitor for use in the treatment of ulcerative colitis, by administration in certain amounts and/or at certain intervals as described herein. In one aspect, the JAK1 inhibitor is upadacitinib or a pharmaceutically acceptable salt or solid state form thereof.

In one aspect, the present disclosure provides for the use of a JAK1 inhibitor for the preparation of a medicament for the treatment of ulcerative colitis, by administration in certain amounts and/or at certain intervals as described herein. In one aspect, the JAK1 inhibitor is upadacitinib or a pharmaceutically acceptable salt or solid state form thereof.

In one aspect, the present disclosure is directed to methods for inducing clinical remission and/or endoscopic remission of ulcerative colitis. In one aspect, the present disclosure provides methods for inducing clinical remission and/or endoscopic remission of ulcerative colitis, in particular methods comprising administering a JAK1 inhibitor to a patient in certain amounts and/or at certain intervals as described herein. In one aspect, the present disclosure is further directed to methods for inducing clinical remission wherein the patient has a SF score ≤1, RBS of 0 and endoscopy score ≤1 at week 48 following administration of the JAK1 inhibitor. In one aspect the patient achieves clinical remission per Full Mayo score ≤2 with no subscore >1) plus fecal calprotectin below 150 mg/kg at Week 8 following administration of the JAK1 inhibitor. In one aspect the patient has an increase of IBDQ≥16 from baseline at week 8 following administration of the JAK1 inhibitor. In one aspect, the patient has a RBS≥1 or an absolute RBS≤1 at week 8 following administration of the JAK1 inhibitor. In one aspect, the patient has a SF subscore ≤1 at week 8 following administration of the JAK1 inhibitor. In one aspect, the patient achieves a RBS of 0 at week 8. In one aspect the patient achieves a fecal calprotectin below 150 mg/kg at week 8 following administration of the JAK1 inhibitor. In one aspect the patient achieves histologic improvement at week 8 following administration of the JAK1 inhibitor. In one aspect, the JAK1 inhibitor is upadacitinib or a pharmaceutically acceptable salt or solid state form thereof.

In one aspect, the present disclosure provides a JAK1 inhibitor for use in inducing clinical remission of ulcerative colitis by administration in certain amounts and/or at certain intervals as described herein. In one aspect, the present disclosure provides a JAK1 inhibitor for use in inducing clinical remission and/or clinical response and/or endoscopic improvement and/or endoscopic remission of ulcerative colitis by administration in certain amounts and/or at certain intervals as described herein. In one aspect, the JAK1 inhibitor is upadacitinib or a pharmaceutically acceptable salt or solid state form thereof.

In one aspect, the present disclosure provides for the use of a JAK1 inhibitor for the preparation of a medicament for inducing clinical remission of ulcerative colitis by administration in certain amounts and/or at certain intervals as described herein. In one aspect, the present disclosure provides for the use of a JAK1 inhibitor for the preparation of a medicament for inducing clinical remission and/or clinical response and/or endoscopic improvement and/or endoscopic remission of ulcerative colitis by administration in certain amounts and/or at certain intervals as described herein. In one aspect, the JAK1 inhibitor is upadacitinib or a pharmaceutically acceptable salt or solid state form thereof.

In one particular aspect, the disease is moderately to severely active ulcerative colitis. In one aspect, in the context of the present disclosure, a patient is naïve to, or was previously treated with immunosuppressants (e.g., methotrexate), aminosalicylate, corticosteroid, and/or a biologic agent (e.g., vedolizumab, ustekinumab, natalizumab, etc.). In one aspect, the patient is naïve to, or was previously treated with an anti-TNF therapy (e.g., infliximab, adalimumab, certolizumab pegol, golimumab, etc.). In one aspect, in the context of a method of the present disclosure a patient was previously treated with one, two, three or more TNF antagonist(s) (also referred to herein as anti-TNF agents). In one embodiment, the patient is a patient who had an inadequate response with, lost response, or was intolerant to a TNF antagonist. In one aspect, in the context of a method of the present disclosure a patient was previously treated with one, two, three or more biologic agent(s). In one embodiment, the patient is a patient who had an inadequate response with, lost response, or was intolerant to a biologic agent. In one embodiment, the patient is a patient who had an inadequate response with, lost response, or was intolerant to a TNF antagonist, aminosalicylates, corticosteroids, immunosuppressants, and/or a biologic agent. In one embodiment, the patient is a refractory patient who has moderately to severely active ulcerative colitis. In one embodiment, the patient is either naïve to or has stopped using corticosteroids prior to treatment with the JAK1 inhibitor.

Disease severity for ulcerative colitis may be measured using a variety of indexes, including the Mayo Scoring System for Assessment of Ulcerative Colitis Activity ("Full Mayo"), the Adapted Mayo Score (consisting of the stool frequency subscore, rectal bleeding subscore and endoscopy subscore of the Full Mayo), the Ulcerative Colitis Endoscopic Index of Severity (UCEIS) score system, the Inflammatory Bowel Disease Questionnaire (IBDQ), the Work Productivity and Activity Impairment Questionnaire for Ulcerative Colitis (version 2.0) (WPAI:UC), the European Quality of Life 5 Dimensions 5 Levels (EQ-5D-5L), the Short Form 36 Item (SF-36) Health Survey (version 2), the Functional Assessment of Chronic Illness Therapy-Fatigue (FACIT-F), Ulcerative Colitis Symptoms Questionnaire (UC-SQ), and the Patient Global Impression of Change (PGIC).

The Mayo Scoring System for Assessment of Ulcerative Colitis Activity, shown below, is a composite of the following subscores: Stool Frequency Subscore, Rectal Bleeding Subscore (RBS), Endoscopy Subscore, and Physician's Global Assessment Subscore.

TABLE 5

Mayo Scoring System for Assessment of Ulcerative Colitis Activity (Full Mayo)

Stool frequency Subscore*
0 = Normal number of stools for this subject
1 = 1 - 2 stools more than normal
2 = 3 - 4 stools more than normal
3 = 5 or more stools more than normal

*Each patient serves as his or her own control to establish normal stool frequency and the degree of abnormal stool frequency.

Rectal bleeding Subscore**
0 = No blood seen
1 = Streaks of blood with stool less than half the time
2 = Obvious blood with stool most of the time
3 = Blood alone passed

**The daily bleeding score represents the most severe bleeding of the day.

Endoscopy Subscore: Findings of flexible sigmoidoscopy
0 = Normal or inactive disease
1 = Mild disease (erythema, decreased vascular pattern, mild friability)
2 = Moderate disease (marked erythema, absent vascular pattern, friability, erosions)
3 = Severe disease (spontaneous bleeding, ulceration)

Physician's Global Assessment Subscore***
0 = Normal (Subscores are 0)
1 = Mild disease (Subscores are mostly 1's)
2 = Moderate disease (Subscores are 1 to 2)
3 = Severe disease (Subscores are 2 to 3)

***The physician's global assessment acknowledges the three other subscores, the subject's daily record of abdominal discomfort and functional assessment, and other observations such as physical findings, and the subject's performance status.

The IBDQ is a well-known 32 item validated questionnaire that assesses a patient's inflammatory bowel disease symptoms, general well-being, and mood, and may be used as a tool to evaluate a patient's quality of life (Guyatt, et al., Gastroenterology, 1989, 96:804-810). The IBDQ questions and answer options are set forth below in Table 6.

TABLE 6

| | IBDQ |
|---|---|
| Question | Answer Options |
| 1. How frequent have your bowel movements been during the last two weeks? | 1 Bowel movements as or more frequent than they have ever been<br>2 Extremely Frequent<br>3 Very frequent<br>4 Moderate increase in frequency of bowel movements<br>5 Some increase in frequency of bowel movements<br>6 Slight increase in frequency of bowel movements<br>7 Normal, no increase in frequency of bowel movements |
| 2. How often has the feeling of fatigue or of being tired and worn out been a problem for you during the last 2 weeks? | 1 All of the time<br>2 Most of the time<br>3 A good bit of the time<br>4 Some of the time<br>5 A little of the time<br>6 Hardly any of the time<br>7 None of the time |
| 3. How often during the last 2 weeks have you felt frustrated, impatient, or restless? | 1 All of the time<br>2 Most of the time<br>3 A good bit of the time<br>4 Some of the time<br>5 A little of the time<br>6 Hardly any of the time<br>7 None of the time |
| 4. How often during the last 2 weeks have you been unable to attend school or do your work because of your bowel problem? | 1 All of the time<br>2 Most of the time<br>3 A good bit of the time<br>4 Some of the time<br>5 A little of the time<br>6 Hardly any of the time<br>7 None of the time |
| 5. How much of the time during the last 2 weeks have your bowel movements been loose? | 1 All of the time<br>2 Most of the time<br>3 A good bit of the time<br>4 Some of the time<br>5 A little of the time<br>6 Hardly any of the time<br>7 None of the time |
| 6. How much energy have you had during the last 2 weeks? | 1 No energy at all<br>2 Very little energy<br>3 A little energy<br>4 Some energy<br>5 A moderate amount of energy<br>6 A lot of energy<br>7 Full of energy |
| 7. How often during the last 2 weeks did you feel worried about the possibility of needing to have surgery because of your bowel problem? | 1 All of the time<br>2 Most of the time<br>3 A good bit of the time<br>4 Some of the time<br>5 A little of the time<br>6 Hardly any of the time<br>7 None of the time |
| 8. How often during the last 2 weeks have you had to delay or cancel a social engagement because of your bowel problem? | 1 All of the time<br>2 Most of the time<br>3 A good bit of the time<br>4 Some of the time<br>5 A little of the time<br>6 Hardly any of the time<br>7 None of the time |
| 9. How often during the last 2 weeks have you been troubled by cramps in your abdomen? | 1 All of the time<br>2 Most of the time<br>3 A good bit of the time<br>4 Some of the time<br>5 A little of the time<br>6 Hardly any of the time<br>7 None of the time |
| 10. How often during the last 2 weeks have you felt generally unwell? | 1 All of the time<br>2 Most of the time<br>3 A good bit of the time<br>4 Some of the time<br>5 A little of the time<br>6 Hardly any of the time<br>7 None of the time |

TABLE 6-continued

IBDQ

| Question | Answer Options |
|---|---|
| 11. How often during the last 2 weeks have you been troubled because of fear of not finding a washroom? | 1 All of the time<br>2 Most of the time<br>3 A good bit of the time<br>4 Some of the time<br>5 A little of the time<br>6 Hardly any of the time<br>7 None of the time |
| 12. How much difficulty have you had, as a result of your bowel problems, doing leisure or sports activities you would have liked to have done during the last 2 weeks? | 1 A great deal of difficulty; activities made impossible<br>2 A lot of difficulty<br>3 A fair bit of difficulty<br>4 Some difficulty<br>5 A little difficulty<br>6 Hardly any difficulty<br>7 No difficulty; the bowel problems did not limit sports or leisure activities |
| 13. How often during the last 2 weeks have you been troubled by pain in the abdomen? | 1 All of the time<br>2 Most of the time<br>3 A good bit of the time<br>4 Some of the time<br>5 A little of the time<br>6 Hardly any of the time<br>7 None of the time |
| 14. How often during the last 2 weeks have you had problems getting a good night's sleep, or been troubled by waking up during the night? | 1 All of the time<br>2 Most of the time<br>3 A good bit of the time<br>4 Some of the time<br>5 A little of the time<br>6 Hardly any of the time<br>7 None of the time |
| 15. How often during the last 2 weeks have you felt depressed or discouraged? | 1 All of the time<br>2 Most of the time<br>3 A good bit of the time<br>4 Some of the time<br>5 A little of the time<br>6 Hardly any of the time<br>7 None of the time |
| 16. How often during the last 2 weeks have you had to avoid attending events where there was no washroom close at hand? | 1 All of the time<br>2 Most of the time<br>3 A good bit of the time<br>4 Some of the time<br>5 A little of the time<br>6 Hardly any of the time<br>7 None of the time |
| 17. Overall, in the last 2 weeks, how much of a problem have you had with passing large amounts of gas? | 1 A major problem<br>2 A big problem<br>3 A significant problem<br>4 Some trouble<br>5 A little trouble<br>6 Hardly any trouble<br>7 No trouble |
| 18. Overall, in the last 2 weeks, how much of a problem have you had maintaining or getting to, the weight you would like to be at? | 1 A major problem<br>2 A big problem<br>3 A significant problem<br>4 Some trouble<br>5 A little trouble<br>6 Hardly any trouble<br>7 No trouble |
| 19. Many patients with bowel problems often have worries and anxieties related to their illness. These include worries about getting cancer, worries about never feeling any better, and worries about having a relapse. In general, how often during the last 2 weeks have you felt worried or anxious? | 1 All of the time<br>2 Most of the time<br>3 A good bit of the time<br>4 Some of the time<br>5 A little of the time<br>6 Hardly any of the time<br>7 None of the time |
| 20. How much of the time during the last 2 weeks have you been troubled by a feeling of abdominal bloating? | 1 All of the time<br>2 Most of the time<br>3 A good bit of the time<br>4 Some of the time<br>5 A little of the time<br>6 Hardly any of the time<br>7 None of the time |

TABLE 6-continued

IBDQ

| Question | Answer Options |
| --- | --- |
| 21. How often during the last 2 weeks have you felt relaxed and free of tension? | 1 None of the time<br>2 A little of the time<br>3 Some of the time<br>4 A good bit of the time<br>5 Most of the time<br>6 Almost all of the time<br>7 All of the time |
| 22. How much of the time during the last 2 weeks have you had a problem with rectal bleeding with your bowel movements? | 1 All of the time<br>2 Most of the time<br>3 A good bit of the time<br>4 Some of the time<br>5 A little of the time<br>6 Hardly any of the time<br>7 None of the time |
| 23. How much of the time during the last 2 weeks have you felt embarrassed as a result of your bowel problem? | 1 All of the time<br>2 Most of the time<br>3 A good bit of the time<br>4 Some of the time<br>5 A little of the time<br>6 Hardly any of the time<br>7 None of the time |
| 24. How much of the time during the last 2 week shave you been troubled by a feeling of having to go to the bathroom even though your bowels were empty? | 1 All of the time<br>2 Most of the time<br>3 A good bit of the time<br>4 Some of the time<br>5 A little of the time<br>6 Hardly any of the time<br>7 None of the time |
| 25. How much of the time during the last 2 weeks have you felt tearful or upset? | 1 All of the time<br>2 Most of the time<br>3 A good bit of the time<br>4 Some of the time<br>5 A little of the time<br>6 Hardly any of the time<br>7 None of the time |
| 26. How much of the time during the last 2 weeks have you been troubled by accidental soiling of your underpants? | 1 All of the time<br>2 Most of the time<br>3 A good bit of the time<br>4 Some of the time<br>5 A little of the time<br>6 Hardly any of the time<br>7 None of the time |
| 27. How much of the time during the last 2 weeks have you felt angry as a result of your bowel problem? | 1 All of the time<br>2 Most of the time<br>3 A good bit of the time<br>4 Some of the time<br>5 A little of the time<br>6 Hardly any of the time<br>7 None of the time |
| 28. To what extent has your bowel problem limited sexual activity during the last 2 weeks? | 1 No sex as a result of bowel disease<br>2 Major limitation as a result of bowel disease<br>3 Moderate limitation as a result of bowel disease<br>4 Some limitation as a result of bowel disease<br>5 A little limitation as a result of bowel disease<br>6 Hardly any limitation as a result of bowel disease<br>7 No limitation as a result of bowel disease |
| 29. How much of the time during the last 2 weeks have you been troubled by nausea or feeling sick to your stomach? | 1 All of the time<br>2 Most of the time<br>3 A good bit of the time<br>4 Some of the time<br>5 A little of the time<br>6 Hardly any of the time<br>7 None of the time |
| 30. How much of the time during the last 2 weeks have you felt irritable? | 1 All of the time<br>2 Most of the time<br>3 A good bit of the time<br>4 Some of the time<br>5 A little of the time<br>6 Hardly any of the time<br>7 None of the time |

TABLE 6-continued

IBDQ

| Question | Answer Options |
|---|---|
| 31. How often during the past 2 weeks have you felt a lack of understanding from others? | 1 All of the time<br>2 Most of the time<br>3 A good bit of the time<br>4 Some of the time<br>5 A little of the time<br>6 Hardly any of the time<br>7 None of the time |
| 32. How satisfied, happy, or leased have you been with your personal life during the past 2 weeks? | 1 Very dissatisfied, unhappy most of the time<br>2 Generally dissatisfied, unhappy<br>3 Somewhat dissatisfied, unhappy<br>4 Generally satisfied, pleased<br>5 Satisfied most of the time, happy<br>6 Very satisfied most of the time, happy<br>7 Extremely satisfied, could not have been more happy or pleased |

The Work Productivity and Activity Impairment Questionnaire for Ulcerative Colitis (WPAI:UC) and Crohn's Disease (WPAI:CD) assesses the impact of the condition on work productivity losses and impairment in daily activity. WPAI:UC has six items covering four domains: Absenteeism (work time missed), measured as the number of hours missed from work in the past 7 days due to a condition related problem. Scores are expressed as impairment percentages, adjusting for hours actually worked according to the WPAI:UC or WPAI:CD scoring algorithm; Presenteeism (impairment at work/reduced on-the-job effectiveness), measured as the impact of the condition on productivity while at work (i.e., reduced amount or kind of work, or not as focused as usual). Responses are recorded on a 0-10 Likert scale (where, 0=no effect of UC or CD on work and 10=severe impact of UC or CD while at work); productivity loss (overall work impairment), measured as the sum of hours missed due to condition i.e., absenteeism and number of hours worked with impairment i.e., product of number of hours worked and presenteeism; and activity impairment (i.e., activities other than paid work like work around house, cleaning, shopping, traveling, studying), recorded and scored in the same way as presenteeism. Higher numbers indicate greater impairment and less productivity. The WPAI:UC/WPAI:CD questions and answer options are set forth in Table 7.

TABLE 7

WPAI:UC* and WPAI:CD

| Questions | Answer Options |
|---|---|
| 1. Are you currently employed (working for pay)? If no, skip to question 6. | No or yes |
| 2. During the past seven days, how many hours did you miss from work because of problems associated with your ulcerative colitis? Include hours you missed on sick days, times you went in late, left early, etc., because of your ulcerative colitis. Do not include time you missed to participate in this study. | Number of hours |
| 3. During the past seven days, how many hours did you miss from work because of any other reason, such as vacation, holidays, time off to participate in this study? | Number of hours |
| 4. During the past seven days, how many hours did you actually work? | Number of hours (if 0, skip to question 6) |
| 5. During the past seven days, how much did your ulcerative colitis affect your productivity while you were working? Think about days you were limited in the amount or kind of work you could do, days you accomplished less than you would like, or days you could not do your work as carefully as usual. If ulcerative colitis affected your work only a little, choose a low number. Choose a high number if ulcerative colitis affected your work a great deal. | Select number on a scale of 0 (UC had no effect on work) to 10 (UC completely prevented me from working), representing how much ulcerative colitis affected productivity while at work |
| 6. During the past 7 days, how much did your ulcerative colitis affect your ability to do your regular daily activities, other than work at a job? Regular activities means usual activities, such as work around the house, shopping, childcare, exercising, studying, etc. Consider times you were limited in the amount or kind of activities you could do and times you accomplished less than you would like. If ulcerative colitis affected your activities only a little, choose a low number. Choose a high number if ulcerative colitis affected your activities a great deal. | Select number on a scale of 0 (UC had no effect on daily activities) to 10 (UC completely prevented me from doing daily activities), representing how much ulcerative colitis affected ability to do regular daily activities, other than work at a job |

*Questions 2-7 are about the previous seven days, not including the day the questionnaire is completed.

The European Quality of Life 5 Dimensions 5 Levels (EQ-5D-5L) is a standardized non-disease specific instrument for describing and valuing health-related quality of life. The EQ-5D-5L consists of 5 dimensions: mobility, self-care, usual activity, pain/discomfort, and anxiety/depression. Each dimension has 5 levels: no problem, slight problem, moderate problem, severe problem or unable to do the activity. It also contains a Visual Analogue Scale (VAS). Subjects are asked to indicate the level that describes their current level of function or experience for each dimension. As a measure of health status, it provides a descriptive profile and can be used to generate a single index value for health status, where full health is equal to 1 and death is equal to 0. The VAS records the subject's assessment of his/her own health along a vertical 20 cm line, which has health state scores between 0 and 100. The EQ-5D-5L questions and answer options are set forth in Table 8.

TABLE 8

EQ-5D-5L Questionnaire

| Dimension | Answer Options | Score |
|---|---|---|
| Mobility | I have no problems walking | MB1 |
| | I have slight problems walking | MB2 |
| | I have moderate problems walking | MB3 |
| | I have severe problems walking | MB4 |
| | I am unable to walk | MB5 |
| Self-Care | I have no problems washing or dressing myself | SC1 |
| | I have slight problems washing or dressing myself | SC2 |
| | I have moderate problems washing or dressing myself | SC3 |
| | I have severe problems washing or dressing myself | 5C4 |
| | I am unable to wash or dress myself | 5C5 |
| Usual Activities* | I have no problems doing my usual activities | UA1 |
| | I have slight problems doing my usual activities | UA2 |
| | I have moderate problems doing my usual activities | UA3 |
| | I have severe problems doing my usual activities | UA4 |
| | I am unable to do my usual activities | UA5 |
| Pain/Discomfort | I have no pain or discomfort | PD1 |
| | I have slight pain or discomfort | PD2 |
| | I have moderate pain or discomfort | PD3 |
| | I have severe pain or discomfort | PD4 |
| | I have extreme pain or discomfort | PD5 |
| Anxiety/Depression | I am not anxious or depressed | AD1 |
| | I am slightly anxious or depressed | AD2 |
| | I am moderately anxious or depressed | AD3 |
| | I am severely anxious or depressed | AD4 |
| | I am extremely anxious or depressed | AD5 |
| How good or bad is your health today? | We would like to know how good or bad your health is TODAY. This scale is numbered from 0 to 100. 100 means the best health you can imagine. 0 means the worst health you can imagine. Mark an X on the scale to indicate how your health is TODAY. Now, please write the number you marked on the scale in the box below. | |

*E.g., work, study, housework, family or leisure activities

The SF-36 questionnaire is a self-administered multi-domain scale with 36 items. Eight subscales cover a range of functioning: physical functioning (PF), role-physical (RP), bodily pain (BP), general health (GH), vitality (VT), social functioning (SF), role-emotional (RE), and mental health (MH). The scoring yields a physical component score, a mental component summary score, and subscale scores. Higher scores represent better outcomes. The concepts measured by the SF-36 are not specific to any age, disease, or treatment group, allowing comparison of relative burden of different diseases and the benefit of different treatments. The SF-36 questions and answer options are set forth below in Table 9.

TABLE 9

SF-36 Health Survey

| Function - Question number | Question | Answer Options |
|---|---|---|
| GH - 1 | In general, would you say your health is: | Excellent Very good Good Fair Poor |

TABLE 9-continued

SF-36 Health Survey

| Function - Question number | Question | Answer Options |
|---|---|---|
| | Compared to one year ago, how would you rate your health in general now? | Much better now than one year ago<br>Somewhat better now than one year ago<br>About the same as one year ago<br>Somewhat worse now than one year ago<br>Much worse now than one year ago |
| PF - 1[1] | Does your health now limit you in vigorous activities, such as running, lifting heavy objects, participating in strenuous sports? If so, how much? | Yes, limited a lot<br>Yes, limited a little<br>No, not limited at all |
| PF - 2[1] | Does your health now limit you in moderate activities, such as moving a table, pushing a vacuum cleaner, bowling, or playing golf? If so, how much? | Yes, limited a lot<br>Yes, limited a little<br>No, not limited at all |
| PF - 3[1] | Does your health now limit you in lifting or carrying groceries? If so, how much? | Yes, limited a lot<br>Yes, limited a little<br>No, not limited at all |
| PF - 4[1] | Does your health now limit you in climbing several flights of stairs? If so, how much? | Yes, limited a lot<br>Yes, limited a little<br>No, not limited at all |
| PF - 5[1] | Does your health now limit you in climbing one flight of stairs? If so, how much? | Yes, limited a lot<br>Yes, limited a little<br>No, not limited at all |
| PF - 6[1] | Does your health now limit you in bending, kneeling, or stooping? If so, how much? | Yes, limited a lot<br>Yes, limited a little<br>No, not limited at all |
| PF - 7[1] | Does your health now limit you in walking more than a mile? If so, how much? | Yes, limited a lot<br>Yes, limited a little<br>No, not limited at all |
| PF - 8[1] | Does your health now limit you in walking several hundred yards? If so, how much? | Yes, limited a lot<br>Yes, limited a little<br>No, not limited at all |
| PF - 9[1] | Does your health now limit you in walking one hundred yards? If so, how much? | Yes, limited a lot<br>Yes, limited a little<br>No, not limited at all |
| PF - 10[1] | Does your health now limit you in bathing or dressing yourself? If so, how much? | Yes, limited a lot<br>Yes, limited a little<br>No, not limited at all |
| RP - 1[2] | Cut down on the amount of time you spent on work or other activities as a result of your physical health | All of the time<br>Most of the time<br>Some of the time<br>A little of the time<br>None of the time |
| RP - 2[2] | Accomplished less than you would like as a result of your physical health | All of the time<br>Most of the time<br>Some of the time<br>A little of the time<br>None of the time |
| RP - 3[2] | Were limited in the kind of work or other activities as a result of your physical health | All of the time<br>Most of the time<br>Some of the time<br>A little of the time<br>None of the time |
| RP - 4[2] | Had difficulty performing the work or other activities as a result of your physical health (for example, it took extra effort) | All of the time<br>Most of the time<br>Some of the time<br>A little of the time<br>None of the time |
| RE - 1[2] | Cut down on the amount of time you spent on work or other activities as a result of any emotional problems (such as feeling depressed or anxious) | All of the time<br>Most of the time<br>Some of the time<br>A little of the time<br>None of the time |
| RE - 2[2] | Accomplished less than you would like as a result of any emotional problems (such as feeling depressed or anxious) | All of the time<br>Most of the time<br>Some of the time<br>A little of the time<br>None of the time |
| RE - 3[2] | Did work or other activities less carefully than usual as a result of any emotional problems (such as feeling depressed or anxious) | All of the time<br>Most of the time<br>Some of the time<br>A little of the time<br>None of the time |

TABLE 9-continued

SF-36 Health Survey

| Function - Question number | Question | Answer Options |
|---|---|---|
| SF - 1 | During the past 4 weeks, to what extent has your physical health or emotional problems interfered with your normal social activities with family, friends, neighbors, or groups? | Not at all<br>Slightly<br>Moderately<br>Quite a bit<br>Extremely |
| BP - 1 | How much bodily pain have you had during the past 4 weeks? | None<br>Very mild<br>Mild<br>Moderate<br>Severe<br>Very severe |
| BP - 2 | During the past 4 weeks, how much did pain interfere with your normal work (including both work outside the home and housework)? | Not at all<br>A little bit<br>Moderately<br>Quite a bit<br>Extremely |
| VT - 1[3] | How much of the time during the past 4 weeks did you feel full of life? | All of the time<br>Most of the time<br>Some of the time<br>A little of the time<br>None of the time |
| MH - 1[3] | How much of the time during the past 4 weeks have you been very nervous? | All of the time<br>Most of the time<br>Some of the time<br>A little of the time<br>None of the time |
| MH - 2[3] | How much of the time during the past 4 weeks have you felt so down in the dumps that nothing could cheer you up? | All of the time<br>Most of the time<br>Some of the time<br>A little of the time<br>None of the time |
| MH - 3[3] | How much of the time during the past 4 weeks have you felt calm and peaceful? | All of the time<br>Most of the time<br>Some of the time<br>A little of the time<br>None of the time |
| VT - 2[3] | How much of the time during the past 4 weeks did you have a lot of energy? | All of the time<br>Most of the time<br>Some of the time<br>A little of the time<br>None of the time |
| MH - 4[3] | How much of the time during the past 4 weeks have you felt downhearted and depressed? | All of the time<br>Most of the time<br>Some of the time<br>A little of the time<br>None of the time |
| VT - 3[3] | How much of the time during the past 4 weeks did you feel worn out? | All of the time<br>Most of the time<br>Some of the time<br>A little of the time<br>None of the time |
| MH - 5[3] | How much of the time during the past 4 weeks have you been happy? | All of the time<br>Most of the time<br>Some of the time<br>A little of the time<br>None of the time |
| VT - 4[3] | How much of the time during the past 4 weeks did you feel tired? | All of the time<br>Most of the time<br>Some of the time<br>A little of the time<br>None of the time |
| SF - 2 | During the past 4 weeks, how much of the time has your physical health or emotional problems interfered with your social activities (like visiting with friends, relatives, etc.)? | All of the time<br>Most of the time<br>Some of the time<br>A little of the time<br>None of the time |
| GH - 2[4] | I seem to get sick a little easier than other people. | Definitely true<br>Mostly true<br>Don't know<br>Mostly false<br>Definitely false |

TABLE 9-continued

SF-36 Health Survey

| Function - Question number | Question | Answer Options |
|---|---|---|
| GH - 3[4] | I am as healthy as anybody I know. | Definitely true<br>Mostly true<br>Don't know<br>Mostly false<br>Definitely false |
| GH - 4[4] | I expect my health to get worse. | Definitely true<br>Mostly true<br>Don't know<br>Mostly false<br>Definitely false |
| GH - 5[4] | My health is excellent. | Definitely true<br>Mostly true<br>Don't know<br>Mostly false<br>Definitely false |

[1]Instructions: The following question is about activities you might do during a typical day
[2]Instructions: During the past 4 weeks, how much of the time have you had any of the following problems with your work or other regular daily activities?
[3]Instructions: This question is about how you feel and how things have been with you during the past 4 weeks. Please give the one answer that comes closest to the way you have been feeling.
[4]Instructions: How TRUE or FALSE is the following statement for you?

The Functional Assessment of Chronic Illness Therapy (FACIT) system is a collection of quality of life (QOL) questionnaires targeted to the management of cancer and other chronic illnesses. The FACIT fatigue (FACIT-F) questionnaire was developed to assess fatigue associated with anemia. It consists of 13 fatigue-related questions. The responses to the 13 items on the FACIT fatigue questionnaire are each measured on a 4-point Likert scale. The responses to the answers are the following: (i) not at all: 0 points; (ii) a little bit: 1 point; (iii) somewhat: 2 points; (iv) quite a bit: 3 points; and (v) very much: 4 points. Thus, the total score ranges from 0 to 52. High scores represent less fatigue. The FACIT-F questions and answer options are set forth below in Table 10.

TABLE 10

FACIT-F Questionnaire

| Question | Answer Options |
|---|---|
| I feel fatigued. . . | 0 Not at all |
| I feel weak all over. . . | 1 A little bit |
| I feel listless ("washed out"). . . | 2 Somewhat |
| I feel tired. . . | 3 Quite a bit |
| I have trouble starting things because I am tired. . . | 4 Very much |
| I have trouble finishing things because I am tired. . . | |
| I have energy. . . | |
| I am able to do my usual activities. . . | |
| I need to sleep during the day. . . | |
| I am too tired to eat. . . | |
| I need help doing my usual activities. . . | |
| I am frustrated by being too tired to do the things I want to do. . . | |
| I have to limit my social activity because I am tired. . . | |

The Ulcerative Colitis Symptoms Questionnaire (UC-SQ) is a UC-specific instrument composed of 17 Likert-type items. UC-SQ was developed to assess UC related gastrointestinal and non-gastrointestinal symptoms such as frequent bowel movements, abdominal discomfort, nausea, loss of appetite, pain, and anemia along with the impact on patients' sleep. Each question can be answered using Likert-type options such as (i) Not at all: 0 points; (ii) A little bit: 1 point; (iii) Somewhat: 2 points; (iv) Quite a bit: 3 points; and (v) Very much: 4 points based on how the patient felt during the past week (i.e., 7 days). The total score ranges can vary from 0 to 68 with lower scores indicating improvement. The UC-SQ questions and answer options are set forth below in Table 11.

TABLE 11

UC-SQ Questionnaire

| Question | Answer Options |
|---|---|
| During the past week, were your bowel movements more frequent than usual? | Not at all<br>A little bit |
| During the past week, did you pass gas more than usual? | Somewhat |
| During the past week, did you have abdominal pain? | Quite a bit |
| During the past week, did you have rectal pain? | Very much |
| During the past week, did you have cramping? | |
| During the past week, have you felt tired or lacking energy? | |
| During the past week, did you feel nauseated? | |
| During the past week, did you experience loss of appetite? | |
| During the past week, did you have joint pain? | |
| During the past week, did you have difficulty sleeping? | |
| During the past week, did you experience bloating? | |
| During the past week, did you have diarrhea? | |
| During the past week, did you pass blood or have blood in your stool? | |
| During the past week, did you have mucus in your stool? | |
| During the past week, were you constipated? | |
| During the past week, did you feel that you needed to have a bowel movement - even when your bowels were empty? | |
| During the past week, did you experience a sudden or intense need to have a bowel movement? | |

The Patient Global Impression of Change (PGIC) is a self-administered instrument that assesses change in the overall symptoms due to Ulcerative Colitis. The PGIC is one item in which subjects are asked to rate overall improvement since start of the treatment. Patients are asked the question "Compared to before your treatment began, how would you rate the change in your overall symptoms due to your ulcerative colitis?", and rate their change as "Very much improved," "Much improved," "Minimally improved", "No change," "Minimally worse," "Much worse" and "Very much worse".

In one aspect, the patient to be treated has moderately to severely active ulcerative colitis. Moderately to severely active ulcerative colitis is characterized by an Adapted Mayo score of 5 to 9 points and an endoscopy subscore of 2 to 3.

In one embodiment, the patient is a patient who had an inadequate response with, lost response, or was intolerant to a conventional therapy (e.g., aminosalicylate, corticosteroids, immunosuppressants), or to a biologic agent. In one embodiment, the patient is a patient who had an inadequate response with, lost response, or was intolerant to biologic therapies. Examples of such biologic therapies include infliximab, adalimumab, vedolizumab, golimumab, ustekinumab and certolizumab pegol. Criteria for determining if a patient has had an inadequate response to, lost response, or experienced intolerance to previous treatment with corticosteroids, immunosuppressants, and/or a biologic therapy are defined below:

Corticosteroids:
1) Signs and symptoms of persistently active disease despite a history of at least one induction regimen that included a dose equivalent to prednisone ≥40 mg/day orally for 3 to 4 weeks or intravenously for 1 week, or
2) Unable to taper corticosteroid to below a dose equivalent to prednisone 10 mg daily orally without recurrent active disease, or
3) History of intolerance to corticosteroids (including, but no limited to Cushing's syndrome, osteopenia/osteoporosis, hyperglycemia, insomnia, infection).

Immunosuppressants:
1) Signs and symptoms of persistently active disease despite a history of at least one 90-day regimen of oral azathioprine (≥1.5 mg/kg/day; for subjects in Japan and China only: ≥1.0 mg/kg/day), 6-mercaptopurine (≥1 mg/kg/day [for subjects in Japan and China only: ≥0.6 mg/kg/day, rounded to the nearest available tablet of half tablet formulation]; or a documented 6-TGN level of 230-450 pmol/8×$10^8$ RBC or higher on the current dosing regimen), injectable methotrexate (MTX≥15 mg/week subcutaneous [SC] or intramuscular), or tacrolimus (for subjects in Japan only: documented trough level of 5-10 ng/mL), or
2) History of intolerance to at least one immunosuppressant (including, but not limited to nausea/vomiting, abdominal pain, pancreatitis, liver enzyme abnormalities, lymphopenia, infection)

Biologic Agents for UC:
1) Signs and symptoms of persistently active disease despite a history of any of the following:
    a. at least one 6-week induction regimen of infliximab (≥5 mg/kg intravenous [IV] at 0, 2 and 6 weeks),
    b. at least one 4-week induction regimen of adalimumab (one 160 mg SC dose followed by one 80 mg SC dose [or one 80 mg SC dose, in countries where this dosing regimen is allowed] followed by one 40 mg SC dose at least 2 weeks apart),
    c. at least one 2-week induction regimen of golimumab (one 200 mg SC dose followed by one 100 mg SC dose at least 2 weeks apart),
    d. at least one 6-week induction regimen of vedolizumab (300 mg IV at 0, 2 and 6 weeks), or
2) Recurrence of symptoms during scheduled maintenance dosing following prior clinical benefit (discontinuation despite clinical benefit does not qualify), or
3) History of intolerance to at least one biologic agent (including, but not limited to infusion-related reaction, demyelination, congestive heart failure (CHF), infection)

In one aspect, the patient is one who has previously been treated with, or is currently being treated with aminosalicylate, immunosuppressants, corticosteroids, and/or a biologic agent.

In one aspect, the Mayo Scoring System for Assessment of Ulcerative Colitis Activity or any of the evaluations described hereinbefore or in the Examples herein below is/are used to assess the efficacy of upadacitinib in the treatment of ulcerative colitis, for example moderately to severely active ulcerative colitis. In one embodiment, the evaluation used to assess the efficacy of upadacitinib in the treatment of ulcerative colitis is selected from the group consisting of the Full Mayo score, the Partial Mayo score, the Adapted Mayo score, the IBDQ, the WPAI:UC, the EQ-5D-5L, the SF-36, the FACIT-F, the UC-SQ, the PGIC, and combinations thereof.

In one embodiment, in the context of the present disclosure, the treatment of a patient having ulcerative colitis, and/or the induction of clinical remission of ulcerative colitis and/or the induction of clinical response and/or endoscopic improvement and/or endoscopic remission in a patient comprises an induction phase and a maintenance phase. In the induction phase, one or more doses of the JAK1 inhibitor, for example referred to herein as induction doses, are administered to the patient, for example, orally. In the maintenance phase, a first dose of the JAK1 inhibitor, for example referred to herein as the maintenance dose, is administered to the patient followed by at least one additional dose of the JAK1 inhibitor, for example, also referred to herein as a maintenance dose. The maintenance doses are, for example, administered orally. The JAK1 inhibitor may be, for example, upadacitinib, or a pharmaceutically acceptable salt or solid state form thereof. Examples of induction phases and maintenance phases are described herein.

In one aspect, a certain therapeutic result is achieved by the patient during or at the end of the induction phase, for example clinical remission. In other embodiments, the therapeutic result achieved by the patient during or at the end of the induction phase is selected from the group consisting of endoscopic subscore of 0 or 1 at week 8, endoscopic subscore of 0 at week 8, fecal calprotectin below 150 mg/kg at week 8, IBDQ response (increase of IBDQ≥16 from baseline) at week 8, RBS≥1 or absolute RBS≤1 at week 8, or RBS of 0 at week 8. In one aspect, the patient achieves clinical remission during or by the end of the induction phase. In one aspect, the patient achieves endoscopic remission during or by the end of the induction phase.

In one aspect, the patient achieves endoscopic improvement of ulcerative colitis during or by the end of the induction phase. In one aspect, the patient achieves clinical remission and endoscopic improvement of ulcerative colitis during or at the end of the induction phase.

In one embodiment, the induction phase lasts for up to 16 weeks (e.g., for up to 16 weeks following initiation of administration of upadacitinib, or a pharmaceutically acceptable salt or solid state form thereof). Thus, in one embodiment, the induction phase is 16 weeks. In another embodiment, the induction phase optionally lasts for less than 16 weeks, for instance, for 2 weeks, for 3 weeks, for 4 weeks, for 5 weeks, for 6 weeks, for 7 weeks, for 8 weeks, for 9 weeks, for 10 weeks, for 11 weeks, for 12 weeks, for 13 weeks, for 14 weeks, or for 15 weeks. In one aspect, the patient achieves an endoscopic remission within 8 weeks, or within 12 weeks, or within 16 weeks of initiating administration of upadacitinib, or a pharmaceutically acceptable salt or solid state form thereof. In one aspect, the patient achieves a clinical remission within 8 weeks, or within 12 weeks, or within 16 weeks of initiating administration of upadacitinib, or a pharmaceutically acceptable salt or solid state form thereof. In one aspect, the patient achieves an endoscopic improvement within 8 weeks, or within 12 weeks, or within 16 weeks of initiating administration of upadacitinib, or a pharmaceutically acceptable salt or solid state form thereof. In one aspect, the patient achieves a clinical response within 8 weeks, or within 12 weeks, or within 16 weeks of initiating administration of upadacitinib, or a pharmaceutically acceptable salt or solid state form thereof. In one aspect, the patient achieves a clinical remission within 8 weeks, or within 12 weeks, or within 16 weeks of initiating administration of upadacitinib, or a pharmaceutically acceptable salt or solid state form thereof.

In one embodiment, the patient achieves clinical remission within 2 weeks of initiating administration of upadacitinib, or a pharmaceutically acceptable salt or solid state form thereof. In one embodiment, the patient achieves clinical remission within 4 weeks of initiating administration of upadacitinib, or a pharmaceutically acceptable salt or solid state form thereof.

In one embodiment, the patient achieves clinical response within 2 weeks of initiating administration of upadacitinib, or a pharmaceutically acceptable salt or solid state form thereof. In one embodiment, the patient achieves clinical response within 4 weeks of initiating administration of upadacitinib, or a pharmaceutically acceptable salt or solid state form thereof.

In one embodiment, the patient achieves endoscopic improvement or endoscopic remission within 2 weeks of initiating administration of upadacitinib, or a pharmaceutically acceptable salt or solid state form thereof. In one embodiment, the patient achieves endoscopic improvement or endoscopic remission within 4 weeks of initiating administration of upadacitinib, or a pharmaceutically acceptable salt or solid state form thereof. In one embodiment, the patient achieves endoscopic improvement or endoscopic remission within 12 weeks of initiating administration of upadacitinib, or a pharmaceutically acceptable salt or solid state form thereof. In one embodiment, the patient achieves endoscopic improvement or endoscopic remission within 16 weeks of initiating administration of upadacitinib, or a pharmaceutically acceptable salt or solid state form thereof.

In one embodiment, the patient achieves corticosteroid-free remission within 12 weeks of initiating administration of upadacitinib, or a pharmaceutically acceptable salt or solid state form thereof. In one embodiment, the patient achieves corticosteroid-free remission within 8 weeks of initiating administration of upadacitinib, or a pharmaceutically acceptable salt or solid state form thereof. In one embodiment, the corticosteroid-free remission is a clinical remission. In one embodiment, the corticosteroid-free remission is endoscopic remission.

In some embodiments, during or by the end of the induction phase (e.g., lasting for up to 16 weeks, including for 2 weeks, 4 weeks, 6 weeks, 8 weeks, 10 weeks, 12 weeks or for 16 weeks), the patient achieves at least one therapeutic result selected from the group consisting of:

1) endoscopic improvement (defined as endoscopic subscore ≤1 within 8 weeks of initiating administration of upadacitinib or a pharmaceutically acceptable salt or solid state form thereof,
2) a Full Mayo score ≤2 with no subscore >1 within 8 weeks of initiating administration of upadacitinib or a pharmaceutically acceptable salt or solid state form thereof,
3) clinical response (defined as decrease from baseline in the Adapted Mayo score ≤2 points and ≤30% from baseline, plus a decrease in rectal bleeding subscore (RBS)≤1 or an absolute RBS of 0 or 1) within 8 weeks of initiating administration of upadacitinib or a pharmaceutically acceptable salt or solid state form thereof,
4) clinical response within 2 weeks of initiating administration of upadacitinib or a pharmaceutically acceptable salt or solid state form thereof,
5) change in Full Mayo score from Baseline to Week 8 after initiating administration of upadacitinib or a pharmaceutically acceptable salt or solid state form thereof,
6) endoscopic remission (defined as endoscopic subscore of 0) within 8 weeks of initiating administration of upadacitinib or a pharmaceutically acceptable salt or solid state form thereof,
7) histologic improvement (defined as a decrease from baseline in Geboes score) within 8 weeks of initiating administration of upadacitinib or a pharmaceutically acceptable salt or solid state form thereof,
8) decrease in RBS≥1 or an absolute RBS≤1 within 8 weeks of initiating administration of upadacitinib or a pharmaceutically acceptable salt or solid state form thereof,
9) RBS of 0 within 8 weeks of initiating administration of upadacitinib or a pharmaceutically acceptable salt or solid state form thereof,
10) endoscopic improvement (endoscopic subscore of 0 or 1) within 8 weeks of initiating administration of upadacitinib or a pharmaceutically acceptable salt or solid state form thereof,
11) stool frequency subscore ≤1 within 8 weeks of initiating administration of upadacitinib or a pharmaceutically acceptable salt or solid state form thereof,
12) maintenance of clinical remission at Week 52 following initial administration of upadacitinib or a pharmaceutically acceptable salt or solid state form thereof in patients who achieved clinical remission within 8 weeks of initiating administration of upadacitinib or a pharmaceutically acceptable salt or solid state form thereof,
13) endoscopic improvement within 52 weeks of initiating administration of upadacitinib or a pharmaceutically acceptable salt or solid state form thereof,
14) a Full Mayo score ≤2 with no subscore >1 within 52 weeks of initiating administration of upadacitinib or a pharmaceutically acceptable salt or solid state form thereof,
15) clinical remission within 52 weeks of initiating administration of upadacitinib or a pharmaceutically acceptable salt or solid state form thereof in patients who discontinued corticosteroid use prior to initiating administration of upadacitinib or a pharmaceutically acceptable salt or solid state form thereof,
16) subjects who are taking corticosteroids at Baseline and are steroid-free at within 52 weeks of initiating administration of upadacitinib or a pharmaceutically acceptable salt or solid state form thereof,
17) endoscopic improvement at Week 52 following initial administration of upadacitinib or a pharmaceutically acceptable salt or solid state form thereof in patients who achieved clinical remission within 8 weeks of initiating administration of upadacitinib or a pharmaceutically acceptable salt or solid state form thereof,
18) clinical response within 44 weeks of initiating administration of upadacitinib or a pharmaceutically acceptable salt or solid state form thereof,
19) endoscopic remission within 52 weeks of initiating administration of upadacitinib or a pharmaceutically acceptable salt or solid state form thereof, 20) histologic improvement within 52 weeks of initiating administration of upadacitinib or a pharmaceutically acceptable salt or solid state form thereof,
21) clinical remission per Adapted Mayo score (defined as SFS≤1, RBS of 0, and endoscopy subscore ≤1), and combinations thereof.

In some embodiments, the patient achieves a clinical remission within 16 weeks or within 12 weeks of initiating administration of upadacitinib, or a pharmaceutically acceptable salt or solid state form thereof, and further achieves any combination of additional therapeutic results selected from the group consisting of therapeutic results 1), 2), 3), 4), 5), 6), 7), 8), 9), 10), 11), 12), 13), 14), 15), 16), 17), 18), 19) 20), 21) and combinations thereof. In one such embodiment, the induction phase is 16 weeks. In one embodiment, the additional therapeutic result is achieved within 8 weeks of initiating administration of upadacitinib, or a pharmaceutically acceptable salt or solid state form thereof, and is selected from the group consisting of therapeutic results 1), 2), 3), 4), 5), 6), 7), 8), 9), 10), 11) and combinations thereof.

In one embodiment, the induction phase is 8 weeks, and the patient achieves a clinical remission within 8 weeks of initiating administration of upadacitinib, or a pharmaceutically acceptable salt or solid state form thereof, and further achieves any combination of additional therapeutic results selected from the group consisting of therapeutic results 1), 2), 3), 4), 5), 6), 7), 8), 9), 10), 11), 12), 13), 14), 15), 16), 17), 18), 19) 20), 21) and combinations thereof. In one embodiment, the additional therapeutic result is achieved within 8 weeks of initiating administration of upadacitinib, or a pharmaceutically acceptable salt or solid state form thereof. In one embodiment, the additional therapeutic result is achieved within 8 weeks of initiating administration of upadacitinib, or a pharmaceutically acceptable salt or solid state form thereof, and is selected from the group consisting of therapeutic results 1), 2), 3), 4), 5), 6), 7), 8), 9), 10), 11) and combinations thereof.

In one embodiment, the induction phase is 4 weeks, and the patient achieves a clinical remission within 4 weeks of initiating administration of upadacitinib, or a pharmaceutically acceptable salt or solid state form thereof, and further achieves any combination of additional therapeutic results selected from the group consisting of therapeutic results 1), 2), 3), 4), 5), 6), 7), 8), 9), 10), 11), 12), 13), 14), 15), 16), 17), 18), 19) 20), 21) and combinations thereof. In one embodiment, the additional therapeutic result is achieved within 4 weeks of initiating administration of upadacitinib, or a pharmaceutically acceptable salt or solid state form thereof. In one embodiment, the additional therapeutic result is achieved within 4 weeks of initiating administration of upadacitinib, or a pharmaceutically acceptable salt or solid state form thereof, and is selected from the group consisting of endoscopic improvement, clinical remission, clinical response, endoscopic remission, histologic improvement, and combinations thereof.

In one embodiment, the patient achieves a clinical remission within 4 weeks, within 8 weeks, within 12 weeks, or within 16 weeks of initiating administration of upadacitinib, or a pharmaceutically acceptable salt or solid state form thereof, and/or achieves an endoscopic improvement within 4 weeks, within 8 weeks, within 12 weeks or within 16 weeks of initiating administration of upadacitinib, or a pharmaceutically acceptable salt or solid state form thereof, and further achieves an additional therapeutic result selected from the group consisting of a decrease from baseline in Partial Mayo score ≥2 points and ≥30% from baseline plus a decrease in RBS≥1 or an absolute RBS≤1 over time within 16 weeks of initiating administration of upadacitinib, or a pharmaceutically acceptable salt or solid state form thereof; clinical response per Partial Mayo score within 12 weeks of initiating administration of upadacitinib, or a pharmaceutically acceptable salt or solid state form thereof; a decrease from baseline in Partial Mayo score ≥2 points and ≥30% from baseline plus a decrease in RBS≥1 or an absolute RBS≤1 over time within 8 weeks of initiating administration of upadacitinib, or a pharmaceutically acceptable salt or solid state form thereof; a decrease from baseline in Partial Mayo score ≥2 points and ≥30% from baseline plus a decrease in RBS≥1 or an absolute RBS≤1 over time within 4 weeks of initiating administration of upadacitinib, or a pharmaceutically acceptable salt or solid state form thereof; a decrease from baseline in Partial Mayo score ≥2 points and ≥30% from baseline plus a decrease in RBS≥1 or an absolute RBS≤1 over time within 2 weeks of initiating administration of upadacitinib, or a pharmaceutically acceptable salt or solid state form thereof; an endoscopic remission within 16 weeks of initiating administration of pharmaceutically upadacitinib, or a pharmaceutically acceptable salt or solid state form thereof; an endoscopic remission within 12 weeks of initiating administration of upadacitinib, or an acceptable salt or solid state form thereof; an endoscopic remission within 8 weeks of initiating administration of upadacitinib, or a pharmaceutically acceptable salt or solid state form thereof; an endoscopic remission within 4 weeks of initiating administration of upadacitinib, or a pharmaceutically acceptable salt or solid state form thereof; a clinical response within 16 weeks of initiating administration of upadacitinib, or a pharmaceutically acceptable salt or solid state form thereof; a clinical response within 12 weeks of initiating administration of upadacitinib, or a pharmaceutically acceptable salt or solid state form thereof; a clinical response within 8 weeks of initiating administration of upadacitinib, or a pharmaceutically acceptable salt or solid state form thereof; a clinical response within 4 weeks of initiating administration of upadacitinib, or a pharmaceutically acceptable salt or solid state form thereof; a Full Mayo score ≤2 with no subscore >1 within 16 weeks of initiating administration of upadacitinib, or a pharmaceutically acceptable salt or solid state form thereof; a Full Mayo score ≤2 with no subscore >1 within 12 weeks of initiating administration of upadacitinib, or a pharmaceutically acceptable salt or solid state form thereof; a Full Mayo score ≤2 with no subscore >1 within 8 weeks of initiating administration of upadacitinib, or a pharmaceutically acceptable salt or solid state form thereof; a Full Mayo score ≤2 with no subscore >1 within 4 weeks of initiating administration of upadacitinib, or a pharmaceutically acceptable salt or solid state form thereof; an endoscopic improvement within 16 weeks of initiating administration of upadacitinib, or a pharmaceutically acceptable salt or solid state form thereof; an endoscopic improvement within 12 weeks of initiating administration of upadacitinib, or a pharmaceutically acceptable salt or solid state form thereof; an endoscopic improvement within 8 weeks of initiating administration of upadacitinib, or a pharmaceutically acceptable salt or solid state form thereof; an endoscopic improvement within 4 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 16 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 12 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 8 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 4 weeks of initiating administration of upadacitinib, or a pharmaceutically acceptable salt or solid state form thereof; and combinations thereof. In one embodiment, the patient achieves a clinical remission within 12 weeks or within 16 weeks of initiating administration of upadacitinib or a pharmaceutically acceptable salt or solid state form thereof, and/or achieves a clinical remission per Adapted Mayo score (defined as SFS $\lesssim$ 1, RBS or 0, and endoscopy subscore $\lesssim$ 1) within 12 weeks of initiation administration of upadacitinib, or a pharmaceutically acceptable salt or solid state form thereof. In one embodiment, the patient achieves a clinical response per Adapted Mayo score (defined as decrease from BL in the Adapted Mayo score $\gtrsim$ 2 points and $\gtrsim$ 30% from BL, plus a decrease in RBS $\gtrsim$ 1 or an absolute RBS $\lesssim$ 1 at week 12 or 16. In one such embodiment, the induction phase is 16 weeks, and the additional therapeutic result is selected from the group consisting of a decrease from baseline in Partial Mayo score ≥2 points and ≥30% from baseline plus a decrease in RBS≥1 or an absolute RBS≤1 over time within 16 weeks, within 12 weeks, within 8 weeks, within 4 weeks or within 2 weeks of initiating administration of upadacitinib, or a pharmaceutically acceptable salt or solid state form thereof; an endoscopic remission within 16 weeks, within 12 weeks, within 8 weeks, or within 4 weeks of initiating administration of upadacitinib, or a pharmaceutically acceptable salt or solid state form thereof; a clinical response within 16, within 12 weeks, within 8 weeks, or within 4 weeks of initiating administration of upadacitinib, or a pharmaceutically acceptable salt or solid state form thereof; an endoscopic improvement within 16 weeks, within 12 weeks, within 8 weeks, or within 4 weeks of initiating administration of upadacitinib, or a pharmaceutically acceptable salt or solid state form thereof; a Full Mayo score ≤2 with no subscore >1 within 16 weeks, within 12 weeks, within 8 weeks, or within 4 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 16 weeks, within 12 weeks, within 8 weeks, or within 4 weeks of initiating administration of upadacitinib, or a pharmaceutically acceptable salt or solid state form thereof; and combinations thereof. In one such embodiment, the induction phase is 12 weeks, and the additional therapeutic result is selected from the group consisting of a decrease from baseline in Partial Mayo score ≥2 points and ≥30% from baseline plus a decrease in RBS≥1 or an absolute RBS≤1 over time within 12 weeks, within 8 weeks, within 4 weeks, or within 2 weeks of initiating administration of upadacitinib, or a pharmaceutically acceptable salt or solid state form thereof; an endoscopic remission within 12 weeks, within 8 weeks, or within 4 weeks of initiating administration of upadacitinib, or a pharmaceutically acceptable salt or solid state form thereof; a clinical response within 12 weeks, within 8 weeks, or within 4 weeks of initiating administration of upadacitinib, or a pharmaceutically acceptable salt or solid state form thereof; an endoscopic improvement within 12 weeks, within 8 weeks, or within 4 weeks of initiating administration of upadacitinib, or a pharmaceutically acceptable salt or solid state form thereof; a Full Mayo score ≤2 with no subscore >1 within 12 weeks, within 8 weeks, or within 4 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 12 weeks, within 8 weeks, or within 4 weeks of initiating administration of upadacitinib, or a pharmaceutically acceptable salt or solid state form thereof; and combinations thereof. In one such embodiment, the induction phase is 8 weeks, and the additional therapeutic result is selected from the group consisting of a decrease from baseline in Partial Mayo score ≥2 points and ≥30% from baseline plus a decrease in RBS≥1 or an absolute RBS≤1 over time within 48 weeks, 8 weeks, within 4 weeks, or within 2 weeks of initiating administration of upadacitinib, or a pharmaceutically acceptable salt or solid state form thereof; an endoscopic remission within 8 weeks or within 4 weeks of initiating administration of upadacitinib, or a pharmaceutically acceptable salt or solid state form thereof; a clinical response within 8 weeks or within 4 weeks of initiating administration of upadacitinib, or a pharmaceutically acceptable salt or solid state form thereof; an endoscopic improvement within 8 weeks or within 4 weeks of initiating administration of upadacitinib, or a pharmaceutically acceptable salt or solid state form thereof; a Full Mayo score ≤2 with no subscore >1 within 8 weeks or within 4 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 8 weeks or within 4 weeks of initiating administration of upadacitinib, or a pharmaceutically acceptable salt or solid state form thereof; and combinations thereof.

In one embodiment, the patient achieves clinical remission within 16 weeks, or within 12 weeks, or within 8 weeks, or within 4 weeks of initiating administration of upadacitinib, or a pharmaceutically acceptable salt or solid state form thereof. In one such embodiment, the patient is one who was taking corticosteroids at baseline but who discontinued corticosteroid use during treatment with the JAK1 inhibitor.

In one embodiment, the additional therapeutic result may be a Full Mayo score ≤2 with no subscore >1 within 16 weeks, or within 12 weeks, or within 8 weeks, or within 4 weeks of initiating administration of upadacitinib, or a pharmaceutically acceptable salt or solid state form thereof. In one such embodiment, the patient is one who was taking corticosteroids at baseline but who discontinued corticosteroid use during treatment with the JAK1 inhibitor. In another embodiment, the additional therapeutic result may be selected from the group consisting of an endoscopic remission within 16 weeks, within 12 weeks, within 8 weeks, or within 4 weeks of initiating administration of upadacitinib, or a pharmaceutically acceptable salt or solid state form thereof; a clinical response within 16 weeks, or 12 weeks, or 8 weeks, or 4 weeks of initiating administration of upadacitinib, or a pharmaceutically acceptable salt or solid state form thereof; a decrease from baseline in Partial Mayo score ≥2 points and ≥30% from baseline, plus a decrease in RBS≥1 or an absolute RBS≤1 over time within 16 weeks, or 12 weeks, or 8 weeks, or 4 weeks, or 2 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 16 weeks, or 12 weeks, or 8 weeks, or 4 weeks of initiating administration of upadacitinib, or a pharmaceutically acceptable salt or solid state form thereof; and an endoscopic improvement within 16 weeks, or 12 weeks, or 8 weeks, or 4 weeks of initiating administration of upadacitinib, or a pharmaceutically acceptable salt or solid state form thereof; and combinations thereof. In one such embodiment, the patient is one who was taking corticosteroids at baseline but who discontinued corticosteroid use during treatment with the JAK1 inhibitor.

In one embodiment, the additional therapeutic result may be an Adapted Mayo score (defined as SFS $\lesssim$ 1, RBS of 0, and endoscopy subscore $\lesssim$ 1) at 16 weeks, or within 12 weeks, or within 8 weeks of initiating administration of upadacitinib, or a pharmaceutically acceptable salt or solid state form thereof. In one such embodiment, the patient is one who was taking corticosteroids at baseline but who discontinued corticosteroid use during treatment with the JAK1 inhibitor. In another embodiment, the additional therapeutic result may be selected from the group consisting of an endoscopic remission within 16 weeks, within 12 weeks, or within 8 weeks of initiating administration of upadacitinib, or a pharmaceutically acceptable salt or solid state form thereof; a clinical response within 16 weeks, or 12 weeks, or 8 weeks of initiating administration of upadacitinib, or a pharmaceutically acceptable salt or solid state form thereof; a decrease from baseline in Partial Mayo score $\geqslant$ 2 points and $\geqslant$ 30% from baseline, plus a decrease in RBS $\geqslant$ 1 or an absolute RBS $\lesssim$ 1 over time within 16 weeks, or 12 weeks, or 8 weeks of initiating administration of upadacitinib, or a pharmaceutically acceptable salt or solid state form thereof; a decrease from baseline in Full Mayo score $\geqslant$ 3 points and $\geqslant$ 30% accompanied by a decrease in RBS of $\geqslant$ 1 or an absolute RBS of 0 or 1 within 16 weeks, or 12 weeks, or 8 weeks, or 4 weeks of initiating administration of upadacitinib, or a pharmaceutically acceptable salt or solid state form thereof; and an endoscopic improvement within 16 weeks, or 12 weeks, or 8 weeks, or 4 weeks of initiating administration of upadacitinib, or a pharmaceutically acceptable salt or solid state form thereof; and combinations thereof. In one such embodiment, the patient is one who was taking corticosteroids at baseline but who discontinued corticosteroid use during treatment with the JAK1 inhibitor.

In one particular embodiment, the induction phase is 8 weeks, and the patient achieves a clinical remission (SF subscore ≤1, RBS of 0 and endoscopic subscore ≤1) within 8 weeks of initiating administration of upadacitinib, or a pharmaceutically acceptable salt or solid state form thereof and an endoscopic improvement (i.e., an endoscopic subscore ≤1) within 6 weeks or within 8 weeks of initiating administration of upadacitinib, or a pharmaceutically acceptable salt or solid state form thereof. In another embodiment, the induction phase is 4 weeks, and the patient achieves a clinical remission within 4 weeks of initiating administration of upadacitinib, or a pharmaceutically acceptable salt or solid state form thereof and an endoscopic improvement within 4 weeks of initiating administration of upadacitinib, or a pharmaceutically acceptable salt or solid state form thereof.

In one particular embodiment, the induction phase is 8 weeks, and the patient achieves a clinical remission within 8 weeks of initiating administration of upadacitinib, or a pharmaceutically acceptable salt or solid state form thereof and further achieves a full Mayo score ≤2, with no subscore >1 within 8 weeks of initiating administration of upadacitinib, or a pharmaceutically acceptable salt or solid state form thereof; an endoscopic improvement (i.e., an endoscopic subscore ≤1) within 6 weeks or within 8 weeks of initiating administration of upadacitinib, or a pharmaceutically acceptable salt or solid state form thereof; or combinations thereof. In another embodiment, the induction phase is 4 weeks, and the patient achieves a clinical remission within 4 weeks of initiating administration of upadacitinib, or a pharmaceutically acceptable salt or solid state form thereof and further achieves a full Mayo score ≤2, with no subscore >1 within 4 weeks of initiating administration of upadacitinib, or a pharmaceutically acceptable salt or solid state form thereof; an endoscopic improvement within 4 weeks of initiating administration of upadacitinib, or a pharmaceutically acceptable salt or solid state form thereof; or combinations thereof.

In one embodiment, the patient is administered upadacitinib, or a pharmaceutically acceptable salt or solid state form thereof, for at least 52 weeks. The administration of upadacitinib, or a pharmaceutically acceptable salt or solid state form thereof, may include an induction phase (e.g., an induction phase of up to 16 weeks), and additional weeks (e.g., 36 weeks or longer) of a maintenance phase (discussed hereinafter). In other embodiments, the administration of upadacitinib, or a pharmaceutically acceptable salt or solid state form thereof, may include a shorter induction phase (e.g., up to 4 weeks, 6 weeks, 8 weeks, 10 weeks, 12 weeks, etc.), and a longer maintenance phase (e.g., a 12 week induction phase and a 40 week or longer maintenance phase).

In one embodiment, the induction phase is 8 weeks and the maintenance phase is 44 weeks. In some such embodiments, the patient may achieve at least one therapeutic result selected from the group consisting of: clinical remission within 52 weeks of initiating administration of upadacitinib, or a pharmaceutically acceptable salt or solid state form thereof; endoscopic remission within 52 weeks of initiating administration of upadacitinib, or a pharmaceutically acceptable salt or solid state form thereof; full Mayo score ≤2, with no subscore >1 within 52 weeks of initiating administration of upadacitinib, or a pharmaceutically acceptable salt or solid state form thereof; clinical response within 52 weeks of initiating administration of upadacitinib, or a pharmaceutically acceptable salt or solid state form thereof; endoscopic improvement within 52 weeks of initiating administration of upadacitinib, or a pharmaceutically acceptable salt or solid state form thereof; decrease from baseline in Partial Mayo score ≥2 points and ≥30% from baseline, plus a decrease in RBS≥1 or an absolute RBS≤1 over time within 52 weeks of initiating administration of upadacitinib, or a pharmaceutically acceptable salt or solid state form thereof; a decrease from baseline in Full Mayo score ≥3 points and ≥30% accompanied by a decrease in RBS of ≥1 or an absolute RBS of 0 or 1 within 52 weeks of initiating administration of upadacitinib, or a pharmaceutically acceptable salt or solid state form thereof; histologic improvement within 52 weeks of initiating administration of upadacitinib, or a pharmaceutically acceptable salt or solid state form thereof; stool frequency subscore ≤1 within 52 weeks of initiating administration of upadacitinib, or a pharmaceutically acceptable salt or solid state form thereof; a RBS of 0 within 52 weeks of initiating administration of upadacitinib, or a pharmaceutically acceptable salt or solid state form thereof; an endoscopic subscore ≤1 within 52 weeks of initiating administration of upadacitinib, or a pharmaceutically acceptable salt or solid state form thereof; a change in IBDQ score from baseline within 52 weeks of initiating administration of upadacitinib, or a pharmaceutically acceptable salt or solid state form thereof; and combinations thereof.

In some embodiment when the patient is administered upadacitinib, or a pharmaceutically acceptable salt or solid state form thereof, for at least 52 weeks, the patient is one who was taking corticosteroids at baseline but who discontinued corticosteroid use during treatment with the JAK1 inhibitor, and the therapeutic result may be selected from the group consisting of clinical remission within 52 weeks of initiating administration of upadacitinib, or a pharmaceutically acceptable salt or solid state form thereof; a endoscopic remission within 52 weeks of initiating administration of upadacitinib, or a pharmaceutically acceptable salt or solid state form thereof; a Full Mayo score ≤2 with no subscore >1 within 52 weeks of initiating administration of upadacitinib, or a pharmaceutically acceptable salt or solid state form thereof; clinical response within 52 weeks of initiating administration of upadacitinib, or a pharmaceutically acceptable salt or solid state form thereof; decrease from baseline in Partial Mayo score ≥2 points and ≥30% from baseline, plus a decrease in RBS≥1 or an absolute RBS≤1 over time within 52 weeks of initiating administration of upadacitinib, or a pharmaceutically acceptable salt or solid state form thereof; decrease from baseline in Full Mayo score ≥3 points and ≥30% accompanied by a decrease in RBS of ≥1 or an absolute RBS of 0 or 1 within 52 weeks of initiating administration of upadacitinib, or a pharmaceutically acceptable salt or solid state form thereof; an endoscopic improvement within 52 weeks of initiating administration of upadacitinib, or a pharmaceutically acceptable salt or solid state form thereof; and combinations thereof.

In one embodiment, in a method of the present disclosure, a patient is evaluated during or at the end of the induction phase for a therapeutic result selected from the group consisting of clinical remission, a Full Mayo score ≤2 with no subscore >1, endoscopic improvement, endoscopic remission, clinical response, decrease from baseline in Full Mayo score ≥3 points and ≥30% accompanied by a decrease in RBS of ≥1 or an absolute RBS of 0 or 1, a decrease from baseline in Partial Mayo score ≥2 points and ≥30% from baseline, plus a decrease in RBS≥1 or an absolute RBS≤1 over time, SF sub score, rectal bleeding subscore, endoscopic subscore, histologic improvement, fecal calprotectin level, hs-CRP, IBDQ score, and combinations thereof. In one embodiment, in a method of the present disclosure, a patient is evaluated for clinical remission during or at the end of the induction phase. In one embodiment, in a method of the present disclosure, a patient is evaluated for endoscopic improvement during or at the end of the induction phase. In one embodiment, in a method of the present disclosure, a patient is evaluated for achievement of Full Mayo score ≤2 with no subscore >1 during or at the end of the induction phase. In one embodiment, in a method of the present disclosure, a patient is evaluated for endoscopic remission during or at the end of the induction phase. In one embodiment, in a method of the present disclosure, a patient is evaluated for clinical response during or at the end of the induction phase. In one embodiment, in a method of the present disclosure, a patient is evaluated for decrease from baseline in Partial Mayo score ≥2 points and ≥30% from baseline, plus a decrease in RBS≥1 or an absolute RBS≤1 over time during or at the end of the induction phase. In one embodiment, in a method of the present disclosure, a patient is evaluated for change in Full Mayo score from baseline during or at the end of the induction phase. In one embodiment, in a method of the present disclosure, a patient is evaluated for histologic improvement during or at the end of the induction phase. In one embodiment, the induction phase is 2 weeks. In one embodiment, the induction phase is 8 weeks. In one embodiment, the induction phase is 12 weeks.

In one embodiment, in a method of the present disclosure, a patient is evaluated during or at the end of the maintenance phase for a therapeutic result selected from the group consisting of endoscopic improvement, achievement of Full Mayo score ≤2 with no subscore >1, discontinuation of corticosteroid use and clinical remission per Adapted Mayo score, maintenance of clinical remission among subjects who achieved clinical remission during the induction phase, endoscopic improvement among subjects who achieved clinical remission during the induction phase, clinical response, endoscopic remission, histologic improvement, and combinations thereof.

In one embodiment, in a method of the present disclosure, a patient is evaluated for a therapeutic result by being corticosteroid-free for 44 weeks after discontinuing corticosteroids. In one embodiment, in a method of the present disclosure, a patient is evaluated for a therapeutic result by achieving clinical remission 4 weeks after initial administration of upadacitinib or a pharmaceutically acceptable salt or solid state form thereof. In one embodiment, in a method of the present disclosure, a patient is evaluated for a therapeutic result by achieving clinical remission 8 weeks after initial administration of upadacitinib or a pharmaceutically acceptable salt or solid state form thereof. In one embodiment, in a method of the present disclosure, a patient is evaluated for a therapeutic result by achieving clinical remission 12 weeks after initial administration of upadacitinib or a pharmaceutically acceptable salt or solid state form thereof. In one embodiment, in a method of the present disclosure, a patient is evaluated for a therapeutic result by achieving Full Mayo score ≤2 with no subscore >1 within 52 weeks after initial administration of upadacitinib or a pharmaceutically acceptable salt or solid state form thereof. In one embodiment, in a method of the present disclosure, a patient is evaluated for a therapeutic result by achieving clinical remission defined as stool frequency subscore ≤1, rectal bleeding subscore of 0, and endoscopic subscore ≤1 with absence of friability within 52 weeks after initial administration of upadacitinib or a pharmaceutically acceptable salt or solid state form thereof. In one embodiment, in a method of the present disclosure, a patient is evaluated for a therapeutic result by achieving a SF subscore of 0, a RBS of 0, and endoscopic subscore of 0. In one embodiment, in a method of the present disclosure, a patient is evaluated for a therapeutic result by achieving a decrease from baseline in Partial Mayo score ≥2 points and ≥30% from baseline, plus a decrease in RBS≥1 or an absolute RBS≤1 over time within 2 weeks after initial administration of upadacitinib or a pharmaceutically acceptable salt or solid state form thereof. In one embodiment, in a method of the present disclosure, a patient is evaluated for a therapeutic result by achieving a decrease from baseline in Partial Mayo score ≥2 points and ≥30% from baseline, plus a decrease in RBS≥1 or an absolute RBS≤1 over time within 4 weeks after initial administration of upadacitinib or a pharmaceutically acceptable salt or solid state form thereof. In one embodiment, in a method of the present disclosure, a patient is evaluated for a therapeutic result by achieving a decrease from baseline in Partial Mayo score ≥2 points and ≥30% from baseline, plus a decrease in RBS≥1 or an absolute RBS≤1 over time within 12 weeks after initial administration of upadacitinib or a pharmaceutically acceptable salt or solid state form thereof. In one embodiment, in a method of the present disclosure, a patient is evaluated for a therapeutic result by achieving clinical response or a decrease from baseline in Full Mayo score ≥3 points and ≥30% accompanied by a decrease in RBS of ≥1 or an absolute RBS of 0 or 1. In one embodiment, in a method of the present disclosure, a patient is evaluated for a therapeutic result by achieving a decrease from baseline in Partial Mayo score ≥2 points and ≥30% from baseline, plus a decrease in RBS≥1 or an absolute RBS≤1 over time within 2 weeks after initial administration of upadacitinib or a pharmaceutically acceptable salt or solid state form thereof. In one embodiment, in a method of the present disclosure, a patient is evaluated for a therapeutic result by achieving clinical response or a decrease from baseline in Full Mayo score ≥3 points and ≥30% accompanied by a decrease in RBS of ≥1 or an absolute RBS of 0 or 1. In one embodiment, in a method of the present disclosure, a patient is evaluated for a therapeutic result by achieving a decrease from baseline in Partial Mayo score ≥2 points and ≥30% from baseline, plus a decrease in RBS≥1 or an absolute RBS≤1 over time within 4 weeks after initial administration of upadacitinib or a pharmaceutically acceptable salt or solid state form thereof. In one embodiment, in a method of the present disclosure, a patient is evaluated for a therapeutic result by achieving clinical response or a decrease from baseline in Full Mayo score ≥3 points and ≥30% accompanied by a decrease in RBS of ≥1 or an absolute RBS of 0 or 1. In one embodiment, in a method of the present disclosure, a patient is evaluated for a therapeutic result by achieving a decrease from baseline in Partial Mayo score ≥2 points and ≥30% from baseline, plus a decrease in RBS≥1 or an absolute RBS≤1 over time within 12 weeks after initial administration of upadacitinib or a pharmaceutically acceptable salt or solid state form thereof. In one embodiment, in a method of the present disclosure, a patient is evaluated for a therapeutic result by achieving stool frequency subscore ≤1 within 2 weeks after initial administration of upadacitinib or a pharmaceutically acceptable salt or solid state form thereof. In one embodiment, in a method of the present disclosure, a patient is evaluated for a therapeutic result by achieving stool frequency subscore ≤1 within 4 weeks after initial administration of upadacitinib or a pharmaceutically acceptable salt or solid state form thereof. In one embodiment, in a method of the present disclosure, a patient is evaluated for a therapeutic result by achieving stool frequency subscore ≤1 within 12 weeks after initial administration of upadacitinib or a pharmaceutically acceptable salt or solid state form thereof. In one embodiment, in a method of the present disclosure, a patient is evaluated for a therapeutic result by achieving rectal bleeding subscore of 0 over time. In one embodiment, in a method of the present disclosure, a patient is evaluated for a therapeutic result by achieving an endoscopic subscore of ≤1 within 12 weeks after initial administration of upadacitinib or a pharmaceutically acceptable salt or solid state form thereof. In one embodiment, in a method of the present disclosure, a patient is evaluated for a therapeutic result by achieving an endoscopic improvement within 12 weeks after initial administration of upadacitinib or a pharmaceutically acceptable salt or solid state form thereof. In one embodiment, in a method of the present disclosure, a patient is evaluated for a therapeutic result by achieving fecal calprotectin below 150 mg/kg within 4 weeks after initial administration of upadacitinib or a pharmaceutically acceptable salt or solid state form thereof. In one embodiment, in a method of the present disclosure, a patient is evaluated for a therapeutic result by achieving fecal calprotectin below 150 mg/kg within 8 weeks after initial administration of upadacitinib or a pharmaceutically acceptable salt or solid state form thereof. In one embodiment, in a method of the present disclosure, a patient is evaluated for a therapeutic result by achieving fecal calprotectin below 150 mg/kg within 12 weeks after initial administration of upadacitinib or a pharmaceutically acceptable salt or solid state form thereof. In one embodiment, in a method of the present disclosure, a patient is evaluated for a therapeutic result by achieving an IBDQ response (increase of IBDQ≥16 from Baseline) within 2 weeks after initial administration of upadacitinib or a pharmaceutically acceptable salt or solid state form thereof. In one embodiment, in a method of the present disclosure, a patient is evaluated for a therapeutic result by achieving an IBDQ response (increase of IBDQ≥16 from Baseline) within 8 weeks after initial administration of upadacitinib or a pharmaceutically acceptable salt or solid state form thereof. In one embodiment, in a method of the present disclosure, a patient is evaluated for a therapeutic result by achieving an IBDQ response (increase of IBDQ≥16 from Baseline) within 12 weeks after initial administration of upadacitinib or a pharmaceutically acceptable salt or solid state form thereof. In one embodiment, in a method of the present disclosure, a patient is evaluated for a therapeutic result by achieving a change from Baseline in hs-CRP within 2 weeks after initial administration of upadacitinib or a pharmaceutically acceptable salt or solid state form thereof. In one embodiment, in a method of the present disclosure, a patient is evaluated for a therapeutic result by achieving a change from Baseline in hs-CRP within 8 weeks after initial administration of upadacitinib or a pharmaceutically acceptable salt or solid state form thereof. In one embodiment, in a method of the present disclosure, a patient is evaluated for a therapeutic result by achieving a change from Baseline in hs-CRP within 12 weeks after initial administration of upadacitinib or a pharmaceutically acceptable salt or solid state form thereof. In one embodiment, in a method of the present disclosure, a patient is evaluated for a therapeutic result by achieving a change in Baseline in fecal calprotectin within 8 weeks after initial administration of upadacitinib or a pharmaceutically acceptable salt or solid state form thereof. In one embodiment, in a method of the present disclosure, a patient is evaluated for a therapeutic result by achieving a change in Baseline in fecal calprotectin within 12 weeks after initial administration of upadacitinib or a pharmaceutically acceptable salt or solid state form thereof. In one embodiment, in a method of the present disclosure, a patient is evaluated for a therapeutic result by achieving a change in corticosteroid dose within 12 weeks after initial administration of upadacitinib or a pharmaceutically acceptable salt or solid state form thereof. In one embodiment, in a method of the present disclosure, a patient is evaluated for a therapeutic result by change from Baseline in Adapted Mayo score, Full Mayo score, Partial Mayo score and/or Mayo subscores within 12 weeks after initial administration of upadacitinib or a pharmaceutically acceptable salt or solid state form thereof. In one embodiment, in a method of the present disclosure, a patient is evaluated for a therapeutic result by change form Baseline in UCEIS scores within 12 weeks after initial administration of upadacitinib or a pharmaceutically acceptable salt or solid state form thereof. In one embodiment, in a method of the present disclosure, a patient is evaluated for a therapeutic result by achieving histologic remission (defined as Geboes score <2) within 8 weeks after initial administration of upadacitinib or a pharmaceutically acceptable salt or solid state form thereof. In one embodiment, in a method of the present disclosure, a patient is evaluated for a therapeutic result by achieving histologic remission (defined as Geboes score <2) within 12 weeks after initial administration of upadacitinib or a pharmaceutically acceptable salt or solid state form thereof. In one embodiment, in a method of the present disclosure, a patient is evaluated for a therapeutic result by change from Baseline in histologic score within 8 weeks after initial administration of upadacitinib or a pharmaceutically acceptable salt or solid state form thereof. In one embodiment, in a method of the present disclosure, a patient is evaluated for a therapeutic result by change from Baseline in histologic score within 8 weeks after initial administration of upadacitinib or a pharmaceutically acceptable salt or solid state form thereof. In one embodiment, in a method of the present disclosure, a patient is evaluated for a therapeutic result by change from Baseline in laboratory and nutritional parameters (e.g., hemoglobin, hematocrit, albumin, total protein concentration, and weight) within 8 weeks after initial administration of upadacitinib or a pharmaceutically acceptable salt or solid state form thereof. In one embodiment, in a method of the present disclosure, a patient is evaluated for a therapeutic result by change from Baseline in laboratory and nutritional parameters (e.g., hemoglobin, hematocrit, albumin, total protein concentration, and weight) within 12 weeks after initial administration of upadacitinib or a pharmaceutically acceptable salt or solid state form thereof. In one embodiment, in a method of the present disclosure, a patient is evaluated for a therapeutic result by change in Baseline in subject-reported stool frequency (absolute values) within 8 weeks after initial administration of upadacitinib or a pharmaceutically acceptable salt or solid state form thereof. In one embodiment, in a method of the present disclosure, a patient is evaluated for a therapeutic result by change in Baseline in subject-reported stool frequency (absolute values) within 12 weeks after initial administration of upadacitinib or a pharmaceutically acceptable salt or solid state form thereof. In one embodiment, in a method of the present disclosure, a patient is evaluated for a therapeutic result by change from Baseline in IBDQ score within 8 weeks after initial administration of upadacitinib or a pharmaceutically acceptable salt or solid state form thereof. In one embodiment, in a method of the present disclosure, a patient is evaluated for a therapeutic result by change from Baseline in IBDQ score within 12 weeks after initial administration of upadacitinib or a pharmaceutically acceptable salt or solid state form thereof. In one embodiment, in a method of the present disclosure, a patient is evaluated for a therapeutic result by change from Baseline in EQ-5D-5L score within 8 weeks after initial administration of upadacitinib or a pharmaceutically acceptable salt or solid state form thereof. In one embodiment, in a method of the present disclosure, a patient is evaluated for a therapeutic result by change from Baseline in EQ-5D-5L score within 12 weeks after initial administration of upadacitinib or a pharmaceutically acceptable salt or solid state form thereof. In one embodiment, in a method of the present disclosure, a patient is evaluated for a therapeutic result by change from Baseline in WPAI:UC scores within 8 weeks after initial administration of upadacitinib or a pharmaceutically acceptable salt or solid state form thereof. In one embodiment, in a method of the present disclosure, a patient is evaluated for a therapeutic result by change from Baseline in WPAI:UC scores within 12 weeks after initial administration of upadacitinib or a pharmaceutically acceptable salt or solid state form thereof. In one embodiment, in a method of the present disclosure, a patient is evaluated for a therapeutic result by change in SF-36, PCT, MCS components and domain scores within 8 weeks after initial administration of upadacitinib or a pharmaceutically acceptable salt or solid state form thereof. In one embodiment, in a method of the present disclosure, a patient is evaluated for a therapeutic result by change in SF-36, PCT, MCS components and domain scores within 12 weeks after initial administration of upadacitinib or a pharmaceutically acceptable salt or solid state form thereof. In one embodiment, in a method of the present disclosure, a patient is evaluated for a therapeutic result by change in PGIC score within 8 weeks after initial administration of upadacitinib or a pharmaceutically acceptable salt or solid state form thereof. In one embodiment, in a method of the present disclosure, a patient is evaluated for a therapeutic result by change in PGIC score within 12 weeks after initial administration of upadacitinib or a pharmaceutically acceptable salt or solid state form thereof. In one embodiment, in a method of the present disclosure, a patient is evaluated for a therapeutic result by change from Baseline in FACIT-F score within 8 weeks after initial administration of upadacitinib or a pharmaceutically acceptable salt or solid state form thereof. In one embodiment, in a method of the present disclosure, a patient is evaluated for a therapeutic result by change from Baseline in FACIT-F score within 12 weeks after initial administration of upadacitinib or a pharmaceutically acceptable salt or solid state form thereof. In one embodiment, in a method of the present disclosure, a patient is evaluated for a therapeutic result by change from Baseline in UC-SQ score within 8 weeks after initial administration of upadacitinib or a pharmaceutically acceptable salt or solid state form thereof. In one embodiment, in a method of the present disclosure, a patient is evaluated for a therapeutic result by change from Baseline in UC-SQ score within 8 weeks after initial administration of upadacitinib or a pharmaceutically acceptable salt or solid state form thereof. In one embodiment, the patient is administered at least 14 doses, 28 doses, or at least 42 doses, or at least 56 doses of upadacitinib, or a pharmaceutically acceptable salt or solid state form thereof, during the induction phase.

In one aspect, a certain therapeutic result is maintained by the patient during the maintenance phase. The maintenance phase may last for an indefinite period of time. In one embodiment, the maintenance phase is at least 36 weeks, including at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks after the patient achieves clinical remission or clinical response after the patient achieves clinical remission or clinical response. In one embodiment, the maintenance phase is at least 40 additional weeks. In one embodiment, the maintenance phase is at least 44 additional weeks after the patient achieves clinical remission or clinical response. In one embodiment, the therapeutic result maintained by the patient during the maintenance phase is selected from the group consisting of clinical remission, a Full Mayo score ≤2 with no subscore >1, endoscopic remission, clinical response, a decrease from baseline in Partial Mayo score ≥2 points and ≥30% from baseline plus a decrease in RBS≥1 or an absolute RBS≤1, a decrease from baseline in Full Mayo score ≥3 points and ≥30% accompanied by a decrease in RBS of ≥1 or an absolute RBS of 0 or 1, endoscopic improvement, and combinations thereof. In one embodiment, the therapeutic result maintained by the patient during the maintenance phase is endoscopic remission. In one embodiment, the therapeutic result maintained by the patient during the maintenance phase is endoscopic response. In one embodiment, the therapeutic result maintained by the patient during the maintenance phase is clinical remission. In one embodiment, the therapeutic result maintained by the patient during the maintenance phase is corticosteroid-free remission.

In one embodiment, in a method of the present disclosure, a patient is evaluated for clinical remission during the maintenance phase. In one embodiment, a patient is evaluated for endoscopic improvement during the maintenance phase. In one embodiment, a patient is evaluated for clinical remission a Full Mayo score ≤2 with no subscore >1 during the maintenance phase. In one embodiment, in a method of the present disclosure, a patient is evaluated for endoscopic remission during the maintenance phase. In one embodiment, in a method of the present disclosure, a patient is evaluated for clinical response, or a decrease from baseline in Partial Mayo score ≥2 points and ≥30% from baseline plus a decrease in RBS≥1 or an absolute RBS≤1, or a decrease from baseline in Full Mayo score ≥3 points and ≥30% accompanied by a decrease in RBS of ≥1 or an absolute RBS of 0 or 1 during the maintenance phase.

In one embodiment, the present disclosure provides a method for treating an inflammatory disease, in one aspect for treating ulcerative colitis, comprising (a) administering to a patient a dose of a JAK1 inhibitor (e.g., upadacitinib or a pharmaceutically acceptable salt or solid state form thereof) at week 0 and once daily (QD) thereafter for 8 weeks, wherein the dose is 45 mg QD. In one embodiment, the method further comprises (b) administering to the patient additional doses once daily thereafter for at least 44 additional weeks, wherein the dose is 15 mg or 30 mg QD. In one embodiment the dose is administered orally.

In one embodiment, 8 weeks after initiating administration of upadacitinib, or a pharmaceutically acceptable salt or solid state form thereof, a patient is evaluated for clinical remission and/or for a Full Mayo score ≤2 with no subscore >1. In one embodiment, 8 weeks after initiating administration of upadacitinib, or a pharmaceutically acceptable salt or solid state form thereof, a patient is evaluated for clinical response and/or for a decrease from baseline in Partial Mayo score ≥2 points and ≥30% from baseline plus a decrease in RBS≥1 or an absolute RBS≤1, and/or for a decrease from baseline in Full Mayo score ≥3 points and ≥30% accompanied by a decrease in RBS of ≥1 or an absolute RBS of 0 or 1 and/or for endoscopic improvement and/or for endoscopic remission. In one embodiment, 6 weeks after initiating administration of upadacitinib, or a pharmaceutically acceptable salt or solid state form thereof, a patient is evaluated for clinical remission and/or a Full Mayo score ≤2 with no subscore >1 and/or for endoscopic remission. In one embodiment, 6 weeks after initiating administration of upadacitinib, or a pharmaceutically acceptable salt or solid state form thereof, a patient is evaluated for a decrease from baseline in Full Mayo score ≥3 points and ≥30% accompanied by a decrease in RBS of ≥1 or an absolute RBS of 0 or 1 and/or clinical response and/or a decrease from baseline in Partial Mayo score ≥2 points and ≥30% from baseline plus a decrease in RBS≥1 or an absolute RBS≤1, and/or for endoscopic improvement. In one embodiment, 4 weeks after initiating administration of upadacitinib, or a pharmaceutically acceptable salt or solid state form thereof, a patient is evaluated for clinical remission and/or for a Full Mayo score ≤2 with no subscore >1 and/or for endoscopic remission. In one embodiment, 4 weeks after initiating administration of upadacitinib, or a pharmaceutically acceptable salt or solid state form thereof, a patient is evaluated for a decrease from baseline in Full Mayo score ≥3 points and ≥30% accompanied by a decrease in RBS of ≥1 or an absolute RBS of 0 or 1 and/or for clinical response and/or for a decrease from baseline in Partial Mayo score ≥2 points and ≥30% from baseline plus a decrease in RBS≥1 or an absolute RBS≤1, and/or for endoscopic improvement. In one embodiment, 2 weeks after initiating administration of upadacitinib, or a pharmaceutically acceptable salt or solid state form thereof, a patient is evaluated for clinical remission and/or for a Full Mayo score ≤2 with no subscore >1 and/or for endoscopic remission. In one embodiment, 2 weeks after initiating administration of upadacitinib, or a pharmaceutically acceptable salt or solid state form thereof, a patient is evaluated for a decrease from baseline in Full Mayo score ≥3 points and ≥30% accompanied by a decrease in RBS of ≥1 or an absolute RBS of 0 or 1 and/or for clinical response and/or for a decrease from baseline in Partial Mayo score ≥2 points and ≥30% from baseline plus a decrease in RBS≥1 or an absolute RBS≤1, and/or for endoscopic improvement.

In one embodiment, 48 weeks after initiating administration of upadacitinib, or a pharmaceutically acceptable salt or solid state form thereof, a patient is evaluated for clinical remission per Adapted Mayo score (defined sa SFS≤1, RBS of 0, and endoscopy subscore ≤1), clinical remission per Full Mayo score (defined as a Full Mayo score ≤2 with no subscore ≥1), clinical remission per Partial mayo score (defined as Partial Mayo score ≤2 with no subscore >1) over time; clinical remission defined as stool frequency subscore ≤1, rRBS of 0 and endoscopic subscore ≤1 with absence of friability and clinical response per Adapted mayo score (defined as decrease from BL in the Adapted Mayo score ≥2 points and ≥30% from BL, plus a decrease in RBS≥1).

In one embodiment, the present disclosure provides a method for treating ulcerative colitis, comprising (a) administering to a patient a dose of a JAK1 inhibitor (e.g., upadacitinib or a pharmaceutically acceptable salt or solid state form thereof) at week 0 and once daily thereafter via an oral route, wherein the doses of the JAK1 inhibitor comprise 15 mg, 30 mg, or 45 mg QD, or any combination thereof.

In one embodiment, the present disclosure provides a method for treating ulcerative colitis, comprising administering to a patient 15 mg to 45 mg of a JAK1 inhibitor. In one embodiment, the present disclosure provides a method for treating ulcerative colitis, comprising administering to a patient orally 15 mg of a JAK1 inhibitor QD. In one embodiment, the present disclosure provides a method for treating ulcerative colitis, comprising administering to a patient orally 30 mg of a JAK1 inhibitor QD. In one embodiment, the present disclosure provides a method for treating ulcerative colitis, comprising administering to a patient orally 45 mg of a JAK1 inhibitor QD. In any such embodiments, the JAK1 inhibitor may be upadacitinib or a pharmaceutically acceptable salt or solid state form thereof. In any such embodiment, the JAK1 inhibitor may be in a once daily modified release formulation. In any such embodiment, the patient may have moderately to severely active ulcerative colitis prior to treatment.

In one embodiment, the administration of a JAK1 inhibitor according to the present disclosure is further described in the Examples herein below or in FIG. 13.

In one embodiment, the present disclosure provides a method for treating ulcerative colitis, said method comprising a) administering at least one induction dose of a JAK1 inhibitor (e.g., upadacitinib or a pharmaceutically acceptable salt or solid state form thereof) to a patient, wherein said induction dose comprises 15 mg to 45 mg of the JAK 1 inhibitor. In one aspect, the induction dose comprises 15 mg or 30 mg or 45 mg. In one aspect, the induction dose comprises 45 mg. In one aspect, the induction dose is administered orally. In one aspect, the induction dose is administered QD. In one aspect, the induction dose is administered for 8 weeks. In one aspect the induction dose is administered for 6 weeks. In one aspect the induction dose is administered for 4 weeks. In one embodiment, the induction dose is administered for up to 12 weeks, including for 2 weeks, 4 weeks, 5 weeks, 6 weeks, 7 weeks, 8 weeks, 9 weeks, 10 weeks, 11 weeks, or 12 weeks.

In one embodiment, the induction dose comprises 45 mg of the JAK1 inhibitor administered QD.

In one embodiment, the induction dose comprises 30 mg of the JAK1 inhibitor administered QD.

In one embodiment, the induction dose comprises 15 mg of the JAK1 inhibitor administered QD.

In one embodiment, the JAK1 inhibitor is upadacitinib or a pharmaceutically acceptable salt or solid state form thereof.

In one embodiment, the induction dose is in a once daily modified release formulation.

In one embodiment, the method further comprises b) administering a first maintenance dose of a JAK1 inhibitor (e.g., upadacitinib, or pharmaceutically acceptable salt or solid state form thereof), to the patient after the last induction dose is administered; and c) administering at least one additional maintenance dose to the patient once daily thereafter.

In one embodiment, the first maintenance dose comprises 15 mg to 30 mg of the JAK1 inhibitor. In one aspect, the first maintenance dose comprises 15 mg or 30 mg of the JAK1 inhibitor. In one aspect, the first maintenance dose is smaller than the induction dose. In one aspect, the first maintenance dose is administered QD. In one aspect the first maintenance dose is 15 mg. In one aspect the first maintenance dose is 30 mg. In one aspect, the first maintenance dose is administered orally. In one aspect, the first maintenance dose is in a once daily modified release formulation.

In one aspect, the at least one additional maintenance dose comprises 15 mg to 30 mg of the JAK 1 inhibitor. In one aspect, the at least one additional maintenance dose comprises 15 mg or 30 mg. In one aspect, the at least one additional maintenance dose is administered orally. In one aspect, the at least one additional maintenance dose is administered QD. In one embodiment, the at least one additional maintenance dose comprises 15 mg of the JAK1 inhibitor administered QD. In one embodiment, the at least one additional maintenance dose comprises 30 mg of the JAK1 inhibitor administered QD. In one aspect, the at least one additional maintenance dose is in a once daily modified release formulation.

In any of the foregoing embodiments, the JAK1 inhibitor may be upadacitinib or a pharmaceutically acceptable salt or solid state form thereof.

In one aspect, in any of the foregoing embodiments, the patient is one who had an inadequate response to or experienced a loss of response to or intolerance to conventional treatment (e.g., aminosalicylate, corticosteroids, immunosuppressants) or to a previous treatment with a biologic agent. In one aspect, in any of the foregoing embodiments, the patient is one who had an inadequate response to, a loss of response to, or experienced intolerance to a previous treatment with an anti-TNF agent.

In one aspect, in any of the foregoing embodiments, the patient is one who is naïve to previous treatment with an aminosalicylate, a corticosteroid, an immunosuppressant, a biologic agent or an anti-TNF agent.

In one aspect, in any of the foregoing embodiments, the patient is one who had moderately to severely active ulcerative colitis prior to treatment or administration of the induction dose.

In one embodiment, the present disclosure further provides a method for inducing clinical remission of ulcerative colitis or a Full Mayo score of ≤2 with no subscore >1 in a patient, said method comprising a) administering to the patient at least one induction dose of a JAK1 inhibitor as described above or herein (e.g., upadacitinib or a pharmaceutically acceptable salt or solid state form thereof). In one embodiment, the induction dose comprises 30 mg to 45 mg of upadacitinib, or a pharmaceutically acceptable salt or solid state form thereof. In one embodiment, an induction dose is administered at week 0 and once daily (QD) thereafter for up to 12 weeks (e.g., for 4 weeks, 5 weeks, 6 weeks, 7 weeks, or 8 weeks, or 9 weeks, or 10 weeks, or 11 weeks, or 12 weeks), wherein the dose is 30 mg QD or 45 mg QD. In one embodiment, the method further comprises maintaining clinical remission of ulcerative colitis or a Full Mayo score of ≤2 with no subscore >1, said method further comprising b) administering a first maintenance dose of said JAK1 inhibitor to the patient after the last induction dose is administered and c) administering at least one additional maintenance dose to the patient thereafter as described above or herein. In one embodiment, the at least one additional maintenance dose is administered once daily. In one embodiment, the additional maintenance doses are administered once daily for at least 36 additional weeks, including for at least 36 weeks, at least 37 weeks, at least 38 weeks, at least 39 weeks, at least 40 weeks, at least 41 weeks, at least 42 weeks, at least 43 weeks, at least 44 weeks, at least 56 weeks, at least 112 weeks, at least 308 weeks, or at least 420 weeks. In one embodiment, the additional maintenance doses are administered once daily for at least 44 additional weeks. In one embodiment, the maintenance dose is 15 mg or 30 mg QD. In one embodiment the induction and maintenance doses are administered orally. In one embodiment, the patient has active ulcerative colitis with an Adapted Mayo score of 5 to 9 points and endoscopy subscore of 2 or 3 before administration of the first induction dose. In one embodiment, the patient has moderately to severely active ulcerative colitis prior to administration of the first induction dose. In one embodiment, the patient has had an inadequate response to or experienced intolerance to conventional treatment (e.g., aminosalicylates, corticosteroids, immunosuppressants) or to a previous treatment with a biologic agent and/or an anti-TNF agent. In one embodiment, the patient is naïve to previous treatment with aminosalicylates, a corticosteroid, an immunosuppressant, a biologic agent, and/or an anti-TNF agent. In one embodiment, the clinical remission or Full Mayo score of ≤2 with no subscore >1 is achieved within 4 weeks or within 8 weeks of initiating administration of upadacitinib, or a pharmaceutically acceptable salt or solid state form thereof. In one embodiment, the clinical remission or a Full Mayo score of ≤2 with no subscore >1 is achieved within 12 weeks of initiating administration of upadacitinib, or a pharmaceutically acceptable salt or solid state form thereof. In one embodiment, the clinical remission or Full Mayo score of ≤2 with no subscore >1 is achieved within 10 weeks of initiating administration of upadacitinib, or a pharmaceutically acceptable salt or solid state form thereof. In one embodiment, the clinical remission or Full Mayo score of ≤2 with no subscore >1 is achieved within 8 weeks of initiating administration of upadacitinib, or a pharmaceutically acceptable salt or solid state form thereof. In one embodiment, the patient achieves a stool frequency subscore ≤1, RBS of 0 and endoscopic subscore ≤1 before administration of the first maintenance dose. In one embodiment, the patient achieves a full Mayo score of ≤2 with no subscore >1 before administration of the first maintenance dose. In one embodiment, the induction and maintenance doses are in once-daily, modified release formulations.

In one embodiment, the present disclosure provides a method for inducing endoscopic remission of ulcerative colitis, the method comprising (a) administering to a patient at least one induction dose of a JAK1 inhibitor (e.g., upadacitinib or a pharmaceutically acceptable salt or solid state form thereof), wherein the induction dose comprises 30 to 45 mg of upadacitinib, or a pharmaceutically acceptable salt or solid state form thereof. In one embodiment, an induction dose is administered at week 0 and once daily (QD) thereafter for up to 12 weeks (e.g., for 4 weeks, 5 weeks, 6 weeks, 7 weeks, or 8 weeks, or 9 weeks, or 10 weeks, or 11 weeks, or 12 weeks), wherein the dose is 30 mg QD or 45 mg QD. In one embodiment, the method further comprises maintaining endoscopic remission of ulcerative colitis, said method further comprising (b) administering to the patient a first maintenance dose of upadacitinib, or a pharmaceutically acceptable salt or solid state form thereof, after the last induction dose is administered, and (c) administering at least one additional maintenance dose once daily thereafter as described above or herein. In one embodiment, the at least one additional maintenance dose is administered once daily. In one embodiment, the additional maintenance doses are administered once daily for at least 36 additional weeks, including for at least 36 weeks, at least 37 weeks, at least 38 weeks, at least 39 weeks, at least 40 weeks, at least 41 weeks, at least 42 weeks, at least 43 weeks, at least 44 weeks, at least 56 weeks, at least 112 weeks, at least 308 weeks, or at least 420 weeks. In one embodiment, the additional maintenance doses are administered once daily for at least 44 additional weeks. In one embodiment, the maintenance dose is 15 mg or 30 mg QD. In one embodiment the induction and maintenance doses are administered orally. In one embodiment, the patient has active ulcerative colitis with an Adapted Mayo score of 5 to 9 points and an endoscopy subscore of 2 or 3 before administration of the first induction dose. In one embodiment, the patient has moderately to severely active ulcerative colitis prior to administration of the first induction dose. In one embodiment, the patient has had an inadequate response to or experienced intolerance to conventional treatment (e.g., aminosalicylates, corticosteroids, immunosuppressants) or to a previous treatment with a biologic and/or an anti-TNF agent. In one embodiment, the patient is naïve to previous treatment with an aminosalicylate, a corticosteroid, an immunosuppressant, an anti-TNF agent and/or a biologic agent. In one embodiment, the endoscopic remission is achieved within 4 weeks or within 8 weeks of initiating administration of upadacitinib, or a pharmaceutically acceptable salt or solid state form thereof. In one embodiment, the endoscopic remission is achieved within 12 weeks of initiating administration of upadacitinib, or a pharmaceutically acceptable salt or solid state form thereof. In one embodiment, the endoscopic remission is achieved within 10 weeks of initiating administration of upadacitinib, or a pharmaceutically acceptable salt or solid state form thereof. In one embodiment, the endoscopic remission is achieved within 8 weeks of initiating administration of upadacitinib, or a pharmaceutically acceptable salt or solid state form thereof. In one embodiment, the patient achieves an endoscopic subscore of 0 before administration of the first maintenance dose. In one embodiment, the induction and maintenance doses are in once-daily, modified release formulations.

In one embodiment, the present disclosure further provides a method for inducing clinical response or inducing a decrease from baseline in Full Mayo score ≥3 points and 30% accompanied by a decrease in RBS of ≥1 or an absolute RBS or 0 or 1 or inducing a decrease from baseline in Partial Mayo score ≥2 points and ≥30%, accompanied by a decrease in RBS of ≥1 or an absolute rectal bleeding subscore of ≤1 in an ulcerative colitis in a patient, said method comprising a) administering to the patient at least one induction dose of a JAK1 inhibitor as described above or herein (e.g., upadacitinib or a pharmaceutically acceptable salt or solid state form thereof). In one embodiment, the induction dose comprises 30 mg to 45 mg of upadacitinib, or a pharmaceutically acceptable salt or solid state form thereof. In one embodiment, an induction dose is administered at week 0 and once daily (QD) thereafter for up to 8 weeks (e.g., for 4 weeks, 5 weeks, 6 weeks, 7 weeks, or 8 weeks), wherein the dose is 30 mg QD or 45 mg QD. In one embodiment, the method further comprises maintaining clinical response of ulcerative colitis or maintaining a decrease from baseline in Full Mayo score ≥3 points and ≥30%, accompanied by a decrease in RBS of ≥1 or an absolute RBS or 0 or 1 or maintaining a decrease from baseline in Partial Mayo score ≥2 points and ≥30%, accompanied by a decrease in RBS of ≥1 or an absolute rectal bleeding subscore of ≤1, said method further comprising b) administering a first maintenance dose of said JAK1 inhibitor to the patient after the last induction dose is administered and c) administering at least one additional maintenance dose to the patient thereinafter as described above or herein. In one embodiment, the at least one additional maintenance dose is administered once daily. In one embodiment, the additional maintenance doses are administered once daily for at least 36 additional weeks, including for at least 36 weeks, at least 37 weeks, at least 38 weeks, at least 39 weeks, at least 40 weeks, at least 41 weeks, at least 42 weeks, at least 43 weeks, at least 44 weeks, at least 56 weeks, at least 112 weeks, at least 308 weeks, or at least 420 weeks. In one embodiment, the additional maintenance doses are administered once daily for at least 44 additional weeks. In one embodiment, the maintenance dose is 15 mg or 30 mg QD. In one embodiment the induction and maintenance doses are administered orally. In one embodiment, the patient has active ulcerative colitis with an Adapted Mayo score of 5 to 9 points and an endoscopy subscore of 2 or 3 before administration of the first induction dose. In one embodiment, the patient has moderately to severely active ulcerative colitis prior to administration of the first induction dose. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with aminosalicylates, a corticosteroid, an immunosuppressant, a biologic agent and/or an anti-TNF agent. In one embodiment, the clinical response or the decrease from baseline in Full Mayo score ≥3 points and ≥30%, accompanied by a decrease in RBS of ≥1 or an absolute RBS or 0 or 1 or the decrease from baseline in Partial Mayo score ≥ 2 points and ≥ 30%, accompanied by a decrease in RBS of ≥ 1 or an absolute rectal bleeding subscore of ≤1 is achieved within 4 weeks or within 8 weeks of initiating administration of upadacitinib, or a pharmaceutically acceptable salt or solid state form thereof. In one embodiment, the clinical response or the decrease from baseline in Full Mayo score ≥3 points and ≥30%, accompanied by a decrease in RBS of ≥1 or an absolute RBS or 0 or 1 is achieved within 12 weeks of initiating administration of upadacitinib, or a pharmaceutically acceptable salt or solid state form thereof. In one embodiment, the clinical response or the decrease from baseline in Full Mayo score ≥3 points and ≥30%, accompanied by a decrease in RBS of ≥1 or an absolute RBS or 0 or 1 or the decrease from baseline in Partial Mayo score ≥ 2 points and ≥ 30%, accompanied by a decrease in RBS of ≥ 1 or an absolute rectal bleeding subscore of ≤1 is achieved within 10 weeks of initiating administration of upadacitinib, or a pharmaceutically acceptable salt or solid state form thereof. In one embodiment, the clinical response, or the decrease from baseline in Full Mayo score ≥3 points and ≥30%, accompanied by a decrease in RBS of ≥1 or an absolute RBS or 0 or 1 or the decrease from baseline in Partial Mayo score ≥ 2 points and ≥ 30%, accompanied by a decrease in RBS of ≥ 1 or an absolute rectal bleeding subscore of ≤1 is achieved within 8 weeks of initiating administration of upadacitinib, or a pharmaceutically acceptable salt or solid state form thereof. In one embodiment, the patient achieves a decrease from baseline in Adapted Mayo score ≥ 2 points and ≥ 30%, accompanied by a decrease in RBS of ≥ 1 or an absolute rectal bleeding subscore of 0 or 1 before administration of the first maintenance dose. In one embodiment, the patient achieves a decrease from baseline in Partial Mayo score ≥ 2 points and ≥ 30%, accompanied by a decrease in RBS of ≥ 1 or an absolute rectal bleeding subscore of ≤1 before administration of the first maintenance dose. In one embodiment, the patient achieves a decrease from baseline in Full Mayo score ≥ 3 points and ≥ 30%, accompanied by a decrease in RBS from baseline of ≥ 1 or an absolute rectal bleeding subscore of 0 or 1 before administration of the first maintenance dose. In one embodiment, the induction and maintenance doses are in once-daily, modified release formulations.

In one embodiment, the present disclosure further provides a method for inducing endoscopic improvement of ulcerative colitis in a patient, said method comprising a) administering to the patient at least one induction dose of a JAK1 inhibitor as described above or herein (e.g., upadacitinib or a pharmaceutically acceptable salt or solid state form thereof). In one embodiment, the induction dose comprises 30 to 45 mg of upadacitinib, or a pharmaceutically acceptable salt or solid state form thereof. In one embodiment, an induction dose is administered at week 0 and once daily (QD) thereafter for up to 12 weeks (e.g., for 4 weeks, 5 weeks, 6 weeks, 7 weeks, 8 weeks, 9 weeks, 10 weeks, 11 weeks or 12 weeks) wherein the dose is 30 mg QD or 45 mg QD. In one embodiment, the method further comprises maintaining endoscopic improvement of ulcerative colitis, said method further comprising b) administering a first maintenance dose of said JAK1 inhibitor to the patient after the last induction dose is administered and c) administering at least one additional maintenance dose to the patient thereinafter as described above or herein. In one embodiment, the at least one additional maintenance dose is administered once daily. In one embodiment, the additional maintenance doses are administered once daily for at least 36 additional weeks, including for at least 36 weeks, at least 37 weeks, at least 38 weeks, at least 39 weeks, at least 40 weeks, at least 41 weeks, at least 42 weeks, at least 43 weeks, at least 44 weeks, at least 56 weeks, at least 112 weeks, at least 308 weeks, or at least 420 weeks. In one embodiment, the additional maintenance doses are administered once daily for at least 44 additional weeks. In one embodiment, the maintenance dose is 15 mg or 30 mg QD. In one embodiment the induction and maintenance doses are administered orally. In one embodiment, the patient has active ulcerative colitis with an Adapted Mayo score of 5 to 9 points and an endoscopy subscore of 2 or 3 before administration of the first induction dose. In one embodiment, the patient has moderately to severely active ulcerative colitis prior to administration of the first induction dose. In one embodiment, the patient has had an inadequate response to or experienced intolerance to a conventional treatment (e.g., aminosalicylate, corticosteroids, and immunosuppressants) or to a previous treatment with a biologic agent and/or an anti-TNF agent. In one embodiment, the patient is naïve to previous treatment with an aminosalicylate a corticosteroid, an immunosuppressant, a biologic agent and/or an anti-TNF agent. In one embodiment, the endoscopic improvement is achieved within 8 weeks or within 16 weeks of initiating administration of upadacitinib, or a pharmaceutically acceptable salt or solid state form thereof. In one embodiment, the endoscopic improvement is achieved within 12 weeks of initiating administration of upadacitinib, or a pharmaceutically acceptable salt or solid state form thereof. In one embodiment, the endoscopic improvement is achieved within 10 weeks of initiating administration of upadacitinib, or a pharmaceutically acceptable salt or solid state form thereof. In one embodiment, the endoscopic improvement is achieved within 8 weeks of initiating administration of upadacitinib, or a pharmaceutically acceptable salt or solid state form thereof. In one embodiment, the patient achieves an endoscopic subscore ≤1 before administration of the first maintenance dose. In one embodiment, the induction and maintenance doses are in once-daily, modified release formulations.

In one embodiment, the present disclosure further provides a method of maintaining clinical remission or a method of maintaining a Full Mayo score ≤2 with no subscore ≥1 of ulcerative colitis in a patient, said method comprising administering 15 mg or 30 mg of upadacitinib or a pharmaceutically acceptable salt or solid state form thereof to the patient. In one embodiment, the upadacitinib or a pharmaceutically acceptable salt or solid state form thereof is administered once daily for at least 36 weeks, including for at least 37 weeks, at least 38 weeks, at least 39 weeks, at least 40 weeks, at least 41 weeks, at least 42 weeks, at least 43 weeks, or at least 44 weeks. In one embodiment the upadacitinib or a pharmaceutically acceptable salt or solid state form thereof is administered orally. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with aminosalicylates, a corticosteroid, an immunosuppressant, a biologic agent and/or an anti-TNF agent. In one embodiment, the patient is a refractory patient. In one embodiment, the upadacitinib or a pharmaceutically acceptable salt or solid state form thereof is a in once-daily, modified release formulation.

In one embodiment, the present disclosure further provides a method of maintaining clinical response or a method of maintaining a decrease from baseline in Full Mayo score ≥3 points and ≥30%, accompanied by a decrease in RBS of ≥1 or an absolute RBS or 0 or 1 or a method of maintaining a decrease from baseline in Partial Mayo score ⩾ 2 points and ⩾ 30%, accompanied by a decrease in RBS of ⩾ 1 or an absolute rectal bleeding subscore of ≤1 in a patient, said method comprising administering 15 mg or 30 mg of upadacitinib or a pharmaceutically acceptable salt or solid state form thereof to the patient. In one embodiment, the upadacitinib or a pharmaceutically acceptable salt or solid state form thereof is administered once daily for at least 36 weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment the upadacitinib or a pharmaceutically acceptable salt or solid state form thereof is administered orally. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with aminosalicylates, a corticosteroid, an immunosuppressant, a biologic agent and/or an anti-TNF agent. In one embodiment, the patient is a refractory patient. In one embodiment, the upadacitinib or a pharmaceutically acceptable salt or solid state form thereof is a in once-daily, modified release formulation.

In one embodiment, the present disclosure further provides a method of maintaining endoscopic improvement or endoscopic remission of ulcerative colitis in a patient, said method comprising administering 15 mg or 30 mg of upadacitinib or a pharmaceutically acceptable salt or solid state form thereof to the patient. In one embodiment, the upadacitinib or a pharmaceutically acceptable salt or solid state form thereof is administered once daily for at least 36 weeks, including for at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, or at least 48 weeks. In one embodiment the upadacitinib or a pharmaceutically acceptable salt or solid state form thereof is administered orally. In one embodiment, the patient has had an inadequate response to or experienced intolerance to a conventional treatment (e.g., aminosalicylates, corticosteroids, immunosuppressants) or to a previous treatment with a biologic agent and/or an anti-TNF agent. In one embodiment, the patient is naïve to previous treatment with aminosalicylates, a corticosteroid, an immunosuppressant, a biologic agent and/or an anti-TNF agent. In one embodiment, the patient is a refractory patient. In one embodiment, the upadacitinib or a pharmaceutically acceptable salt or solid state form thereof is a in once-daily, modified release formulation.

In one aspect, induction doses for the methods disclosed herein are administered for 8 weeks in a dose regimen described in Table 12. In one aspect, induction doses are administered for 8 weeks in a dose regimen described in Table 12. In one aspect, maintenance doses are administered for 44 weeks or more in a dose regimen described in Table 12. In one aspect, induction doses for the methods disclosed herein are administered for 8 weeks and the maintenance doses are administered for 44 weeks in a dosing regimen as described in Table 12.

TABLE 12

Doses and Dosing Regimens (QD)

| Induction Dose (mg) | Frequency of induction doses | Maintenance dose (mg) | Frequency of maintenance dose |
|---|---|---|---|
| 7.5 | QD | 7.5 | QD |
| 15 | QD | 15 | QD |
| 30 | QD | 15 | QD |
| 30 | QD | 30 | QD |
| 45 | QD | 15 | QD |
| 45 | QD | 30 | QD |

In one particular embodiment, the induction dose is 45 mg of upadacitinib or a pharmaceutically acceptable salt or solid state form thereof administered QD, and the maintenance dose, and any additional maintenance dose administered thereafter, is 30 mg of upadacitinib or a pharmaceutically acceptable salt or solid state form thereof administered QD. In another embodiment, the induction dose is 45 mg of upadacitinib or a pharmaceutically acceptable salt or solid state form thereof administered QD, and the maintenance dose, and any additional maintenance dose administered thereafter, is 15 mg of upadacitinib or a pharmaceutically acceptable salt or solid state form thereof administered QD. In one embodiment, the induction dose is 30 mg of upadacitinib or a pharmaceutically acceptable salt or solid state form thereof administered QD, and the maintenance dose, and any additional maintenance dose administered thereafter, is 30 mg of upadacitinib or a pharmaceutically acceptable salt or solid state form thereof administered QD. In one embodiment, the induction dose is 30 mg of upadacitinib or a pharmaceutically acceptable salt or solid state form thereof administered QD, and the maintenance dose, and any additional maintenance dose administered thereafter, is 15 mg of upadacitinib or a pharmaceutically acceptable salt or solid state form thereof administered QD. In one embodiment, the induction dose is 30 mg or 45 mg of upadacitinib or a pharmaceutically acceptable salt or solid state form thereof administered QD, and the maintenance dose, and any additional maintenance dose administered thereafter, is 15 mg of upadacitinib or a pharmaceutically acceptable salt or solid state form thereof administered QD. In one embodiment, the induction dose is 30 mg or 45 mg of upadacitinib or a pharmaceutically acceptable salt or solid state form thereof administered QD, and the maintenance dose, and any additional maintenance dose administered thereafter, is 7.5 mg of upadacitinib or a pharmaceutically acceptable salt or solid state form thereof administered QD.

In one aspect, induction doses for the methods disclosed herein are administered for 16 weeks in a dose regimen described in Table 13. In one aspect, induction doses are administered for 16 weeks in a dose regimen described in Table 13. In one aspect, maintenance doses are administered for 44 weeks or more in a dose regimen described in Table 13. In one aspect, induction doses for the methods disclosed herein are administered for 16 weeks and the maintenance doses are administered for 36 weeks in a dosing regimen as described in Table 13.

TABLE 13

Doses and Dosing Regimens (QD)

| Induction Dose (mg) | Frequency of induction doses | Maintenance dose (mg) | Frequency of maintenance dose |
|---|---|---|---|
| 45 | QD | 15 | QD |
| 45 | QD | 30 | QD |

In one embodiment, the present disclosure provides a method of maintaining clinical remission of ulcerative colitis in a patient, said method comprising administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains clinical remission.

In one embodiment, the present disclosure provides a method of maintaining endoscopic improvement of ulcerative colitis in a patient, said method comprising administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains endoscopic improvement.

In one embodiment, the present disclosure provides a method of maintaining endoscopic remission of ulcerative colitis in a patient, said method comprising administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains endoscopic remission.

In one embodiment, the present disclosure provides a method of maintaining clinical remission of ulcerative colitis in a patient, said method comprising administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains clinical remission.

In one embodiment, the present disclosure provides a method of maintaining endoscopic improvement of ulcerative colitis in a patient, said method comprising administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains endoscopic improvement.

In one embodiment, the present disclosure provides a method of maintaining endoscopic remission of ulcerative colitis in a patient, said method comprising administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains endoscopic remission.

In one embodiment of the method of maintaining clinical remission, endoscopic improvement, or endoscopic remission of ulcerative colitis, the patient has moderately to severely active ulcerative colitis.

In one embodiment, the clinical remission, endoscopic improvement or endoscopic remission is corticosteroid free.

In one embodiment, the clinical remission, endoscopic improvement or endoscopic remission is maintained for at least 52 weeks.

In one embodiment, the patient demonstrated an inadequate response to, loss of response to or intolerance to one or more corticosteroids, immunosuppressants, or biologic therapies.

In one embodiment, the immunosuppressants are selected form oral azathioprine, 6-mercaptopurine, injectable methotrexate and tacrolimus. In one embodiment, the biologic therapy is selected from infliximab, adalimumab, golimumab and vedolizumab.

In one embodiment, the inadequate response in said patient taking corticosteroids is defined as said patient experiencing signs and symptoms of persistently active disease despite a history of at least one induction regimen that included a dose equivalent to prednisone ≥40 mg/day orally for 3 to 4 weeks or intravenously for one week. In one embodiment, the patient is unable to taper corticosteroid below a dose equivalent to prednisone 10 mg daily orally without recurrent active disease.

In one embodiment, the intolerance of said patient to corticocosteroids leads to Cushing's syndrome, osteopenia, osteoporosis, hyperglycemia, insomnia or infection. In one embodiment, the patient experiencing intolerance to immunosuppressants experienced nausea, vomiting, abdominal pain, pancreatitis, liver enzyme abnormalities, lymphopenia or infection.

In one embodiment, the patient experiencing the inadequate response to immunosuppressants experienced signs and symptoms of persistently active disease despite a history of at least one 90-day regimen of oral azathioprine, 6-mercaptopurine, injectable methotrexate or tacrolimus. In one embodiment, the patient experiencing the inadequate response to biologic therapies experienced signs and symptoms of persistently active disease despite a history of at least one 6-week induction regimen of infliximab comprising a greater than or equal to 5 mg/kg intravenous dose at 0, 2 and 6 weeks; at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; at least one 2-week induction regimen of golimumab comprising one 200 mg subcutaneous dose followed by one 100 mg subcutaneous dose at least 2 weeks apart; or at least one 6-week induction regimen of vedolizumab comprising a 300 mg intravenous dose at 0, 2 and 6 weeks.

In one embodiment, the patient experiencing inadequate response to biologic therapies experienced recurrence of symptoms during scheduled maintenance dosing following prior clinical benefit. In one embodiment, the patient experiencing intolerance to biologic therapies experienced infusion-related reaction, demyelination, congestive heart failure of infection.

In one embodiment, the clinical remission achieved is defined by an Adapted Mayo score ≤2. In one embodiment, the clinical remission comprises an SFS≤1 and not greater than baseline, a RBS of 0, and an endoscopic subscore ≤1.

In one embodiment, the clinical remission is defined by an Adapted Mayo score ≤2, and is corticosteroid free. In one embodiment, the patient in clinical remission has been corticosteroid free for 90 days or more immediately preceding week 52 of daily maintenance dose administration. For example, in some embodiments, the patient discontinued corticosteroid use at least 90 days prior to the end of a 52 week period of administration of the maintenance dose.

In one embodiment, the patient exhibits a Histologic Endoscopic Mucosal Improvement (HEMI) comprising an endoscopic score ≤1 and a Geboes score ≤3.1 at week 52 (i.e., following 52 weeks of daily maintenance dose administration), In one embodiment, the patient exhibits mucosal healing comprising an endoscopic score of 0 and a Geboes score <2 at week 52 (i.e., following 52 weeks of daily maintenance dose administration), In one embodiment, the patient does not exhibit bowel urgency during the maintenance period. In one embodiment, the patient does not exhibit bowel urgency at week 52 (i.e., following 52 weeks of daily maintenance dose administration), In one embodiment, the patient does not exhibit abdominal pain during the maintenance period. In one embodiment, the patient does not exhibit abdominal pain at week 52 (i.e., following 52 weeks of daily maintenance dose administration).

In one embodiment, the present disclosure further provides a method of inducing clinical remission of ulcerative colitis in a patient, said method comprising: (a) administering to the patient an induction dose of upadacitinib, or a pharmaceutically acceptable salt thereof, wherein said induction dose is administered orally once a day for up to 16 weeks and comprises 45 mg of upadacitinib, or a 45 mg free base equivalent amount of a pharmaceutically acceptable salt thereof; and (b) wherein said patient achieves clinical remission within 16 weeks of administration of the first induction dose.

In one embodiment, the present disclosure further provides a method of inducing clinical remission of ulcerative colitis in a patient, said method comprising: (a) administering to the patient an induction dose of upadacitinib, or a pharmaceutically acceptable salt thereof, wherein said induction dose is administered orally once a day and comprises 45 mg of upadacitinib, or a 45 mg free base equivalent amount of a pharmaceutically acceptable salt thereof; and (b) continuing the administering until said patient achieves clinical remission.

In one embodiment, the clinical remission is defined by an Adapted Mayo score ≤2.

In one embodiment, the method comprises an SFS≤1 and not greater than baseline, a RBS of 0, and an endoscopic subscore ≤1.

In one embodiment, the clinical remission is achieved after more than 8 weeks, but within 16 weeks of administration of the first 45 mg induction dose.

In one embodiment, the present disclosure further provides a method of inducing clinical remission of ulcerative colitis, said method comprising: (a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and (b) wherein the patient achieves clinical response within 8 weeks of administration of the first 45 mg induction dose, wherein the patient was previously treated with 45 mg of upadacitinib for at least 8 weeks and did not exhibit a clinical response.

In one embodiment, the present disclosure further provides a method of inducing clinical response in a patient having ulcerative colitis, said method comprising: (a) administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and (b) wherein the patient achieves clinical response within 8 weeks of administration of the first 45 mg induction dose, wherein the patient was previously treated with 45 mg of upadacitinib for at least 8 weeks and did not exhibit a clinical response.

In one embodiment, the present disclosure further provides a method of inducing a clinical response in a patient with moderately to severely active ulcerative colitis, said method comprising: a) administering to the patient at least one induction dose of upadacitinib, or a pharmaceutically acceptable salt or solid state form thereof, wherein said induction dose comprises 45 mg of upadacitinib, or a pharmaceutically acceptable salt or solid state form thereof.

In one such embodiment, the clinical response is a clinical response is wherein the patient has a decrease from a baseline Adapted Mayo score greater than or equal to 2 points and greater than or equal to 30% accompanied by a decrease in rectal bleeding subscore of greater than or equal to 1 or an absolute rectal bleeding subscore of 0 or 1. In another such embodiment, the clinical response is a clinical response is wherein the patient has a decrease from a baseline Full Mayo score greater than or equal to 3 points and greater than or equal to 30% accompanied by a decrease in rectal bleeding subscore from baseline of greater than or equal to 1 or an absolute rectal bleeding subscore of 0 or 1.

In yet another embodiment, the method further comprises maintaining the clinical response, said method further comprising: b) administering a first maintenance dose of upadacitinib, or a pharmaceutically acceptable salt or solid state form thereof to the patient after the last induction dose is administered; and c) administering at least one additional maintenance dose once daily thereafter.

In another embodiment, the induction dose comprises 45 mg of upadacitinib, or a pharmaceutically acceptable salt or solid state form thereof. In another embodiment, the first maintenance dose and/or the at least one additional maintenance dose comprises 15 mg to 30 mg of upadacitinib, or a pharmaceutically acceptable salt or solid state form thereof.

In one embodiment, the present disclosure further provides a method of maintaining clinical remission of ulcerative colitis in a patient, said method comprising: administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains clinical remission.

In one embodiment, the present disclosure further provides a method of maintaining endoscopic improvement of ulcerative colitis in a patient, said method comprising: administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains endoscopic improvement.

In one embodiment, the present disclosure further provides a method of maintaining endoscopic remission of ulcerative colitis in a patient, said method comprising: administering to the patient a daily maintenance dose of upadacitinib, or a pharmaceutically acceptable salt thereof, wherein said daily maintenance dose is administered orally once a day and comprises 30 mg of upadacitinib, or a 30 mg free base equivalent amount of the pharmaceutically acceptable salt thereof; wherein said patient maintains endoscopic remission.

In one embodiment, the present disclosure further provides a method of maintaining clinical remission of ulcerative colitis in a patient, said method comprising: administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains clinical remission.

In one embodiment, the present disclosure further provides a method of maintaining endoscopic improvement of ulcerative colitis in a patient, said method comprising: administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains endoscopic improvement.

In one embodiment, the present disclosure further provides a method of maintaining endoscopic remission of ulcerative colitis in a patient, said method comprising: administering to the patient a daily maintenance dose of upadacitinib, or a pharmaceutically acceptable salt thereof, wherein said daily maintenance dose is administered orally once a day and comprises 15 mg of upadacitinib, or a 15 mg free base equivalent amount of the pharmaceutically acceptable salt thereof; wherein said patient maintains endoscopic remission.

In some embodiments, said patient has moderately to severely active ulcerative colitis.

In some embodiments, the clinical remission, endoscopic improvement or endoscopic remission is corticosteroid free.

In some embodiments, the clinical remission, endoscopic improvement or endoscopic remission is maintained for at least 52 weeks.

In some embodiments, said patient demonstrated an inadequate response to, loss of response to or intolerance to one or more corticosteroids, immunosuppressants, or biologic therapies.

In some embodiments, the immunosuppressants are selected form oral azathioprine, 6-mercaptopurine, injectable methotrexate and tacrolimus.

In some embodiments, the biologic therapy is selected from infliximab, adalimumab, golimumab and vedolizumab.

In some embodiments, the inadequate response in said patient taking corticosteroids is defined as said patient experiencing signs and symptoms of persistently active disease despite a history of at least one induction regimen that included a dose equivalent to prednisone ≥40 mg/day orally for 3 to 4 weeks or intravenously for one week.

In some embodiments, the said patient is unable to taper corticosteroid below a dose equivalent to prednisone 10 mg daily orally without recurrent active disease.

In some embodiments, the intolerance of said patient to corticocosteroids leads to Cushing's syndrome, osteopenia, osteoporosis, hyperglycemia, insomnia or infection.

In some embodiments, the said patient experiencing the inadequate response to immunosuppressants experienced signs and symptoms of persistently active disease despite a history of at least one 90-day regimen of oral azathioprine, 6-mercaptopurine, injectable methotrexate or tacrolimus.

In some embodiments, said patient experiencing intolerance to immunosuppressants experienced nausea, vomiting, abdominal pain, pancreatitis, liver enzyme abnormalities, lymphopenia or infection.

In some embodiments, said patient experiencing the inadequate response to biologic therapies experienced signs and symptoms of persistently active disease despite a history of: at least one 6-week induction regimen of infliximab comprising a greater than or equal to 5 mg/kg intravenous dose at 0, 2 and 6 weeks; at least one 4-week induction regimen of adalimumab comprising one 160 mg subcutaneous dose followed by one 80 mg subcutaneous dose or one 80 mg subcutaneous dose, followed by one 40 mg subcutaneous dose at least two weeks apart; at least one 2-week induction regimen of golimumab comprising one 200 mg subcutaneous dose followed by one 100 mg subcutaneous dose at least 2 weeks apart; or at least one 6-week induction regimen of vedolizumab comprising a 300 mg intravenous dose at 0, 2 and 6 weeks.

In some embodiments, said patient experiencing inadequate response to biologic therapies experienced recurrence of symptoms during scheduled maintenance dosing following prior clinical benefit.

In some embodiments, said patient experiencing intolerance to biologic therapies experienced infusion-related reaction, demyelination, congestive heart failure of infection.

In some embodiments, the clinical remission is defined by an Adapted Mayo score ≤2.

In some embodiments, the method comprises an SFS≤1 and not greater than baseline, a RBS of 0, and an endoscopic subscore ≤1.

In some embodiments, the clinical remission is defined by an Adapted Mayo score ≤2, and is corticosteroid free.

In some embodiments, the patient has been corticosteroid free for 90 days or more immediately preceding week 52 of daily maintenance dose administration.

In some embodiments, the patient exhibits a Histologic Endoscopic Mucosal Improvement (HEMI) comprising an endoscopic score ≤1 and a Geboes score ≤3.1 at week 52.

In some embodiments, the patient exhibits mucosal healing comprising an endoscopic score of 0 and a Geboes score <2 at week 52.

In some embodiments, the patient does not exhibit bowel urgency at week 52.

In some embodiments, the patient does not exhibit abdominal pain at week 52.

In one embodiment, the present disclosure further provides a method of inducing Histologic Endoscopic Mucosal Improvement (HEMI) in a patient with ulcerative colitis, said method comprising: administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; and wherein said patient achieves Histologic Endoscopic Mucosal Improvement (HEMI) comprising an endoscopic score ≤1 and a Geboes score ≤3.1 within 8 weeks of administration of the induction dose.

In one embodiment, the present disclosure further provides a method of inducing and maintaining Histologic Endoscopic Mucosal Improvement (HEMI) in a patient with ulcerative colitis, said method comprising: administering to the patient an induction dose of upadacitinib, or a pharmaceutically acceptable salt thereof, wherein said induction dose is administered orally once a day for at least 8 weeks and comprises 45 mg of upadacitinib, or a 45 mg free base equivalent amount of a pharmaceutically acceptable salt thereof; wherein said patient achieves Histologic Endoscopic Mucosal Improvement (HEMI) comprising an endoscopic score ≤1 and a Geboes score ≤3.1 within 8 weeks of administration of the first induction dose; administering to the patient a maintenance dose of upadacitinib, or a pharmaceutically acceptable salt thereof, wherein said first maintenance dose is administered orally once a day for at least 52 weeks and comprises 15 mg of upadacitinib or 30 mg of upadacitinib, or a 15 mg or 30 mg free base equivalent amount of a pharmaceutically acceptable salt thereof after the last induction dose is administered; wherein said patient maintains Histologic Endoscopic Mucosal Improvement (HEMI) comprising an endoscopic score ≤1 and a Geboes score ≤3.1 for 52 weeks after administration of the first maintenance dose.

In one embodiment, the present disclosure further provides a method of maintaining Histologic Endoscopic Mucosal Improvement (HEMI) in a patient with ulcerative colitis, said method comprising: administering to the patient a maintenance dose of upadacitinib, or a pharmaceutically acceptable salt thereof, wherein said first maintenance dose is administered orally once a day for at least 52 weeks and comprises 15 mg of upadacitinib or 30 mg of upadacitinib, or a 15 mg or 30 mg free base equivalent amount of a pharmaceutically acceptable salt thereof; wherein said patient maintains Histologic Endoscopic Mucosal Improvement (HEMI) comprising an endoscopic score ≤1 and a Geboes score ≤3.1 for 52 weeks after administration of the first maintenance dose.

V. PREPARATION OF UPADACITINIB

The synthesis of the compounds of the disclosure, including (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide (upadacitinib) and pharmaceutically acceptable salts thereof is provided in U.S. Pat. No. 8,426,411, the entire content of which is incorporated herein by reference. In one embodiment, upadacitinib, and pharmaceutically acceptable salts thereof, may be synthesized according to the methods described in U.S. patent application Ser. No. 15/295,561, which is herein incorporated by referenced. For example, upadacitinib may be synthesized using synthetic transformations such as those illustrated in Schemes I-IIIa. Starting materials are commercially available, may be prepared by the procedures described in U.S. patent application Ser. No. 15/295,561, by literature procedures, or by procedures that would be well known to one skilled in the art of organic chemistry (see, for example, Larock, R. C. "Comprehensive Organic Transformations: A Guide to Functional Group Preparations, $2^{nd}$ edition", 1999, Wiley-VCH or Greene, T. W. and Wuts, P. G. M. "Protective Groups in Organic Synthesis, $3^{rd}$ Edition", 1999, Wiley-Interscience).

A process for preparing upadacitinib is illustrated in Scheme I. Reaction of protected (3R,4S)-4-ethylpyrrolidine-3-carboxylic acid (I) or a pharmaceutically acceptable salt thereof with trimethylsulfoxonium chloride gives sulfur ylide (II). Contacting sulfur ylide (II) with LiX and a sulfonic acid yields the corresponding halomethyl ketone (III). Reaction of (III) with (IV) in the presence of a base yields (V). Cyclization of (V) in the presence of a perfluoro acid anhydride and an organic base produces (VI). Removal of the protecting group and contacting the deprotected compound with an acid yields a pharmaceutically acceptable salt of (VII). Reacting the pharmaceutically acceptable salt of (VII) with 2,2,2-trifluoroethylamine produces upadacitinib.

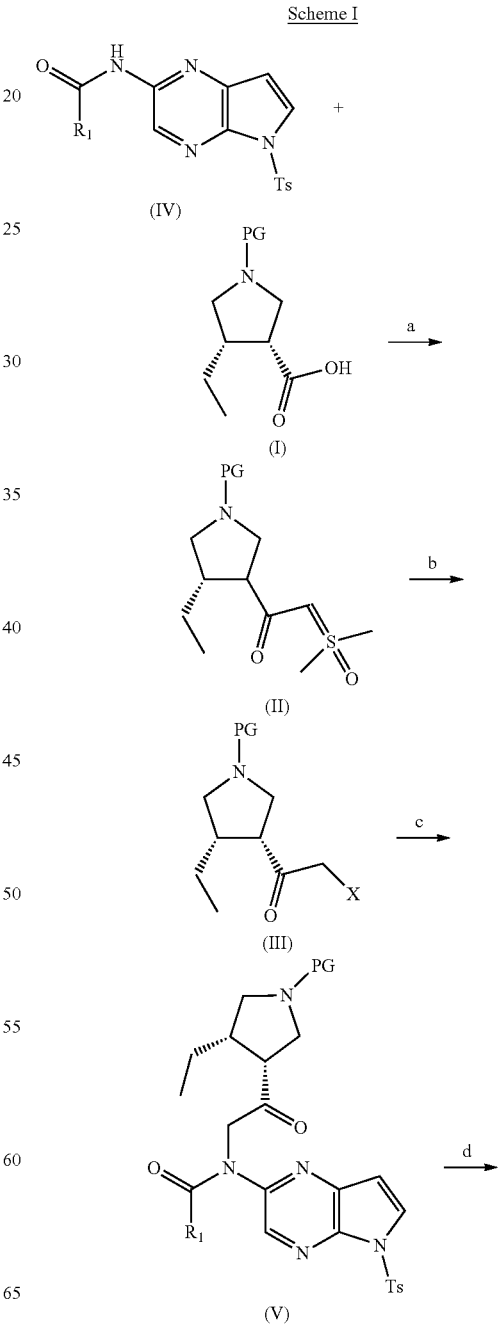

Scheme I

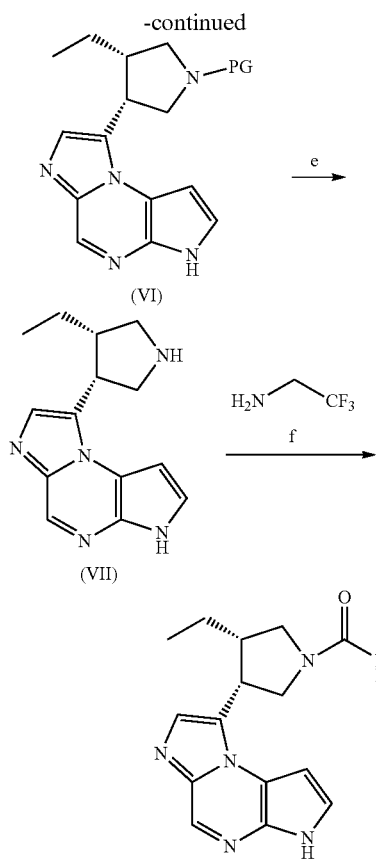

(VI)

(VII)

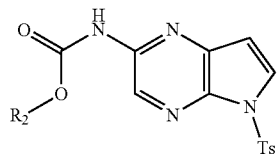

wherein:
PG is a protecting group;
X is Br or Cl;
R₁ is selected from the group consisting of alkyl, aryl, and —OR₂;
R₂ is alkyl; and
Ts is tosyl.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl. In another embodiment, the protecting group is carboxybenzyl.

In another embodiment, R₁ is —OR₂, and R₂ is methyl or ethyl. In such embodiments, the compound of formula (IV) is a compound of formula (IVa):

(IVa)

wherein R₂ is methyl or ethyl.

In certain embodiments, a pharmaceutically acceptable salt of a compound of the compound of formula (I) is used in the reaction of step (a). In one embodiment, the pharmaceutically acceptable salt of the compound of formula (I) is selected from the group consisting of the naphthalenethane amine salt (Ia) and the dicyclohexylamine salt (Ib)

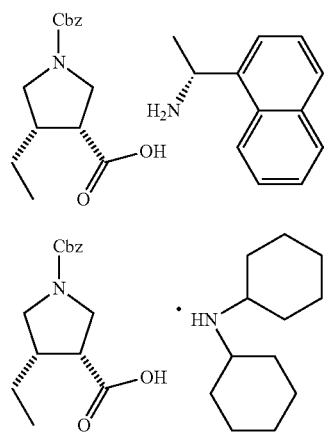

(Ia)

(Ib)

wherein Cbz is carboxybenzyl.

In one embodiment, the pharmaceutically acceptable salt of compound (VII) is selected from the group consisting of (VIIa), (VIIb), and (VIIc)

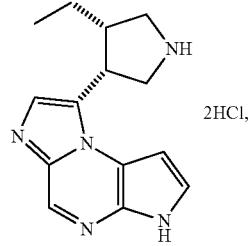

(VIIa) 2HCl,

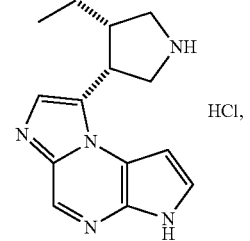

(VIIb) HCl,

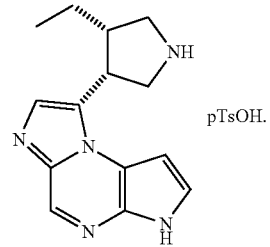

(VIIc) pTsOH.

Another process for preparing upadacitinib is illustrated in Scheme Ia. Reaction of (3R,4S)-1-((benzyloxy)carbonyl)-4-ethylpyrrolidine-3-carboxylate dicyclohexylamine salt (Ib) with trimethylsulfoxonium chloride in the presence of carbonyldiimidazole and a strong base gives sulfur ylide (IIa). Contacting sulfur ylide (IIa) with lithium bromide and a sulfonic acid yields the corresponding bromomethyl ketone (IIIa). Reaction of (IIIa) with alkyl 5-tosyl-5H-pyrrolo[2,3-b]pyrazin-2-ylcarbamate (IVa) in the presence of lithium tert-butoxide yields (Va). Cyclization of (Va) in the presence of a perfluoro acid anhydride and an organic base produces (VIa). Removal of the carboxybenzyl protecting group and contacting the deprotected compound with hydrochloric acid yields the pharmaceutically acceptable salt (VIIa). Reacting the pharmaceutically acceptable salt (VIIa) with 2,2,2-trifluoroethylamine produces upadacitinib.

Scheme Ia

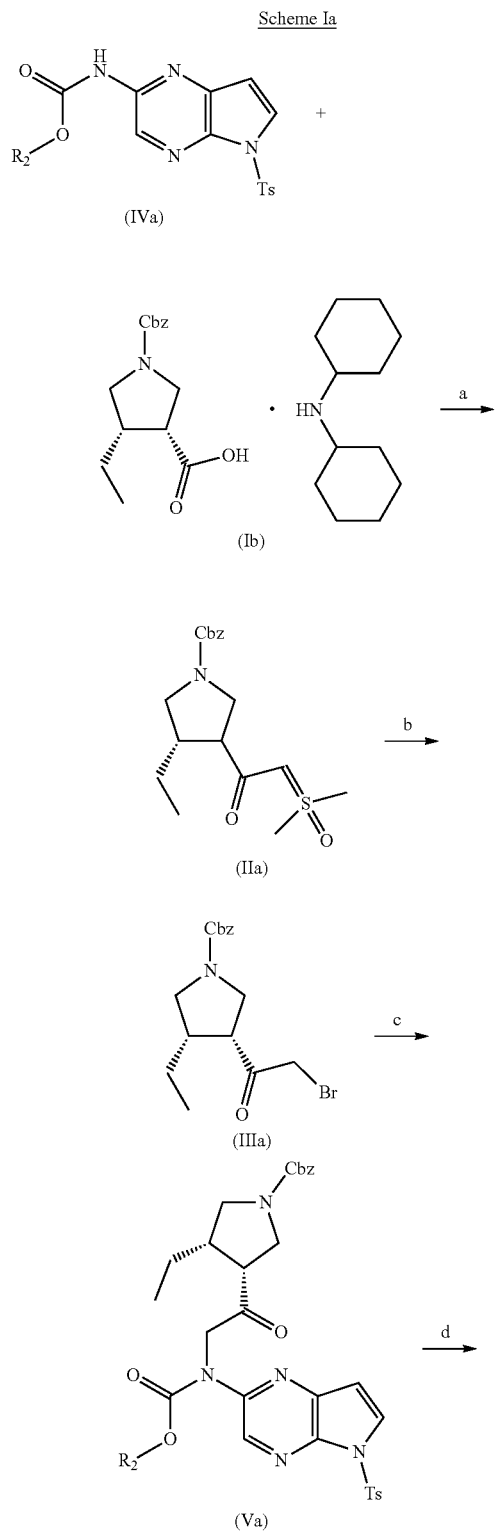

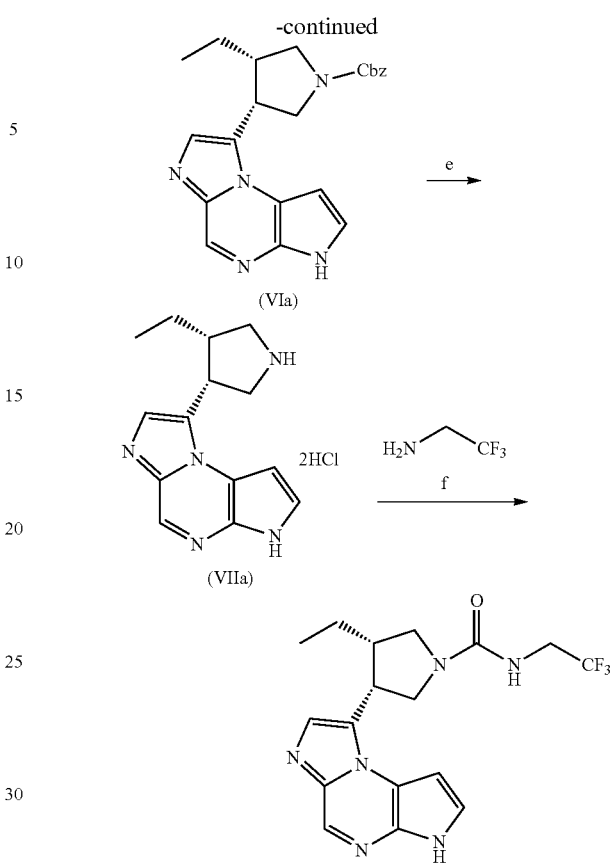

wherein:
Cbz is carboxybenzyl;
Ts is tosyl; and
$R_2$ is methyl or ethyl.

The reaction in step (a) of Schemes I and Ia is generally accomplished in the presence of a coupling agent, such as carbonyldiimidazole (CDI), and a strong base. The strong base may be, for example, potassium tert-butoxide, sodium tert-butoxide, or combinations thereof. The step (a) reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide.

More particularly, in certain embodiments, a solution of a compound of formula (I), (Ia), or (Ib) in solvent is slowly added (e.g., over 30 minutes) to a slurry of CDI in solvent, and the resulting mixture is stirred at room temperature for 30 minutes to 12 hours, and typically for about 1 hour. The resulting solution is slowly added (e.g., over 15 minutes) to a suspension of the trimethylsulfoxonium chloride, strong base, and solvent, while maintaining the internal temperature below −1° C. In another embodiment, the reaction is quenched and the resulting compound of formula (II) or (IIa) is isolated prior to step (b).

In some embodiments, the reaction of step (a) may further involve contact of (Ia) or (Ib) with an acid prior to reaction with the trimethylsulfoxonium chloride, in order to extract the amine to obtain a compound of formula (I). Suitable acids include any mineral acid or organic acid, such as phosphoric acid, hydrochloric acid (HCl), acetic acid (HOAc), citric acid, and the like. The compound of formula (I) may subsequently be taken up in a suitable solvent, and reacted with trimethylsulfoxonium chloride, as described herein. In one embodiment, a pharmaceutically acceptable salt of a compound of formula (I) is used in step (a), wherein the pharmaceutically acceptable salt is (Ia) or (Ib).

In step (b) of Schemes I and Ia, a compound of formula (II) or (IIa) is contacted with LiX and a sulfonic acid to form a compound of formula (III) or (IIIa), respectively. In one embodiment, the sulfonic acid is selected from the group consisting of methanesulfonic acid and p-toluenesulfonic acid. In one embodiment, the sulfonic acid is p-toluenesulfonic acid. LiX may be selected from lithium bromide and lithium chloride. In one embodiment, LiX is lithium bromide. In one embodiment, the reaction is conducted in lithium bromide and p-toluensulfonic acid. The reaction of step (b) may be conducted in any suitable solvent including, but not limited to tetrahydrofuran, ethyl acetate, heptanes, ethanol, water, and combinations thereof.

More particularly, in certain embodiments, the sulfonic acid is added to a solution of the compound of formula (II) or (IIa) and LiX in a solvent. The resulting mixture is warmed to about 35° C. to about 65° C. and stirred overnight. In one embodiment, the mixture is warmed to about 40° C. and stirred overnight. The mixture is cooled to room temperature and washed. The compound of formula (III) or (IIIa) may be isolated, or optionally used in the next step without purification.

In step (c) of Schemes I and Ia a compound of formula (III) or (IIIa) are reacted with a compound of formula (IV) or (IVa) (prepared as described herein). The step (c) reaction is conducted in the presence of a base, such as lithium tert-butoxide, sodium tert-butoxide, or combinations thereof. In one embodiment, the base is lithium tert-butoxide. The reaction of step (c) may be conducted in any suitable solvent including, but not limited to dimethylacetamide, tetrahydrofuran, dichloromethane, ethyl acetate, heptanes, and combinations thereof.

More particularly, in certain embodiments, the base is added to a cooled suspension of the compound of formula (III) or (IIIa) in a solvent. The resulting solution is stirred for about 30 minutes to about 12 hours, or about 30 minutes, and cooled to about –20° C. to about 0°, or about –10° C. In one embodiment, the solution is stirred for about 30 minutes and cooled to about –20° C. to about 0°. A solution of a compound of formula (IV) or (IVa) in a solvent is slowly added (e.g., over 30 minutes), and the resulting mixture is stirred for about 30 minutes to about 6 hours, or about 30 minutes, at a temperature of about –20° C. to about 0° C., or about –10° C. In one embodiment, following addition of the solution of the compound of formula (IV) or (IVa) in a solvent, the resulting mixture is stirred for about 30 minutes at a temperature of about –10° C. In one embodiment, the reaction is quenched, and, in some embodiments, the resulting product (V) or (Va) is isolated prior to step (d).

In step (d) of Schemes I and Ia, a compound of formula (V) or (Va) is contacted with a perfluoro acid anhydride and an organic base to form a compound of formula (VI) or (VIa), respectively. Non-limiting examples of suitable organic bases include pyridine, triethylamine, and combinations thereof. Examples of suitable perfluoro acid anhydrides include trifluoroacetic anhydride, pentafluoropropionic anhydride, heptafluorobutyric anhydride, and combinations thereof. In certain embodiments, the organic base is pyridine and the perfluoro acid anhydride is trifluoroacetic anhydride. In other embodiments, the organic base is triethylamine and the perfluoro acid anhydride is pentafluoropropionic anhydride. Suitable solvents for use in step (d) include, but are not limited to acetonitrile, toluene, and combinations thereof.

More particularly, in certain embodiments, the organic base and the perfluoro acid anhydride are charged into a solution of a compound of formula (V) or (Va) in solvent. The resulting mixture is warmed to about 55° C. to about 75° C., or about 55° C., and stirred for about 4 hours to about 18 hours, or about 6 hours. In one embodiment, the mixture of perfluoro acid anhydride and the compound of formula (V) or (Va) is warmed to about 55° C. and stirred for about 4 hours to about 18 hours. In one embodiment, the mixture is stirred for about 6 hours. Upon completion of the reaction, in some embodiments, the reaction mixture may be cooled, and concentrated prior to contacting with a hydroxide solution to quench excess reagents, and remove the tosyl protecting group. Suitable hydroxide solutions include a sodium hydroxide (NaOH) solution, a potassium hydroxide (KOH) solution, and the like. The resulting mixture may be stirred at room temperature to about 85° C., including at about 55° C., for about 30 minutes to about 8 hours. In one embodiment, the mixture is stirred for about 1 hour. Upon completion, the solvent may optionally be removed and switched to methanol, ethanol, isopropanol, or other suitable solvents prior to step (e).

In step (e) of Schemes I and Ia, a compound of formula (VI) or (VIa) is deprotected, and a pharmaceutically acceptable salt of compound (VII), such as (VIIa), (VIIb), or (VIIc) is formed. The protecting group on the compound of formula (VI) or (VIa) may be removed using any suitable means known in the art. In one embodiment, deprotection occurs by contacting the compound of formula (VI) or (VIa) with palladium on carbon (e.g., Pd/C or Pd(OH$_2$)/C) under hydrogen pressure. In other embodiments, deprotection occurs by contacting the compound of formula (VI) or (VIa) with an acid. Non-limiting examples of suitable acids include hydrochloric acid (HCl), hydrobromic acid (HBr), hydrobromic acid in acetic acid (e.g., HBr/HOAc), and the like. In other embodiments, deprotection occurs by subjecting the compound of formula (VI) or (VIa) to heating, e.g., at a temperature of from room temperature to about 85° C., including about 50° C. Upon deprotection, the compound of formula (VII) is contacted with the appropriate acid (e.g., hydrochloric acid or p-toluenesulfonic acid) to form the pharmaceutically acceptable salt.

Step (e) may occur in any suitable solvent including, but not limited to ethanol, isopropyl acetate, ethyl acetate, and combinations thereof.

More particularly, in some embodiments, palladium on carbon and the compound of formula (VI) or (VIa) in solvent are mixed under hydrogen pressure at about 1 psig to about 100 psig. In another embodiment, the hydrogen pressure is about 20 psig. The mixture is agitated for about 2 hours to about 24 hours, including about 16 hours, at about 20° C. to about 85° C., including about 50° C. In one embodiment, the mixture is agitated for about 16 hours at about 20° C. to about 80° C. In one embodiment, the mixture is agitated for about 16 hours at about 50° C. Upon completion of the reaction, the reaction mixture is cooled and filtered, followed by addition of the appropriate acid. The resulting salt is optionally isolated prior to step (f).

In step (f), the salt produced in step (e) is reacted with 2,2,2-trifluoroethylamine to produce upadacitinib. The step (f) reaction is conducted in the presence of a coupling agent, such as carbonyldiimidazole (CDI), and optionally buffers, such as dipotassium phosphate, potassium hydroxide, and combinations thereof. In one embodiment, the step (f)

reaction is conducted in the presence of CDI, dipotassium phosphate, and potassium hydroxide. The step (f) reaction may be conducted in any suitable solvent including, but not limited to, tetrahydrofuran, ethyl acetate, heptanes, ethanol, water, and combinations thereof.

More particularly, in certain embodiments, 2,2,2-trifluoroethyl amine is added slowly (e.g., over 20 minutes) to a slurry of CDI in solvent, while maintaining an internal temperature of less than 30° C. The resulting solution is stirred for about 10 minutes to about 12 hours, and in one embodiment for about 1 hour, to form an imidazolide solution. The pH of a biphasic mixture of the pharmaceutically acceptable salt from step (e) in buffer and solvent is adjusted to about 7 to about 11, and in one embodiment to about 9, by addition of a base. The imidazolide solution is added, and the resulting mixture is mixed at about 25° C. while maintaining a pH of about 9 by portionwise addition of base for about 30 minutes to about 18 hours. In one embodiment, the mixture formed after addition of the imidazolide solution is mixed at about 25° C. while maintaining a pH of about 9 by portionwise addition of base for about 1 hour. In one embodiment, upon completion, the reaction is quenched and the resulting product isolated.

An alternate process for preparing upadacitinib is illustrated in Scheme II. Reaction of protected (3R,4S)-4-ethylpyrrolidine-3-carboxylic acid (I) or a pharmaceutically acceptable salt thereof with trimethylsulfoxonium chloride gives sulfur ylide (II). Contacting sulfur ylide (II) with LiX and a sulfonic acid yields the corresponding halomethyl ketone (III). Reaction of (III) with (IV) in the presence of a base yields (V). Cyclization of (V) in the presence of a perfluoro acid anhydride and an organic base produces (VI). Removal of the protecting group and contacting the deprotected compound (VII) (not shown) with hydrochloric acid yields pharmaceutically acceptable salt (VIIb). The pharmaceutically acceptable salt (VIIb) is converted to the freebase (VII), which is reacted with 2,2,2-trifluoroethylamine to produce upadacitinib. Upadacitinib is contacted with L-tartaric acid to form the corresponding tartrate salt, followed by formation of the upadacitinib freebase.

Scheme II

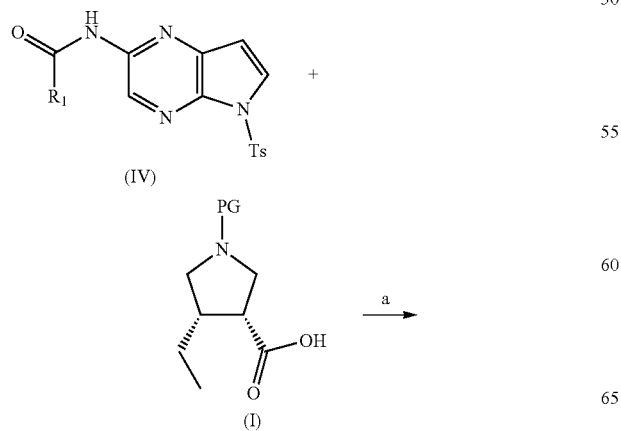

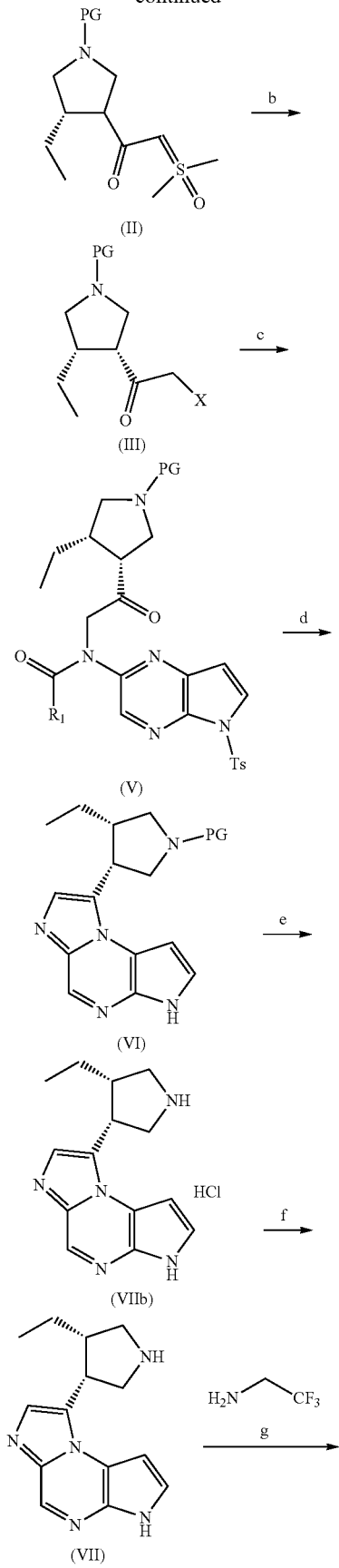

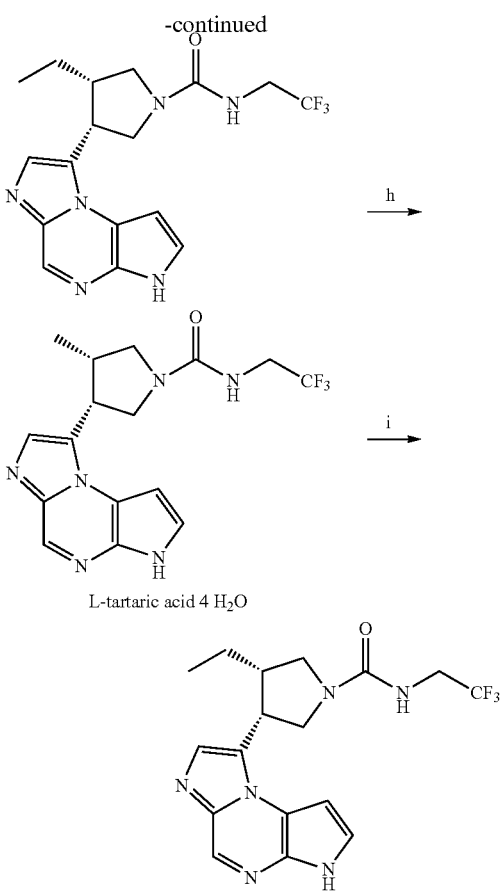

L-tartaric acid 4 H$_2$O wherein PG, Ts, X, and R1 are as defined above.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl. In one embodiment, the protecting group is carboxybenzyl.

In one embodiment, R$_1$ is —OR$_2$, and R$_2$ is ethyl or methyl.

In certain embodiments, a pharmaceutically acceptable salt of the compound of formula (I) is used in the reaction of step (a). In one embodiment, the pharmaceutically acceptable salt of the compound of formula (I) is selected from the group consisting of the naphthalenethane amine salt (Ia) and the dicyclohexylamine salt (Ib).

Steps (a)-(e) of Scheme II are conducted as described above for Scheme I, wherein following deprotection of the compound of formula (VI), deprotected compound (VII) is contacted with hydrochloric acid to form pharmaceutically acceptable salt (VIIb).

In step (f) of Scheme II, salt (VIIb) is contacted with a base to form the corresponding freebase (VII). Suitable bases include, but are not limited to hydroxides, such as sodium hydroxide, potassium hydroxide, and the like, and combinations thereof. In one embodiment, the base is sodium hydroxide. The reaction of step (f) may be conducted in any suitable water-containing solvent including, but not limited to, water alone or in combination with THF, 2-methyl tetrahydrofuran, ethanol, methanol, and the like.

In step (g) compound (VII) is reacted with 2,2,2-trifluoroethylamine to produce upadacitinib. The step (g) reaction is conducted in the presence of a coupling agent, such as CDI. Step (g) in Scheme II is conducted using similar reagents and under similar conditions as those set forth above for step (f) of Scheme I.

In step (h) of Scheme II, upadacitinib is contacted with L-tartaric acid to form the corresponding tartrate salt (step (h)). Formation of the tartrate salt advantageously aids in removal of impurities prior to isolation of the freebase. The tartrate salt is subsequently converted back to the freebase form (step (i)) to produce upadacitinib. In particular, in step (i) the tartrate salt may be contacted with a base, such as an inorganic base, to produce the corresponding freebase. Suitable bases include, but are not limited to, sodium bicarbonate, sodium carbonate, sodium hydroxide, potassium carbonate, potassium bicarbonate, potassium hydroxide, and the like, or combinations thereof. In one embodiment, the tartrate salt is contacted with sodium bicarbonate and sodium carbonate to produce the corresponding freebase.

Suitable solvents for use in step (h) include, but are not limited to, isopropyl acetate, methyl tert-butyl ether, water, isopropyl alcohol, and combinations thereof. Suitable solvents for use in step (i) include, but are not limited to, ethyl acetate, ethanol, water, and combinations thereof.

In some embodiments, the products of steps (d), (e), (g), and (h) of Scheme II are not isolated prior to the subsequent step.

An alternate process for preparing upadacitinib is illustrated in Scheme III. Compound (XIa) is hydrogenated to produce (I). Reaction of protected (3R,4S)-4-ethylpyrrolidine-3-carboxylic acid (I) with trimethylsulfoxonium chloride gives sulfur yilde (II). Contacting sulfur yilde (II) with an anhydrous source of HBr or HCl yields the corresponding halomethyl ketone (III). Reaction of (III) with (IV) in the presence of a base yields (V). Cyclization of (V) in the presence of a perfluoro acid anhydride and an organic base produces (VI). Removal of the protecting group and contacting the deprotected compound with an acid yields a pharmaceutically acceptable salt of (VII). Reacting the pharmaceutically acceptable salt of (VII) with 2,2,2-trifluoroethylamine produces upadacitinib.

Scheme III

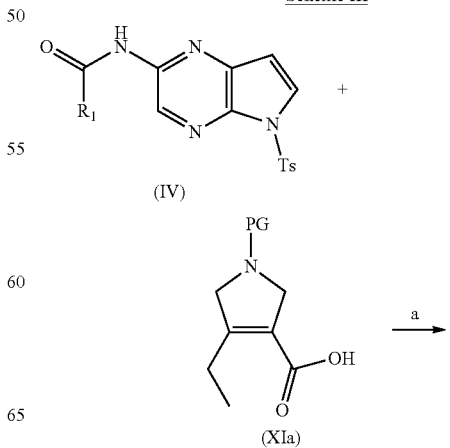

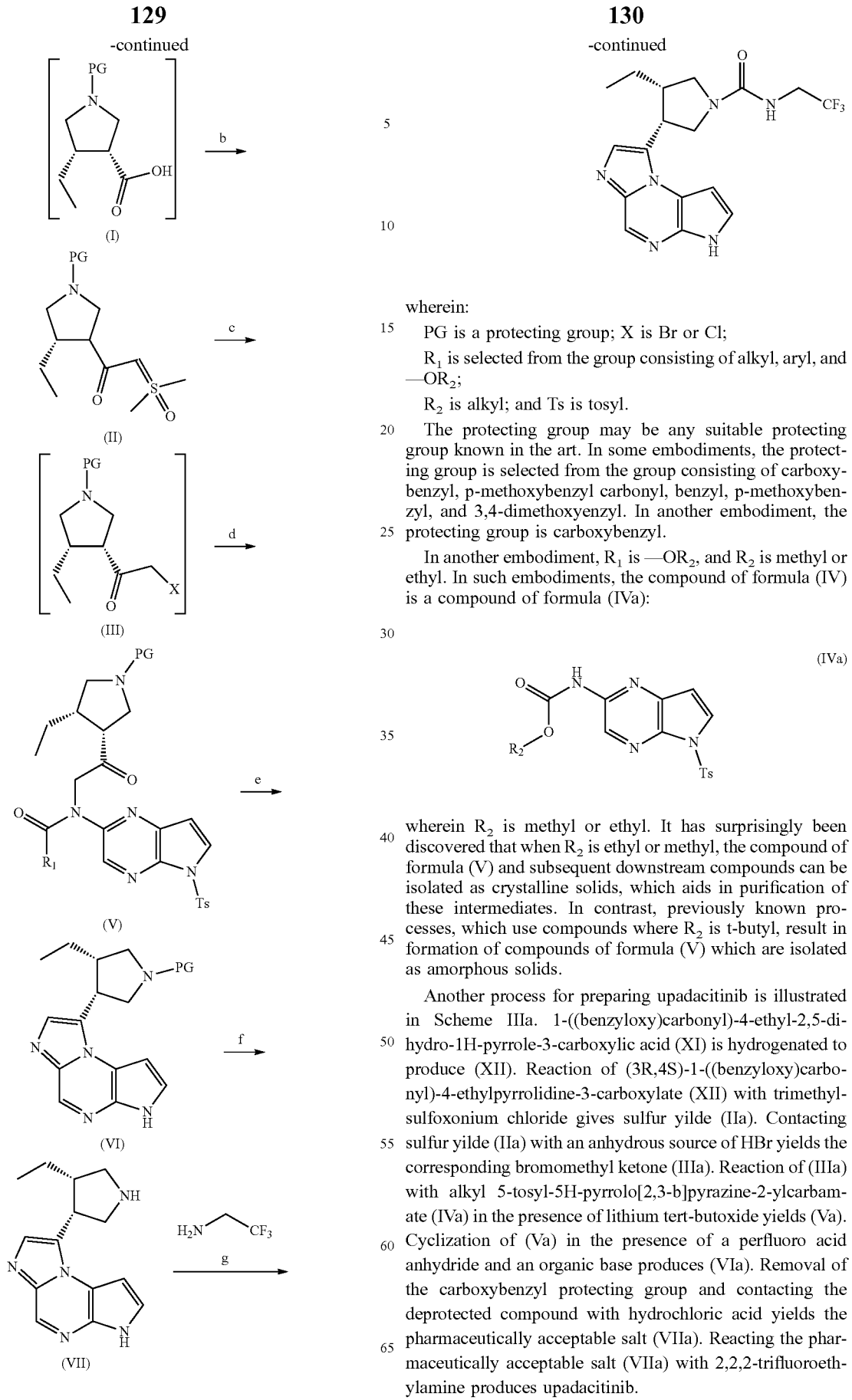

wherein:

PG is a protecting group; X is Br or Cl;

R₁ is selected from the group consisting of alkyl, aryl, and —OR₂;

R₂ is alkyl; and Ts is tosyl.

The protecting group may be any suitable protecting group known in the art. In some embodiments, the protecting group is selected from the group consisting of carboxybenzyl, p-methoxybenzyl carbonyl, benzyl, p-methoxybenzyl, and 3,4-dimethoxyenzyl. In another embodiment, the protecting group is carboxybenzyl.

In another embodiment, R₁ is —OR₂, and R₂ is methyl or ethyl. In such embodiments, the compound of formula (IV) is a compound of formula (IVa):

wherein R₂ is methyl or ethyl. It has surprisingly been discovered that when R₂ is ethyl or methyl, the compound of formula (V) and subsequent downstream compounds can be isolated as crystalline solids, which aids in purification of these intermediates. In contrast, previously known processes, which use compounds where R₂ is t-butyl, result in formation of compounds of formula (V) which are isolated as amorphous solids.

Another process for preparing upadacitinib is illustrated in Scheme IIIa. 1-((benzyloxy)carbonyl)-4-ethyl-2,5-dihydro-1H-pyrrole-3-carboxylic acid (XI) is hydrogenated to produce (XII). Reaction of (3R,4S)-1-((benzyloxy)carbonyl)-4-ethylpyrrolidine-3-carboxylate (XII) with trimethylsulfoxonium chloride gives sulfur ylide (IIa). Contacting sulfur ylide (IIa) with an anhydrous source of HBr yields the corresponding bromomethyl ketone (IIIa). Reaction of (IIIa) with alkyl 5-tosyl-5H-pyrrolo[2,3-b]pyrazine-2-ylcarbamate (IVa) in the presence of lithium tert-butoxide yields (Va). Cyclization of (Va) in the presence of a perfluoro acid anhydride and an organic base produces (VIa). Removal of the carboxybenzyl protecting group and contacting the deprotected compound with hydrochloric acid yields the pharmaceutically acceptable salt (VIIa). Reacting the pharmaceutically acceptable salt (VIIa) with 2,2,2-trifluoroethylamine produces upadacitinib.

Scheme IIIa

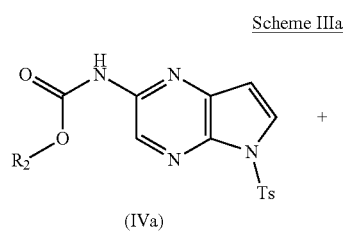

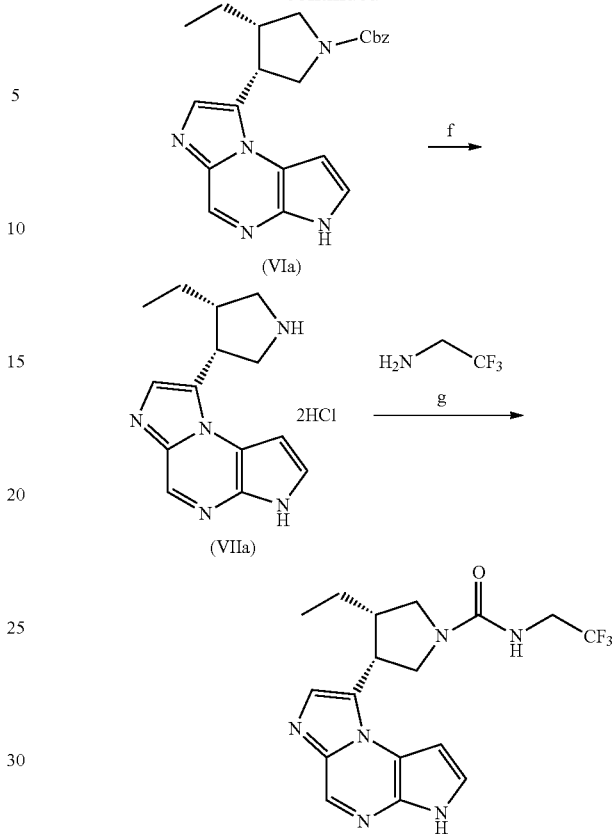

wherein:
Cbz is carboxybenzyl; Ts is tosyl; and R₂ is methyl or ethyl.

In step (a) of Schemes III and IIIa, (XIa) or (XI) (which may be prepared as described in Scheme V) is converted to (I) or (XII), respectively. In particular, in step (a), compound (XI) or (XIa) may be contacted with a catalyst, such as a ruthenium catalyst. Any catalyst comprising a chiral phosphine may be used. One particular example of a suitable catalyst is diacetato[(S)-(−)5,5'-bis(diphenylphosphino)-4,4'-bi-1,3-benzodioxolekuthenium(II) (i.e., (S)-Segphos Ru(OAc)₂). Suitable solvents for use in step (a) include, but are not limited to, methanol, triethylamine, and combinations thereof.

In particular, in certain embodiments, a solution of (XI) or (XIa) and the catalyst in solvent is hydrogenated at about 30° C. to about 100° C. for from about 1 hour to about 18 hours. In one embodiment, the solution of (XI) or (XIa) and the catalyst in solvent is hydrogenated at about 580 psi. In one embodiment, the solution of (XI) or (XIa) and the catalyst in solvent is hydrogenated at about 200 psi gauge (psig). In one embodiment, the solution of (XI) or (XIa) and the catalyst in solvent is hydrogenated at about 80° C. for from about 1 hour to about 8 hours, or for about 2 hours, or for about 4 hours. Upon completion, the reaction mixture is cooled to room temperature, filtered, and concentrated.

The reaction in step (b) of Schemes III and Ma, is generally accomplished in the presence of a coupling agent, such as carbonyldiimidazole (CDI), and a strong base. The strong base may be, for example, potassium tert-butoxide, sodium tert-butoxide, or combinations thereof. The step (b) reaction may be conducted in any suitable solvent including, but not limited to, tetrahydrofuran, water, and methyl tert-butyl ether. In one embodiment, the reaction is conducted in the presence of carbonyldiimidazole and potassium tert-butoxide.

More particularly, in certain embodiments, a suspension of trimethylsulfoxonium chloride, strong base, and solvent is heated (e.g., to about 35° C. to about 65° C., or to about 45° C.) for about 30 minutes to about 8 hours, or for about 1 hour, followed by cooling. In one embodiment, the suspension is cooled to a temperature of about −1° C. or less, or to about −5° C. or less. In some embodiments, the concentrated filtrate from step (a) is diluted with a suitable solvent (e.g., tetrahydrofuran), and to this solution is slowly added (e.g., over 30 minutes to 1 hour, or over 30 minutes) CDI. The resulting mixture is stirred at room temperature for 30 minutes to 12 hours, and typically for about 1 hour. The resulting solution is slowly added (e.g., over 15 minutes to 1 hour, or over 1 hour) to the suspension of the trimethylsulfoxonium chloride, strong base, and solvent, while maintaining the internal temperature below −1° C. In embodiments, the reaction may be stirred for about 30 minutes to about 8 hours, or for about 1 hour at a temperature of below about −1° C., or at about −5° C. In another embodiment, the reaction is quenched and the resulting compound of formula (II) or (IIa) is isolated prior to step (c).

Steps (a) and (b) of Schemes III and IIIa advantageously allow for preparation of a protected (3R,4S)-4-ethylpyrrolidine-3-carboxylic acid without formation and isolation of the naphthalenethane amine salt (Ia) or the dicyclohexylamine salt (Ib), or isolation of (I) or (XI).

In step (c) of Schemes III and IIIa, a compound of formula (II) or (IIa) is contacted with an anhydrous source of HBr or HCl to form a compound of formula (III) or (IIIa), respectively. In particular, the anhydrous source of HBr or HCl comprises no more than 0.2% water (by volume), or no more than about 0.15% water (by volume). The reaction of step (c) may be conducted in any suitable solvent including, tetrahydrofuran.

More particularly, in certain embodiments, (II) or (IIa) is combined with the HBr or HCl in a suitable solvent. In one embodiment, the solvents are tetrahydrofuran and acetic acid. In one embodiment, the solvent comprises no more than 0.2% water (by volume). In one embodiment, (II) or (IIa) is combined with a solvent (e.g., THF) and a solution of HBr in HOAc. The resulting mixture is warmed to about 35° C. to about 65° C., or about 40° C. and agitated. In one embodiment, the mixture is agitated for about 4 to about 12 hours, or for about 5 hours. In one embodiment, the mixture is warmed to about 40° C. and agitated (e.g., stirred) for about 5 hours. In one embodiment, the mixture is cooled to room temperature (e.g., around 20° C.) and distilled, followed by washing. In one particular embodiment, the product (compound (III) or (IIIa)) is concentrated to dryness, and resuspended in a solvent (e.g., N,N-dimethylacetamide) to form a solution of (III) or (IIIa) for use in step (d).

Step (c) advantageously produces the halomethyl ketone (III) or (IIIa) in higher purity than Scheme I or Ia.

In step (d) of Schemes III and IIIa, a compound of formula (III) or (IIIa) is reacted with a compound of formula (IV) or (IVa) (prepared as described herein). The step (d) reaction is conducted in the presence of a base, such as lithium tert-butoxide, sodium tert-butoxide, or combinations thereof. In one embodiment, the base is lithium tert-butoxide. The reaction of step (d) may be conducted in any suitable solvent including, but not limited to dimethylacetamide, tetrahydrofuran, dichloromethane, ethyl acetate, heptanes, and combinations thereof.

More particularly, in certain embodiments, the base is slowly added (e.g., over about 30 minutes) to a cooled suspension of the compound of formula (IV) or (IVa) in a solvent. In one embodiment, the suspension of the compound of formula (IV) or (IVa) is cooled to about 0° C. The resulting solution is stirred for about 30 minutes to about 12 hours, or about 30 minutes, and cooled to about −20° C. to about 0° C., or about −10° C. In one embodiment, the solution is stirred for about 30 minutes and cooled to about −20° C. to about 0° C., or about −10° C. The halomethyl ketone solution prepared in step (c) is then slowly added (e.g., over about 1 hour), and the resulting mixture is agitated (e.g., stirred) for about 30 minutes to about 6 hours, or about 30 minutes, at a temperature of about −20° C. to about 0° C., or about −10° C. In one embodiment, following addition of the step (c) solution, the resulting mixture is stirred for about 30 minutes at a temperature of about −10° C. In one embodiment, the reaction is quenched, and, in some embodiments, the resulting product (V) or (Va) is isolated prior to step (e).

Steps (e)-(g) of Schemes III and IIIa may be conducted as described above for steps (d)-(f) of Scheme I, respectively.

VI. SOLID STATE FORMS

The present disclosure also relates to the use of solid state forms of upadacitinib in the treatment of Crohn's disease and ulcerative colitis. Solid state forms include the Amorphous Freebase form of upadacitinib, Freebase Solvate Form A, Freebase Hydrate Form B, Freebase Hydrate Form C, Tartrate Hydrate, and Freebase Anhydrate Form D. These and other solid state forms of upadacitinib are described in U.S. patent application Ser. No. 15/295,561, which is herein incorporated by reference. The sections below also discuss solid state forms that have been identified and selected properties of those solid state forms.

A. Amorphous Freebase

In one embodiment, the solid state form is amorphous upadacitinib (the "Amorphous Freebase"). In one aspect, the Amorphous Freebase comprises less than about 13% by weight water. In another aspect, the Amorphous Freebase comprises less than about 12% by weight water. In another aspect, the Amorphous Freebase comprises less than about 10% by weight water. In another aspect, the Amorphous Freebase comprises less than about 9% by weight water. In another aspect, the Amorphous Freebase comprises less than about 8% by weight water. In another aspect, the Amorphous Freebase comprises less than about 7% by weight water. In another aspect, the Amorphous Freebase comprises less than about 6% by weight water. In another aspect, the Amorphous Freebase comprises less than about 5% by weight water. In another aspect, the Amorphous Freebase comprises less than about 4% by weight water. In another aspect, the Amorphous Freebase comprises less than about 3% by weight water. In another aspect, the Amorphous Freebase comprises less than about 2% by weight water. In another aspect, the Amorphous Freebase comprises less than about 1% by weight water. In another aspect, the Amorphous Freebase has a glass transition temperature onset at about 119° C. In another aspect, the Amorphous Freebase has a glass transition temperature midpoint at about 122° C. In another aspect, the Amorphous Freebase has a glass transition temperature onset at about 119° C. and a glass transition temperature midpoint at about 122° C.

The Amorphous Freebase generally has greater solubility, and increased bioavailability, relative to the corresponding crystalline forms of the compound. The Amorphous Freebase also has acceptable chemical stability. In addition, the Amorphous Freebase exhibits acceptable stability to light and peroxide. The Amorphous Freebase, however, is hygroscopic and can comprise as much as 12% by weight water at 25° C./90% relative humidity. Environmental controls potentially are required to ensure appropriate control of potency and water content during storage, dispensing, and handling of the Amorphous Freebase.

The Amorphous Freebase can be prepared, for example, using anti-solvent crystallization to prepare the Freebase Solvate Form A or Freebase Hydrate Form B (described below) followed by dehydration or desolvation to yield the Amorphous Freebase. This crystallization/dehydration/desolvation method allows for the large-scale manufacture of the Amorphous Freebase without the need for labor-intensive and expensive techniques such as spray-drying. It also provides for appropriate control of the bulk properties of the Amorphous Freebase (i.e., particle size, flow properties etc.). When the Amorphous Freebase is prepared by desolvation of the Freebase Solvate Form A or dehydration of the Freebase Hydrate Form B, the Amorphous Freebase generally retains the morphology of the Freebase Solvate Form A or Freebase Hydrate Form B (i.e., blades with hexagonal crystal faces when prepared by dehydration of Freebase Hydrate Form B, or irregular when desolvated from Freebase Solvate Form A).

The process volumes required for crystallization during the large-scale manufacture of the Freebase Solvate Form A or Freebase Hydrate Form B generally are within conventional processing volumes, but impurity rejection potentially may be lower than desired. Drying and dehydration/desolvation of the Freebase Hydrate Form B/Freebase Solvate Form A to the Amorphous Freebase generally can be carried out with standard equipment under conventional conditions and the isolated Amorphous Freebase typically can be co-milled without adversely impacting the amorphous state.

B. Crystalline Freebase Solvates and Hydrates

In another embodiment, the solid state form is a crystalline freebase of upadacitinib. In one aspect, the crystalline freebase is a solvate. In another aspect, the crystalline freebase is an isopropyl acetate/water solvate (the "Freebase Solvate Form A"). In another aspect, the crystalline freebase is a hydrate (the "Freebase Hydrate Form B"). The Freebase Solvate Form A and the Freebase Hydrate Form B are further described in the Examples of the application.

In one embodiment, the crystalline freebase solvate or hydrate has an X-ray powder diffraction pattern characterized by peaks at 3.1±0.2, 9.3±0.2, and 12.0±0.2 degrees two theta when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2 degrees two theta, and that is further characterized by a peak at one or more of 13.7±0.2, 20.8±0.2 and 25.0±0.2 degrees two theta when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, and 20.8±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, and 25.0±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, 20.8±0.2, and 25.0±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, 12.0±0.2, 13.7±0.2, 20.8±0.2, and 25.0±0.2 degrees two theta when measured at about 25° C. with monochromatic Kα1 radiation.

In one embodiment, the crystalline freebase solvate or hydrate has an X-ray powder diffraction pattern without a significant peak at one or more of 15.1±0.2, and 21.7±0.2 degrees two theta when measured at about 25° C. with monochromatic Kα1 radiation.

In one embodiment, the crystalline freebase solvate or hydrate has an X-ray powder diffraction pattern without a significant peak at one or more of 3.9±0.2, 6.8±0.2, and 14.1±0.2 degrees two theta when measured at about 25° C. with monochromatic Kα1 radiation.

In one embodiment, the crystalline freebase solvate or hydrate has an X-ray powder diffraction pattern without a significant peak at one or more of 15.1±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2 degrees two theta, and without a significant peak at one or more of 15.1±0.2, and 21.7±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2 degrees two theta, and without a significant peak at one or more of 15.1±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2, 13.7±0.2, 20.8±0.2, and 25.0±0.2 degrees two theta, and without a significant peak at one or more of 15.1±0.2, and 21.7±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2, 13.7±0.2, 20.8±0.2, and 25.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks at 3.1±0.2, 9.3±0.2, and 12.0±0.2, 13.7±0.2, 20.8±0.2, and 25.0±0.2 degrees two theta, and without a significant peak at one or more of 15.1±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the crystalline freebase solvate or hydrate has an X-ray powder diffraction pattern characterized by peaks substantially at the positions listed in Table 15-A±0.2 degrees two theta, when measured at about 25° C. with monochromatic Kα1 radiation.

In one embodiment, the crystalline freebase solvate or hydrate has an X-ray powder diffraction pattern characterized by peaks substantially at the positions listed in Table 15-B±0.2 degrees two theta, when measured at about 25° C. with monochromatic Kα1 radiation.

In one embodiment, the crystalline freebase solvate or hydrate has an X-ray powder diffraction pattern characterized by peaks substantially at the positions listed in Table 17-B±0.2 degrees two theta that have a relative intensity of at least 10.0%, when measured at about 25° C. with monochromatic Kα1 radiation.

In further aspects of each of the above embodiments, the significant peak values have a variation of ±0.1 degrees two theta rather than ±0.2 degrees two theta. In still further aspects of each of the above embodiments, the significant peak values have a variation of ±0.05 degrees two theta rather than ±0.2 degrees two theta.

Figure 19:
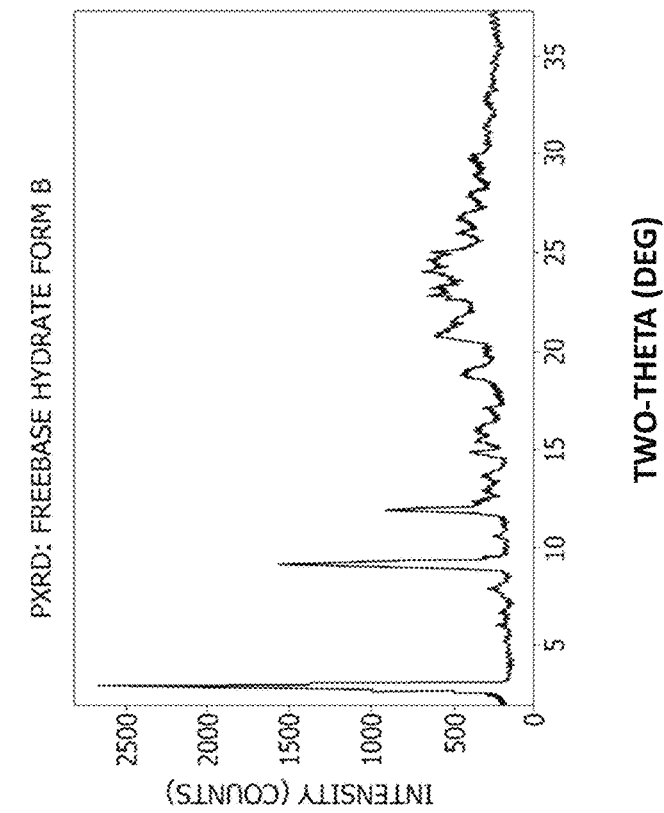
FIG. 19 is a powder X-ray diffraction pattern corresponding to the Freebase Hydrate Form B.

In one embodiment, the crystalline freebase has an X-ray powder diffraction pattern substantially as shown in FIG. 19.

The Freebase Solvate Form A and Freebase Hydrate Form B are not physically stable. As discussed above, they desolvate (or dehydrate) and convert to the Amorphous Freebase upon drying. Although the Freebase Solvate Form A and Freebase Hydrate Form B generally do not exhibit pharmaceutically acceptable physical stability for use as an active ingredient in a pharmaceutical dosage form, they are useful intermediates in the preparation of other solid state forms such as the Amorphous Freebase.

C. Crystalline Freebase Hydrate Form C (Hemihydrate)

In another embodiment, the solid state form is a crystalline hydrate, wherein the crystalline hydrate is a hemihydrate. In another embodiment, the solid state form is crystalline hemihydrate of upadacitinib having a powder X-ray diffraction pattern corresponding to Freebase Hydrate Form C. The Freebase Hydrate Form C is further described in the Examples of the application.

In one embodiment, the Freebase Hydrate Form C has an X-ray powder diffraction pattern characterized by peaks at 13.4±0.2, 15.1±0.2, and 21.7±0.2 degrees two theta when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and that is further characterized by a peak at one or more of 7.7±0.2, 7.9±0.2, 9.6±0.2, 10.3±0.2, 13.9±0.2, 15.5±0.2, 15.9±0.2, 17.0±0.2, 17.2±0.2, 17.8±0.2, 18.1±0.2, 18.3±0.2, 19.3±0.2, 19.7±0.2, 20.5±0.2, 20.9±0.2, 21.9±0.2, 22.2±0.2, 23.5±0.2, 24.4±0.2, 24.9±0.2, 28.2±0.2, and 29.5±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 15.5±0.2, and 21.7±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 17.0±0.2, and 21.7±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 20.9±0.2, and 21.7±0.2 degrees two theta when measured at about 25° C. with monochromatic Kα1 radiation.

In one embodiment, the Freebase Hydrate Form C has an X-ray powder diffraction pattern that is characterized by peaks at 13.4±0.2, 15.1±0.2, 15.5±0.2, 17.0±0.2, 20.9±0.2, and 21.7±0.2 degrees two theta when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta when measured at about 25° C. with monochromatic Kα1 radiation.

In one embodiment, the Freebase Hydrate Form C has an X-ray powder diffraction pattern without a significant peak at one or more of 3.1±0.2, 9.3±0.2, and 12.0±0.2 degrees two theta, when measured at about 25° C. with monochromatic Kα1 radiation.

In one embodiment, the Freebase Hydrate Form C has an X-ray powder diffraction pattern without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern without a significant peak at one or more of 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 13.4±0.2, 15.1±0.2, and 21.7±0.2 degrees two theta, and without a significant peak at one or more of 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks at 15.5±0.2, 13.4±0.2, 15.1±0.2, 19.3±0.2, 20.5±0.2, and 21.7±0.2 degrees two theta, and without a significant peak at one or more of 3.1±0.2, 9.3±0.2, and 12.0±0.2 degrees two theta, and without a significant peak at one or more of 3.9±0.2, 6.8±0.2, and 14.1±0.2 degrees two theta, when measured at about 25° C. with monochromatic Kα1 radiation.

In one embodiment, the Freebase Hydrate Form C has an X-ray powder diffraction pattern characterized by peaks substantially at the positions listed in Table 15-C±0.2 degrees two theta, when measured at about 25° C. with monochromatic Kα1 radiation.

In one embodiment, the Freebase Hydrate Form C has an X-ray powder diffraction pattern characterized by peaks substantially at the positions listed in Table 17-C±0.2 degrees two theta that have a relative intensity of at least 10.0%, when measured at about 25° C. with monochromatic Kα1 radiation.

In further aspects of each of the above embodiments, the significant peak values have a variation of ±0.1 degrees two theta rather than ±0.2 degrees two theta. In still further aspects of each of the above embodiments, the significant peak values have a variation of ±0.05 degrees two theta rather than ±0.2 degrees two theta.

Figure 20:
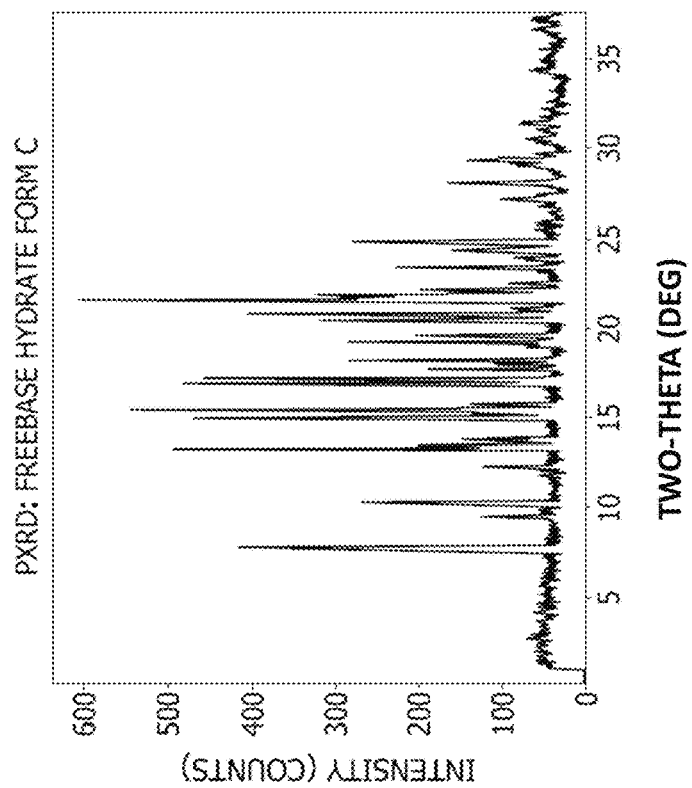
FIG. 20 is a powder X-ray diffraction pattern corresponding to the Freebase Hydrate Form C.

In one embodiment, the Freebase Hydrate Form C has an X-ray powder diffraction pattern substantially as shown in FIG. 20 when measured at about 25° C. with monochromatic Kα1 radiation.

The Freebase Hydrate Form C generally exhibits good chemical stability, physical stability, and solid state properties (including low hygroscopicity). Large-scale manufacture of the Freebase Hydrate Form C is relatively straightforward with minimal scaling, good yield, good impurity rejection, fast filtration, conventional drying, and minimal milling issues (even after subjecting the isolated material to high energy pinmilling) In addition, different particle sizes can be achieved through appropriate control of the crystallization process.

D. Crystalline Freebase Anhydrate Form D

In another embodiment, the solid state form is a crystalline anhydrate freebase of upadacitinib having a powder X-ray diffraction pattern corresponding to Freebase Anhydrate Form D. The Freebase Anhydrate Form D is further described in the Examples of the application.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and that is further characterized by a peak at one or more of 4.0±0.2, 18.4±0.2, 19.0±0.2, 23.0±0.2, and 24.7±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 8.0±0.2, 9.7±0.2, 14.2±0.2, 14.5±0.2, and 20.3±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 18.4±0.2 and 20.3±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 19.0±0.2 and 20.3±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2 and 20.3±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 20.3±0.2, and 23.0±0.2 degrees two theta, when measured at about 25° C. with monochromatic Kα1 radiation.

In one embodiment, the Freebase Anhydrate Form D has an X-ray powder diffraction pattern characterized by peaks at 8.0±0.2, 9.7±0.2, 14.2±0.2, 14.5±0.2, 20.3±0.2, and 24.7±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 14.5±0.2, and 19.0±0.2 degrees two theta, when measured at about 25° C. with monochromatic Kα1 radiation.

In one embodiment, the Freebase Anhydrate Form D has an X-ray powder diffraction pattern characterized by peaks at 4.0±0.2, 14.5±0.2, and 19.0±0.2 degrees two theta, and that is further characterized by a peak at one or more of 8.0±0.2, 9.7±0.2, 14.2±0.2, 18.4±0.2, 20.3±0.2, 23.0±0.2, and 24.7±0.2 degrees two theta, when measured at about 25° C. with monochromatic Kα1 radiation.

In one embodiment, the Freebase Anhydrate Form D has an X-ray powder diffraction pattern without a significant peak at one or more of 3.1±0.2, 9.3±0.2, and 20.8±0.2 degrees two theta, when measured at about 25° C. with monochromatic Kα1 radiation.

In one embodiment, the Freebase Anhydrate Form D has an X-ray powder diffraction pattern without a significant peak at one or more of 6.8±0.2, 15.7±0.2, and 21.9±0.2 degrees two theta, when measured at about 25° C. with monochromatic Kα1 radiation.

In one embodiment, the Freebase Anhydrate Form D has an X-ray powder diffraction pattern without a significant peak at one or more of 13.4±0.2, 15.5±0.2, and 21.7±0.2 degrees two theta, when measured at about 25° C. with monochromatic Kα1 radiation.

In one embodiment, the Freebase Anhydrate Form D has an X-ray powder diffraction pattern without a significant peak at one or more of 13.4±0.2, 15.5±0.2, and 21.7±0.2 degrees two theta, and without a significant peak at one or more of 6.8±0.2, 15.7±0.2, and 21.9±0.2 degrees two theta, and without a significant peak at one or more of 3.1±0.2, 9.3±0.2, and 20.8±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 3.1±0.2, 9.3±0.2, and 20.8±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 6.8±0.2, 15.7±0.2, and 21.9±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment the Freebase Anhydrate Form D has an X-ray powder diffraction pattern characterized by peaks at 8.0±0.2, 9.7±0.2, 14.2±0.2, 14.5±0.2, and 20.3±0.2 degrees two theta, and without a significant peak at one or more of 3.1±0.2, 9.3±0.2, and 20.8±0.2 degrees two theta, and without a significant peak at one or more of 6.8±0.2, 15.7±0.2, and 21.9±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 3.1±0.2, 9.3±0.2, and 20.8±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 6.8±0.2, 15.7±0.2, and 21.9±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment the Freebase Anhydrate Form D has an X-ray powder diffraction pattern characterized by peaks at 4.0±0.2, 8.0±0.2, 9.7±0.2, 14.2±0.2, 14.5±0.2, 19.0±0.2, and 20.3±0.2 degrees two theta, and without a significant peak at one or more of 3.1±0.2, 9.3±0.2, and 20.8±0.2 degrees two theta, and without a significant peak at one or more of 6.8±0.2, 15.7±0.2, and 21.9±0.2 degrees two theta, and without a significant peak at one or more of 13.4±0.2, 15.5±0.2, and 21.7±0.2 degrees two theta, when measured at about 25° C. with monochromatic Kα1 radiation.

In one embodiment, the Freebase Anhydrate Form D has an X-ray powder diffraction pattern characterized by peaks substantially at the positions listed in Table 15-E±0.2 degrees two theta, when measured at about 25° C. with monochromatic Kα1 radiation.

In one embodiment, the Freebase Anhydrate Form D has an X-ray powder diffraction pattern characterized by peaks substantially at the positions listed in Table 15-E±0.2 degrees two theta that have a relative intensity of at least 10.0%, when measured at about 25° C. with monochromatic Kα1 radiation.

In further aspects of each of the above embodiments, the significant peak values have a variation of ±0.1 degrees two theta rather than ±0.2 degrees two theta. In still further aspects of each of the above embodiments, the significant peak values have a variation of ±0.05 degrees two theta rather than ±0.2 degrees two theta.

Figure 22:
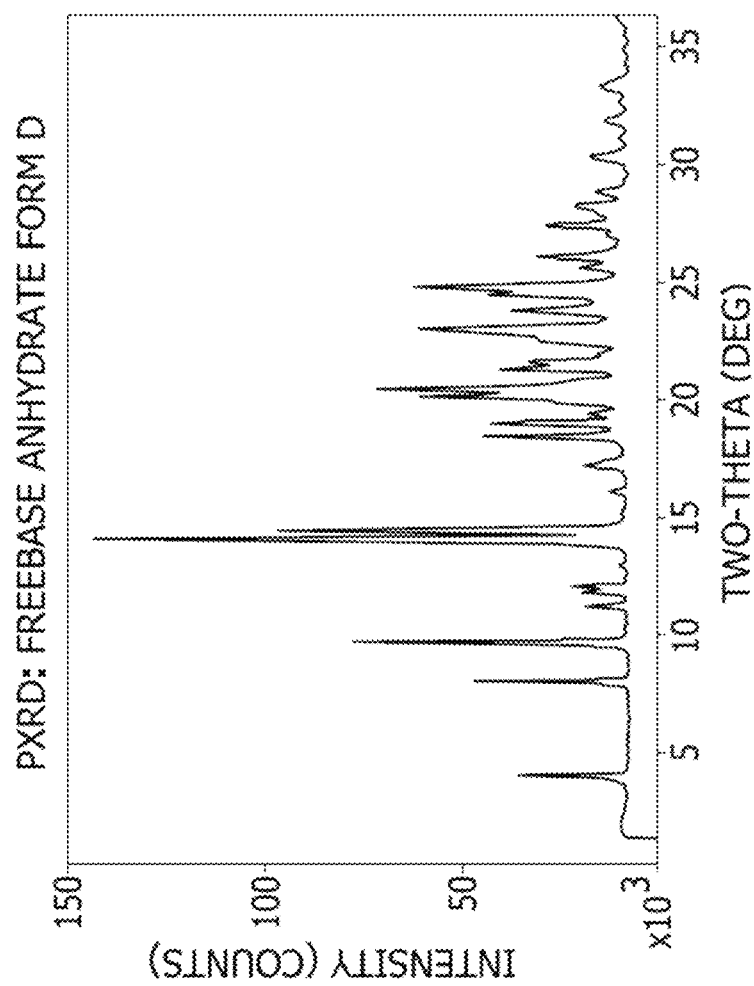
FIG. 22 is a powder X-ray diffraction pattern corresponding to the Freebase Anhydrate Form D.
Figures 23A, 23B, 23C:
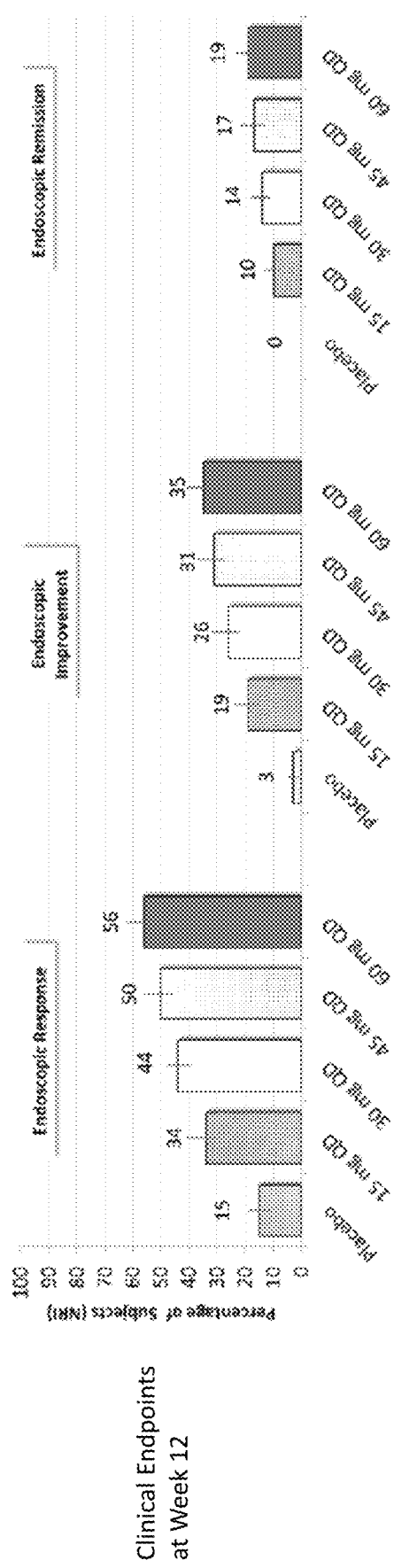
FIGS. 23A-23F are graphs depicting the exposure-response model-predicted efficacy for clinical and endoscopic endpoints for extended-release formulation QD regimens.
Figures 23D, 23E, 23F:
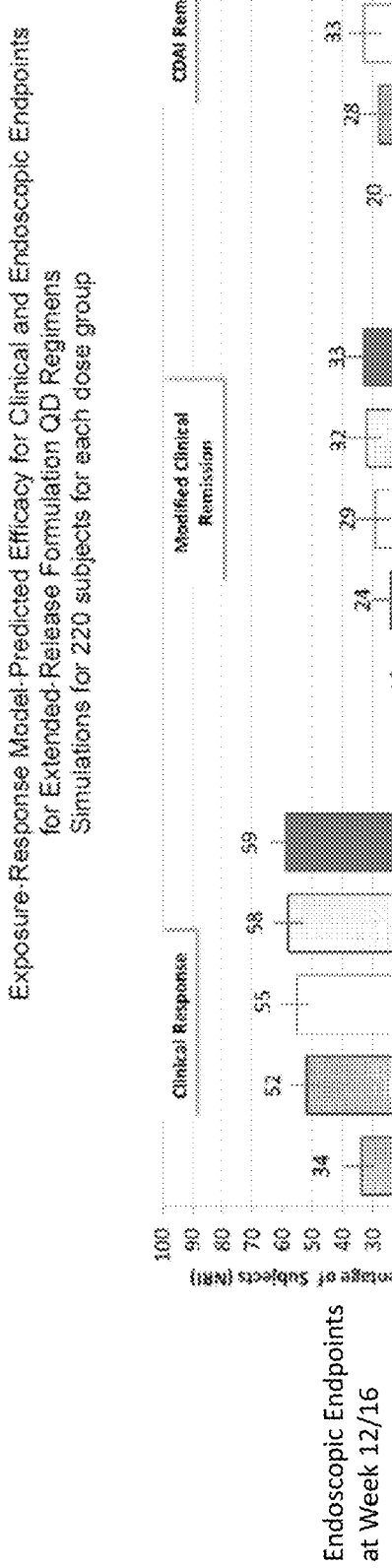
Figure 24:
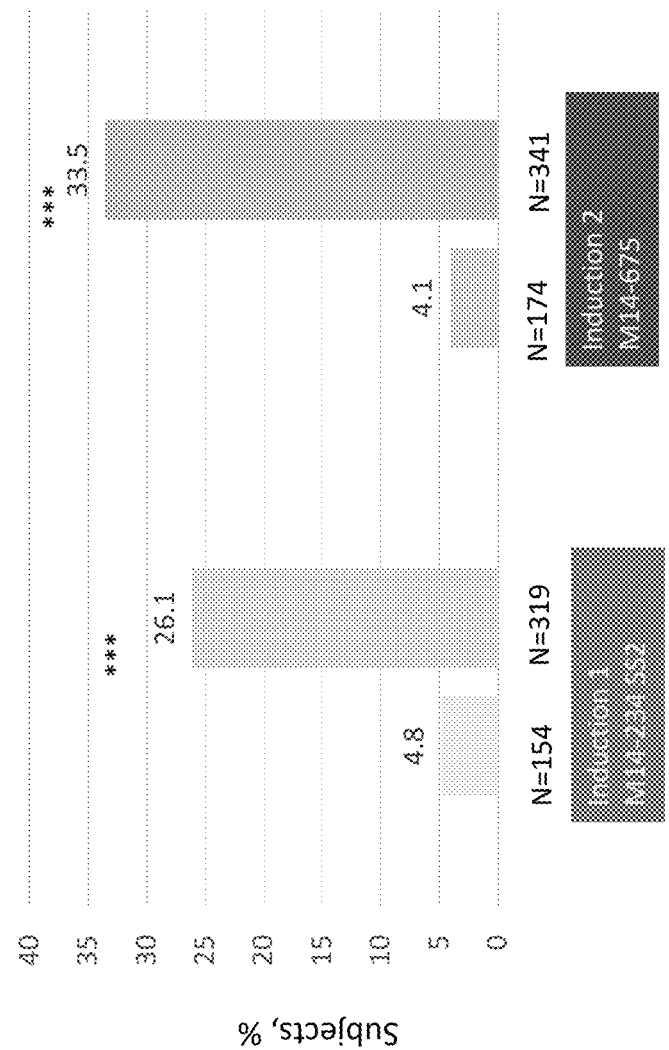
FIG. 24 shows the clinical remission at week 8 in a patient population administered upadacitinib or placebo in the Example 19 ulcerative colitis clinical study, based on achieving an Adapted Mayo score ≤2, with SFS≤1 and not greater than baseline, RBS of 0, and endoscopic subscore ≤1.

In one embodiment, the Freebase Anhydrate Form D has an X-ray powder diffraction pattern substantially as shown in FIG. 22 when measured at about 25° C. with monochromatic Kα1 radiation.

Freebase Anhydrate Form D is reversibly hygroscopic (up to 1.8% water at 90% RH at 25° C.), and is metastable relative to Freebase Hydrate Form C at typical environmental conditions (e.g., above 2.4% RH at 23° C.) used during storage for downstream processing. The manufacture of Freebase Anhydrate Form D requires strict control of water, as the Freebase Anhydrate Form D can be manufactured only when the water content of the crystallization solvent is low (e.g., less than 0.15% at 23° C., corresponding to a water activity of 2.4%), and will convert to Freebase Hydrate Form C in solutions at high water content. Freebase Anhydrate Form D is slow to crystallize, and difficult to manufacture in higher yield.

E. Crystalline Tartrate

In another embodiment, the solid state form is a tartrate of upadacitinib. In one aspect, the tartrate is amorphous. In another aspect, the tartrate is crystalline. In another aspect, the crystalline tartrate is a solvate. In another aspect, the crystalline tartrate is a hydrate. In another aspect, the tartrate is a crystalline L-tartrate. In another aspect, the crystalline L-tartrate is a hydrate. In another aspect, the crystalline tartrate is a tetrahydrate (the "Tartrate Hydrate"). The Tartrate Hydrate (a tetrahydrate) is further described in the Examples of the application.

In one embodiment, the Tartrate Hydrate has an X-ray powder diffraction pattern characterized by peaks at 3.9±0.2, 6.8±0.2, and 14.1±0.2 degrees two theta when measured at about 25° C. with monochromatic Kα1 radiation.

In one embodiment, the Tartrate Hydrate has an X-ray powder diffraction pattern characterized by peaks at 3.9±0.2, 6.8±0.2, 14.1±0.2, 15.7±0.2, 21.9±0.2, and 25.9±0.2 degrees two theta when measured at about 25° C. with monochromatic Kα1 radiation.

In one embodiment, the Tartrate Hydrate has an X-ray powder diffraction pattern without a significant peak at one or more of 13.4±0.2 and 15.1±0.2 degrees two theta, when measured at about 25° C. with monochromatic Kα1 radiation.

In one embodiment, the Tartrate Hydrate has an X-ray powder diffraction pattern without a significant peak at one or more of 3.1±0.2, 9.3±0.2, and 12.0±0.2 degrees two theta, when measured at about 25° C. with monochromatic Kα1 radiation.

In one embodiment, the Tartrate Hydrate has an X-ray powder diffraction pattern without a significant peak at one or more of 13.4±0.2 and 15.1±0.2 degrees two theta, and without a significant peak at one or more of 3.1±0.2 and 9.3±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, and 14.1±0.2 degrees two theta, and without a significant peak at one or more of 13.4±0.2 and 15.1±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, and 14.1±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, and 14.1±0.2 degrees two theta, and without a significant peak at one or more of 13.4±0.2 and 15.1±0.2 degrees two theta, and without a significant peak at one or more of 3.1±0.2, 9.3±0.2, and 12.0±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, 14.1±0.2, 15.7±0.2, 21.9±0.2 degrees two theta, and without a significant peak at one or more of 13.4±0.2 and 15.1±0.2 degrees two theta, when measured at about 25° C. with monochromatic Kα1 radiation.

In one embodiment, the Tartrate Hydrate has an X-ray powder diffraction pattern characterized by peaks at 3.9±0.2, 6.8±0.2, 14.1±0.2, 15.7±0.2, 21.9±0.2 degrees two theta, and without a significant peak at one or more of 3.1±0.2, 9.3±0.2, and 12.0±0.2 degrees two theta.

In one embodiment, the Tartrate Hydrate has an X-ray powder diffraction pattern characterized by peaks at 3.9±0.2, 6.8±0.2, 14.1±0.2, 15.7±0.2, 21.9±0.2 degrees two theta, and without a significant peak at one or more of 13.4±0.2 and 15.1±0.2 degrees two theta, and without a significant peak at one or more of 3.1±0.2, 9.3±0.2, and 12.0±0.2 degrees two theta.

In further aspects of each of the above embodiments, the significant peak values have a variation of ±0.1 degrees two theta rather than ±0.2 degrees two theta. In still further aspects of each of the above embodiments, the significant peak values have a variation of ±0.05 degrees two theta rather than ±0.2 degrees two theta.

Figure 21:
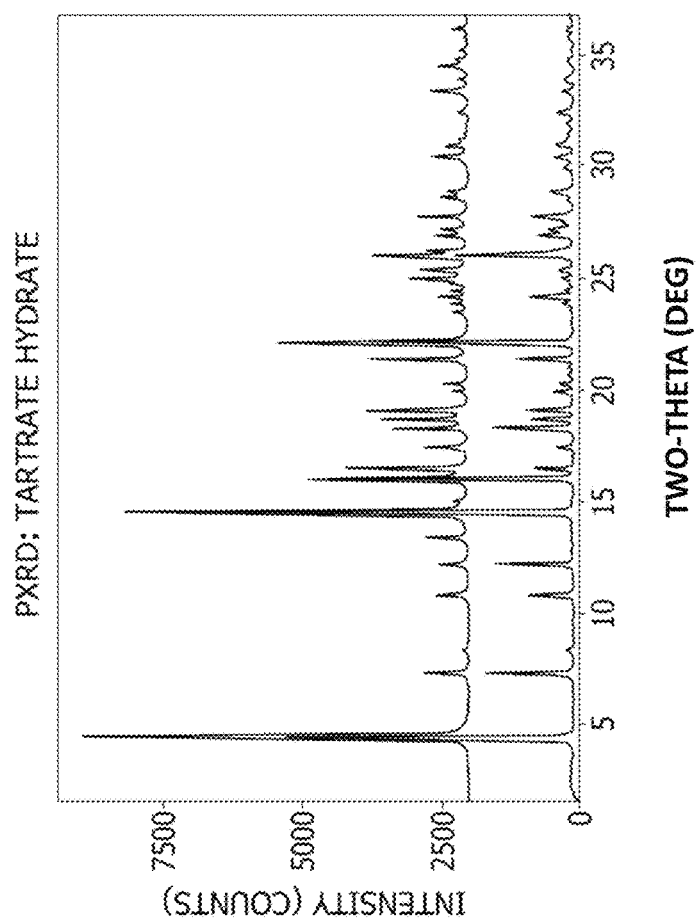
FIG. 21 is a powder X-ray diffraction pattern corresponding to the Tartrate Hydrate. The experimental PXRD pattern is shown at the bottom of FIG. 21 and the calculated PXRD pattern is shown at the top of FIG. 21.

In one embodiment, the Tartrate Hydrate has an X-ray powder diffraction pattern substantially as shown in FIG. 21, when measured at about 25° C. with monochromatic Kα1 radiation.

The Tartrate Hydrate has acceptable chemical stability and exhibits acceptable stability to light and peroxide. The Tartrate Hydrate has good solubility (BCS Class I) and is not hygroscopic. The Tartrate Hydrate, however, potentially will convert to an amorphous tartrate below 10% relative humidity, when heated, or when compressed or under shear.

The Tartrate Hydrate can be manufactured, for example, using anti-solvent crystallization. Impurity rejection during the large-scale manufacture of the Tartrate Hydrate generally is good, but scaling may be greater than desired and specific anti-solvent addition controls and process volume restrictions potentially may be required. In addition, appropriate control of the filtration, washing, and drying steps may be required to minimize consolidation of the wet cake and formation of hard lumps in the isolated material. For example, control of the relative humidity (e.g., greater than 10% and less than 100% relative humidity), temperature (e.g., crystallization at about 10° C. works well), and mixing rate may be required during drying to minimize the formation of hard lumps in the isolated material. Insufficient control of the drying conditions potentially will produce a consolidated, harder material that may be difficult to break up during subsequent processing. As previously noted, shearing and compression potentially will cause conversion to the amorphous tartrate. The dried material typically is milled with mechanical impact mills (e.g., Fitzmills and pin mills) because shear-based mills (e.g., comills) can lead to loss of crystallinity. In addition, loss of crystallinity potentially can result from pressure or compression forces during formulation (such as would be required for tableting).

F. Crystalline Purity

In additional embodiments of the solid state forms discussed above, the solid state form has a pharmaceutically acceptable crystalline purity (or a pharmaceutically acceptable amorphous purity in the case of the Amorphous Freebase). For example, in one aspect, upadacitinib comprises at least about 75% by weight of the desired solid state form. In another aspect, at least 80% by weight is the desired solid state form. In another aspect, at least 85% by weight is the desired solid state form. In another aspect, at least 90% by weight is the desired solid state form. In another aspect, at least 95% by weight is the desired solid state form. In another aspect, at least 96% by weight is the desired solid state form. In another aspect, at least 97% by weight is the desired solid state form. In another aspect, at least 98% by weight is the desired solid state form. In another aspect, at least 99% by weight is the desired solid state form. In another aspect, upadacitinib is present as the substantially crystalline pure (or amorphous pure in the case of the Amorphous Freebase) solid state form. In a preferred aspect, the solid state form is the Amorphous Freebase. In another aspect, the solid state form is Freebase Anhydrate Form D. In a more preferred aspect, the solid state form is the Freebase Hydrate Form B. In a particularly preferred aspect, the solid state form is the Freebase Hydrate Form C. In a preferred aspect, the solid state form is the Tartrate Hydrate.

VII. SOLID STATE PREPARATION

The present disclosure also relates to methods for preparing a solid state form of upadacitinib. In one aspect, the solid state form prepared is the Amorphous Freebase. In another aspect, the solid state form prepared is the Freebase Hydrate Form B. In another aspect, the solid state form prepared is the Freebase Hydrate Form C. In another aspect, the solid state form prepared is the Tartrate Hydrate. In another aspect, the solid state form prepared is the Freebase Anhydrate Form D.

A. Preparation of Amorphous Freebase

Figure 14:
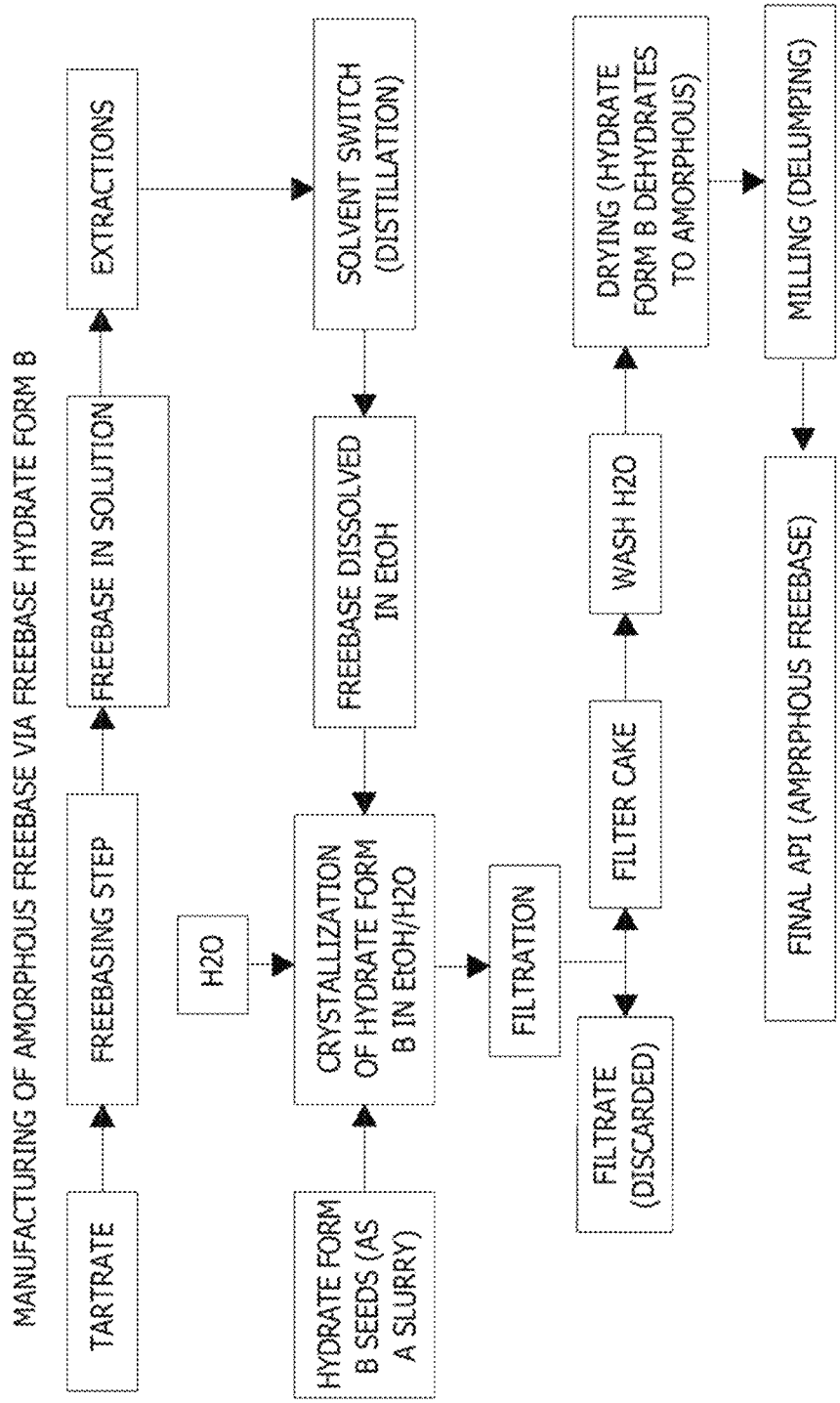
FIG. 14 schematically illustrates one method of preparing the Amorphous Freebase.

The present disclosure relates to methods for preparing the Amorphous Freebase. In one embodiment, the method comprises dehydrating the Freebase Hydrate Form B to provide the Amorphous Freebase. In another embodiment, the method comprises desolvating the Freebase Solvate Form A to provide the Amorphous Freebase. A wide range of process conditions can be employed for the dehydration/desolvation. The dehydration can be conducted, for example, under ambient conditions or in a vacuum oven. FIG. 14 schematically illustrates one method of preparing the Amorphous Freebase by dehydration of the Freebase Hydrate Form B.

In another embodiment, the method comprises dissolving upadacitinib in a solvent or mixture of solvents; and adjusting the pH of the solvent or mixture of solvents to a pH greater than about 8 to initiate precipitation of the Amorphous Freebase. In one aspect, the solvent or mixture of solvents comprises water. In another aspect, the pH is adjusted to a pH greater than about 9. In another aspect, the pH is adjusted to a pH greater than about 10. In another aspect, the pH is adjusted to a pH greater than about 11. In another aspect, the pH is adjusted to a pH of at least about 9.

In still other embodiments, the method comprises preparing the Amorphous Freebase using a method selected from the group consisting of impinging jet, spray drying, and hot-melt extrusion.

B. Preparation of Crystalline Freebase Solvate Form A and Crystalline Freebase Hydrate Form B The present disclosure additionally relates to methods for preparing the Freebase Solvate Form A and Freebase Hydrate Form B. In one embodiment, the method comprises dissolving upadacitinib in a solvent or mixture of solvents comprising an anti-solvent; and maintaining the solvent or mixture of solvents at a temperature less than about 15° C. for an amount of time sufficient to initiate crystallization of the Freebase Solvate Form A or the Freebase Hydrate Form B. The anti-solvent can comprise, for example, water. The solvent or mixture of solvents can comprise a polar solvent such as a solvent is selected from the group consisting of methanol, ethanol, n-butylamine, acetone, acetonitrile, ethyl formate, methyl acetate, ethyl acetate, methyl ethyl ketone, methyl isobutyl ketone, methyl isobutyl ketone, methyl tert-butyl ether, and isopropyl acetate. The Freebase Solvate Form A and Freebase Hydrate Form B exhibit similar PXRD patterns, and are therefore isostructural. The method generally is conducted at sub-ambient temperatures, for example, less than about 10° C., less than about 5° C., or less than about 0° C. In certain aspects, the process further comprises seeding the solvent or mixture of solvents with crystals of the Freebase Solvate Form A or the Freebase Hydrate Form B.

C. Preparation of Crystalline Freebase Hydrate Form C

The present disclosure additionally relates to methods for preparing the Freebase Hydrate Form C. In one embodiment, the method comprises dissolving upadacitinib in a solvent or mixture of solvents; and initiating crystallization to provide the Freebase Hydrate Form C. The solvent or mixture of solvents generally will comprise an anti-solvent (such as water) which can be present in the solvent or mixture of solvents before, or added to the solvent or mixture of solvents after, the upadacitinib is dissolved in the solvent or mixture of solvents. The solvent or mixture of solvents can comprise, for example, one or more polar solvents (such as polar solvent selected from the group consisting of ethanol and ethyl acetate); one or more nonpolar solvents (such as a nonpolar solvent is selected from the group consisting of hexane and heptane); or at least one polar solvent and at least one nonpolar solvent. In one aspect, the solvent or mixture of solvents is a ternary solvent mixture comprising ethyl acetate, heptane, and water. The method generally is conducted at temperatures less than about 30° C., less than about 20° C., or less than about 10° C. In certain aspects, the initiating crystallization step comprises mixing the solvent or mixture of solvents to provide sufficient agitation to initiate crystallization. In certain aspects, the initiating crystallization step comprises seeding the solvent or mixture of solvents with crystals of the Freebase Hydrate Form C. In certain aspects, the initiating crystallization step comprises both mixing the solvent or mixture of solvents and seeding the solvent or mixture of solvents with crystals of the Freebase Hydrate Form C.

In one embodiment, upadacitinib is first prepared according to any of the methods set forth herein, a reaction mixture comprising upadacitinib is filtered, and the resulting solution is suspended in a solvent or mixture of solvents. The solvent or mixture of solvents can comprise, for example, one or more polar solvents (such as polar solvent selected from the group consisting of ethanol and ethyl acetate); one or more nonpolar solvents (such as a nonpolar solvent is selected from the group consisting of hexane and heptane); or at least one polar solvent and at least one nonpolar solvent. In one particular embodiment, the solvent is ethyl acetate, or a mixture of ethyl acetate and water. In certain aspects, the initiating crystallization step comprises seeding the solvent or mixture of solvents with crystals of the Freebase Hydrate Form C. In one particular aspect, the crystallization occurs in a wet mill.

Figure 15:
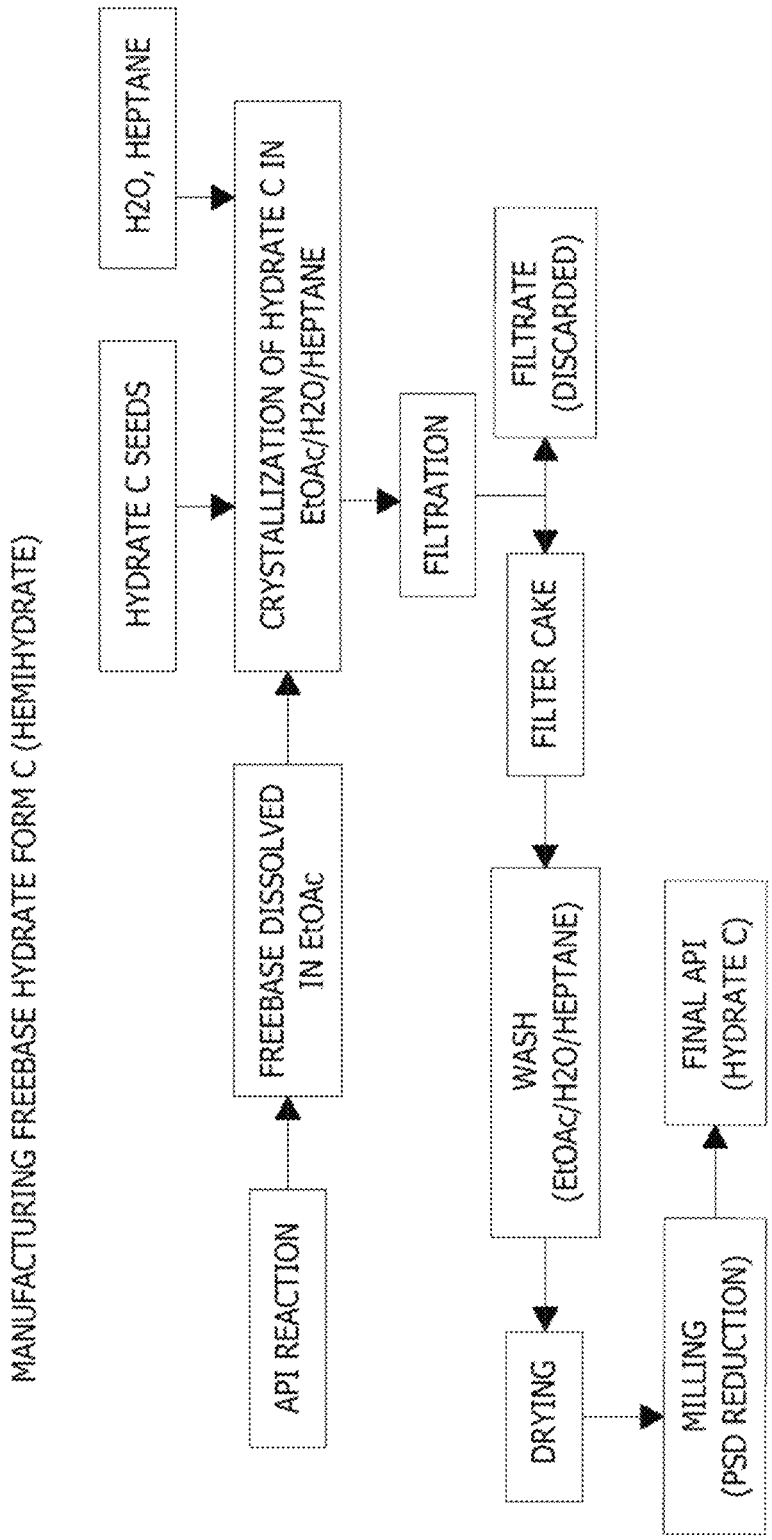
FIG. 15 schematically illustrates one method of preparing the Freebase Hydrate Form C.

FIG. 15 schematically illustrates one method of preparing the Freebase Hydrate Form C.

D. Preparation of Crystalline Freebase Anhydrate Form D

The present disclosure additionally relates to methods for preparing the Freebase Anhydrate Form D. In one embodiment, the method comprises dissolving upadacitinib in a solvent or mixture of solvents; and initiating crystallization to provide the Freebase Anhydrate Form D. The solvent or mixture of solvents will be water-free, or close to water-free. In embodiments, the solvent or mixture of solvents will have a water content of less than about 0.15 wt %, or less than about 0.10 wt. %, or less than about 0.05 wt. %, or about 0 wt. % at 23° C. In one embodiment, the solvent or mixture of solvents will have a water activity of about 2.4% or less, or about 2.2% or less, or about 2.0% or less, or about 1.5% or less. The solvent or mixture of solvents can comprise, for example, ethyl acetate (EtOAc), heptane, and combinations thereof. In one embodiment, the solvent system comprises a mixture of heptane in ethyl acetate. In some embodiments, the solvent system comprises about 10 wt. %, or about 20 wt. %, or about 30 wt. %, or about 40 wt. % heptane in ethyl acetate. The method generally is conducted at temperatures of at least about 7° C., at least about 23° C., at least about 25° C. or less, or at least about 30° C. In one embodiment, the method is conducted at about 23° C. In certain aspects, the initiating crystallization step comprises mixing the solvent or mixture of solvents to provide sufficient agitation to initiate crystallization. In certain aspects, the initiating crystallization step comprises seeding the solvent or mixture of solvents with crystals of the Freebase Anhydrate Form D. In certain aspects, the initiating crystallization step comprises both mixing the solvent or mixture of solvents and seeding the solvent or mixture of solvents with crystals of the Freebase Anhydrate Form D.

E. Preparation of Crystalline Tartrate Hydrate

The present disclosure additionally relates to methods for preparing the Tartrate Hydrate. In one embodiment, the method comprises dissolving upadacitinib and L-tartaric acid in a solvent or mixture of solvents to form a crystallization solution; and crystallizing the Tartrate Hydrate from the crystallization solution. The solvent or mixture of solvents can comprise, for example, water and/or, for example, one or more polar solvents (such as isopropyl acetate). The solvent or mixture of solvents also can comprise an anti-solvent (such as isopropyl acetate). In certain aspects, the process further comprises seeding the solvent or mixture of solvents with crystals of the Tartrate Hydrate.

The crystallization generally is conducted at a temperature less than about 40° C. When an anti-solvent is used, a moderate rate of addition is employed for the anti-solvent as a faster rate of addition typically results in the precipitation of an amorphous tartrate and a slower rate of addition allows the resulting slurry to thicken. Proper control of filtration, washing, and drying may be needed to avoid potential issues associated with consolidation of the filter cake, including solvent entrapment, solid properties (e.g., hard, chunky solids) and handing, and damage to equipment. Depending upon the properties of the dried Tartrate Hydrate material, milling may require a mechanical impact-type of mills rather than a shear-based mill (such as a co-mill).

Figure 16:
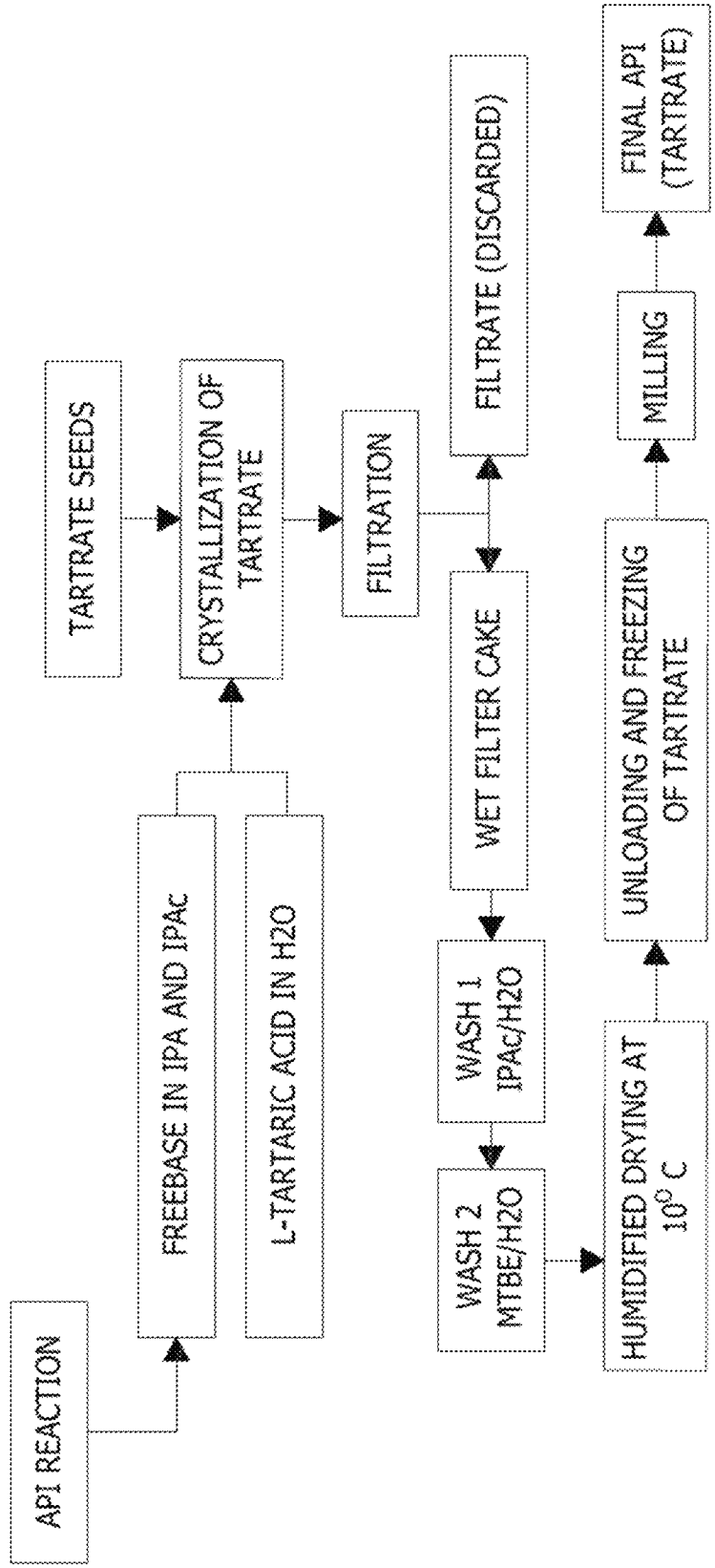
FIG. 16 schematically illustrates one method of preparing the Tartrate Hydrate.

FIG. 16 schematically illustrates one method of preparing the Tartrate Hydrate.

VIII. PHARMACEUTICAL COMPOSITIONS AND ROUTES OF ADMINISTRATION

One or more compounds of this disclosure can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions.

The pharmaceutical compositions of the present disclosure may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

In one embodiment, the active ingredient contained in the dosage unit composition is upadacitinib, or a pharmaceutically acceptable salt or solid state form thereof. In one embodiment, the target or label amount of active ingredient (e.g., upadacitinib) provided for inclusion in the compositions of the present disclosure refers to the amount of upadacitinib freebase. For instance, upadacitinib may be prepared in several solid state forms including Amorphous Freebase, crystalline solvates and hydrates (e.g., Freebase Solvate Form A, Freebase Hydrate Form B), crystalline hemihydrates (e.g., Freebase Hydrate Form C), crystalline anhydrate (e.g., Freebase Anhydrate Form D), and crystalline tartrate (e.g., Tartrate Hydrate). Preparation of these solid state forms is described herein and also in U.S. patent application Ser. No. 15/295,561, which is herein incorporated by reference. It should be understood that in embodiments, where the dosage unit composition comprises, e.g., a solvate, hydrate, hemihydrate, or tartrate of upadacitinib, the amount of solvate, hydrate, hemihydrate, or tartrate of upadacitinib present in the dosage unit composition may be slightly higher than the target amount of upadacitinib (active ingredient), and preferably will be present in the dosage unit composition in an amount sufficient to deliver the target amount of upadacitinib freebase equivalent to a patient. For example, if the target amount of upadacitinib (active ingredient) in a dosage unit composition is 15 mg, a dosage unit composition comprising, for example, a hydrate of upadacitinib, may comprise the hydrate in an amount sufficient to deliver 15 mg of the upadacitinib freebase equivalent.

In one embodiment, the pharmaceutical composition is a tablet dosage form. In one aspect, the tablet is coated with a pharmaceutically acceptable polymer. In one embodiment, the pharmaceutical composition is a capsule dosage form.

In one embodiment, tablet is a controlled-release formulation, such as an extended release tablet dosage form (also referred to herein as a modified release or sustained release formulation). Such formulations permit the sustained release of the active ingredient over an extended period of time, as compared to immediate release solid dosage forms, which permit the release of most or all of the active ingredient over a short period of time (e.g., typically around 60 minutes or less). In one aspect, the tablet comprises an active ingredient (e.g., upadacitinib) and at least one additive selected from the group consisting of a release control polymer, a filler, a glidant, a lubricant (e.g., for use in compacting the granules), a pH modifier, a surfactant, and combinations thereof. In one aspect, the tablet comprises an active ingredient, a release control polymer, a filler, a glidant, and a lubricant. In one aspect, the tablet comprises an active ingredient, a release control polymer, a filler, a glidant, a lubricant, and a pH modifier.

In certain embodiments, the release control polymer will be a hydrophilic polymer. Examples of suitable release control polymers include, but are not limited to a cellulose derivative with a viscosity of between 1000 and 150,000 mPA-s, hydroxypropylmethyl cellulose (e.g., Hypromellose 2208 or controlled release grades of hydroxypropylmethyl cellulose, including the E, F, and K series), copolymers of acrylic acid crosslinked with a polyalkenyl polyether (e.g., Carbopol® polymers), hydroxypropyl cellulose, hydroxyethyl cellulose, non-ionic homopolymers of ethylene oxide (e.g., Polyox™), water soluble natural gums of polysaccharides (e.g., xanthan gum, alginate, locust bean gum, etc.), crosslinked starch, polyvinyl acetates, polyvinylpyrrolidone, mixtures of polyvinyl acetates and polyvinyl pyrrolidone, and combinations thereof. In one embodiment, the release control polymer is selected from the group consisting of hydroxypropylmethyl cellulose, copolymers of acrylic acid crosslinked with a polyalkenyl polyether (e.g., Carbopol® polymers), and combinations thereof. Examples of suitable fillers ("bulking agents") include, but are not limited to, microcrystalline cellulose (e.g., Avicel® PH 101; Avicel® PH 102;), mannitol (e.g., Pearlitol® 100 SD or Pearlitol® 200 SD), lactose, sucrose, sorbitol, and the like. In one embodiment, the filler is selected from the group consisting of microcrystalline cellulose, mannitol, and combinations thereof. Examples of suitable glidants include, but are not limited to, silicone dioxide (e.g., colloidal silicon dioxide), calcium silicate, magnesium silicate, talc, and combinations thereof. In one embodiment, the glidant is colloidal silicone dioxide. Examples of suitable lubricants include, but are not limited to, polyethylene glycol (e.g., having a molecular weight of from 1000 to 6000), magnesium stearate, calcium stearate, sodium stearyl fumarate, talc, and the like. In one embodiment, the lubricant is magnesium stearate. Examples of suitable pH modifiers include, but are not limited to, organic acids, such as tartaric acid, citric acid, succinic acid, fumaric acid; sodium citrate; magnesium or calcium carbonate or bicarbonate; and combinations thereof. In one embodiment, the pH modifier is tartaric acid. Examples of suitable surfactants include sodium lauryl sulfate.

In one embodiment, the pharmaceutical composition comprises from about 10 w/w % to about 35 w/w % of a pH modifier, and in particular, tartaric acid, fumaric acid, citric acid, succinic acid, malic acid, or combinations thereof. In other embodiments, the formulation comprises from about 20 w/w % to about 35 w/w %, or from about 20 w/w % to about 30 w/w %, or from about 20 w/w % to about 25 w/w %, or about 10 w/w %, about 15 w/w.%, about 20 w/w %, about 25 w/w % or about 30 w/w % pH modifier. In one embodiment, the pH modifier is tartaric acid. Sustained peak plasma concentrations can theoretically be achieved by means of sustained release matrix systems. However, when such systems are made of hydrophilic polymers, such as HPMC, they seldom provide pH independent drug release of pH-dependent soluble drugs, and they are normally incapable of attaining zero-order release except for practically insoluble drugs. Is has been discovered that when a pH modifier, such as tartaric acid, fumaric acid, citric acid, succinic acid, malic acid, or combinations thereof, is used in a hydrophilic sustained release matrix system, it allows upadacitinib or a pharmaceutically acceptable salt or solid state form thereof to be released at a steady rate regardless of the pH of the environment. It has been discovered that as a tablet containing the hydrophilic polymer matrix system erodes, upadacitinib reacts with the HPMC, creating a thicker gel layer which slows the release of upadacitinib from the tablet. The resulting gel layer provides an environment suitable for upadacitinib to dissolve.

Thus, in one embodiment, the pharmaceutical composition of the present disclosure exhibits a pH-independent release of the active ingredient (upadacitinib). Advantageously, it has been discovered that including organic acids, such as a tartaric acid, in the composition as a pH modifier improves the release profile, and results in a pH independent release of the active ingredient. Without wishing to be bound to any particular theory, it is believed that the pH modifier and hydrophilic polymer create a microenvironment in which the active ingredient dissolves, and then is released. The release from the microenvironment occurs at approximately the same rate, regardless of pH. This is particularly advantageous, since the pH of the gastrointestinal tract may vary significantly from the stomach (e.g., pH of about 1.5-3), to the duodenum (e.g., pH of about 4-5), to the lower part of the small intestines (e.g., pH of about 6.5-7.5).

Thus, in one embodiment, the pharmaceutical composition is a modified release formulation comprising upadacitinib, or a pharmaceutically acceptable salt or solid state form thereof, a hydrophilic polymer, and a pH modifier, wherein the hydrophilic polymer, in contact with water, forms a gel layer that provides an environment suitable for upadacitinib, or a pharmaceutically acceptable salt or solid state form thereof, to dissolve. In some embodiments, the environment suitable for upadacitinib, or a pharmaceutically acceptable salt or solid state form thereof, to dissolve has a pH equal to or less than about 3.8 at 37° C. In some such embodiments, the environment has a pH of from about 1.5 to about 3.7, or from about 2.0 to about 3.7, or from about 2.5 to about 3.6, or from about 3.0 to about 3.6, or from about 3.0 to about 3.5.

In one such embodiment, the environment suitable for upadacitinib, or a pharmaceutically acceptable salt or solid state form thereof, to dissolve is as set forth above, and the modified release formulation comprises from about 10 w/w % to about 35 w/w % of a pH modifier, and in particular, tartaric acid, fumaric acid, citric acid, succinic acid, malic acid, or combinations thereof. In other embodiments, the formulation comprises from about 20 w/w % to about 35 w/w %, or from about 20 w/w % to about 30 w/w %, or from about 20 w/w % to about 25 w/w %, or about 10 w/w %, about 15 w/w %, about 20 w/w %, about 25 w/w % or about 30 w/w % pH modifier. In any of these embodiments, the pH modifier may be selected from the group consisting of tartaric acid, fumaric acid, citric acid, succinic acid, malic acid, and combinations thereof. In one such embodiment, the pH modifier is selected from the group consisting of tartaric acid, fumaric acid, citric acid, succinic acid, and combinations thereof. In one such embodiment, the pH modifier is selected from the group consisting of tartaric acid and fumaric acid. In one embodiment, the pH modifier is tartaric acid. In one embodiment, the pH modifier is fumaric acid or citric acid. The weight % tartaric acid set forth herein is by weight of the uncoated composition (e.g., uncoated tablet). In any of the foregoing embodiments, the hydrophilic polymer may be a cellulose derivative with a viscosity of between 1000 and 150,000 mPA-s. In one embodiment, the hydrophilic polymer is selected from the group consisting of hydroxypropylmethyl cellulose, hydroxyethyl cellulose, and mixtures or combinations thereof. In one embodiment, the hydrophilic polymer is hydroxypropylmethyl cellulose. In one embodiment, the hydrophilic polymer is hydroxypropylmethyl cellulose Grade E, F, or K. In one embodiment, the hydrophilic polymer is Hypromellose 2208.

In one embodiment, the tablet is a compressed and/or milled tablet. For example, in some embodiments, the tablet is formed by blending the composition components (e.g., including the active ingredient and at least one pharmaceutically acceptable carrier). The composition can then be either directly compressed, or one or more of the composition components can be granulated prior to compression. In one embodiment, milling is performed using a mill fitted with any suitable size screen (e.g., a fitted with a screen size of from about 600 to about 1400 μm or about 610 μm or about 1397 μm). Compression can be done in a tablet press, such as in a steel die between two moving punches.

In other embodiments, the compressed and/or milled tablet is formulated using a wet granulation process. Use of wet granulation helps reduce and/or eliminate sticking that may occur when compression without wet granulation (e.g., direct compression) is used to formulate the tablets. In one embodiment, the wet granulation process may include the following steps: (a) combining the active ingredient (e.g., upadacitinib or a pharmaceutically acceptable salt or solid state form thereof or a solid state form of upadacitinib) and at least a portion of one additional composition component to form a dry granulation mixture; (b) contacting the dry granulation mixture with a granulation fluid to form a wet granulation mixture; (c) drying the wet granulation mixture to form a granulated material; (d) milling the granulated material to form a milled granulated material; (e) combining the milled granulation material with the remaining composition components; and (f) compressing the composition into the solid dosage unit (e.g., a tablet).

In step (a) of this process, the active ingredient may be combined with, for example, a portion of the release control polymer (e.g., HPMC), a portion of the filler (e.g., microcrystalline cellulose, such as Avicel® PH101), or both a portion of the release control polymer and a portion of the filler to form the dry granulation mixture. Any suitable portion of the release control polymer may be used in step (a). In one embodiment, from about 5 to 10 wt. % or from about 6 to 8 wt. % of the total amount of the release control polymer in the composition is used in step (a).

In certain embodiments, the granulation fluid used in step (b) may comprise water, a suitable solvent (e.g., ethanol, isopropanol, etc.), or combinations thereof. In one embodiment, the granulation fluid comprises water. In one embodiment, the active ingredient may be combined with a portion of the filler, while a portion of the release control polymer (e.g., HPMC) is dissolved in a liquid, such as water, to form the granulation fluid. In one embodiment, the granulation fluid is sprayed on the dry granulation mixture.

The dried granulation material may be milled using, for example, a comill fit with any suitable screen size. In one embodiment, the screen size is from about 600 to about 900 microns, or from about 610 to about 813 microns. In one embodiment, the granulated material is milled using a comill fitted with a 610 µm screen. In one embodiment, the granulated material is milled using a comill fitted with a 813 µm screen.

In step (e), the milled granulation material is combined with any remaining composition components, such as any remaining filler (e.g., microcrystalline cellulose, such as Avicel® PH102), any remaining release control polymer, glidants, lubricants, pH modifiers, surfactants, and the like. In one embodiment, the filler and/or release control polymer included in the granulated material may be the same or different than the filler and/or release control polymer added in step (e). For instance, in one embodiment, the filler included in the granulated material (e.g., Avicel®PH101) may have a smaller particle size distribution than the filler added in step (e) (e.g., AvicerPH®102).

In one embodiment, the composition may be sieved, and the sieved composition blended, for example, after step (e), and prior to compressing the composition (step (f)). In one embodiment, the formulation is sieved prior to addition of any lubricant. In one embodiment, the pH modifier (e.g., tartaric acid) is optionally milled prior to combining with the granulated material.

In some embodiments, the tablet further comprises a film coat. A film coat on the tablet further may contribute to the ease with which it can be swallowed. A film coat can also improve taste and provides an elegant appearance. In certain embodiments, the film-coat includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. polysorbates, and optionally a pigment, e.g. titanium dioxide or iron oxides. The film-coating may also comprise talc as anti-adhesive. In one embodiment, the film coat accounts for less than 5% by weight of a pharmaceutical composition of the present disclosure.

In another embodiment, the pharmaceutical composition is a capsule dosage form.

For the prevention or treatment of disease, the appropriate dosage of JAK1 inhibitor will depend on a variety of factors such as the type of disease to be treated, as defined above, the severity and course of the disease, whether the JAK1 inhibitor is administered for preventive or therapeutic purposes, previous therapy, the patient's clinical history and response to the antibody, and the discretion of the attending physician. The JAK1 inhibitor is suitably administered to the patient at one time or over a series of treatments.

The JAK1 inhibitor is formulated, dosed, and administered in a fashion consistent with good medical practice. Factors for consideration in this context include the particular disorder being, treated, the particular mammal being treated, the clinical condition of the individual patient, the cause of the disorder, the scheduling of administration, and other factors known to medical practitioners. The "therapeutically effective amount" of the JAK1 inhibitor will be governed by such considerations.

Pharmaceutical compositions suitable for use in the present disclosure include compositions wherein the active ingredients are contained in an effective amount to achieve its intended purpose. More specifically, a therapeutically effective amount means an amount effective to prevent development of or to alleviate the existing symptoms of the patient being treated. Determination of the effective amounts is well within the capability of those skilled in the art. In one particular embodiment, the composition will be a once-daily modified release formulation comprising 7.5 mg, 15 mg, 30 mg, or 45 mg of upadacitinib or a pharmaceutically acceptable salt or solid state form thereof.

IX. EXAMPLES

Example 1: Preparation of Amorphous Freebase

A. Method A: Precipitation From Water

Upadacitinib (approximately 300 g) was dissolved in water (10 L) and 50% sodium hydroxide (160 g) was added drop-wise over a two hour period to adjust the pH to greater than 12. Solids formed immediately. The solids were filtered, washed with two 500 mL aliquots of water, and then dried in a vacuum oven. The solids were equilibrated for a short period of time at ambient temperature prior to characterization. Conversion to Amorphous Freebase of upadacitinib was confirmed by PXRD analysis.

B. Method B: Dehydration of Freebase Hydrate Form B

A sample of the Freebase Hydrate Form B form of upadacitinib (crystallized from ethanol/water at sub-ambient temperatures as described in Example 2, Method C below) was placed in a vacuum oven at 40° C. overnight. The solids removed from the vacuum oven were equilibrated for a short time at 23° C. prior to characterization. Conversion to Amorphous Freebase of upadacitinib was confirmed by PXRD analysis.

Example 2: Preparation of Freebase Solvate Form A and Freebase Hydrate Form B A. Method A: Freebase Solvate Form A (Isopropyl Acetate/Water Solvate)

A sample of the Amorphous Freebase of upadacitinib (25 mg) was added to a vial followed by isopropyl acetate (125 µL) and water (10 µL). All solids dissolved at ambient temperature. The solution was placed in a freezer at −16° C. for 4 days. The liquor was decanted and the crystallized solids were isolated. The isolated crystals were analyzed by PXRD while still wet. Conversion to Freebase Solvate Form A (isopropyl acetate/water solvate) of upadacitinib was confirmed by PXRD analysis.

B. Method B: Freebase Hydrate Form B from Methanol/Water

A sample of the Amorphous Freebase of upadacitinib (164 mg) and MeOH (621 mg) were added to a vial. The components were mixed at ambient temperature until the solids dissolved. Water (approximately 680 µL) was added to the vial and the vial was placed in an ice/sodium chloride bath at approximately −3° C. Crystal seeds comprising Freebase Hydrate Form B were added to the vial and the vial was placed in a freezer at −16° C. A sample was pulled from the crystallized suspension and the solids were immediately analyzed with PXRD and TGA-MS. Conversion to Freebase Hydrate Form B of upadacitinib was confirmed by PXRD and TGA-MS analysis.

C. Method C: Freebase Hydrate Form B from Ethanol/Water

A sample of the Amorphous Freebase of upadacitinib (4.2 g) was dissolved in EtOH (15.3 g) in a jacketed reactor. Water (23.3 g) was slowly added to the reactor. The reactor solution was cooled to approximately 2° C. A small portion of a seed solution comprising the Freebase Hydrate Form B was charged to the reactor. The suspension was mixed at approximately 2° C. for 3 hours and water (36 g) in was charged to the reactor in small aliquots over several hours while maintaining the suspension at a temperature of approximately 2° C. The crystallized suspension was mixed at approximately 2° C. and the solids were isolated via filtration. Conversion to Freebase Hydrate Form B of upadacitinib was confirmed by PXRD analysis.

The Freebase Solvate Form A and Freebase Hydrate Form B do not readily crystallize from solution. In general, sub-ambient temperatures and sufficient water activity are needed to crystallize Freebase Solvate Form A and Freebase Hydrate Form B from solution.

Crystalline freebase hydrates and solvates have been isolated from several solvent systems either through primary nucleation (without seeding) or through seeding. In addition to crystallization from isopropyl acetate/water (as described in Method A above), crystalline freebase hydrates or solvates also have been isolated through primary nucleation (without seeding) from, e.g., n-butylamine/water and ethanol/water solvent systems. In addition to crystallization from methanol/water (as described in Method B above) and ethanol/water (as described in Method C above), crystalline freebase hydrates or solvates also have been isolated through seeding from, e.g., acetone/water; acetonitrile/water; ethyl formate/water; methyl acetate/water; ethyl acetate/water; methyl ethyl ketone/water; methyl isobutyl ketone/water, methyl isobutyl ketone/methyl tert-butyl ether/water; and isopropyl acetate/methyl tert-butyl ether/water solvent systems. The Freebase Solvate Form A (isopropyl acetate/water solvate) prepared in Method A above, the Freebase Hydrate Form B prepared in Methods B and C above, and these other crystalline freebase solvates or hydrates that have been prepared are isostructural and exhibit similar PXRD patterns. Notably, these crystalline freebase solvates and hydrates are distinguishable from and exhibit a different PXRD pattern than Freebase Hydrate Form C (a hemihydrate), which is described below.

The Freebase Solvate Form A and Freebase Hydrate Form B that were prepared were not stable after isolation at ambient conditions and readily dehydrated to the Amorphous Freebase.

Example 3: Preparation of Freebase Hydrate Form C

A. Method A: Freebase Hydrate Form C from Ethanol/Water

A sample of the Amorphous Freebase of upadacitinib (2 g) was transferred to a 500 mL beaker equipped with a stirring bar. EtOH (50 g) was added to the beaker and stirred until all solids dissolved. The solution was transferred to a 250 mL jacketed flask equipped with a dispersing device. The solution was cooled to 6° C. Water (150 g) was added to the solution and the solution was subjected to high shear for two hours using the dispersing device. After solid formation was observed, an additional amount of water (50 g) was added to the resulting suspension. The suspension was held overnight at ambient temperature. Solids were isolated and examined on the following day. Conversion to upadacitinib Freebase Hydrate Form C was confirmed by PXRD analysis.

B. Method B: Freebase Hydrate Form C From Ethyl Acetate/Heptane/Water

A crude reaction mixture assaying for 11.1 g of upadacitinib was taken up in 2% water in EtOAc (70 g) and seeded with Freebase Hydrate Form C (100 mg). The suspension was stirred overnight and heptane (70 g) was added. The solids were collected by filtration, washed with water saturated EtOAc/heptane (1/1, 100 mL), and dried under vacuum at 50° C. Conversion to upadacitinib Freebase Hydrate Form C was confirmed by PXRD analysis.

As was observed with the Freebase Solvate Form A and the Freebase Hydrate Form B, the Freebase Hydrate Form C also does not readily crystallize from solution.

Example 4: Preparation of Tartrate Hydrate

Three methods for the preparation of upadacitinib tartrate tetrahydrate (the "Tartrate Hydrate") are described below. Method A describes an initial procedure that was used to prepare the tartrate tetrahydrate. Method B describes a modified procedure used to prepare the tartrate tetrahydrate at a larger scale. Method C describes a further modified procedure used to prepare the tartrate tetrahydrate. The modified procedure of Method C relative to the procedure of Method B further reduces solidification of the filter cake, a potential problem that potentially can impact manufacturability and downstream processing.

A. Method A

A sample of the Amorphous Freebase of upadacitinib (28.2 mg) was transferred to an amber vial. Water (200 µL) and L-tartaric acid (34.5 mg (approximately 3 equivalents)) were added to the vial. The suspension was vortexed under ambient conditions until all the solids dissolved. The solution in the vial was magnetically stirred at 0° C. The following day, the solids were isolated from the solution and left at ambient temperature for a short period of time prior to characterization. Conversion to the upadacitinib Tartrate Hydrate (tetrahydrate) was confirmed by PXRD analysis.

B. Method B

Upadacitinib (4.6 g) was added to a jacketed reactor followed by the addition of isopropanol (6.5 mL) and IPAc (7.8 mL). The slurry was mixed at ambient condition until the solids dissolved. In a separate vial, L-tartaric acid (1.96 g) was dissolved in deionized water (3.92 mL). The L-tartaric acid solution was added to the reactor followed by the addition of tartrate tetrahydrate seed crystals (28 mg). The suspension was mixed for 30 minutes under ambient conditions. IPAc (71 mL) was added in small aliquots over 2 hours. The crystallized suspension was cooled to 5° C. and equilibrated at 5° C. overnight. The suspension was discharged onto a filter and the filter cake rinsed with 20 mL of water saturated IPAc. The filtered solids were air-dried for two days. Conversion to the upadacitinib Tartrate Hydrate (tetrahydrate) was confirmed by PXRD analysis.

C. Method C

Crystallization: Upadacitinib (104 g) was added to a flask together with isopropanol (222.7 g) and IPAc (375.8 g). The components were mixed under ambient conditions until the solids dissolved. In a separate flask, L-tartaric acid (61.6 g) was dissolved in water (98.3 g). The contents of the two flasks were then added to a jacketed reactor. Tartrate tetrahydrate seed crystals (1.55 g) were added to the reactor solution. The resulting suspension was mixed overnight under ambient conditions. IPAc (2542 g) was charged to the reactor suspension over an 8 hour period.

Filtration, Washing and Drying: Approximately half of the crystallized tartrate suspension was charged to a jacketed agitated filter dryer. The suspension was cooled inside the filter dryer to approximately 11° C. The suspension was filtered using positive pressure until a wet cake was obtained. Water saturated IPAc (438 g) was charged to the filter dryer and the suspension was mixed overnight at approximately 11° C. The suspension was filtered using positive pressure until a wet cake was obtained. Water saturated MTBE (110 g) was charged to the filter dryer. After 10 minutes, the suspension was filtered with positive pressure until a wet cake was obtained. Water saturated MTBE (261 g) was charged to the filter dryer and the suspension was mixed at approximately 11° C. for 3.5 hours. The suspension was filtered with agitation using positive pressure until a wet cake was obtained. The wet cake was dried with constant agitation at a temperature of approximately 11° C. under humidified nitrogen and positive pressure for two days. Conversion to the upadacitinib Tartrate Hydrate (tetrahydrate) was confirmed by PXRD analysis.

Example 5: Preparation of Freebase Anhydrate Form D

A sample of the Amorphous Freebase of upadacitinib was dissolved in water-free EtOAc at a concentration of 19.6% (w/w). An aliquot comprising approximately 1 mL was transferred to a 4 mL vial equipped with a magnetic stirrer. The vial was sealed with parafilm and mixed at 400 rpm on a magnetic stir plate at around 23° C. for almost 8 weeks. The resulting slurry was filtered and left at ambient conditions for a short period of time prior to characterization. Conversion to Freebase Anhydrate Form D was confirmed by PXRD analysis.

Example 6: Microscopy/Crystal Morphology

The solid state forms of upadacitinib were evaluated by microscopy. Samples were examined by microscopic visual examination using a polarizing microscope (model Eclipse E-600 POL, Nikon Corp., Garden City, N.Y.). A color video camera was used to record digital images (model DXC 390, Fryer Co., Inc., Huntley, Ill.). Images were captured using MetaMorph Imaging System (version 4.6R8, Universal Imaging Corporation, Downingtown, Pa.). Observations regarding the crystal morphology of the samples are reported in Table 14 below. Those of skill in the art will recognize that variation in crystal shape and size may be observed depending upon the specific crystallization conditions employed. The solvation states and PXRD profiles reported in Table 14 correspond to the information presented in the figures and subsequent examples of this application.

TABLE 14

| Solid Form Nomenclature | Species | Solvation/ Hydration State | Morphology |
| --- | --- | --- | --- |
| Amorphous Freebase | Freebase | Anhydrous | Blades (when prepared via precipitation or dehydration of Freebase Hydrate Form B) |
| Freebase Solvate Form A | Freebase | Isopropyl Acetate/Water Solvate | Irregular |
| Freebase Hydrate Form B | Freebase | Labile Hydrate | Blades |
| Freebase Hydrate Form C | Freebase | Hemihydrate | Prisms |
| Tartrate Hydrate | Tartrate | Tetrahydrate | Needles |
| Freebase Anhydrate Form D | Freebase | Anhydrous | Not Determined |

Example 7: PXRD Analysis

The solid state forms of upadacitinib listed in Table 14 were analyzed by X-ray powder diffraction ("PXRD"). The PXRD data were collected with a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromator provided monochromatic Kα1 radiation λ=1.540562 Å). The diffractometer was calibrated using the attenuated direct beam at one-degree intervals. Calibration was checked using a silicon powder line position reference standard (NIST 640c). Samples were prepared by spreading the sample powder in a thin layer on an aluminum sample holder and gently leveling with a glass microscope slide. The instrument was computer controlled using the Symphonix software (Inel Corp., Artenay, France) and the data was analyzed using the Jade software (version 6.5, Materials Data, Inc., Livermore, Calif.). The aluminum sample holder was mounted on the rotating sample holder of the G3000 diffractometer and the diffraction data collected at ambient conditions.

Tables 15-A through 15-E set out the significant parameters of the main peaks in terms of 2Θ values and intensities for the crystalline forms analyzed. It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realize that the relative intensities of peaks may vary according to the orientation of the sample under testing and on the type and setting of the instrument used. The skilled person also will realize that the position of reflections can be affected by the precise height at which the sample sits in the diffractometer and the zero calibration of the diffractometer. The surface planarity of the sample also may have an effect on the results. A person skilled in the art will appreciate that the diffraction pattern data presented below is not to be construed as absolute and any crystalline form that provides a power diffraction pattern substantially identical to those disclosed below fall within the scope of the present disclosure (for further information see Jenkins, R & Snyder, R. L. 'Introduction to X-Ray Powder Diffractometry', John Wiley & Sons, 1996).

Figure 17B:
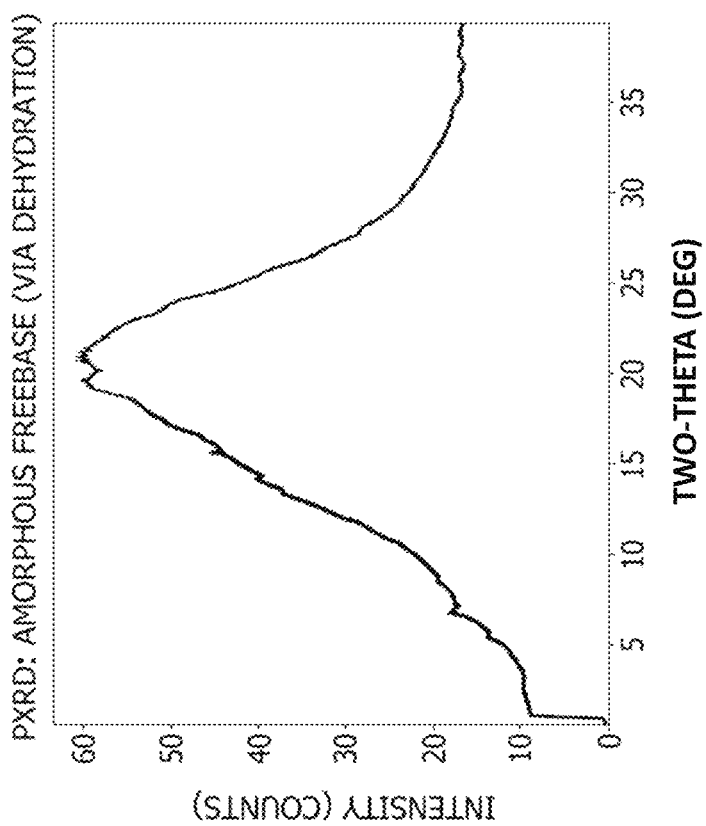
FIGS. 17A and 17B are powder X-ray diffraction patterns corresponding to the Amorphous Freebase (via precipitation) and the Amorphous Freebase (via dehydration), respectively.
Figure 17A:
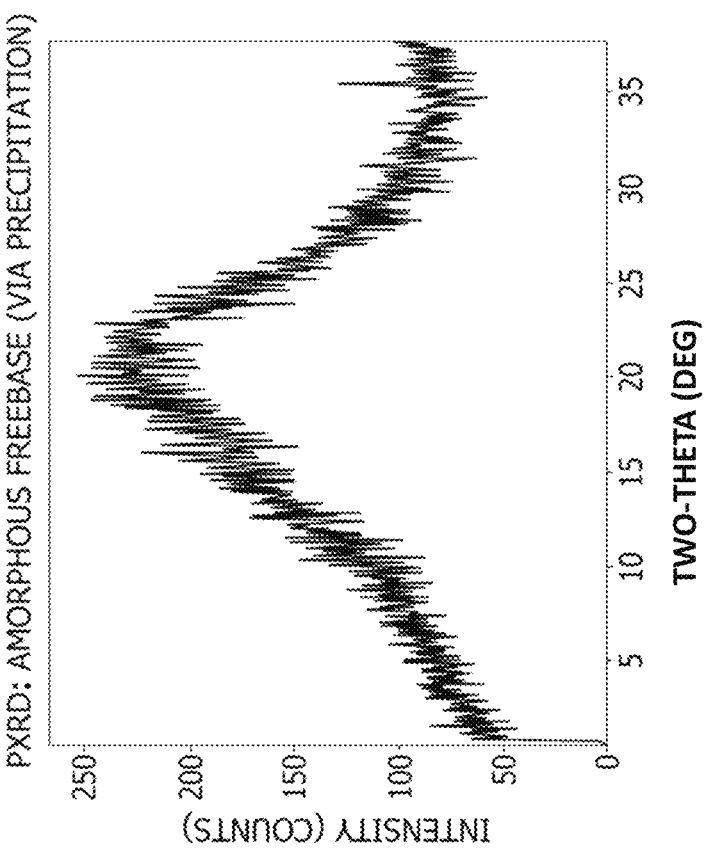

The PXRD pattern corresponding to the Amorphous Freebase (via precipitation) and the Amorphous Freebase (via dehydration) are shown in FIGS. 17A and 17B, respectively.

Figure 18:
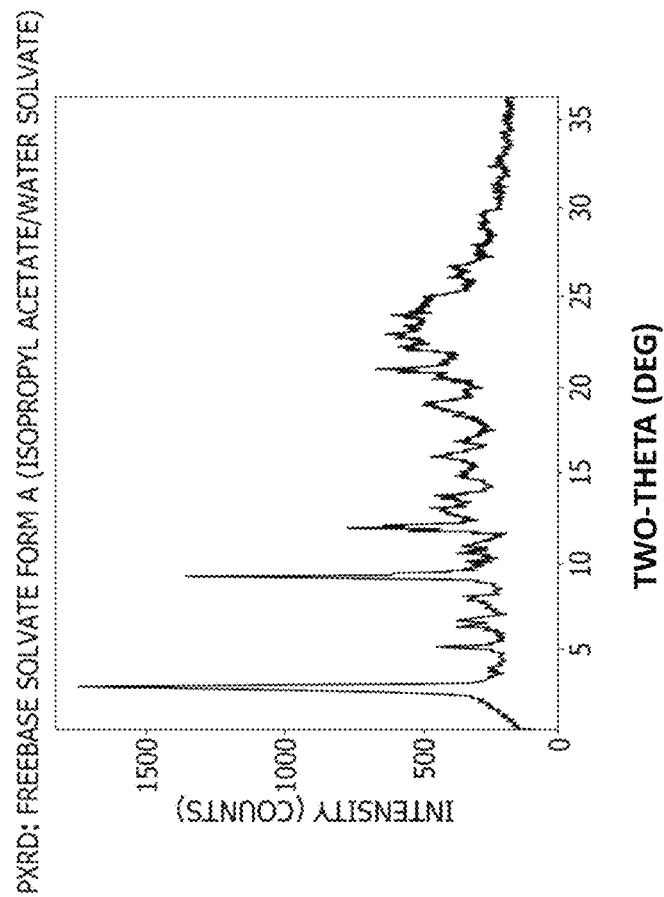
FIG. 18 is a powder X-ray diffraction pattern corresponding to the Freebase Solvate Form A (Isopropyl Acetate/Water Solvate).

The PXRD pattern corresponding to the Freebase Solvate Form A is shown in FIG. 18. Peak listing of the experimental PXRD pattern with relative intensities is given in Table 15-A below.

TABLE 145A

PXRD Peak Listing Freebase Solvate Form A (Isopropyl Acetate/Water Solvate)

| PEAK POSITION (°2Θ) | RELATIVE INTENSITY |
| --- | --- |
| 3.1 | 100.0 |
| 5.4 | 15.4 |
| 6.6 | 10.7 |
| 8.2 | 8.7 |
| 9.4 | 74.7 |
| 10.8 | 9.2 |
| 11.1 | 6.7 |
| 12.1 | 33.5 |
| 13.1 | 7.4 |
| 15.1 | 6.4 |
| 16.2 | 11.6 |
| 17.0 | 7.1 |
| 19.1 | 13.3 |
| 21.1 | 20.7 |
| 22.3 | 7.2 |

TABLE 145A-continued

PXRD Peak Listing Freebase Solvate
Form A (Isopropyl Acetate/Water Solvate)

| PEAK POSITION (°2Θ) | RELATIVE INTENSITY |
|---|---|
| 22.9 | 11.9 |
| 26.2 | 5.8 |
| 29.6 | 4.4 |

The PXRD pattern corresponding to the Freebase Hydrate Form B is shown in FIG. 19. Peak listing of the experimental PXRD pattern with relative intensities is given in Table 15-B below.

TABLE 15-B

PXRD Peak Listing Freebase Hydrate Form B

| PEAK POSITION (°2Θ) | RELATIVE INTENSITY |
|---|---|
| 3.1 | 100.0 |
| 6.1 | 3.4 |
| 7.9 | 4.6 |
| 9.3 | 54.8 |
| 10.7 | 3.1 |
| 12.0 | 27.1 |
| 12.4 | 6.3 |
| 13.0 | 3.3 |
| 13.7 | 4.3 |
| 14.9 | 7.5 |
| 15.6 | 4.2 |
| 16.0 | 3.5 |
| 17.1 | 3.7 |
| 18.8 | 7.0 |
| 20.8 | 13.4 |
| 22.9 | 6.6 |
| 23.3 | 4.5 |
| 24.0 | 6.6 |
| 24.6 | 4.2 |
| 25.0 | 12.4 |
| 26.0 | 4.7 |
| 26.9 | 5.1 |
| 28.1 | 3.3 |
| 28.9 | 2.5 |
| 29.8 | 4.1 |

The PXRD pattern corresponding to the Freebase Hydrate Form C is shown in FIG. 20. Peak listing of the experimental PXRD pattern with relative intensities is given in Table 15-C below.

TABLE 15-C

PXRD Peak Listing Freebase Hydrate Form C

| PEAK POSITION (°2Θ) | RELATIVE INTENSITY |
|---|---|
| 7.7 | 28.8 |
| 7.9 | 41.1 |
| 9.6 | 10.2 |
| 10.3 | 35.0 |
| 12.4 | 9.8 |
| 13.4 | 72.5 |
| 13.9 | 16.9 |
| 15.1 | 74.6 |
| 15.5 | 93.7 |
| 15.9 | 11.7 |
| 17.0 | 76.1 |
| 17.2 | 46.8 |
| 17.8 | 21.6 |
| 18.1 | 10.0 |
| 18.3 | 37.2 |
| 19.3 | 33.0 |
| 19.7 | 24.7 |
| 20.5 | 52.4 |
| 20.9 | 54.9 |

TABLE 15-C-continued

PXRD Peak Listing Freebase Hydrate Form C

| PEAK POSITION (°2Θ) | RELATIVE INTENSITY |
|---|---|
| 21.2 | 7.9 |
| 21.7 | 100.0 |
| 21.9 | 34.6 |
| 22.2 | 21.7 |
| 22.6 | 6.2 |
| 23.5 | 27.2 |
| 24.0 | 5.0 |
| 24.4 | 18 |
| 24.9 | 35.1 |
| 27.4 | 9.8 |
| 28.2 | 19.8 |
| 29.2 | 8.2 |
| 29.5 | 13.7 |
| 31.5 | 6.9 |

The PXRD pattern corresponding to the Tartrate Hydrate is shown in FIG. 21. Peak listing of the experimental PXRD pattern with relative intensities is given in Table 15-D below. The experimental PXRD pattern is shown at the bottom of FIG. 21 and the calculated PXRD pattern is shown at the top of FIG. 21.

TABLE 15-D

PXRD Peak Listing Tartrate Hydrate

| PEAK POSITION (°2Θ) | RELATIVE INTENSITY |
|---|---|
| 3.9 | 80.3 |
| 6.8 | 24.6 |
| 10.4 | 12.8 |
| 11.8 | 21.6 |
| 14.1 | 100.0 |
| 15.7 | 63.3 |
| 16.1 | 10.4 |
| 17.1 | 4.5 |
| 18.0 | 22.1 |
| 18.4 | 11.6 |
| 18.8 | 12.4 |
| 19.7 | 5.2 |
| 20.0 | 3.1 |
| 21.2 | 15.2 |
| 21.9 | 55.9 |
| 24.0 | 11.9 |
| 24.8 | 3.0 |
| 25.2 | 3.6 |
| 25.9 | 32.6 |
| 26.7 | 9.2 |
| 27.0 | 6.8 |
| 27.6 | 11.5 |
| 28.7 | 6.3 |
| 30.4 | 4.9 |
| 30.9 | 4.9 |
| 32.4 | 4.3 |
| 33.4 | 3.0 |

The PXRD pattern corresponding to the Freebase Anhydrate Form D is shown in FIG. 22. Peak listing of the experimental PXRD pattern with relative intensities is given in Table 15-E below.

TABLE 15-E

PXRD Peak Listing Freebase Anhydrate Form D

| PEAK POSITION (°2Θ) | RELATIVE INTENSITY |
|---|---|
| 4.0 | 20.6 |
| 8.0 | 29.3 |
| 9.7 | 52.1 |
| 11.2 | 7.5 |

TABLE 15-E-continued

PXRD Peak Listing Freebase Anhydrate Form D

| PEAK POSITION (°2Θ) | RELATIVE INTENSITY |
|---|---|
| 12.0 | 9.8 |
| 13.0 | 1.4 |
| 14.2 | 100.0 |
| 14.5 | 65.7 |
| 16.1 | 3.1 |
| 17.2 | 7.5 |
| 18.4 | 24.3 |
| 19.0 | 23.5 |
| 20.3 | 43.1 |
| 21.4 | 18.5 |
| 23.0 | 35.7 |
| 23.8 | 18.3 |
| 24.7 | 35.8 |
| 25.6 | 6.0 |
| 26.1 | 14.5 |
| 27.4 | 11.7 |
| 28.2 | 9.3 |
| 28.7 | 5.2 |
| 30.3 | 6.6 |
| 31.1 | 1.3 |
| 31.9 | 3.8 |
| 32.7 | 1.0 |
| 33.3 | 5.1 |
| 34.8 | 0.7 |

Example 8: Clinical Study for Crohn's Disease

This trial was a multicenter, randomized, double-blind placebo-controlled study of upadacitinib for the induction of symptomatic and endoscopic remission in patient with moderately to severely active Crohn's disease who have inadequately responded to or are intolerant to immunosuppressants or anti-TNF therapy.

The trial consisted of a screening period of up to 30 days, a 16 week double blind induction period, re-randomization at week 16, a 36 week double blind and open label phase and a 30 day follow up period.

Figure 1:
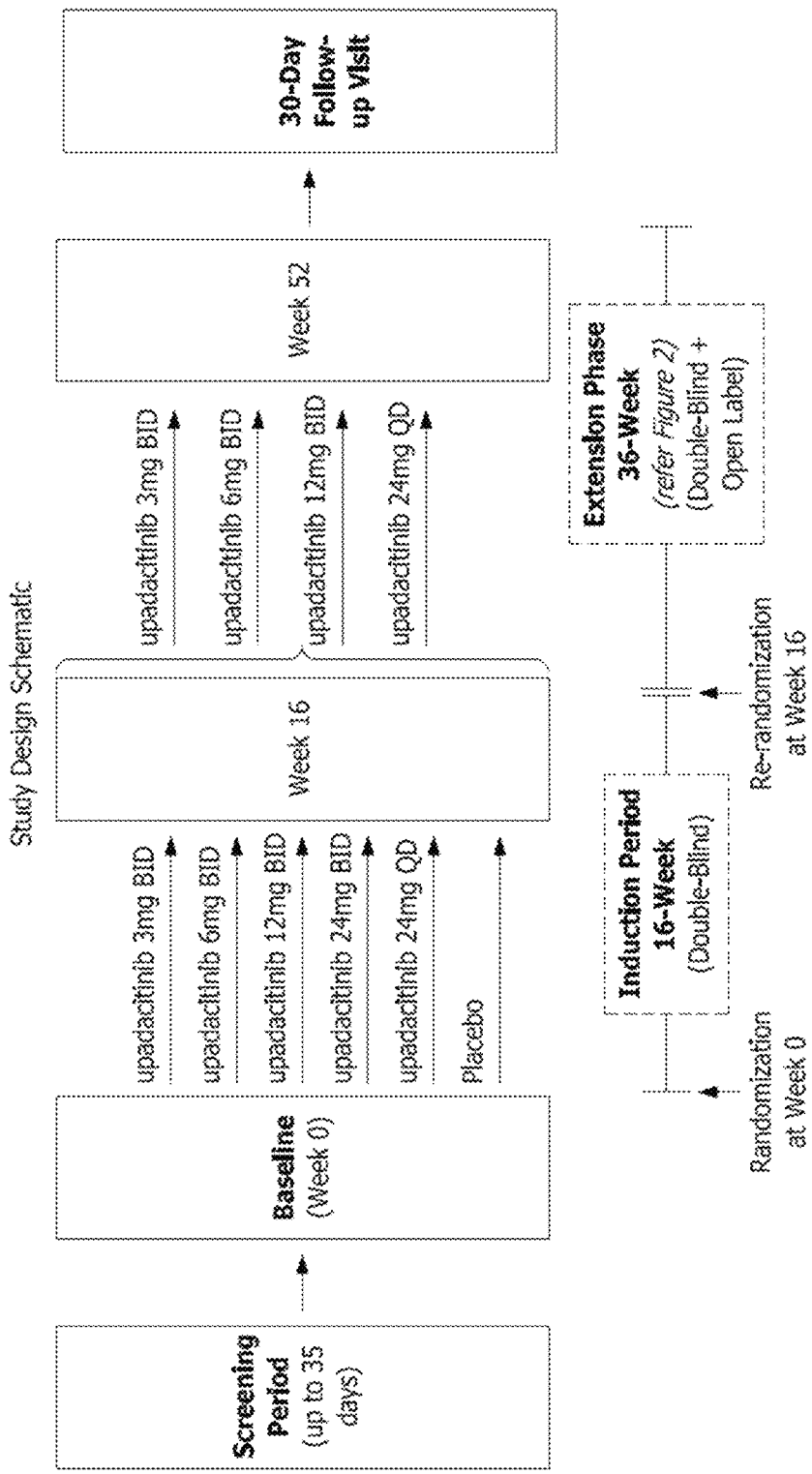
FIG. 1 is a schematic representation of the study design for the clinical study described in Example 8.
Figure 2:
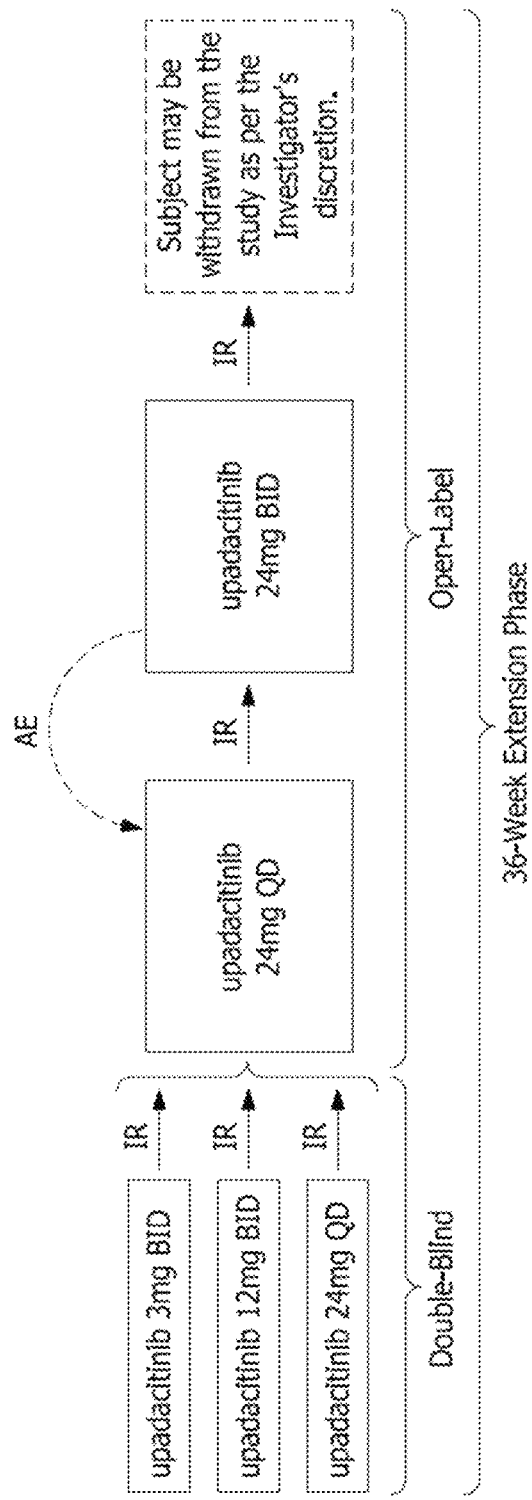
FIG. 2 is a schematic representation of the 36 week extension phase for the clinical study described in Example 8. Patients who did not adequately respond during the double-blind portion of the extension phase were eligible to receive open-label therapy.
Figure 3A:
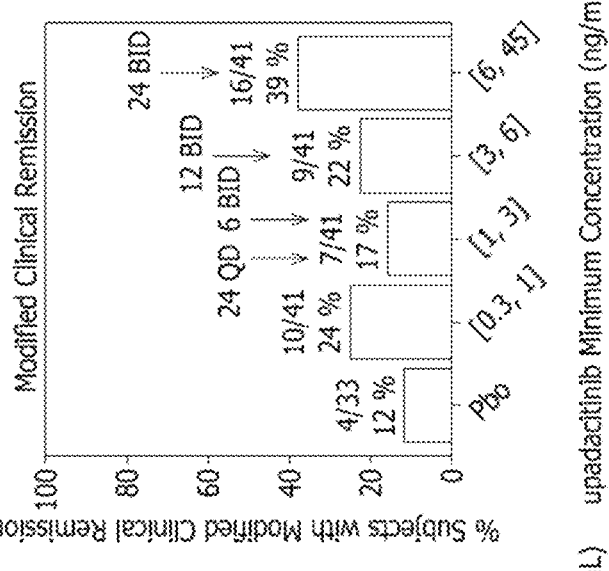
Figure 3B:
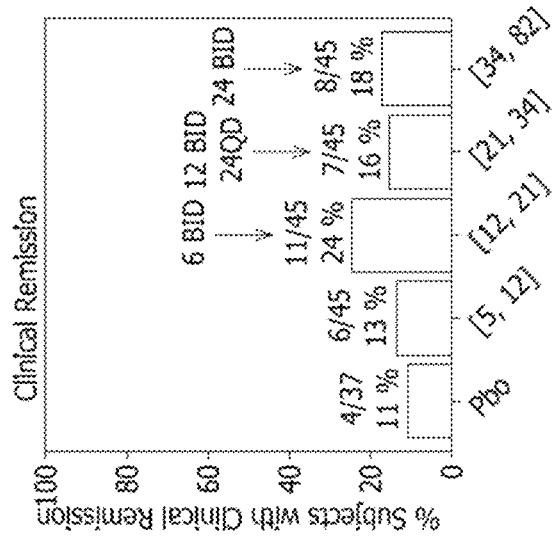
Figure 3C:
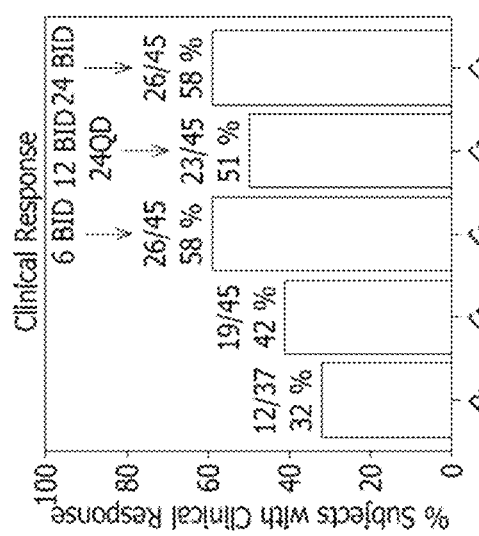
Figure 3G:
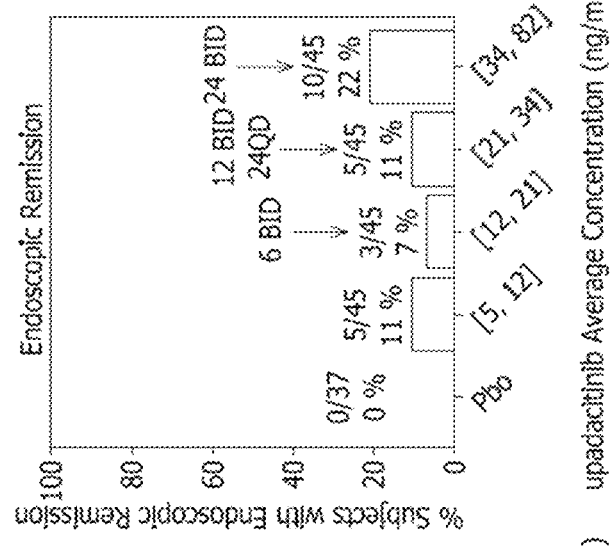
Figure 3H:
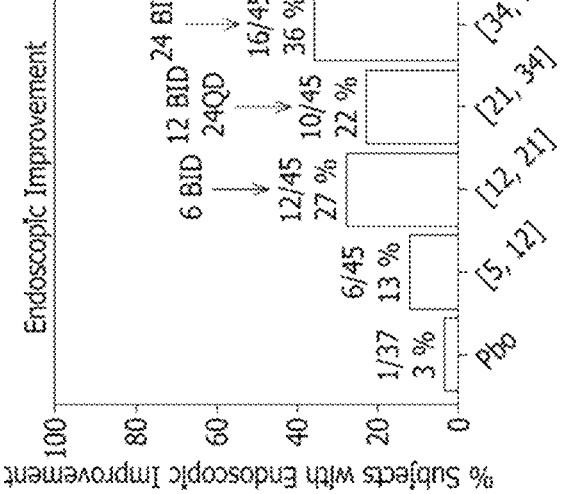
Figure 3I:
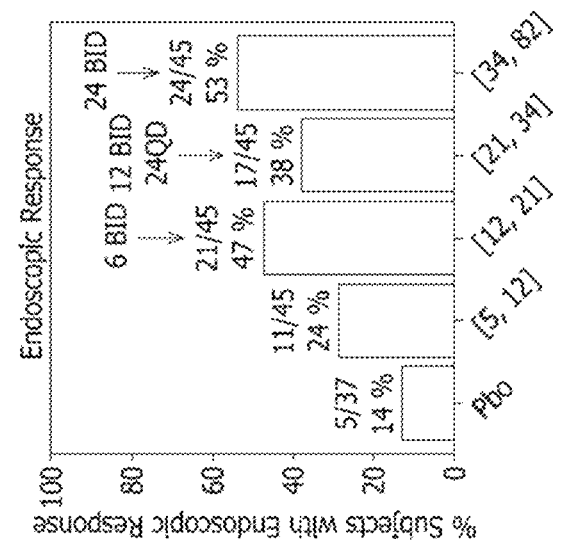
Figures 4A, 4B:
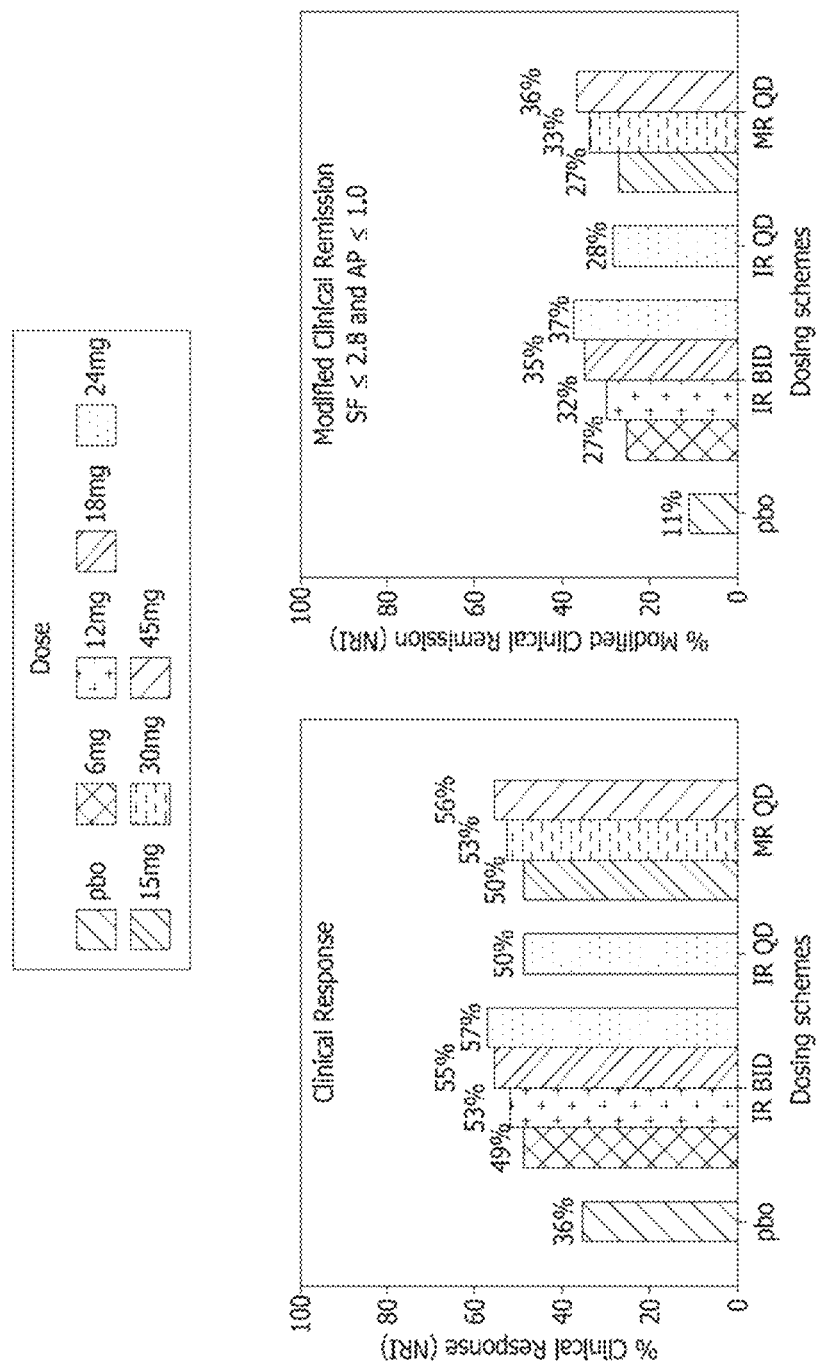
Figures 4C, 4D:
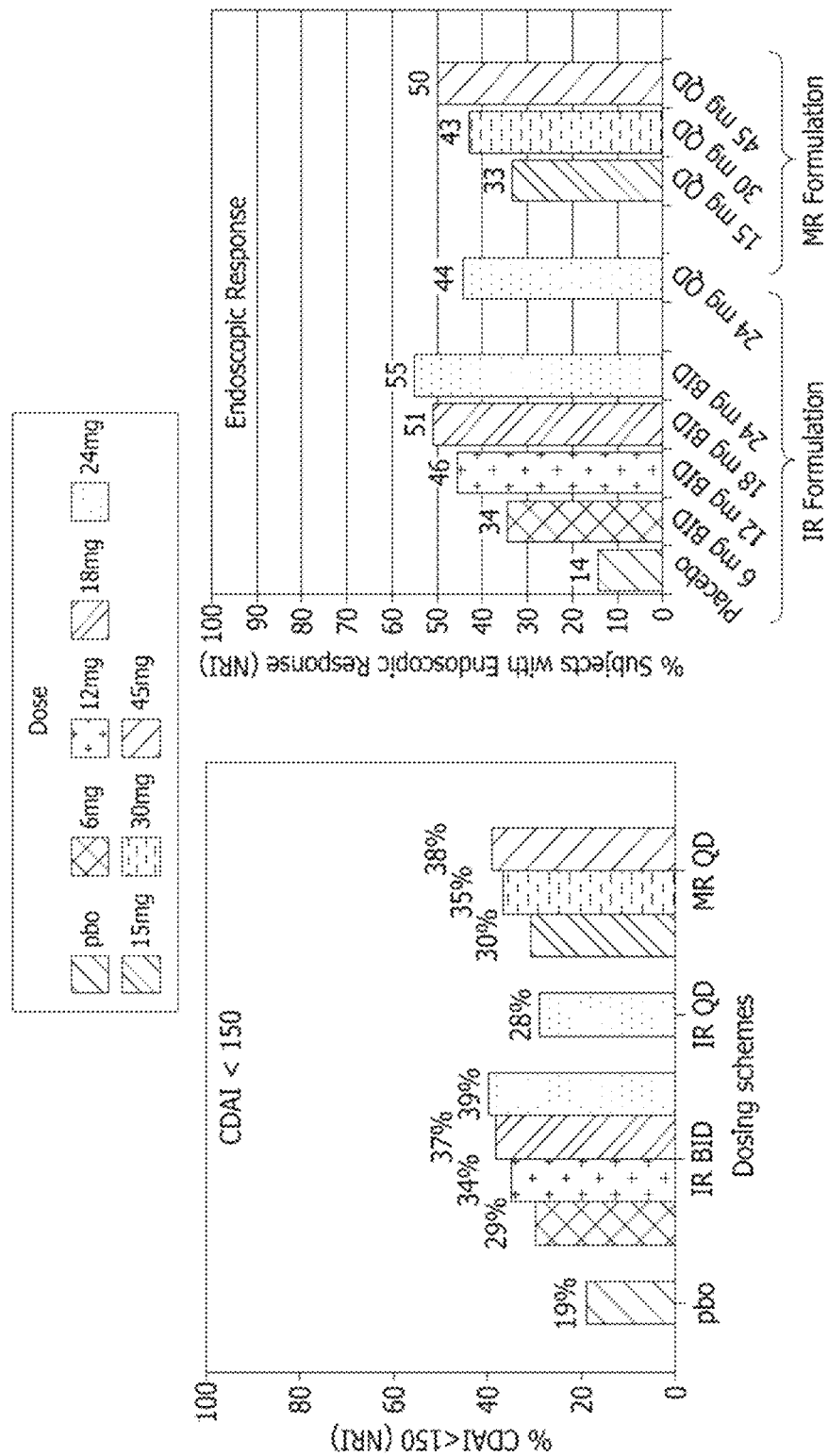

Approximately 220 patients with moderately to severely active Crohn's disease—defined for purposes of this study as having 1) Simplified Endoscopic Score for CD (SES-CD) ≥6, (or SES-CD≥4 for patients with disease limited to the ileum), 2) a CDAI≥220 and ≤450, and 3) an average daily liquid/soft stool frequency (SF)≥2.5 or an average daily abdominal pain (AP) score ≥2.0)—were randomized in a 1:1:1:1:1:1 ratio to one of the schematics of the overall study design shown in FIG. 1.

1. Group 1: upadacitinib 3 mg BID capsules (IR)
2. Group 2: upadacitinib 6 mg BID capsules (IR)
3. Group 3: upadacitinib 12 mg BID capsules (IR)
4. Group 4: upadacitinib 24 mg BID capsules (IR)
5. Group 5: upadacitinib 24 mg QD dose (IR) (two 12 mg capsules administered simultaneously)
6. Group 6: Placebo The 16 week induction period began at the BL visit (week 0) and ended at the week 16 visit. The randomization at BL was stratified by endoscopic disease severity (SES-CD<15 and ≥15). Safety and efficacy evaluations were performed through the end of the study. The end of the study was defined as the date the last patient completed the last follow up visit.

At week 16, patients who had completed the induction period were re-randomized to one of four double-blinded doses of upadacitinib: 3 mg BID, 6 mg BID, 12 mg BID, or 24 mg QD (patients administered two 12 mg capsules simultaneously). The re-randomization was stratified by dose received during the first 16 weeks and overall response (responder versus non-responder) at week 16.

Each treatment group received the corresponding dose of upadacitinib or placebo orally twice daily. Patients receiving the 24 mg QD dose were administered two 12 mg capsules simultaneously orally once daily. At week 12 and week 16, patients were evaluated for clinical remission (average daily SF≤1.5 and not worse than baseline and average daily AP≤1.0 and not worse than baseline). Patients were randomly assigned (1:1) to have an endoscopy at either week 12 or at week 16, and were evaluated for endoscopic remission (SES-CD≤4 and at least a two point reduction in SES-CD versus BL and no subscore ≥1 in any individual variable used to calculate SES-CD) at week 12 or week 16.

The central reader endoscopic score was used for calculating the endoscopic response for the evaluation of the efficacy endpoints. However, for stratification at the time of re-randomization, the endoscopic score at BL from central reader and the endoscopic score at week 12 or week 16 from site local reader were used in order to determine response status.

The co-primary endpoints for efficacy were:
endoscopic remission at week 12 or 16
clinical remission at week 16
Secondary endpoints to measure efficacy included:
CDAI<150 at week 16
decrease in CDAI of ≥70 points from BL at week 16
clinical remission at week 12
remission at week 16 (endoscopic remission at week 12 or 16 and clinical remission at week 16)
response at week 16 (endoscopic response at week 12 or 16 and clinical response at week 16)
endoscopic response at week 12 or 16
clinical response at week 16
whether a subject with an average daily SF≥2.5 and an average daily AP score ≥2.0 at BL achieves clinical remission at week 16
whether a subject taking corticosteroids at BL who discontinues corticosteroid use achieves
CDAI<150 at week 16
whether a subject taking corticosteroids at BL who discontinues corticosteroid use achieves endoscopic remission at week 12 or week 16 and clinical remission at week 16
whether a subject taking corticosteroids at BL who discontinues corticosteroid use achieves clinical remission at week 16
whether a subject taking corticosteroids at BL who discontinues corticosteroid use achieves endoscopic remission at week 12 or week 16
change from BL in fecal calprotectin level at week 16
change from BL in hs-CRP (high sensitivity C-reactive protein) at week 16
change in the Inflammatory Bowel Disease Questionnaire (IBDQ) from BL at week 16
whether a subject with isolated ileal Crohn's Disease achieves remission at week 16
whether a subject achieves remission at week 52
whether a subject achieves endoscopic remission at week 52
whether a subject achieves clinical remission at week 52
whether a subject achieves response at week 52
endoscopic response at week 52
clinical response at week 52
whether a subject taking corticosteroids at BL who discontinued corticosteroid use achieves CDAI<150 at week 52 whether a subject taking corticosteroids at BL who discontinued corticosteroid use achieves remission at week 52
whether a subject taking corticosteroids at BL who discontinued corticosteroid use achieves clinical remission at week 52
whether a subject taking corticosteroids at BL who discontinued corticosteroid use achieves endoscopic remission at week 52
CDAI<150 at week 52
decrease in CDAI≥70 points from BL at week 52
change from BL in fecal calprotectin level at week 52
change from BL in hs-CRP at week 52
change in IBDQ from BL at week 52
whether subject with isolated ileal Crohn's Disease achieves remission at week 52
change in extra-intestinal manifestations (EIMS) from BL at week 52

Methods

The study comprised two treatment periods: a 16 week double-blind induction period and a 36 week double-blind extension phase. In the induction period, patients with a diagnosis of ileal, colonic, or ileocolonic Crohn's disease for ≥3 months prior to BL and confirmed by endoscopy during the screening period, a CDAI≥220 and ≤450, and who have inadequately responded to or experienced intolerance to previous treatment with an anti-TNF agent (e.g. infliximab, adalimumab or certolizumab pegol), were assigned to receive one of the following doses of upadacitinib 3 mg BID, 6 mg BID, 12 mg BID, 24 mg BID or 24 mg QD or placebo. The co-primary endpoints were endoscopic remission at week 12 or week 16 and clinical remission at week 16. Secondary endpoints included CDAI<150 at week 16 and endoscopic response at week 12 or 16.

Eligible patients were aged 18 to 75 years. They had a diagnosis of CD for at least three months and at screening had moderate-to-severe CD, defined as a 1) SES-CD≥6 (or ≥4 for patients with disease limited to the ileum), 2) a CDAI of 220-450, and 3) an average daily liquid/soft SF score ≥2.5 or an average daily AP score ≥2.0. Patients had inadequately responded to or experienced intolerance to previous treatment with an anti-TNF agent. Patients with a current diagnosis of ulcerative colitis, collagenous colitis or indeterminate colitis as well as patients with previous exposure to a JAK inhibitor were excluded. See Table 16 below for key demographics and BL characteristics.

TABLE 16

Key Demographics and Baseline Characteristics

| Demographics and Characteristics | PBO N = 37 | 3 mg BID N = 39 | 6 mg BID N = 37 | 12 mg BID N = 36 | 24 mg BID N = 36 | 24 mg QD* N = 35 |
|---|---|---|---|---|---|---|
| Female, n (%) | 24 (64.9) | 19 (48.7) | 21 (56.8) | 17 (47.2) | 25 (69.4) | 19 (54.3) |
| Median Age, yrs | 40.0 | 37.0 | 39.0 | 41.0 | 43.5 | 41.0 |
| Disease duration, yrs | 11.80 | 13.25 | 11.82 | 13.29 | 14.83 | 14.22 |
| CDAI, mean | 288.4 | 298.0 | 316.1 | 305.1 | 294.3 | 315.1 |
| SF, mean | 5.85 | 5.63 | 7.38 | 6.45 | 5.64 | 6.73 |
| AP score, mean | 1.67 | 1.87 | 1.80 | 1.82 | 1.63 | 1.89 |
| SES-CD, mean | 15.8 | 14.7 | 16.2 | 15.6 | 14.3 | 13.4 |
| hsCRP, mean (mg/dL) | 20.8 | 23.6 | 17.9 | 26.9 | 17.1 | 17.1 |
| IBDQ, mean | 118.0 | 115.2 | 113.7 | 115.2 | 113.8 | 120.7 |
| Prior anti-TNFs, n (%) | | | | | | |
| 0 | 2 (5.4) | 2 (5.1) | 1 (2.7) | 2 (5.6) | 0 | 2 (5.7) |
| 1 | 15 (40.5) | 18 (46.2) | 12 (32.4) | 6 (16.7) | 10 (27.8) | 10 (28.6) |
| 2 | 15 (40.5) | 15 (38.5) | 20 (54.1) | 24 (66.7) | 15 (41.7) | 16 (45.7) |
| 3 | 5 (13.5) | 4 (10.3) | 4 (10.8) | 4 (11.1) | 9 (25.0) | 7 (20.0) |
| ≥4 | 0 | 0 | 0 | 0 | 2 (5.6) | 0 |
| Steroid use at BL, n (%) | 15 (40.5) | 20 (51.3) | 18 (48.6) | 18 (50.0) | 15 (41.7) | 10 (28.6) |
| Prior non-anti-TNF biologics (%) | 14 (38) | 15 (39) | 19 (51) | 15 (42) | 16 (44) | 14 (40) |
| vedolilzumab, n (%) | 10 (27) | 12 (31) | 14 (38) | 15 (42) | 12 (33) | 12 (34) |

*24 mg QD dose is two 12 mg doses given simultaneously

TABLE 17

Analysis of Primary Efficacy Endpoints

| | PBO N = 37 | 3 mg BID N = 39 | 6 mg BID N = 37 | 12 mg BID N = 36 | 24 mg BID N = 36 | 24 mg QD* N = 35 |
|---|---|---|---|---|---|---|
| Endoscopic Remission[1] (week 12 or 16) | 0 (0.0%) | 4 (10.3%) | 3 (8.1%) | 3 (8.3%) | 8 (22.2%) | 5 (14.3%) |
| Risk Difference | | 10.3 | 8.1 | 8.3 | 22.2 | 14.3 |
| P-value | | 0.056 | 0.108 | 0.099 | 0.004 | 0.025 |
| 94% CI | | −(0.3, 201.) | (−1.6, 16.4) | (−1.5, 6.8) | (6.8, 35.2) | (1.8, 25.5) |
| Clinical Remission[2] (week 16) | 4 (10.8%) | 5 (12.8%) | 10 (27.0%) | 4 (11.1%) | 8 (22.2%) | 5 (14.3%) |

TABLE 17-continued

Analysis of Primary Efficacy Endpoints

|  | PBO<br>N = 37 | 3 mg BID<br>N = 39 | 6 mg BID<br>N = 37 | 12 mg BID<br>N = 36 | 24 mg BID<br>N = 36 | 24 mg QD*<br>N = 35 |
|---|---|---|---|---|---|---|
| Risk difference |  | 2.0 |  | 0.3 | 11.4 | 3.5 |
| P-value |  | 0.740 | 0.082 | 0.952 | 0.205 | 0.607 |
| 95% CI |  | (−12.3, 17.3) | (−2.0, 34.3) | (−14.1, 15.0) | (−6.1, 28.5) | (−11.5, 19.6) |

Note:
Statistical significance was indicated by p value ≤0.10

[1] Endoscopic remission: SES-CD ≤4 and at least two point reduction in SES-CD versus BL and no subscore >1 in any individual variable

[2] clinical remission: average daily liquid/very soft SF score ≤1.5 and not worse than BL AND average daily AP score ≤1.0 and not worse than BL

*24 mg QD dose is two 12 mg doses given simultaneously

TABLE 18

Analysis of Secondary Efficacy Endpoints (NRI)

|  | PBO<br>N = 37 | 3 mg BID<br>N = 39 | 6 mg BID<br>N = 37 | 12 mg BID<br>N = 36 | 24 mg BID<br>N = 36 | 24 mg QD[&]<br>N = 35 |
|---|---|---|---|---|---|---|
| Week 16 |  |  |  |  |  |  |
| Clinical Response[1] | 12 (32.4%) | 17 (43.6%) | 21 (56.8%)* | 17 (47.2%) | 22 (61.1%)* | 17 (48.6%) |
| Endoscopic Response (weeks 12/16)[2] | 5 (13.5%) | 9 (23.1%) | 16 (43.2%)* | 14 (38.9%)* | 18 (50.0%)* | 17 (48.6%)* |
| Clinical Remission and Endoscopic Remission | 0 | 1 (2.6%) | 2 (5.4%) | 1 (2.8%) | 3 (8.3%)* | 2 (5.7%) |
| Clinical and Endoscopic Response | 1 (2.7%) | 6 (15.4%)* | 12 (32.4%)* | 10 (27.8%)* | 14 (38.9%)* | 12 (34.3%)* |
| CDAI <150 | 6 (16.2%) | 8 (20.5%) | 11 (29.7%) | 14 (38.9%)* | 11 (30.6%) | 7 (20.0%) |
| CR100[5] | 10 (27.0%) | 13 (33.3%) | 15 (40.5%) | 16 (44.4%) | 20 (55.6%)* | 11 (31.4%) |
| CR70[6] | 13 (35.1%) | 18 (46.2%) | 20 (54.1%) | 16 (44.4%) | 23 (63.9%)* | 17 (48.6%) |
| Steroid-free remisison[3] | 0/15 (0%) | 0/20 (0)%) | 1/18 (5.6%) | 1/18 (5.6%) | 2/15 (13.3%) | 0/10 (0%) |
| Steroid-free and CDAI <150[3] | 0/15 (0%) | 4/20 (20.0%) | 4/18 (22.2%) | 7/18 (38.9%)* | 5/15 (33.3%)* | 1/10 (10.0%) |
| Steroid-free and clinical response[3] | 0/15 (0%) | 5/20 (25%) | 9/18 (50%) | 8/18 (44%) | 10/15 (67%) | 3/10 (30%) |
| Week 12 |  |  |  |  |  |  |
| Clinical Remission[4] | 4 (10.8%) | 4 (10.3%) | 11 (29.7%)* | 5 (13.9%) | 9 (25.0%) | 3 (8.6%) |
| Clinical Response[1] | 13 (35.1%) | 21 (53.8%) | 24 (64.9%)* | 19 (52.8%) | 20 (55.6%) | 18 (51.4%) |
| CDAI <150 | 24.3% | 18.4% | 41.7% | 47.2%* | 38.9% | 22.9% |
| CR70[6] | 35.1% | 38.5% | 59.5%* | 47.2% | 58.3%* | 51.4% |
| CR100[5] | 29.7% | 30.8% | 51.4%* | 41.7% | 52.8%* | 40.0% |

*Statistical significance was indicated by p value ≤0.10
[&] 24 mg QD dose is two 12 mg doses given simultaneously
[1] Clinical response: average daily liquid/very soft SF score ≥30% reduction from BL and average daily AP not greater than BL and/or average daily AP score ≥30% reduction from BL and average daily liquid/very soft SF score not greater than BL
[2] Endoscopic response: >25% decrease in SES-CD from BL, as scored by central reviewer
[3] Among subjects taking steroids at BL
[4] Clinical remission: average daily liquid/very soft stool frequency score ≤1.5 and not worse than BL AND average daily AP ≤1.0 and not worse than BL
[5] Decrease in CDAI score ≥100 from baseline
[6] Decrease in CDAI score ≥70 from baseline

TABLE 19

Analysis of Additional Efficacy Endpoints

| Endpoints[&] | PBO<br>N = 33 | 3 mg BID<br>N = 38 | 6 mg BID<br>N = 33 | 12 mg BID<br>N = 34 | 24 mg BID<br>N = 30 | 24 mg QD**<br>N = 32 |
|---|---|---|---|---|---|---|
| Modified Clinical Remission[1] (week 16) | 4 (12.1%) | 6 (15.8%) | 10 (30.3%)* | 9 (26.5%) | 11 (36.7%)* | 6 (18.8%) |

TABLE 19-continued

Analysis of Additional Efficacy Endpoints

| Endpoints[&] | PBO<br>N = 33 | 3 mg BID<br>N = 38 | 6 mg BID<br>N = 33 | 12 mg BID<br>N = 34 | 24 mg BID<br>N = 30 | 24 mg QD**<br>N = 32 |
|---|---|---|---|---|---|---|
| Endoscopic Improvement[2]<br>(Week 12 or 16) | 1 (3.0%) | 12.8% | 18.9%* | 27.8%* | 36.1%* | 25.7%* |

Figures 6A, 6B:
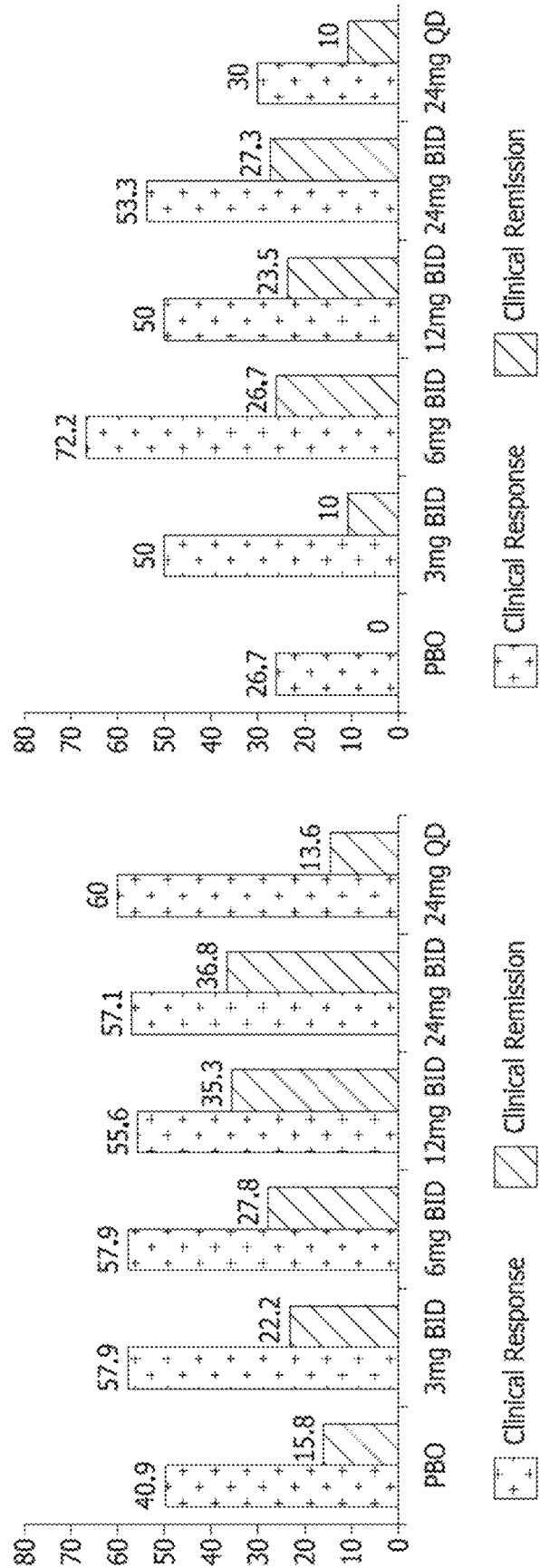
FIGS. 6A and 6B are graphs depicting the percent of subjects who achieved clinical response or clinical remission at week 12 of the Example 8 study.

[&]Includes subjects with baseline SF ≥4.0 or AP ≥2.0.
*Statistical significance was indicated by p value ≤0.10.
**24 mg QD dose is two 12 mg doses given simultaneously
[1]Clinical remission: average daily SF ≤2.8 and not greater than Baseline AND average daily AP ≤1.0 and not greater than Baseline
[2]Endoscopic improvement: SES-CD >50% reduction from BL or at least a 2 point reduction in SES-CD from BL or endoscopic remission Results Baseline demographics and disease characteristics were similar between study arms. In total there were 95 males and 125 females, with a mean age of 42.5 years and mean CDAI of 302.83; 96.0% percent of patients had previously been exposed to ≥1 TNF antagonists. At week 12/16, endoscopic remission was achieved by 10.3%, 8.1%, 8.3%, 22.2% and 14.3% of patients treated with 3 mg BID, 6 mg BID, 12 mg BID, 24 mg BID and 24 mg QD, respectively, of upadacitinib, compared with 0% of patients treated with placebo (p=0.056, p=0.108, p=0.099, p=0.004, p=0.025, respectively, see Table 17). At week 16, clinical remission was achieved by 12.8%, 27.0%, 11.1%, 22.2% and 14.3% of patients treated with 3 mg BID, 6 mg BID, 12 mg BID, 24 mg BID and 24 mg QD, respectively, of upadacitinib, compared 10.8% of patients treated with placebo (p=0.740, p=0.082, p=0.952, p=0.205, p=0.607, respectively, see Table 17). Clinical remission was observed in some patients as early as week 12. The percentage of patients achieving clinical remission at week 12 is shown in FIG. 6A (patients not on baseline steroids) and FIG. 6B (patients who were on steroids at baseline, and underwent mandatory taper of steroid dose starting at week 2). The steroid taper consisted of a weekly decrease by 5 mg/day of prednisone (or equivalent) for doses >10/mg/day of prednisone (or equivalent) until a 10 mg/day (or equivalent) dose was reached, then a weekly decrease by 2.5 mg/day (or equivalent) until discontinuation. Upadacitinib was shown to induce clinical remission as early as week 12.

Clinical response was achieved at week 16 by 43.6%, 56.8%, 47.2%, 61.1% and 48.6% of patients treated with 3 mg BID, 6 mg BID, 12 mg BID, 24 mg BID and 24 mg QD, respectively, of upadacitinib, compared with 32.4% of patients treated with placebo. Endoscopic response was achieved at week 12 or week 16 by 23.1%, 43.2%, 38.9%, 50.0% and 48.6% of patients treated with 3 mg BID, 6 mg BID, 12 mg BID, 24 mg BID and 24 mg QD, respectively, of upadacitinib, compared with 13.5% of patients treated with placebo.

Clinical remission and endoscopic remission was achieved at week 16 by 2.6%, 5.4%, 2.8%, 8.3% and 5.7% of patients treated with 3 mg BID, 6 mg BID, 12 mg BID, 24 mg BID and 24 mg QD, respectively, of upadacitinib, compared with 0% of patients treated with placebo. Clinical and endoscopic response was achieved at week 16 by 15.4%, 32.4%, 27.8%, 38.9% and 34.3% of patients treated with 3 mg BID, 6 mg BID, 12 mg BID, 24 mg BID and 24 mg QD, respectively, of upadacitinib, compared with 2.7% of patients treated with placebo. Results are shown in Table 18.

Clinical remission was achieved at week 12 by 10.3%, 29.7%, 13.9%, 25.0% and 8.6% of patients treated with 3 mg BID, 6 mg BID, 12 mg BID, 24 mg BID and 24 mg QD, respectively, of upadacitinib, compared with 10.8% of patients treated with placebo. Clinical response was achieved at week 12 by 53.8%, 64.9%, 52.8%, 55.6% and 51.4% of patients treated with 3 mg BID, 6 mg BID, 12 mg BID, 24 mg BID and 24 mg QD, respectively, of upadacitinib, compared with 35.1% of patients treated with placebo. Results are shown in Table 18. The percentage of patients achieving clinical response at week 12 is shown in FIG. 6A (patients not on baseline steroids) and FIG. 6B (patients who were on steroids at baseline, and underwent mandatory taper of steroid dose starting at week 2).

Modified clinical remission was achieved at week 16 by 15.8%, 30.3%, 26.5%, 36.7%, and 18.8% of patients treated with 3 mg BID, 6 mg BID, 12 mg BID, 24 mg BID and 24 mg QD, respectively, of upadacitinib, compared with 12.1% of patients treated with placebo. Results are shown in Table 19.

Endoscopic improvement was achieved at week 12 or week 16 by 12.8%, 18.9%, 27.8%, 36.1%, and 25.7% of patients treated with 3 mg BID, 6 mg BID, 12 mg BID, 24 mg BID and 24 mg QD, respectively, of upadacitinib, compared with 3.0% of patients treated with placebo. Results are shown in Table 19. Of the patients who were evaluated for endoscopic improvement at week 12, 10.5%, 13.3%, 25%, 33.3%, and 12.5% of patients treated with 3 mg BID, 6 mg BID, 12 mg BID, 24 mg BID and 24 mg QD, respectively, of upadacitinib, achieved endoscopic improvement by week 12, compared with 0% of patients treated with placebo. Of the patients who were evaluated for endoscopic improvement at week 16, 15.8%, 27.8%, 27.3%, 25%, and 31.3% of patients treated with 3 mg BID, 6 mg BID, 12 mg BID, 24 mg BID and 24 mg QD, respectively, of upadacitinib, achieved endoscopic improvement by week 16, compared with 6.7% of patients treated with placebo. These results are shown in Table 20. These results show that endoscopic improvement was observed as early as week 12.

By week 4 of the induction period, among Crohn's patients tapering corticosteroids, 13.3%, 9.5%, 11.1%, 11.8%, 6.7% and 10% respectively were able to discontinue steroids with placebo, 3 mg BID, 6 mg BID, 12 mg BID, 24 mg BID and 24 mg BID, respectively. By week 8 of the induction period, among Crohn's patients tapering corticosteroids, 26.7%, 23.8%, 44.4%, 64.7%, 53.3% and 40% respectively were able to discontinue steroids 3 mg BID, 6 mg BID, 12 mg BID, 24 mg BID and 24 mg BID, respectively. By week 12 of the induction period, among Crohn's patients were able to discontinue steroids, 33.3%, 28.6%, 55.6%, 76.5%, 60% and 40% respectively were able to reduce their steroid dose by ≥50% with placebo, 3 mg BID, 6 mg BID, 12 mg BID, 24 mg BID and 24 mg BID, respectively. By week 16 of the induction period, among Crohn's patients tapering corticosteroids, 20%, 38.1%, 55.6%, 64.7%, 74.3% and 40% respectively were able to reduce their steroid dose by ≥50% with placebo, 3 mg BID, 6 mg BID, 12 mg BID, 24 mg BID and 24 mg BID, respectively.

By week 4 of the induction period, among Crohn's patients tapering corticosteroids, 20%, 42.9%, 50%, 82.4%, 46.7% and 40% respectively were able to reduce their steroid dose by ≥50% with placebo, 3 mg BID, 6 mg BID, 12 mg BID, 24 mg BID and 24 mg BID, respectively. By week 8 of the induction period, among Crohn's patients tapering corticosteroids, 55.3%, 42.9%, 66.7%, 88.2%, 66.7% and 60% respectively were able to reduce their steroid dose by ≥50% with placebo, 3 mg BID, 6 mg BID, 12 mg BID, 24 mg BID and 24 mg BID, respectively. By week 12 of the induction period, among Crohn's patients tapering corticosteroids, 46.7%, 38.1%, 61.1%, 88.2%, 60% and 40% respectively were able to reduce their steroid dose by ≥50% with placebo, 3 mg BID, 6 mg BID, 12 mg BID, 24 mg BID and 24 mg BID, respectively. By week 16 of the induction period, among Crohn's patients tapering corticosteroids, 33.3%, 38.1%, 66.7%, 88.4%, 77.3% and 40% respectively were able to reduce their steroid dose by ≥50% with placebo, 3 mg BID, 6 mg BID, 12 mg BID, 24 mg BID and 24 mg BID, respectively.

At the end of the 16 week induction period, among Crohn's patients who discontinued corticosteroids, 11.1%, 5.9%, 20% and 10% achieved endoscopic remission with, 6 mg BID, 12 mg BID, 24 mg BID and 24 mg BID, respectively. At the end of the 16 week induction period, among patients who discontinued corticosteroids, 6.7%, 4.8%, 16.7%, 17.6%, 20% and 20% achieved endoscopic response with placebo, 3 mg BID, 6 mg BID, 12 mg BID, 24 mg BID and 24 MG BID, respectively. At the end of the 16 week induction period, among patients who discontinued corticosteroids, 14.3%, 22.2%, 11.8%, 33.3% and 10% achieved clinical remission with 3 mg BID, 6 mg BID, 12 mg BID, 24 mg BID and 24 MG BID, respectively. At the end of the 16 week induction period, among patients who discontinued corticosteroids 14.3%, 26.7%, 25.0%, 36.4% and 10% achieved modified clinical remission with 3 mg BID, 6 mg BID, 12 mg BID, 24 mg BID and 24 MG BID, respectively. At the end of the 16 week induction period, among patients who discontinued corticosteroids 19.0%, 22.2%, 41.2%, 33.3% and 10% achieved CDAI<150 with 3 mg BID, 6 mg BID, 12 mg BID, 24 mg BID and 24 MG BID, respectively. The taper consisted of a weekly decrease by 5 mg/day of prednisone (or equivalent) for doses ≥10/mg/day of prednisone (or equivalent) until a 10 mg/day (or equivalent) dose was reached, then a weekly decrease by 2.5 mg/day (or equivalent) until discontinuation.

TABLE 20

Analysis of Endoscopic Improvement by Week Evaluated

| Week 12 | PBO<br>N = 18 | 3 mg<br>BID<br>N = 19 | 6 mg<br>BID<br>N = 15 | 12 mg<br>BID<br>N = 12 | 24 mg<br>BID<br>N = 18 | 24 mg<br>QD<br>N = 16 |
|---|---|---|---|---|---|---|
| Endoscopic Improvement | 0% | 10.5%* | 13.3% | 25%* | 33.3%* | 12.5% |

TABLE 20-continued

Analysis of Endoscopic Improvement by Week Evaluated

| Week 16 | PBO<br>N = 15 | 3 mg<br>BID<br>N = 19 | 6 mg<br>BID<br>N = 18 | 12 mg<br>BID<br>N = 22 | 24 mg<br>BID<br>N = 12 | 24 mg<br>QD<br>N = 16 |
|---|---|---|---|---|---|---|
| Endoscopic Improvement | 6.7% | 15.8% | 27.8% | 27.3% | 25% | 31.3%* |

*Statistical significance was indicated by p value ≤0.10.

This study included refractory patients with moderately to severely active Crohn's disease, who have had Crohn's disease for more than ten years and who have failed several treatments, including biologic treatments. Table 16 above shows the number of patients in the study that received prior anti-TNF treatment, treatment with prior non-anti-TNF biologics, treatment with vedolilzumab, and who were being treated with steroids at baseline, as well as the average duration of Crohn's disease at baseline. Typically, because refractory patients are treated with different therapeutics, the efficacy of each treatment progressively decreases. Surprisingly, however, the current study demonstrated that when treated with upadacitinib, the refractory patients showed unprecedented efficacy. The results for refractory patients in the study are shown in FIG. 9.

As shown by FIG. 9, refractory patients treated with upadacitinib achieved clinical remission and endoscopic response at unprecedented rates. At week 16, 15.8% of refractory patients treated with 3 mg BID of upadacitinib achieved clinical remission. At week 16, 30.3% of refractory patients treated with 6 mg BID of upadacitinib achieved clinical remission. At week 16, 26.5% of refractory patients treated with 12 mg BID of upadacitinib achieved clinical remission. At week 16, 36.7% of refractory patients treated with 24 mg QD (two 12 mg BID doses given simultaneously) achieved clinical remission.

In addition, as also shown in FIG. 9, a surprising proportion of refractory patients treated with upadacitinib achieved endoscopic remission at 12 or 16 weeks. 13.2% of refractory patients treated with 3 mg BID of upadacitinib achieved endoscopic remission at 12 or 16 weeks. 21.2% of refractory patients treated with 6 mg BID of upadacitinib achieved endoscopic remission at 12 or 16 weeks. 29.4% of refractory patients treated with 2 mg BID of upadacitinib achieved endoscopic remission at 12 or 16 weeks. 33.3% of refractory patients treated with 24 mg QD (two 12 mg doses given simultaneously) of upadacitinib achieved endoscopic remission at 12 or 16 weeks.

The relationship between upadacitinib plasma concentrations and the primary endpoints and certain secondary and additional endpoints is set forth in FIGS. 3A-3I. Exposure-response relationships were observed for clinical response, clinical remission, CDAI remission (CDAI<150), endoscopic response, endoscopic improvement, and endoscopic remission.

Safety

The incident of adverse events was numerically higher (~3-13%) in upadacitinib dose groups, compared to placebo, with no clear dose-relationship. Severe adverse events and treatment discontinuations due to adverse events were lower/comparable across all upadacitinib dose groups compared to placebo except in the 12 mg BID dose group. There were no treatment emergent deaths in the study. Overall, the incidence of adverse events of special interest were low (except for infections) and similar across all treatment groups. Infections were increased in all upadacitinib BID dose groups compared to placebo. Two adjudicated major adverse cardiac events (MACE) were observed in the 12 mg BID dose group (two had an acute myocardial infarction).

Figure 5A:
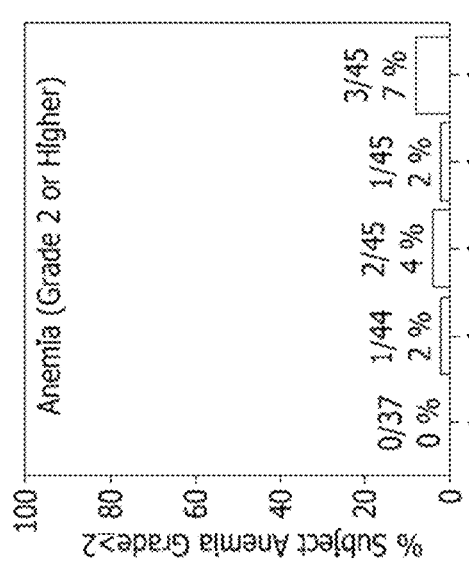
FIGS. 5A-5H are graphs depicting the relationship between upadacitinib plasma concentration and the change from baseline for select measured laboratory parameters at week 16 (LOCF) of the Example 8 clinical study. The maximum and minimum plasma concentrations for each data point are indicated in brackets.
Figure 5B:
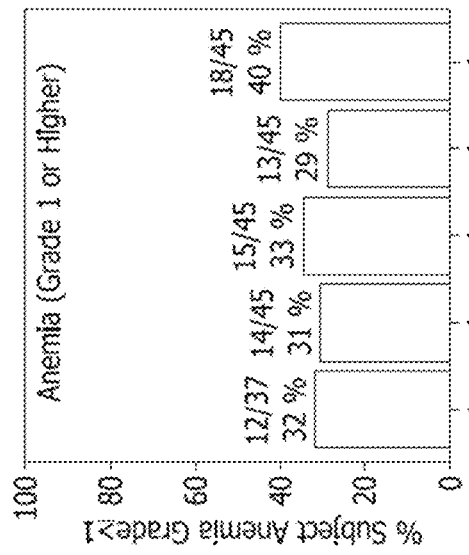
Figure 5C:
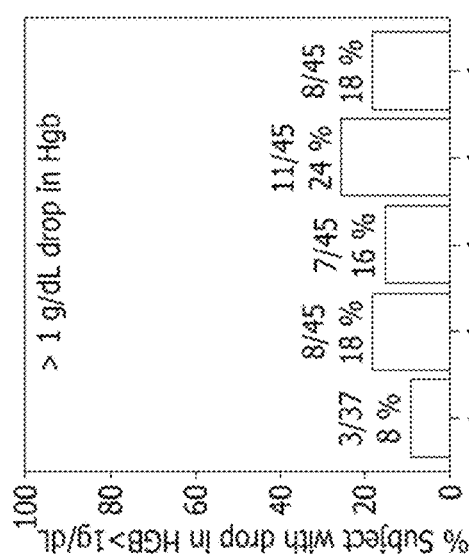
Figure 5F:
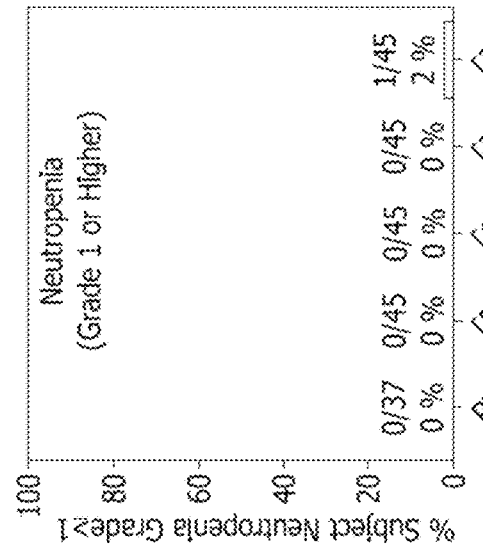
Figure 5E:
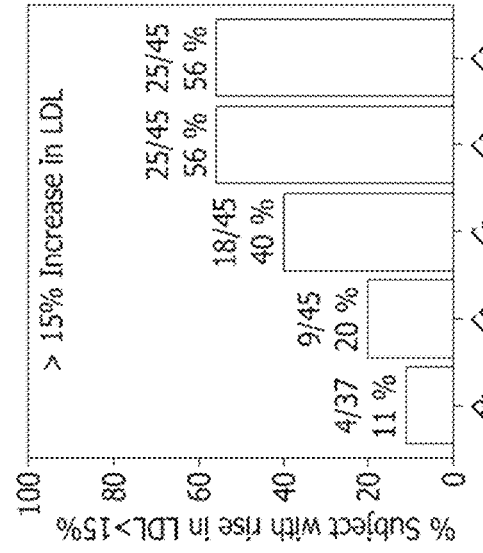
Figure 5D:
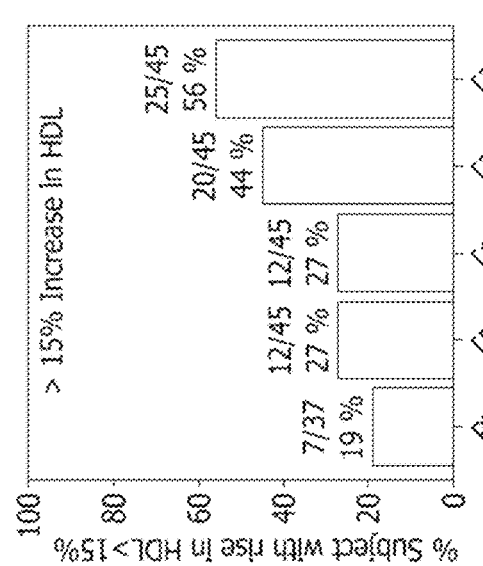
Figure 5H:
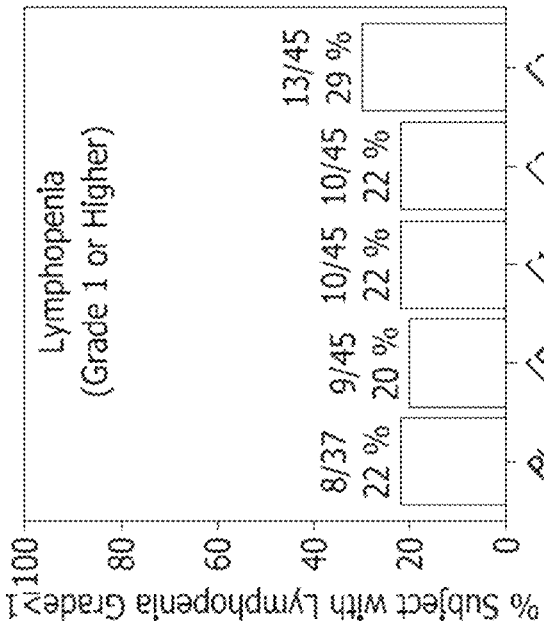
Figure 5G:
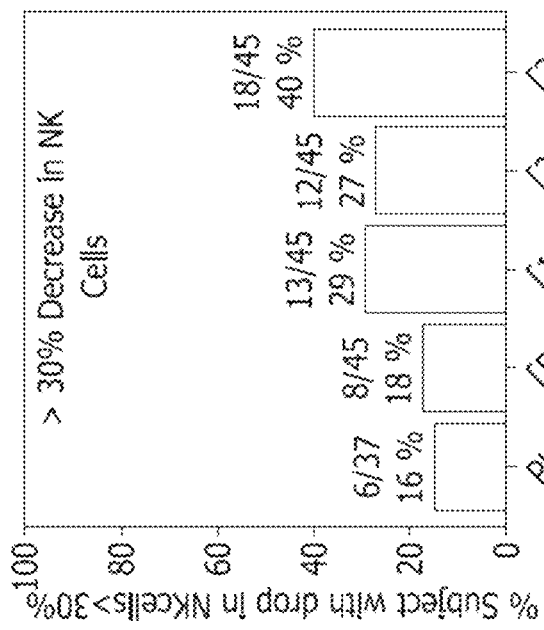

The relationship between upadacitinib plasma concentration and the change from baseline in hemoglobin levels, anemia, LDL and HDL cholesterol, neutropenia, lymphopenia, and natural killer (NK) cell levels was determined, and the results shown in FIGS. 5A-5H. Exposure-response relationships for effects of upadacitinib on NK cells, neutrophils, LDL and HDL cholesterol in Crohn's patients were generally consistent with those previously observed in RA patients. Compared to RA patients (data not shown), subjects with Crohn's had lower decreases in hemoglobin (FIG. 5A).

Example 9: Model Predicted Efficacy for Once-Daily Doses

Based on the data obtained in Example 8 for administration of an immediate release (IR) formulation of upadacitinib BID, the exposure-response relationships (simulating for 200 patients/arm) for 15 mg, 30 mg, and 45 mg modified-release QD doses of upadacitinib, for placebo, for 6 mg, 12 mg, 18 mg, and 24 mg IR BID doses of upadacitinib, and for 24 mg IR QD doses of upadacitinib was predicted. The full time-course for the different clinical endpoints was analyzed using Markov analyses. The Marko models allowed transition between response, no response, and dropouts. The models evaluated $C_p$, $C_{ave}$, $C_{min}$, and $C_{max}$ as predictors for drug efficacy. The different endoscopic endpoints at Week 12/16 were analyzed using logistic regression analyses. Then, the models were used to simulate clinical response, clinical remission, CDAI<150, endoscopic response, endoscopic improvement and endoscopic remission at Weeks 12 and 16 (when applicable) for different dose regimens for both the immediate and modified release formulation by back transforming exposures to doses. The results are set forth in FIGS. 4A-4F.

This modelling suggests 1-3% improvements in clinical parameters between doses with the MR formulation.

Example 10: Clinical Study for Crohn's Disease: Long-Term Efficacy and Safety of Upadacitinib in Moderate to Severe Crohn's Disease In Example 10, the extension phase of the Example 8 clinical study was studied and discussed. The trial was a multicenter, randomized, double-blind placebo-controlled study of upadacitinib for the induction of symptomatic and endoscopic remission in patient with moderately to severely active Crohn's disease who have inadequately responded to or are intolerant to immunosuppressants or anti-TNF therapy.

The trial consisted of a screening period of up to 30 days, a 16 week double blind induction period, re-randomization at week 16, a 36 week double blind and open label phase and a 30 day follow up period.

Approximately 220 patients with moderately to severely active Crohn's disease—defined for purposes of this study as having 1) Simplified Endoscopic Score for CD (SES-CD) ≥6, (or SES-CD≥4 for patients with disease limited to the ileum), 2) a CDAI≥220 and ≤450, and 3) an average daily liquid/soft stool frequency (SF)≥2.5 or an average daily abdominal pain (AP) score ≥2.0)—were randomized in a 1:1:1:1:1:1 ratio to one of the schematics of the overall study design shown in FIG. 1.

1. Group 1: upadacitinib 3 mg BID capsules (IR)
2. Group 2: upadacitinib 6 mg BID capsules (IR)
3. Group 3: upadacitinib 12 mg BID capsules (IR)
4. Group 4: upadacitinib 24 mg BID capsules (IR)
5. Group 5: upadacitinib 24 mg QD dose (IR) (two 12 mg capsules administered simultaneously)
6. Group 6: Placebo The 16 week induction period began at the BL visit (week 0) and ended at the week 16 visit. The randomization at BL was stratified by endoscopic disease severity (SES-CD<15 and ≥15). Safety and efficacy evaluations were performed through the end of the study. The end of the study was defined as the date the last patient completed the last follow up visit.

At week 16, patients who completed the 16-week induction phases were re-randomised 1:1:1 to double-blind upadacitinib at 3 mg twice daily (BID), 12 mg BID or 24 mg daily (QD) for 36 weeks. A protocol amendment stopped enrolment in the 24 mg QD arm and initiated a 6 mg BID arm. A total of 180 patients were re-randomised to one of four double-blinded doses of upadacitinib:

1. Group 1: upadacitinib 3 mg BID capsules (IR)
2. Group 2: upadacitinib 6 mg BID capsules (IR)
3. Group 3: upadacitinib 12 mg BID capsules (IR)
4. Group 4: upadacitinib 24 mg QD dose (IR) (two 12 mg capsules administered simultaneously)

The re-randomization was stratified by dose received during the first 16 weeks and overall response (responder versus non-responder) at week 16.

Each treatment group received the corresponding dose of upadacitinib orally once or twice daily. Patients receiving the 24 mg QD dose were administered two 12 mg capsules simultaneously orally once daily. At week 52, patients were evaluated for clinical remission (average daily SF≤1.5 and not worse than baseline and average daily AP≤1.0 and not worse than baseline), CDAI≤150, modified clinical remission (SF≤2.8 and AP≤1.0, both not worse than BL in patients with SF≥4, AP≥2.0 at BL), clinical response (≥30% decrease in SF or AP, both not worse than BL), endoscopic remission (SES-CD≤4 and ≥2-point reduction from BL and no subscore >1), endoscopic response (SES-CD reduction >50% from BL or endoscopic remission) and change from BL in C-reactive protein (CRP) and faecal calprotectin (FC).

The co-primary endpoints for efficacy were the same as the endpoints in Example 8 study.

Methods

The study comprised two treatment periods: a 16 week double-blind induction period and a 36 week double-blind extension phase. In the induction period, patients with a diagnosis of ileal, colonic, or ileocolonic Crohn's disease for ≥3 months prior to BL and confirmed by endoscopy during the screening period, a CDAI≥220 and ≤450, and who have inadequately responded to or experienced intolerance to previous treatment with an anti-TNF agent (e.g. infliximab, adalimumab or certolizumab pegol), were assigned to receive one of the following doses of upadacitinib 3 mg BID, 6 mg BID, 12 mg BID, 24 mg BID or 24 mg QD or placebo. The co-primary endpoints were endoscopic remission at week 12 or week 16 and clinical remission at week 16. Secondary endpoints included CDAI<150 at week 16 and endoscopic response at week 12 or 16. In the extension phase, patients who completed the 16-week induction phases were re-randomised 1:1:1 to double-blind upadacitinib at 3 mg twice daily (BID), 12 mg BID or 24 mg daily (QD) for 36 weeks. A protocol amendment stopped enrolment in the 24 mg QD arm and initiated a 6 mg BID arm. Clinical remission (average daily stool frequency [SF]≤1.5 and abdominal pain score [AP] ≤1.0, both not worse than Baseline [BL]), CDAI<150, modified clinical remission (SF≤2.8 and AP≤1.0, both not worse than BL in patients with SF≥4, AP≥2.0 at BL), clinical response (≥30% decrease in SF or AP, both not worse than BL), endoscopic remission (SES-CD≤4 and ≥2-point reduction from BL and no subscore >1), endoscopic response (SES-CD reduction >50% from BL or endoscopic remission) and change from BL in C-reactive protein (CRP) and faecal calprotectin (FC) were analysed at week 52 in patients with either both clinical and endoscopic response or clinical response at week 16. Endoscopies were evaluated at BL, 12/16 and 52 weeks by a central reader. Patients who received open label upadacitinib (escape) or prematurely discontinued prior to week 52 were considered non-responders (non-responder imputation). Adverse events were collected throughout the study up to 30 days after the last upadacitinib dose.

Eligibility, key demographics and BL characteristics of the patients were essentially the the same as those in Example 8 study.

Among subjects who achieved clinical response and endoscopic response at week 16, endoscopic response was achieved at week 52 by 50.0%, 50.0%, 68.8%, and 30.0% of patients treated with 3 mg BID, 6 mg BID, 12 mg BID, and 24 mg QD, respectively, of upadacitinib. Among subjects who achieved clinical response at week 16, endoscopic response was achieved at week 52 by 34.4%, 35.7%, 44.8%, and 36.8% of patients treated with 3 mg BID, 6 mg BID, 12 mg BID, and 24 mg QD, respectively, of upadacitinib. Results are shown in Table 21. Among subjects who achieved clinical response and endoscopic response at week 16, endoscopic response was achieved at week 52 by 34.4, 35.7, 44.8 and 36.8% of patients treated with 3 mg BID, 6 mg BID, 12 mg BID and 24 mg QD, respectively.

Among subjects who achieved clinical response and endoscopic response at week 16, modified clinical remission was achieved at week 52 by 41.2%, 62.5%, 73.3%, and 40.0% of patients treated with 3 mg BID, 6 mg BID, 12 mg BID, and 24 mg QD, respectively, of upadacitinib. Among

TABLE 21

Analysis of Primary and Secondary Efficacy Endpoints (Clinical and endoscopic endpoints at Week 52 in the CELEST study)

| Endpoint at Week 52 | 3 mg BID N = 32 | 6 mg BID N = 14 | 12 mg BID N = 29 | 24 mg QD[&] N = 19 |
|---|---|---|---|---|
| Among subjects who achieved clinical response and endoscopic response at Week 16 | | | | |
| Modified clinical remission[a], n (%) | 7 (41.2)[b] | 5 (62.5)[b] | 11 (73.3)[b] | 4 (40.0)[b] |
| Endoscopic response, % | 10 (50.0)[d] | 4 (50.0)[d] | 11 (68.8)[d] | 3 (30.0)[d] |
| Among subjects who achieved clinical response at Week 16 | | | | |
| Modified clinical remission, n (%) | 8 (28.6)[e] | 6 (42.9)[e] | 14 (51.9)[e] | 7 (38.9)[e] |
| Endoscopic response, % | 11 (34.4)[f] | 5 (35.7)[f] | 13 (44.8)[f] | 7 (36.8)[f] |
| Clinical remission[g], n (%) | 8 (25) | 4 (29) | 12 (41) | 6 (32) |
| CDAI <150, % (n) | 14 (44) | 7 (50) | 16 (55) | 7 (37) |
| Enhanced clinical response[h], n (%) | 15 (47) | 10 (71) | 18 (62) | 8 (42) |
| Clinical response[i], n (%) | 16 (50) | 10 (71) | 18 (62) | 8 (42) |
| Endoscopic remission[j], n (%) | 5 (16) | 3 (21) | 7 (24) | 5 (26) |
| Mean change from BL in hs-CRP ± SD | −2.8 ± 18.9 | −2.1 ± 18.4 | −13.9 ± 37.1 | 10.2 ± 55.7 |
| Mean change from BL in FC ± SD | 1.0 ± 2457.2 | −239.3 ± 1443.1 | −2617.4 ± 3232.0 | −1510.3 ± 2773.9 |

[&]24 mg QD dose is two 12 mg doses given simultaneously
[a]Modified clinical remission: SF ≤2.8 and AP ≤1.0, both not worse than BL in patients with SF ≥4 or AP ≥2.0 at BL
[b]For 3, 6, and 12 mg BID and 24 mg QD, n = 17, 8, 15, and 10
[c]Endoscopic response: SES-CD reduction >50% from BL or endoscopic remission. in responders and 28, 14, 27, and 18 in clinical responders, respectively
[d]For 3, 6, and 12 mg BID and 24 mg QD, n = 20, 8, 16, and 10
[e]For 3, 6, and 12 mg BID and 24 mg QD, n = 28, 14, 27, and 18
[f]For 3, 6, and 12 mg BID and 24 mg QD, n = 32, 14, 29, and 19
[g]Clinical remission: SF ≤1.5 and AP ≤1.0 and both not worse than BL
[h]Enhanced clinical response: ≥60% reduction from induction BL in SF or ≥35% reduction from induction BL in AP and both not worse than BL or modified clinical remission
[i]Clinical response: ≥30% reduction from BL in SF or ≥30% reduction from BL in AP and both not worse than BL.
[j]Endoscopic remission: SES-CD ≤4 and at least 2-point reduction from BL and no subscore >1

Results

Baseline demographics and disease characteristics were similar between study arms. At week 52, endoscopic remission was achieved by 16%, 21%, 24%, and 26% of patients treated with 3 mg BID, 6 mg BID, 12 mg BID, and 24 mg QD, respectively, of upadacitinib. At week 52, clinical remission was achieved by 25%, 29%, 41%, and 32% of patients treated with 3 mg BID, 6 mg BID, 12 mg BID, and 24 mg QD, respectively, of upadacitinib. Results are shown in Table 21.

Clinical response was achieved at week 52 by 50%, 71%, 62%, and 42% of patients treated with 3 mg BID, 6 mg BID, 12 mg BID, and 24 mg QD, respectively, of upadacitinib. Enhanced clinical response was achieved at week 52 by 47%, 71%, 62%, and 42% of patients treated with 3 mg BID, 6 mg BID, 12 mg BID and 24 mg QD, respectively, of upadacitinib. Results are shown in Table 21.

subjects who achieved clinical response at week 16, modified clinical remission was achieved at week 52 by 28.6%, 42.9%, 51.9%, and 38.9% of patients treated with 3 mg BID, 6 mg BID, 12 mg BID, and 24 mg QD, respectively, of upadacitinib. Results are shown in Table 21.

Safety

The incident of adverse events (AEs) was numerically higher with upadacitinib 3 and 12 mg BID (45 [75.0%] and 43 [72.9%]) than that with 6 mg BID and 24 mg QD (14 [60.9%] and 23 [63.9%]), respectively. Serious AEs were numerically higher with 3 mg BID and infections with 3 and 12 mg BID than that in the other arms. Two malignancies occurred with 12 mg BID.

Conclusion

Dose-dependent improvements in clinical and endoscopic outcomes and markers of inflammation were observed with 36-week upadacitinib treatment in patients who responded to a 16-week induction regimen. The overall safety profile of upadacitinib is consistent with other studies in rheumatoid arthritis.

Example 11: Clinical Study for Crohn's Disease: Rapidity of Clinical and Laboratory Improvements Following Upadacitinib Induction Treatment This analysis evaluates the rapidity of clinical remission, clinical response, and changes in markers of inflammation during the induction phase of the clinical study discussed in Example 8.

Methods

Adult patients with Crohn's Disease Activity Index (CDAI) 220-450, average daily liquid/very soft stool frequency (SF)≥2.5 or daily abdominal pain score (AP)≥2.0, and Simplified Endoscopic Score for CD (SES-CD)≥6 [or ≥4 for those with isolated ileal disease], were randomized to double-blind therapy with placebo (PBO) or immediate release formulation of upadacitinib at 3, 6, 12, 24 mg twice daily (BID) or 24 mg once daily (QD) for 16 weeks. Patients were randomized at baseline for follow-up ileocolonoscopy at either Week 12 or 16. Proportion of patients with modified clinical remission and enhanced clinical response, both defined in Figure, mean change from baseline in C-reactive protein (CRP) and faecal calprotectin (FC) were assessed over time in all patients unless otherwise mentioned. Comparisons between each upadacitinib dose with PBO was tested by Cochran-Mantel-Haenszel test stratified by SES-CD at BL. Non-responder imputation was applied to patients who received open-label upadacitinib or prematurely discontinued prior to Week 16 or initiated corticosteroids or had dose increase higher than baseline.

Results

Figure 12:
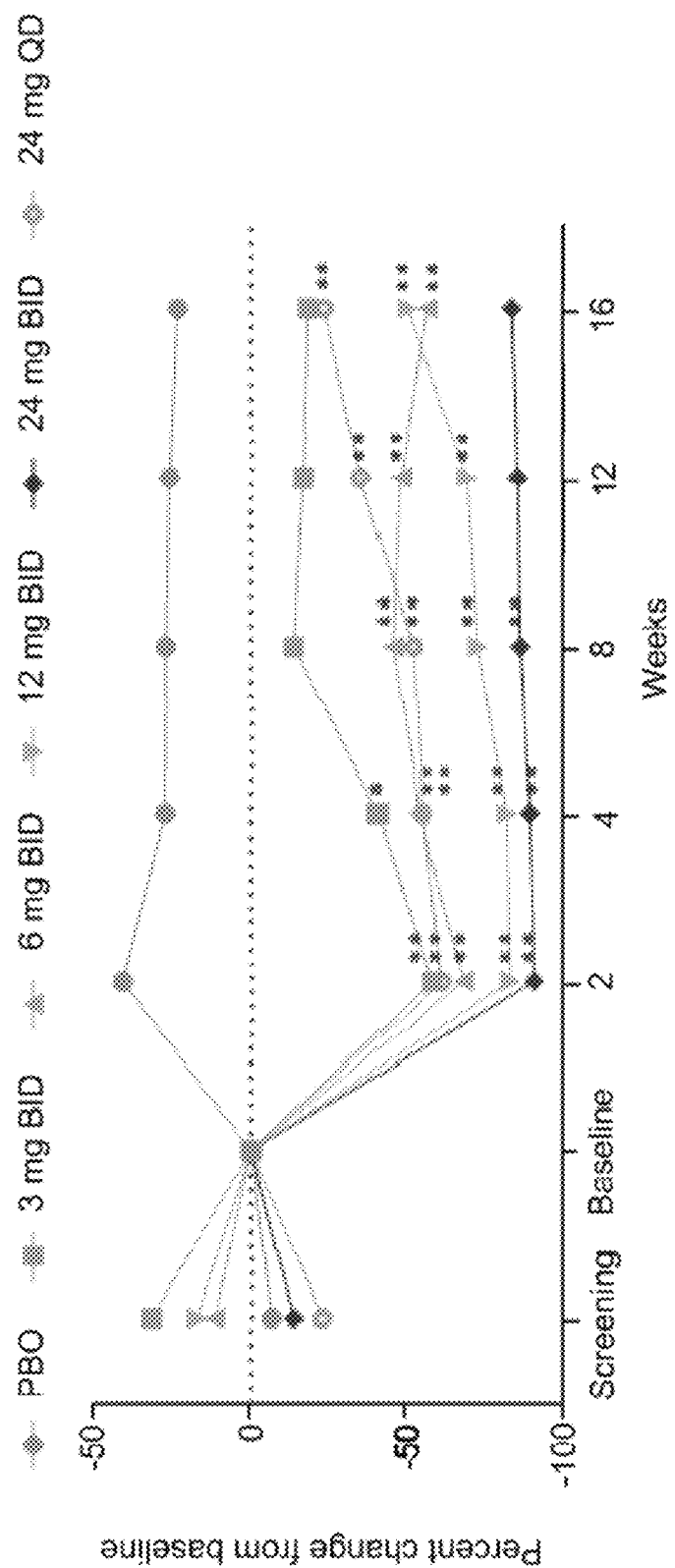
FIG. 12 shows the mean change in hs-CRP (percentage over baseline) versus time (weeks) following administration of placebo (PBO), upadacitinib at 3, 6, 12, 24 mg twice daily (BID) and 24 mg once daily (QD) for 16 weeks. Modified clinical remission was analyzed in patients with SF ≥ AP ≥ 2.0 at baseline.

Baseline demographics and disease characteristics were similar between study arms. A total of 220 patients were enrolled (mean age 40.7±12.9 years, CDAI 302.7±63.4, disease duration 13.2±10.0 years). Overall, patients receiving upadacitinib achieved modified clinical remission as early as week 4 and enhanced clinical response at week 8. Over time, there were sustained clinical improvements in several upadacitinib dosage groups for up to 16 weeks (FIGS. 10A-10E and FIGS. 11A-11E). Mean C-reactive protein (CRP) levels significantly decreased in all upadacitinib doses at week 4 and were sustained for up to 16 weeks in the 12 and 24 mg BID and 24 mg QD arms (FIG. 12). Statistically significant decrease in mean faecal calprotectin (FC) from baseline was observed with upadacitinib at 12 and 24 mg BID at week 4 and 24 mg BID at week 16.

Conclusions

Early and significant effects of upadacitinib in clinical parameters were demonstrated in a refractory patient population with active Crohn's disease, concurrent with rapid and sustainable decrease in the markers of inflammation hsCRP and faecal calprotectin.

Example 12: Clinical Study for Ulcerative Colitis

This trial is a multicenter, randomized, double-blind placebo-controlled study of upadacitinib for the induction and maintenance of clinical remission (using the Mayo Scoring System for Assessment of Ulcerative Colitis Activity, excluding Physician's Global Assessment [i.e., Adapted Mayo score]) in patients with moderately to severely active ulcerative colitis.

The trial consists of a screening period of up to 35 days, an 8 week double blind induction period (Substudy 1), a second 8 week double blind and open label induction period (Substudy 2), re-randomization at week 8, a 44 week double blind and open label maintenance phase (Substudy 3), and a 30 day follow up period.

Figure 13:
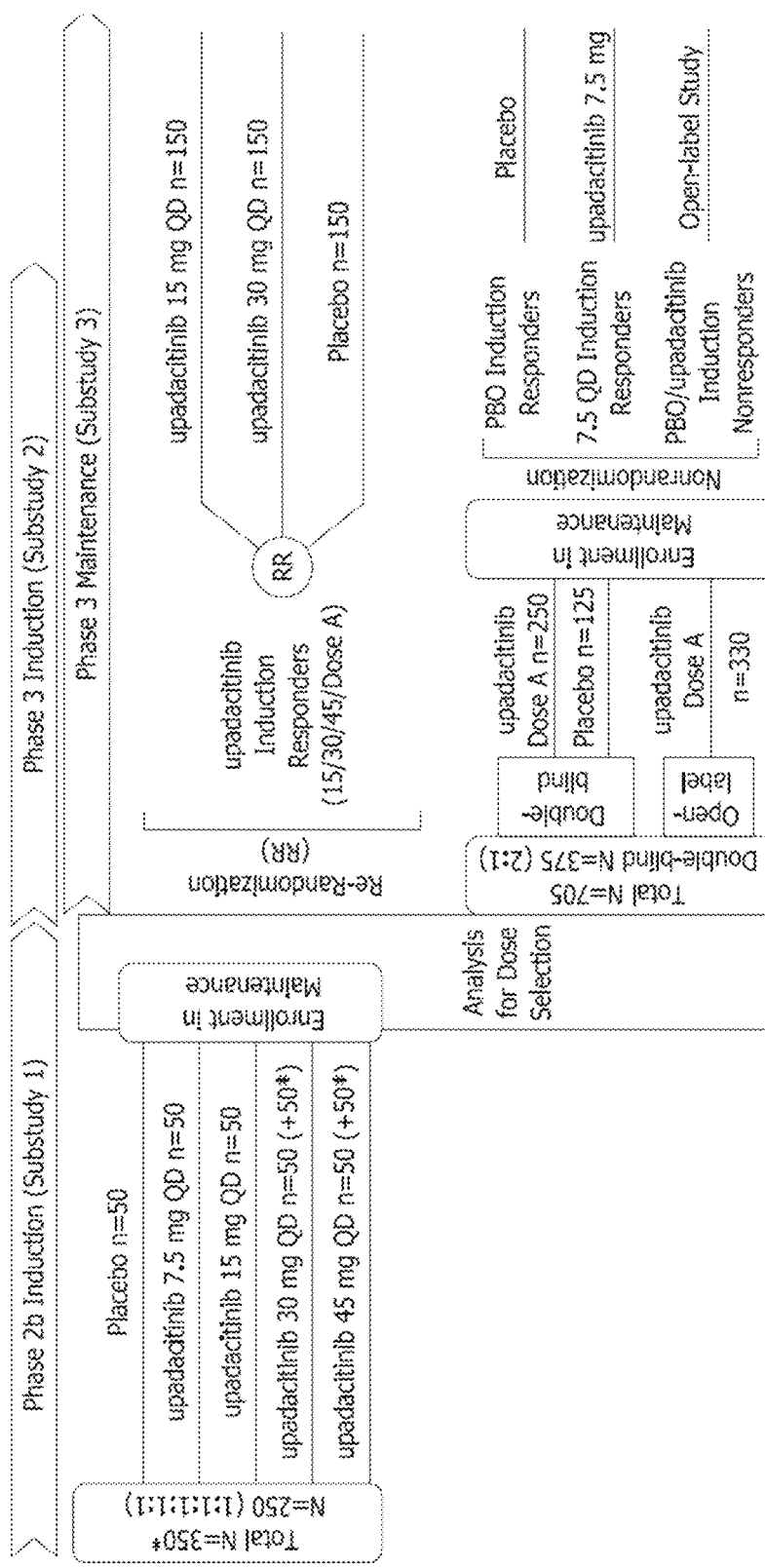
FIG. 13 is a schematic representation of the study design for the ulcerative colitis clinical study described in Example 12.

Approximately 250 patients with moderately to severely active ulcerative colitis are randomized in a 1:1:1:1:1 ratio for Substudy 1 to one of the treatment arms of the overall study design shown in FIG. 13.

1. Group 1: upadacitinib 7.5 mg QD MR capsules
2. Group 2: upadacitinib 15 mg QD MR capsules
3. Group 3: upadacitinib 30 mg QD MR capsules
4. Group 4: upadacitinib 45 mg QD MR capsules
5. Group 5: Placebo QD dose The first 8 week induction period begins at the BL visit (week 0) and ends at the week 8 visit. Once the 250 randomized patients have completed an 8 week induction, an analysis of efficacy and safety of upadacitinib versus placebo will be performed. Based on this analysis, one induction dose of upadacitinib (Dose A) will be identified for further evaluation in Substudy 2. During the analysis period, approximately 100 additional subjects will continue to be randomized into Groups 3 and 4 of Substudy 1 to receive either 30 mg QD or 45 mg QD treatment (50 patients per dose group).

Substudy 2 consists of two parts. In Part 1, approximately 375 patients with moderately to severely active ulcerative colitis are randomized in a 2:1 ratio to one of the double-blinded induction treatment arms as shown in FIG. 13: upadacitinib Dose A mg QD or placebo QD. Dose A is the dose determined in Substudy 1 for further evaluation. Part 2 of Substudy 2 is open label. Approximately 330 subjects will be enrolled in Part 2 of Substudy 2 to receive open-label upadacitinib Dose A QD. This second 8 week induction period begins at the BL visit (week 0) and ends at the week 8 visit.

Approximately 450 patients who received the 15, 30 or 45 mg QD of upadacitinib in Substudy 1 and those who received the selected induction dose in Substudy 2 and who also achieved a clinical response (i.e., a decrease from baseline in the Adapted Mayo score ≥2 points and 30% from baseline accompanied by a decrease in RBS≥1 or an absolute RBS≤1) will be re-randomized in the maintenance portion of the study (Substudy 3). This period will begin at the baseline visit (Week 8 of Substudy 1 or Substudy 2) and will end at the Week 44 visit. The treatment assignment in Substudy 3 will depend on the treatment received in Substudies 1 and 2, as follows:

Placebo: continue placebo 7.5 mg QD upadacitinib: continue 7.5 mg QD upadacitinib 15 mg QD upadacitinib: randomized 1:1 to receive either upadacitinib 15 mg QD or matching placebo 30 mg QD or 45 mg QD upadacitinib: randomized 1:1:1 to receive either upadacitinib 15 mg QD, upadacitinib 30 mg QD, or matching placebo.

During Substudy 3, subjects who meet the criteria for loss of response after at least 4 weeks of follow up will have the option receive open label upadacitinib. Loss of response is defined as follows: a subject who presents with an stool frequency subscore and RBS score at least 1 point greater than the end-of-induction value (Week 8 of Substudy 1 or 2) on two consecutive visits at least 14 days apart. The schematics of the overall study design are shown in FIG. 13.

The primary endpoints for efficacy for Substudy 1 and Substudy 2 are the proportion of patients who achieve clinical remission per Adapted Mayo score (defined as stool frequency subscore ≤1, rectal bleeding subscore of 0, and endoscopic subscore ≤1) at week 8. The primary efficacy endpoint for Substudy 3 is the proportion of patients who achieve clinical remission per Adapted Mayo score at week 44. Secondary efficacy endpoints for both Substudy 1 and Substudy 2 are:

endoscopic improvement (defined as endoscopic subscore ≤1)

achieving Full Mayo score ≤2 with no subscore >1) at week 8

Clinical response (i.e., decrease from baseline in the Adapted Mayo score ≥2 points and ≥30% from baseline, plus a decrease in rectal bleeding subscore (RBS) ≥1 or an absolute RBS≤1) at week 8 decrease from baseline in the Partial Mayo score ≥2 points and ≥30% from baseline plus a decrease in rectal bleeding subscore (RBS)≥1 or an absolute RBS≤1) at week 2

Change in Full Mayo score from Baseline to Week 8

Endoscopic remission (defined as endoscopic subscore of 0) at Week 8

Histologic improvement (defined as decrease from baseline in Geboes score) at week 8

Secondary efficacy endpoints for Substudy 3 maintenance are:

Endoscopic improvement at week 44

Full Mayo score ≤2 with no subscore ≥1) at week 44

Subjects who discontinued corticosteroid use and achieved clinical remission per Adapted Mayo score at week 44

Subjects who maintain clinical remission at Week 44 among subjects who achieved clinical remission per Adapted Mayo score in Substudy 1 or 2

Subjects who are taking corticosteroids at baseline and are corticosteroid-free at week 44

Subjects with endoscopic improvement at week 44 among subjects who achieved clinical remission in Substudy 1 or 2

Subjects achieving clinical response (i.e., decrease from baseline in the Adapted Mayo score ≥2 points and 30% from baseline accompanied by a decrease in RBS≥1 or an absolute RBS≤1) at week 44

Subjects with endoscopic remission at week 44

Subjects who achieved histologic improvement at week 44

Methods

The study comprised three treatment periods: Substudy 1 comprising an 8 week double-blind induction period; Substudy 2 comprising two parts: Part 1 is an 8 week double-blind induction period and Part 2 is an 8 week open-label option of the substudy; Substudy 3 evaluates patients from Substudy 1 and Substudy 2 who achieved clinical response.

Eligible patients are aged 18 to 75 years. They have a diagnosis of ulcerative colitis for 90 days or greater prior to baseline, confirmed by colonoscopy during the screening period, with exclusion of current infection, colonic dysplasia and/or malignancy. Patients have active ulcerative colitis with an Adapted Mayo score of 5 to 9 points and an endoscopic subscore of 2 to 3 at baseline. Eligible patients are those who have demonstrated an inadequate response to or experienced intolerance to corticosteroids, immunosuppressants and/or biologic therapies, as defined below:

Corticosteroids:

Signs and symptoms of persistently active disease despite a history of at least one induction regimen that included a dose equivalent to prednisone ≥40 mg/day orally for 3 to 4 weeks or intravenously for 1 week or Unable to taper corticosteroids to below a doses equivalent to prednisone 10 mg daily orally without recurrent active disease or History of intolerance to corticosteroids (including, but not limited to Cushing's syndrome, osteopenia/osteoporosis, hyperglycemia, insomnia, infection)

Immunosuppressants:

Signs and symptoms of persistently active disease despite a history of at least one 90-day regimen of oral azathioprine (≥1.5 mg/kg/day; for subjects in Japan and China only: ≥1.0 mg/kg/day), 6-mercaptopurine (≥1 mg/kg/day; for subjects in Japan and China only: ≥0.6 mg/kg/day) or a documents 6-TGN level of 230-450 pmol/8×$10^8$ RBC or higher on the current dosing regimen), injectable methotrexate (MTX≥15 mg/week subcutaneously or intramuscular), or tacrolimus or History of intolerance to at least one immunosuppressant (including, but not limited to nausea/vomiting, abdominal pain, pancreatitis, liver enzyme abnormalities, lymphopenia, infection)

Biologic agents for UC:

Signs and symptoms of persistently active disease despite a history of any of the following:

At least one 6-week induction regimen of infliximab (≥5 mg/kg intravenous at 0, 2 and 6 weeks), At least one 4-week induction regimen of adalimumab (one 160 mg subcutaneous dose followed by 80 mg subcutaneous dose [or one 80 mg subcutaneous dose) followed by one 40 mg subcutaneous dose at least 2 weeks apart), At least one 2-week induction regimen of golimumab (one 200 mg subcutaneous dose followed by one 100 mg subcutaneous dose at least two weeks apart), At least one 6-week induction regimen of vedolizumab (300 mg intravenous at 0, 2 and 6 weeks), or Recurrence of symptoms during scheduled maintenance dosing following prior clinical benefit (discontinuation despite clinical benefit does not qualify) or History of intolerance to at least one biologic agent (including, but not limited to infusion-related reaction, demyelination, congestive heart failure CHF), infection)

Oral MTX use is allowed during the study, however prior or current use of oral MTX is not sufficient for inclusion into the study unless these subjects were previously treated with corticosteroids or immunosuppressants (azathioprine or 6-MP) and in the judgment of the investigator have failed to respond to or could not tolerate their treatment.

Examples 13-16: Modified Release Tablets

Modified release tablets containing either 7.5 mg (Example 13) 15 mg (Example 14), 30 mg (Example 15), or 45 mg (Example 16) of upadacitinib were prepared using a wet granulation process.

Upadacitinib (hemi-hydrate), microcrystalline cellulose (MCC), and hydroxypropyl methylcellulose (HPMC) were added to a granulator and mixed. Water was sprayed to granulate. The granulated material was then dried and milled using a comill fitted with a 610 micron screen to form a granulate composition containing 25% drug load. The granulate composition is summarized in Table 22.

TABLE 22

Granulate Composition (25% Drug Load)

| Component | Function | Amount in Granulation Composition (%) |
|---|---|---|
| Upadacitinib freebase (hemi-hydrate)[1] | Active | 25.0% |
| Microcrystalline cellulose (Avicel® PH 101) | Filler | 67.0% |
| HPMC (Hypromellose 2208) | Release control polymer | 8.0% |

[1]Upadacitinib used in Examples 13-16 was a hemi-hydrate (Freebase Hydrate Form C, as described herein and in U.S. patent application Ser. No. 15/295,561). As used herein, the amount of upadacitinib present in the Examples 13-16 formulations refers to the amount of upadacitinib freebase equivalent provided by the hemi-hydrate.

The granulation composition was combined with the remaining formulation components other than magnesium stearate, and sieved using a comill fitted with a 1397 micron screen, followed by blending. The magnesium stearate was then added to the bin and blended. The lubricated granulation was compressed into tablets using a rotary tablet press. The tablets were coated using a film coater, which sprayed a solution containing the Opadry® II Yellow film coat and purified water until the desired amount of coating had been applied to the tablets.

The formulations of the tablets are set forth in Table 23.

TABLE 23

Modified Release Tablets

| Component | Function | Ex. 13 (mg) | Ex. 14 (mg) | Ex. 15 (mg) | Ex. 16 (mg) |
|---|---|---|---|---|---|
| Tablet Core | | | | | |
| Granulation composition (25% drug load) | Active | 30.7[1] | 61.4[2] | 122.8[3] | 184.3[4] |
| Microcrystalline cellulose (Avicel® PH 102) | Filler | 149.5 | 121.3 | 64.8 | 8.3 |
| Mannitol (Pearlitol® 100SD) | Filler | 100.6 | 100.6 | 100.6 | 100.6 |
| Tartaric acid (crystalline or powder) | pH modifier | 96.0 | 96.0 | 96.0 | 96.0 |
| HPMC (Hypromellose 2208) | Release control polymer | 93.5 | 91.1 | 96.2 | 81.3 |
| Colloidal silicon dioxide | Glidant | 2.4 | 2.4 | 2.4 | 2.4 |
| Magnesium stearate | Lubricant | 7.2 | 7.2 | 7.2 | 7.2 |
| Uncoated weight of tablet | | 479.9 | 480.0 | 480.0 | 480.1 |
| Opadry® II Yellow | Film coat | 14.4 | 14.4 | 14.4 | 14.4 |
| Purified Water[5] | Processing aid | n/a | n/a | n/a | n/a |
| Total weight of tablet | | 494.3 | 494.4 | 494.4 | 494.5 |

[1]Provides 7.5 mg of upadacitinib freebase equivalent.
[2]Provides 15 mg of upadacitinib freebase equivalent.
[3]Provides 30 mg of upadacitinib freebase equivalent.
[4]Provides 45 mg of upadacitinib freebase equivalent.
[5]Processing aid removed during coating.

Example 17: Observed Steady State Exposures for 15 mg Modified Release Tablets and 6 mg Immediate Release Capsules Under Fasting Conditions The steady state pharmacokinetic profile of a 15 mg once daily modified release (MR) tablet (comprising upadacitinib hemi-hydrate) under fasting conditions was evaluated, and compared to that of a 6 mg immediate release (IR) twice daily (BID) capsule comprising upadacitinib (tartrate tetrahydrate) as the active. The 15 mg MR tablet had the following formulation set forth in Table 24.

TABLE 24

15 mg Modified Release Tablet

| Component | Function | Amount (mg) (ER7) |
|---|---|---|
| Upadacitinib (hemi-hydrate)[1] | Active | 15.4 |
| Microcrystalline cellulose (Avicel® PH 102) | Filler | 162.4 |
| Mannitol (Pearlitol® 100 SD) | Filler | 52.6 |
| Tartaric acid | pH modifier | 144.0 |
| HPMC (Hypromellose 2208) | Release control polymer | 96.0 |
| Colloidal silicon dioxide | Glidant | 2.4 |
| Magnesium stearate impalpable powder | Lubricant | 7.2 |
| Uncoated weight of tablet | | 480.0 |
| Opadry® II Yellow (PVA based) | Film coat | 14.40 |
| Total weight of tablet | | 494.39 |

[1]Upadacitinib was a hemi-hydrate (Freebase Hydrate Form C, as described herein and in U.S. patent application Ser. No. 15/295,561). The hemi-hydrate provides about 15 mg of upadacitinib freebase equivalent.

The tablet was prepared by first milling the tartaric acid through a Fitz mill Model M5A, fitted with a 1512-0027 screen. The upadacitinib hemi-hydrate, microcrystalline cellulose, mannitol (when present), milled tartaric acid, release control polymer, and colloidal silicone dioxide (when present) were combined and blended. The blend was milled using a Mobil Mill fitted with a 610 or 1397 micron screen. The magnesium stearate was screened through mesh #30 and was then added to the bin and blended. The lubricated granulation was compressed into about 480 mg weight tablets using a rotary tablet press. The tablet was coated using a film coater, which sprayed a solution containing the Opadry® II Yellow film coat and purified water until 14.40 mg of coating had been applied to the tablets.

Healthy human subjects were assigned to one of two regimens under fasting conditions in a randomized, two-period, cross-over study design. Subjects in Regimen K (n=12 at onset; n=11 on Day 7) were administered the 6 mg IR capsule twice daily for seven days under fasting conditions. Subjects in Regimen L (n=12) were administered the 15 mg MR tablet once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for upadacitinib using appropriate liquid chromatography mass spectrometry procedures. Pharmacokinetic parameters were estimated using non-compartmental methods, and summary statistics were computed for each parameter by regimen.

Figure 7:
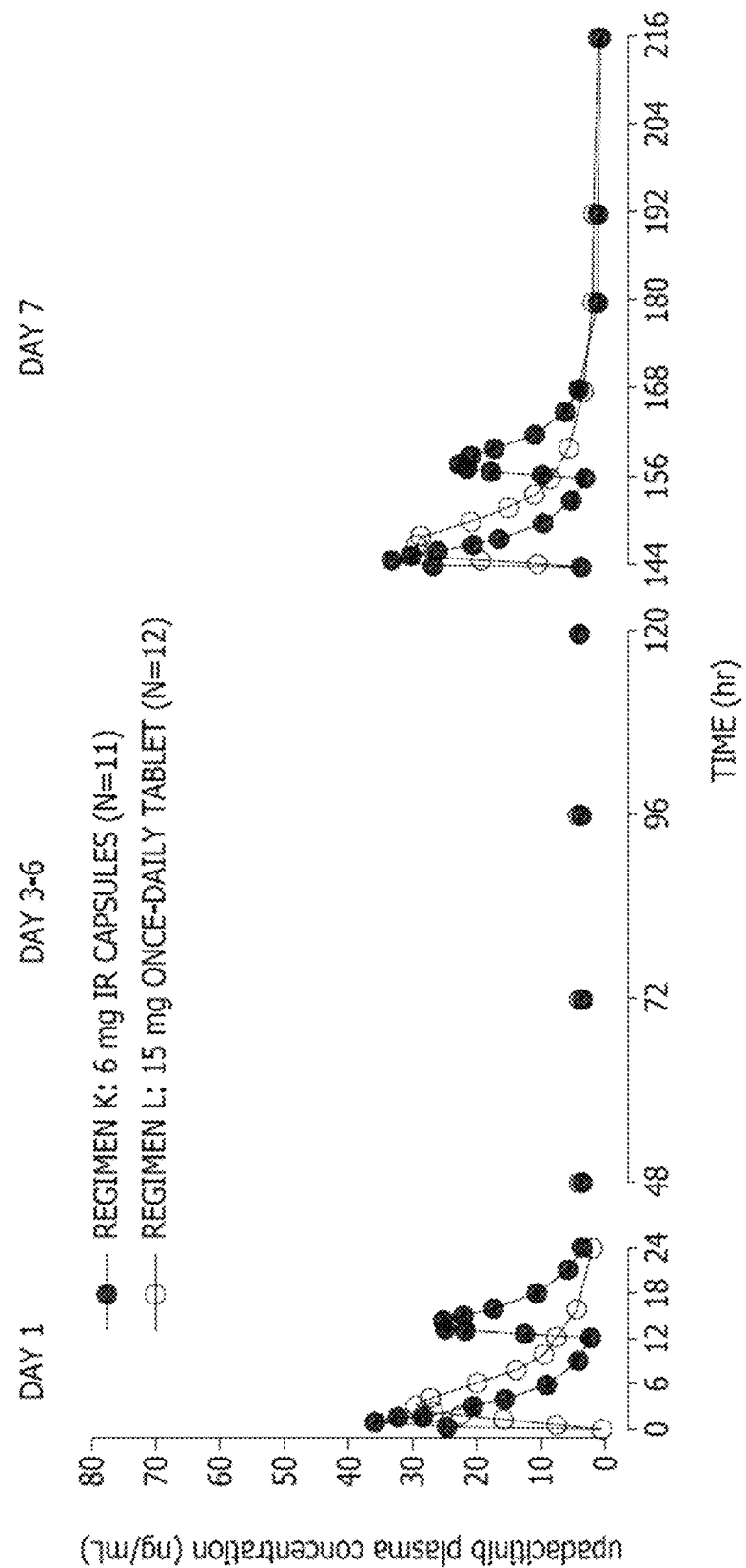
FIG. 7 shows the upadacitinib mean plasma concentration versus time following administration of 6 mg twice daily immediate release capsules (Regimen K) or a 15 mg once-daily modified release tablet (Regimen L) for seven days under fasting conditions.

The results are summarized in Table 25. The mean plasma concentration of upadacitinib at each time point measured for each of the two regimens is set forth in FIG. 7.

TABLE 25

Mean (% CV)[e] Pharmacokinetic Parameters for Upadacitinib Following Administration of 6 mg BID (IR) Capsules and 15 mg QD (MR) Tablets for Seven Days (Fasting Conditions)

| PK Parameter | Units | Regimen K (6 mg IR Capsules (BID)) | | Regimen L (15 mg MR Tablet (QD)) | |
|---|---|---|---|---|---|
| | | Day 1 | Day 7 | Day 1 | Day 7 |
| $C_{max}$ | ng/mL | 36.5 (25) | 33.9 (26) | 31.7 (40) | 31.9 (35) |
| $T_{max}$[a] | hours | 1.0 (1.0-13) | 1.0 (0.5-14) | 3.0 (1.5-6.0) | 2.5 (1.5-4.0) |
| $AUC_{24}$ | ng · h/mL | 289 (21) | 288 (22) | 249 (29) | 279 (26) |
| $C_{12}$ | ng/mL | 2.0 (30) | 2.8 (24) | — | — |
| $C_{24}$ | ng/mL | 3.2 (36) | 3.6 (23) | 1.9 (42) | 3.1 (37) |
| $C_{min}$ | ng/mL | — | 2.7 (26) | — | 3.1 (37) |
| Fluctuation Index | % | 303 (13) | 259 (13) | 299 (22) | 246 (21) |
| $t_{1/2}$[b] | hours | — | 14.7 (77) | — | 10.3 (76) |
| $C_{max}$ to $C_{24}$ ratio[a] | — | 12 (7.7-19) | 8.8 (7.4-13) | 22 (5.8-43) | 12 (4.2-20) |
| $C_{max}$ to $C_{min}$ ratio[a] | — | — | 13 (8.3-18) | — | 12 (4.2-20) |
| $AUC_{24}$/Dose | (ng · h/mL)/mg | 24.8 (23) | 24.0 (22) | 16.6 (29) | 18.6 (26) |
| $R_{AUC}$[c] | — | — | 1.02 (0.88-1.09) | — | 1.11 (0.87-1.99) |
| $R_{Cmax}$[d] | — | — | 0.97 (0.68-1.17) | — | 1.01 (0.65-3.01) |

[a]Median (minimum-maximum)
[b]Harmonic mean (pseudo-% CV)
[c]$R_{AUC}$ = $AUC_{24}$Day7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for the once-daily (MR) tablet formulation (Regimen L) relative to the twice daily (IR) capsule formulation (Regimen K) at steady state was also determined based on analysis of the natural logarithms of $C_{max}$, $AUC_{24}$, $C_{min}$, and $C_{24}$. The results are summarized in Table 26 below.

TABLE 265

Relative Bioavailability Estimates and 90% Confidence Intervals for 15 mg QD Tablets Relative to 6 mg BID Capsules at Steady State under Fasting Conditions

| | Relative Bioavailability | |
|---|---|---|
| PK Parameter | Point Estimate | 90% Confidence Interval |
| $C_{max}$ | 0.909 | 0.736-1.122 |
| $AUC_{24}$ | 0.939 | 0.837-1.053 |
| $C_{min}$ | 1.090 | 0.852-1.395 |

The ratio of steady-state AUC for the 15 mg QD tablets relative to the 6 mg BID capsules was approximately 1, with the 90% confidence intervals within the equivalence boundaries. The ratio of the steady-state $C_{min}$ was approximately 1 for the 15 mg QD tablet relative to the 6 mg BID capsules.

As can be seen from this data, at steady state under fasting conditions, the 15 mg QD tablets provided equivalent $AUC_{24}$ and comparable $C_{max}$ and $C_{min}$ relative to the 6 mg BID capsules. The steady state $C_{max}$ was 10% lower for the 15 mg QD tablet compared to the 6 mg BID capsule.

Example 18: Observed Steady State Exposures for 30 mg Modified Release Tablets and 12 mg Immediate Release Capsules Under Fasting Conditions The steady state pharmacokinetic profile of a 30 mg once daily modified release (MR) tablet (comprising upadacitinib hemi-hydrate) under fasting conditions was evaluated, and compared to that of a 12 mg immediate release (IR) twice daily (BID) capsule comprising upadacitinib (tartrate tetrahydrate) as the active. The 30 mg MR tablet had the following formulation set forth in Table 27.

TABLE 27

30 mg Modified Release Tablet

| Component | Function | Amount (mg) (ER8) |
|---|---|---|
| Upadacitinib (hemi-hydrate)[1] | Active | 30.7 |
| Microcrystalline cellulose (Avicel ® PH 102) | Filler | 147.1 |
| Mannitol (Pearlitol ® 100 SD) | Filler | 52.6 |
| Tartaric acid | pH modifier | 144.0 |
| HPMC (Hypromellose 2208) | Release control polymer | 96.0 |
| Colloidal silicon dioxide | Glidant | 2.4 |
| Magnesium stearate impalpable powder | Lubricant | 7.2 |
| Uncoated weight of tablet | | 480.0 |
| Opadry ® II Yellow (PVA based) | Film coat | 14.40 |
| Total weight of tablet | | 494.43 |

[1]Upadacitinib was a hemi-hydrate (Freebase Hydrate Form C, as described in U.S. patent application Ser. No. 15/295,561).
The hemi-hydrate provides about 30 mg of upadacitinib freebase equivalent.

The tablet was prepared by first milling the tartaric acid through a Fitz mill Model M5A, fitted with a 1512-0027 screen. The upadacitinib hemi-hydrate, microcrystalline cellulose, mannitol (when present), milled tartaric acid, release control polymer, and colloidal silicone dioxide (when present) were combined and blended. The blend was milled using a Mobil Mill fitted with a 610 or 1397 micron screen. The magnesium stearate was screened through mesh #30 and was then added to the bin and blended. The lubricated granulation was compressed into about 480 mg weight tablets using a rotary tablet press. The tablet was coated using a film coater, which sprayed a solution containing the Opadry® II Yellow film coat and purified water until 14.40 mg of coating had been applied to the tablets.

Healthy human subjects were assigned to one of two regimens under fasting conditions in a randomized, two-period, cross-over study design. Subjects in Regimen M (n=11) were administered the 12 mg IR capsule twice daily for seven days under fasting conditions. Subjects in Regimen N (n=12 at onset; n=11 at Day 7) were administered the 30 mg MR tablet once daily for seven days under fasting conditions. On days one and seven, serial blood samples were collected from each subject prior to the daily dosing and up to 24 hours after dosing. Blood samples were also collected at 48, 72, 96 and 120 hours after initial dosing. Upon collection, the samples were promptly placed in an ice bath, and within 2 hours after sample collection they were centrifuged at about 4° C. The resulting plasma samples were placed in clean polypropylene-tubes and stored in a freezer until analysis. The plasma samples were assayed for upadacitinib using appropriate liquid chromatography mass spectrometry procedures. Pharmacokinetic parameters were estimated using non-compartmental methods, and summary statistics were computed for each parameter by regimen.

Figure 8:
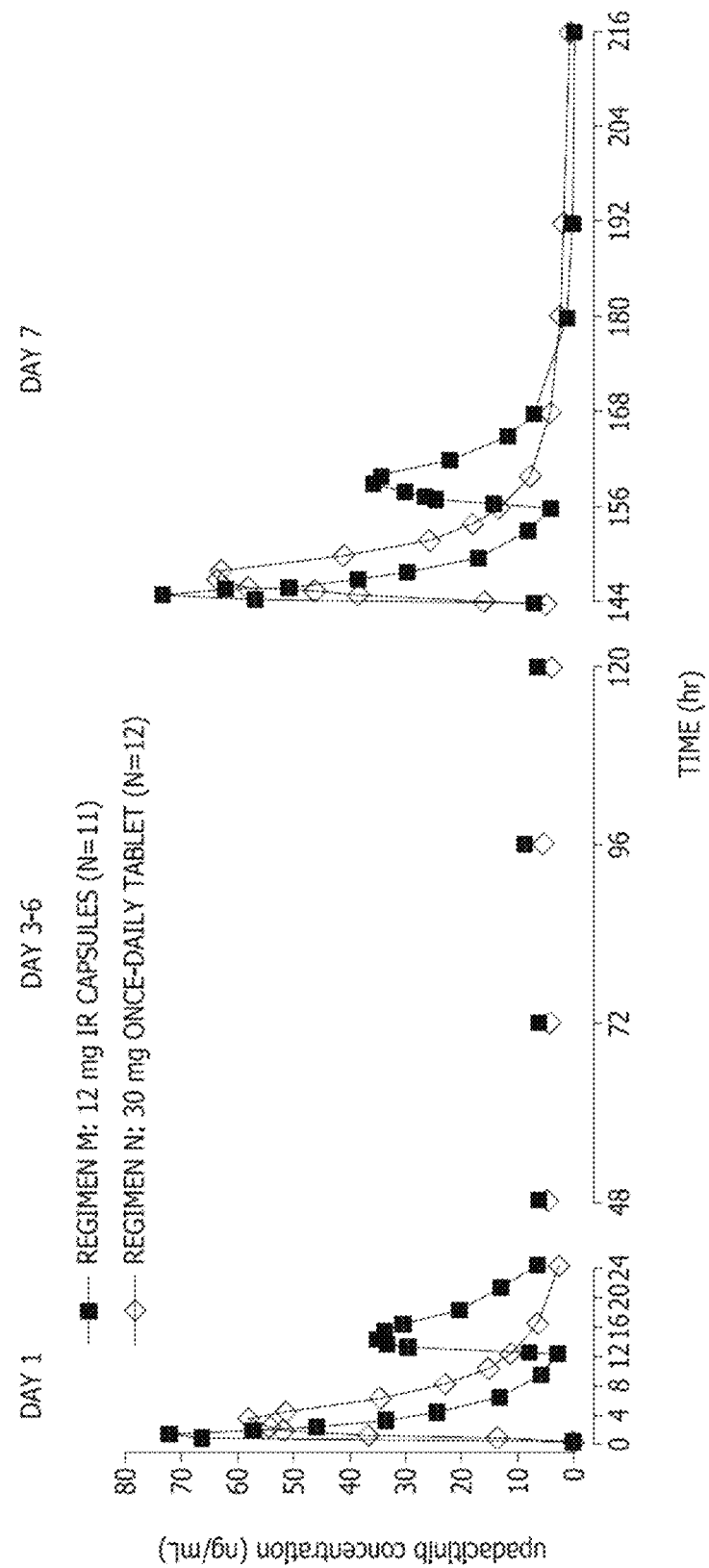
FIG. 8 shows the upadacitinib mean plasma concentration versus time following administration of 12 mg twice daily immediate release capsules (Regimen M) or a 30 mg once-daily modified release tablet (Regimen N) for seven days under fasting conditions.
Figure 10A:
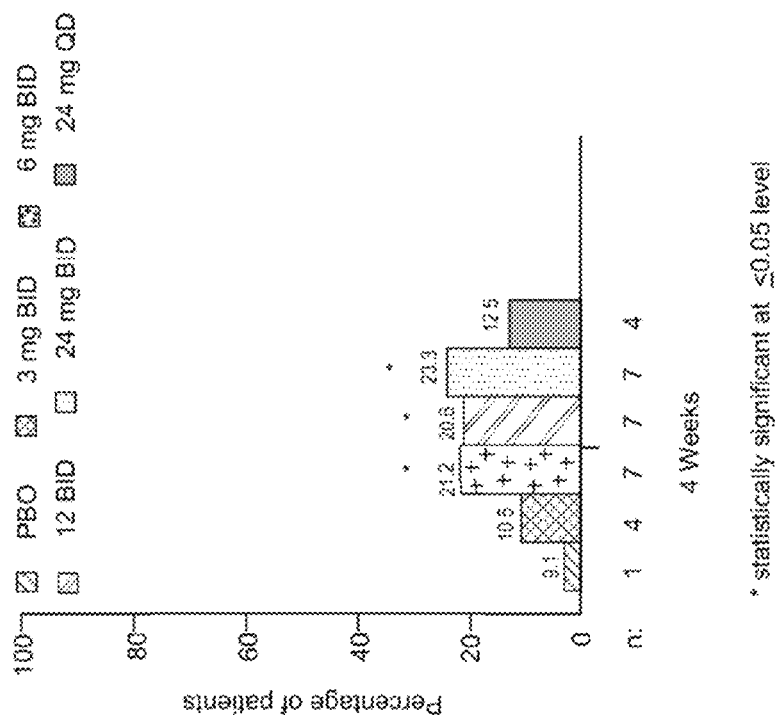
Figure 10B:
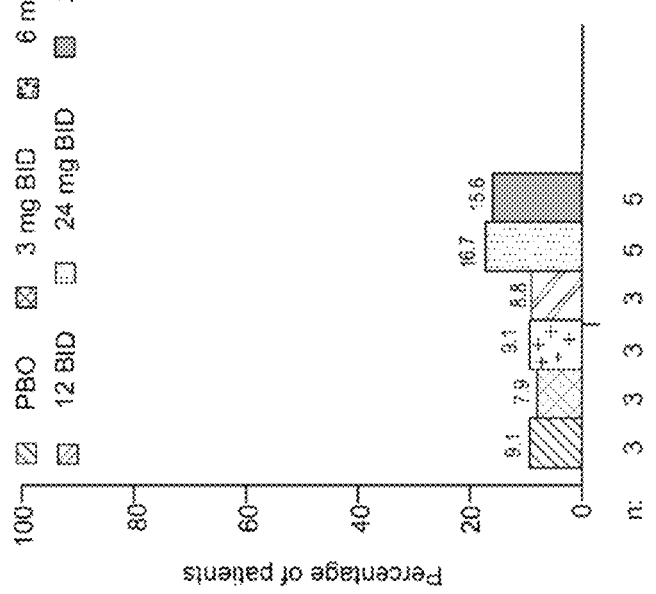
Figure 10E:
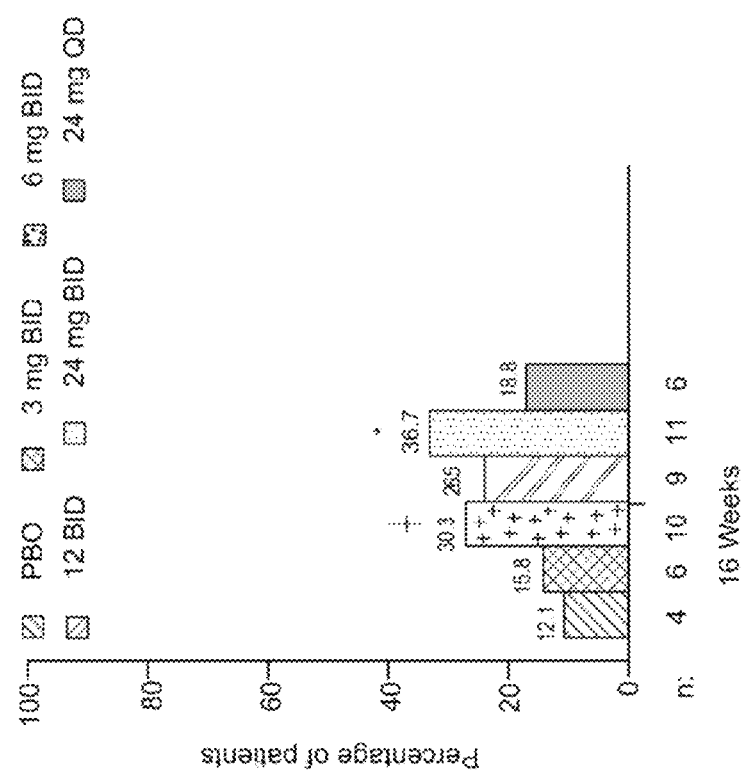
Figure 11A:
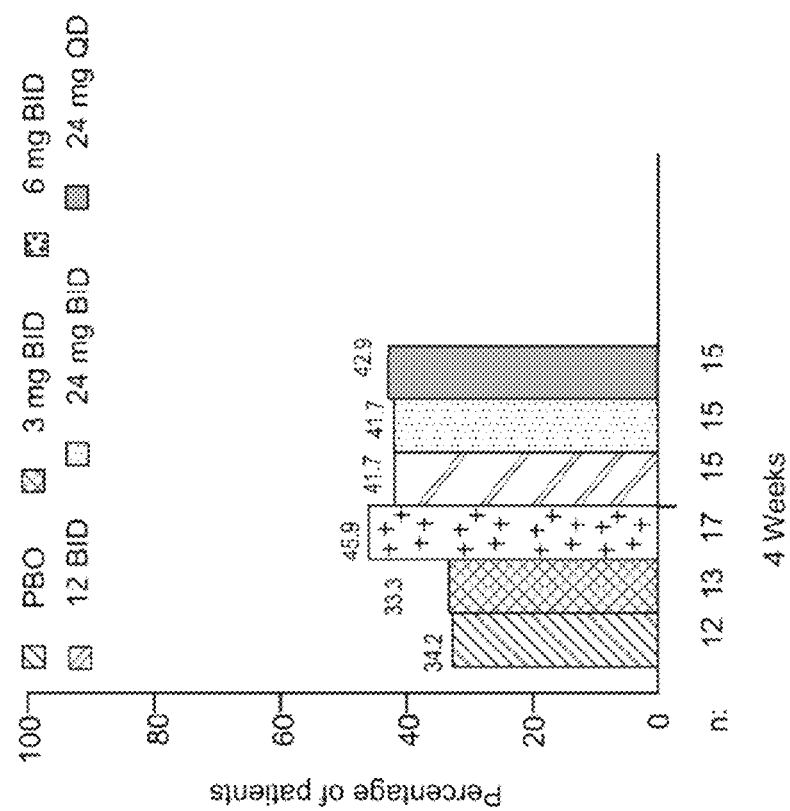
FIGS. 11A-11E are graphs depicting the percentage of subjects who achieved enhanced clinical response at week 2 (FIG. 11A), week 4 (FIG. 11B), week 8 (FIG. 11C), week 12 (FIG. 11D) and week 16 (FIG. 11E) of the Example 8 study.
Figure 11B:
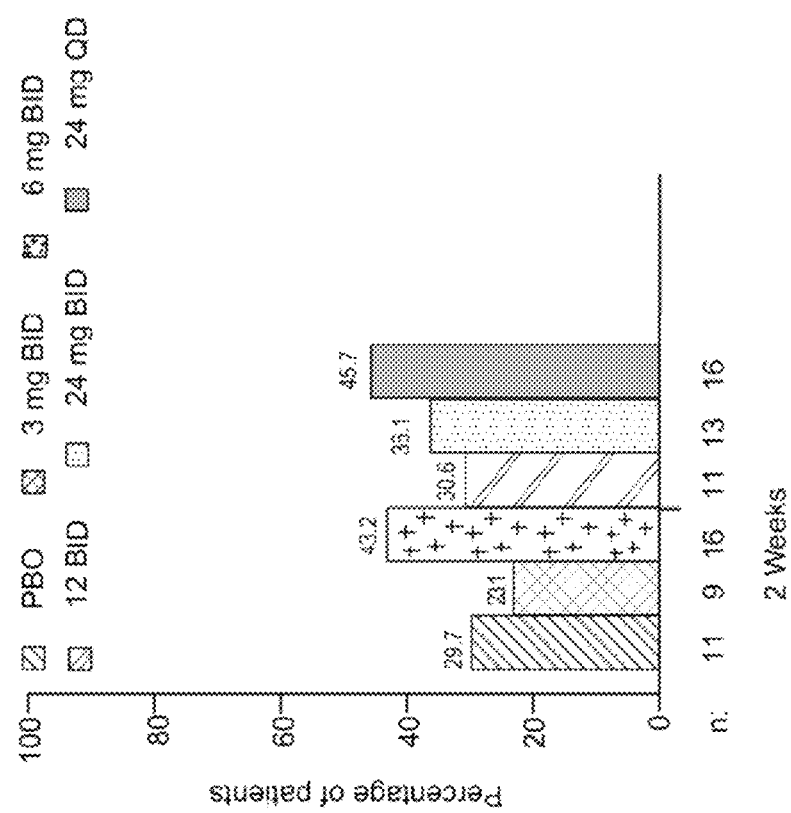
Figure 11D:
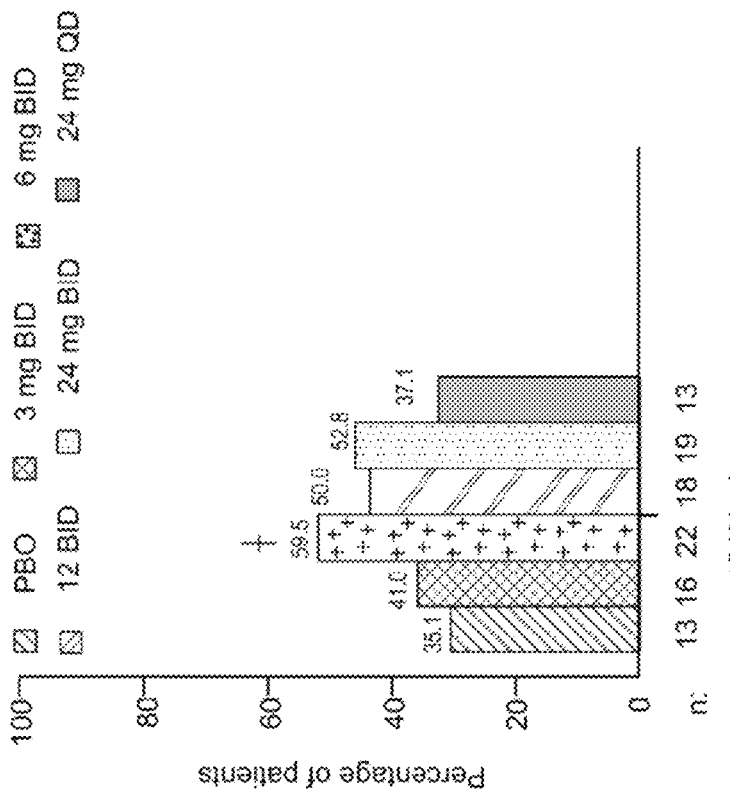
Figure 11C:
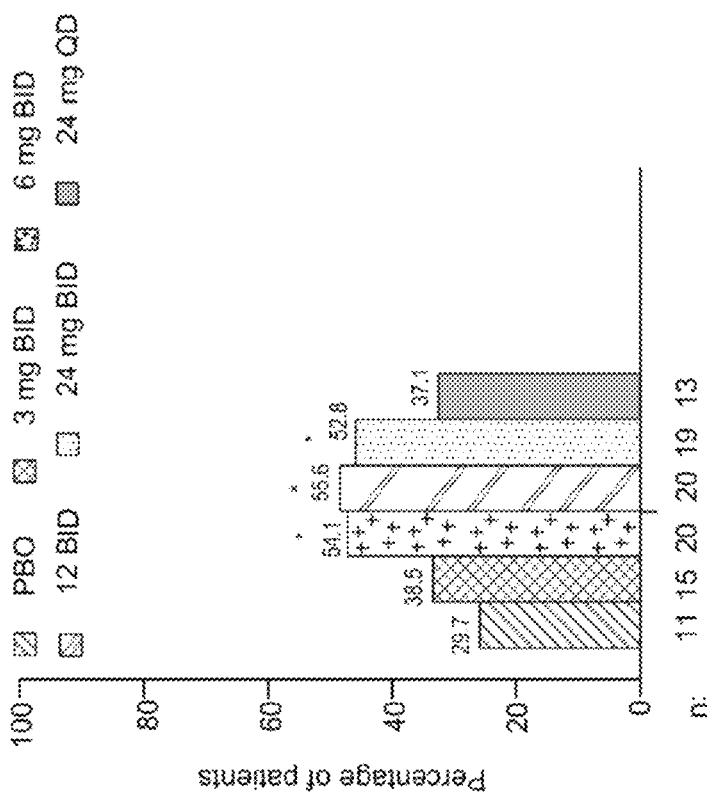
Figure 11E:
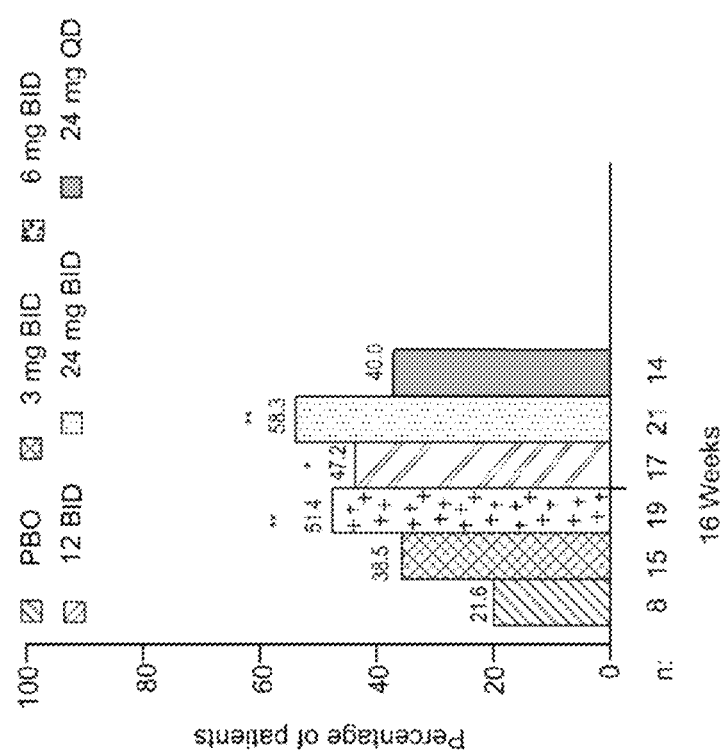

The results are summarized in Table 28. The mean plasma concentration of upadacitinib at each time point measured for each of the two regimens is set forth in FIG. 8.

The ratio of steady-state AUC for the 30 mg QD tablets relative to the 12 mg BID capsules was approximately 1, with the 90% confidence intervals within the equivalence boundaries. The steady-state $C_{min}$ for the 30 mg QD tablet was approximately 13% lower than for the 12 mg BID capsules. Outliers with high $C_{min}$ in the 12 mg BID dose may have contributed to this difference.

As can be seen from this data, at steady state under fasting conditions, the 30 mg QD tablets provided equivalent $AUC_{24}$ and comparable $C_{max}$ and $C_{min}$ relative to the 12 mg BID capsules. The steady state $C_{max}$ was 10% lower for the 30 mg QD tablet compared to the 12 mg BID capsules.

Example 19. Clinical Study for Ulcerative Colitis

This study is a Phase 3, multicenter, randomized, double-blind, placebo-controlled efficacy and safety study to evaluate the efficacy and safety of upadacitinib (ABT-494) in subjects with moderately to severely active ulcerative colitis.

TABLE 28

Mean (% CV)[e] Pharmacokinetic Parameters for Upadacitinib Following Administration of 12 mg BID (IR) Capsules and 30 mg QD (MR) Tablets for Seven Days (Fasting Conditions)

| PK Parameter | Units | Regimen M (12 mg IR Capsules (BID)) | | Regimen N (30 mg MR Tablet (QD)) | |
|---|---|---|---|---|---|
| | | Day 1 | Day 7 | Day 1 | Day 7 |
| | ng/mL | 80.8 (23) | 73.9 (19) | 65.7 (22) | 68.2 (30) |
| $T_{max}$[a] | hours | 1.0 (0.5-13) | 1.0 (0.5-1.5) | 2.5 (1.5-4.0) | 3.0 (2.0-4.0) |
| $AUC_{24}$ | ng · h/mL | 497 (15) | 534 (18) | 454 (23) | 525 (23) |
| $C_{12}$ | ng/mL | 3.0 (46) | 4.1 (55) | — | — |
| $C_{24}$ | ng/mL | 6.5 (54) | 6.9 (37) | 2.8 (37) | 4.4 (39) |
| $C_{min}$ | ng/mL | — | 3.8 (58) | — | 3.8 (43) |
| Fluctuation Index | % | 388 (15) | 317 (14) | 349 (12) | 291 (17) |
| $t_{1/2}$[b] | hours | — | 7.3 (60) | — | 14.4 (64) |
| $C_{max}$ to $C_{24}$ ratio[a] | — | 15 (5.4-20) | 12 (5.9-16) | 29 (13-38) | 17 (4.1-33) |
| $C_{max}$ to $C_{min}$ ratio[a] | — | — | 19 (8.4-31) | — | 17 (11-37) |
| $AUC_{24}$/Dose | (ng · h/mL)/mg | 21.1 (15) | 22.3 (18) | 15.1 (22) | 17.5 (23) |
| $R_{AUC}$[c] | — | — | 1.08 (0.97-1.18) | — | 1.11 (0.79-1.67) |
| $R_{Cmax}$[d] | — | — | 0.98 (0.65-1.18) | — | 1.03 (0.40-1.82) |

[a]Median (minimum-maximum)
[b]Harmonic mean (pseudo-% CV)
[c]$R_{AUC}$ = $AUC_{24}$Day7/$AUC_{24}$Day 1; median (range)
[d]$R_{Cmax}$ = $C_{max}$Day 7/$C_{max}$Day 1; median (range)
[e]Data in parentheses is the coefficient of variance of the PK parameter (% CV), unless otherwise indicated The relative bioavailability for a single dose of the once-daily (MR) tablet formulation (Regimen N) relative to the twice daily (IR) capsule formulation (Regimen M) was also determined based on analysis of the natural logarithms of $C_{max}$, $AUC_{24}$, $C_{min}$, and $C_{24}$. The results are summarized in Table 29 below.

TABLE 29

Relative Bioavailability Estimates and 90% Confidence Intervals for 30 mg QD Tablets Relative to 12 mg BID Capsules at Steady State under Fasting Conditions

| | Relative Bioavailability | |
|---|---|---|
| PK Parameter | Point Estimate | 90% Confidence Interval |
| $C_{max}$ | 0.900 | 0.732-1.107 |
| $AUC_{24}$ | 0.974 | 0.869-1.092 |
| $C_{min}$ | 0.874 | 0.747-1.022 |

Objective

The primary objective of this study is to evaluate the efficacy and safety of upadacitinib 45 mg once daily (QD) compared to placebo in inducing clinical remission (per Adapted Mayo score) in subjects with moderately to severely active ulcerative colitis (UC). Particularly, the primary objective is to evaluate the efficacy and safety of upadacitinib 45 mg once daily (QD) compared to placebo in inducing clinical remission (per Adapted Mayo score) in subjects with moderately to severely active UC who have demonstrated inadequate response, loss of response, or intolerance to oral aminosalicylates, immunosuppressants, corticosteroids, and/or biologic therapies.

The secondary objectives of the study are to evaluate the efficacy of upadacitinib 45 mg QD comparing with placebo in ranked secondary endpoints of achieving endoscopic improvement, endoscopic remission, clinical response per Adapted Mayo Score, clinical response per Partial Adapted Mayo score, histologic-endoscopic mucosal improvement, no bowel urgency, no abdominal pain, histologic improvement, mucosal healing, and change in IBDQ total score and FACIT-F score.

The study will allow enrollment of up to 30% of enrolled bio-IR subjects who have failed 3 or more biologics. Among non-bio-IR subjects, subjects who have used a biologic up to 1 year and have discontinued for reasons other than inadequate response, loss of response, or intolerance (e.g., change of insurance/reimbursement, well-controlled disease, etc.) may be enrolled but must meet other criteria for inadequate response, loss of response, or intolerance to aminosalicylates, corticosteroids, or immunosuppressants as defined in the protocol. The study will allow for enrollment of up to 20% enrolled non-bio-IR subjects who could also have previous use of a biologic therapy but discontinued based on reasons other than inadequate response, loss of response, or intolerance. The study will also evaluate the efficacy of an additional 8-week upadacitinib 45 mg QD treatment in subjects who did not achieve clinical response in the initial 8-week induction phase.

Study Population:

Males and females between 18 and 75 years of age with a diagnosis of moderately to severely active UC. Adolescent males and females 16 and 17 years of age with body weight ≥40 kg and meet the definition of Tanner Stage 5 will be enrolled if approved by the country or regulatory/health authority. If these approvals have not been granted, only subjects ≥18 years old will be enrolled. The study will consist of a mixed population: biologic-inadequate responders (bio-IR) and non-biologic-inadequate responders (non-bio-IR). The number of enrolled non-biologic-inadequate responders (non-bio-IR) subjects will be at least 25% and not exceed 50%.

This study will allow enrollment of up to 30% of enrolled bio-IR subjects who have failed 3 or more biologics. Among non-bio-IR subjects, subjects who have used a biologic up to 1 year and have discontinued for reasons other than inadequate response, loss of response, or intolerance (e.g., change of insurance/reimbursement, well-controlled disease, etc.) may be enrolled but must meet other criteria for inadequate response, loss of response, or intolerance to aminosalicylates, corticosteroids, or immunosuppressants as defined in the protocol. The study will allow for enrollment of up to 20% enrolled non-bio-IR subjects who could also have previous use of biologic therapy but discontinued based on reasons other than inadequate response, loss of response, or intolerance.

The study duration could be up to 25 weeks (excluding a possible washout period), including a Screening Period of up to 5 weeks, an 8-week double-blind Induction Period, an 8-week Open Label Extended Treatment Period (for eligible subjects), and a 30-day Follow-Up Period, if the subject does not meet eligibility to proceed to Study M14-234 Substudy 3.

Number of Subjects to be Enrolled:

A total of approximately 462 subjects will be enrolled worldwide. The number of non-bio-IR subjects enrolled will be at least 25% and not exceed 50% of the total number of subjects enrolled.

Methodology:

At the end of either Week 8 (Part 1) or Week 16 (Part 2), if subjects are eligible, they will be offered an opportunity to participate in Study M14-234 Substudy 3 which is a Phase 3 study designed to evaluate the efficacy and safety of oral administration of upadacitinib 15 mg or 30 mg compared to placebo as maintenance therapy in subjects with moderately to severely active UC who achieved clinical response following induction with upadacitinib in Study M14-675.

Subjects who consent and meet all of the inclusion criteria and none of the exclusion criteria will be enrolled into Study M14-675, which consists of two parts: (Part 1) a randomized, double-blind, placebo-controlled 8-week induction study; and (Part 2) an 8-week Extended Treatment Period for clinical non-responders from Part 1.

Part 1

In Part 1, approximately 462 subjects will be randomized in a 2:1 ratio to double-blind upadacitinib 45 mg QD or matching placebo for 8 weeks. The randomization will be stratified by bio-IR status (bio-IR vs non-bio-IR), corticosteroid use (yes or no) and Adapted Mayo score $\leq 7$ or $>7$) at Baseline. Within bio-IR, the randomization will be further stratified by number of prior biologic treatments $\leq 1$ or $>1$). Within non-bio-IR, the randomization will be further stratified by previous biologic use (yes or no).

Treatment Groups for Part 1 Include:
 Group 1: Upadacitinib 45 mg QD (blinded, n=308)
 Group 2: Placebo QD (blinded, n=154)

At Week 8, subjects achieving clinical response, defined as a decrease from Baseline in the Adapted Mayo score $\geq 2$ points and $\geq 30\%$ from Baseline, PLUS a decrease in rectal bleeding subscore (RBS) $\geq 1$ or an absolute RBS $\leq 1$ may be eligible to enter the 52-week, double-blind, maintenance portion of Study M14-234 (Substudy 3).

All subjects who do not achieve clinical response at Week 8 will be eligible to participate in Part 2 (Extended Treatment Period) to receive open-label upadacitinib 45 mg QD for an additional 8 weeks.

Part 2

Part 2 is an open-label, 8-week Extended Treatment Period for subjects who do not achieve clinical response at Week 8 in Part 1. The objectives of Part 2 are to offer upadacitinib induction treatment to placebo clinical non-responders from Part 1 and to evaluate delayed clinical response of upadacitinib in subjects who do not initially respond during Part 1. The blind from Part 1 will not be broken for the duration of the study as subjects will be assessed as clinical non-responders at the 8 Week Visit of Part 1 and will be moved to Part 2 for further treatment in the study without identifying their initial treatment assignment. All eligible subjects entering Part 2 will receive open-label treatment with upadacitinib 45 mg QD for 8 additional weeks (until Week 16). At Week 16, an endoscopy will be performed to evaluate the treatment effect. A flexible rectosigmoidoscopy is recommended. However, the use of flexible sigmoidoscopy or colonoscopy is at the investigators' discretion based on local practice.

During Part 2, subject with persistent symptoms or worsening UC may be discontinued at any time. At Week 16, subjects who achieve clinical response may be eligible to enter Study M14-234 (Substudy 3) for further blinded treatment. Subjects who do not achieve clinical response at Week 16 will be discontinued from the study and will not be eligible to enroll in Study M14-533 (long term extension)

All subjects will be provided with a Subject Diary (eDiary) at Screening in Study M14-675 where they will record UC-related symptoms, use of anti-diarrheals, and use of medications for endoscopy preparation. For the assessment of the clinical endpoints, the stool frequency and the rectal bleeding subscore will be calculated as an average of the entries recorded into the subject's diary from the most recent consecutive 3-day period prior to each study visit. If diary entries from the 3 consecutive days prior to the visit are not available, the 3 most recent consecutive days in the last 10 days will be utilized. If data is not available for 3 consecutive days, the average of the entries from the most recent 3 non-consecutive days in the last 10 days will be utilized. Clinical endpoints of abdominal pain and bowel urgency from subject diaries will be measured at the same time period as the stool frequency and rectal bleeding subscores. Proportion of subjects who report no abdominal pain and proportion of subjects who report no bowel urgency in the 3 days will be estimated.

At each study visit, a routine physical examination including evaluation of vital signs, evaluation of extra-intestinal manifestations (EIMs), diary review, monitoring for adverse events (AEs), review of concomitant medications, and completion of laboratory assessments will be performed. A full physical examination will be performed at Screening, Baseline, Week 8 and Week 16/Premature Discontinuation (PD) (for subjects who enter the Extended Treatment Period) and must include an evaluation of extra-intestinal manifestations. Symptom based physical examinations will be performed at all other visits at a minimum, but evaluation of EIMs will still be completed at every study visit.

Subjects will undergo a full colonoscopy with biopsy for histologic assessment during Screening with local investigator assessment for Mayo endoscopic subscore for initial eligibility assessment, confirmed by a central reader prior to randomization. At end of treatment (Week 8 in Part 1) a full colonoscopy or flexible sigmoidoscopy, depending on the extent of disease at Screening, will be performed.

For subjects in Part 2, an endoscopy will be performed at Week 16/PD. A flexible rectosigmoidoscopy is recommended at Week 16/PD, however, the use of flexible rectosigmoidoscopy or colonoscopy will be based on the investigator's discretion per local practice.

The endoscopic subscore result from the central reader during the screening period will be used to evaluate the eligibility of a subject to enroll in the study and for all efficacy assessments at Week 8 of Part 1. However, for re randomization into Substudy 3, the endoscopic subscore at Week 8 (Study M14 675 Part 1) or Week 16 (Study M14-675 Part 2) based on the local reader's assessment will be used to determine clinical response status compared to the Baseline assessment of the central reader for enrollment into Study M14-234 Substudy 3.

In addition to the Mayo endoscopic subscore, the central reader will assess the endoscopy findings using the Ulcerative Colitis Endoscopic Index of Severity (UCEIS) scoring system for additional exploratory analyses. Blood samples will be collected for high sensitivity C-reactive protein (hs-CRP), upadacitinib plasma concentrations and other biomarker analyses. In addition, stool samples for fecal calprotectin will be collected. The stool samples should be taken before starting bowel preparations for scheduled endoscopies.

Subjects will be asked to fill out the Inflammatory Bowel Disease Questionnaire (IBDQ), Work Productivity and Activity Impairment (WPAI), European Quality of Life 5 Dimensions 5 Levels (EQ 5D-5L), Short Form 36 Item (SF-36), and Functional Assessment of Chronic Illness Therapy-Fatigue (FACIT-F), Ulcerative Colitis Symptoms Questionnaire (UC-SQ), and Patient Global Impression of Severity (PGIS; only in select sites) during the study at Baseline, Week 2, and Week 8/PD for Part 1. These same questionnaires will be completed at Week 16/PD for Part 2. Subjects will be asked to fill out the Patient Global Impression of Change (PGIC) during the study at Week 2, and Week 8/PD for Part 1. This same questionnaire will be completed at Week 16/PD for Part 2. During each study visit subjects will also be asked to report UC-related hospitalizations and surgeries which will be captured as a part of the supplemental Health Care Resource Utilization (HCRU) form of Adverse Event collection in electronic data capture.

Subjects will be discontinued from the study if they withdraw consent or if they are deemed unsuitable to continue for any reason by the investigator.

Washout Period:

Subjects, who have been taking exclusionary medications prior to screening must complete medication washout. The duration is based on the excluded medication as described in the protocol. However, for subjects who have discontinued infliximab, certolizumab, adalimumab, golimumab, vedolizumab, natalizumab, ustekinumab, if there is proper documentation of an undetectable drug level measured by a commercially available assay for any of the approved biologics above, there is no minimum washout prior to Baseline. Protocol-related adverse events should be reviewed and subjects must complete the washout prior to the Baseline Visit.

Concomitant UC-Related Medications (Oral Corticosteroids, Antibiotics, Aminosalicylates, and/or Methotrexate): Parts 1 and 2

All UC-related concomitant medications should be kept on stable doses in Parts 1 and 2. All subjects receiving stable dose of UC-related antibiotics (those subjects who did not discontinue), aminosalicylates, or MTX at Week 0 will maintain their concomitant treatments and respective doses through the end of the study. Dose may be decreased or terminated in the event of moderate to severe treatment related toxicity (e.g., leukopenia or elevated liver enzymes) in the opinion of the investigator.

Diagnosis and Main Criteria for Inclusion/Exclusion:

Main Inclusion:

1. Male or female between 16 and 75 years of age at Baseline. Adolescent subjects 16 and 17 years old will only be enrolled if approved by the country or regulatory/health authority and must weigh ≥40 kg and meet the definition of Tanner Stage 5 (refer to Appendix H) at the screening visit. If these approvals have not been granted, only subjects 18 years old will be enrolled.

2. Diagnosis of UC for 90 days or greater prior to Baseline, confirmed by colonoscopy during the Screening Period, with exclusion of current infection, colonic dysplasia and/or malignancy. Appropriate documentation of biopsy results consistent with the diagnosis of UC, in the assessment of the Investigator, must be available.

3. Active UC with an Adapted Mayo score of 5 to 9 points and endoscopic subscore of 2 to 3 (confirmed by central reader).

4. Demonstrated an inadequate response, loss of response, or intolerance to at least one of the following treatments including, oral aminosalicylates, corticosteroids, immunosuppressants, and/or biologic therapies, in the opinion of the investigator, as defined below:

Note: An inadequate response, loss of response, or intolerance to Oral Aminosalicylates will NOT count towards eligibility for the following countries: Austria, Czechia, Finland, France, Ireland, Italy, Latvia, Lithuania, Norway, Poland, Portugal, Spain, Sweden and United Kingdom.

Oral aminosalicylates (e.g., mesalamine, sulfasalazine, olsalazine, balsalazide)

Signs and symptoms of persistently active disease, in the opinion of the investigator, during a current or prior course of at least 4 weeks of treatment with 2.4 g/day mesalamine, 4 g/day sulfasalazine, 1 g/day olsalazine, or 6.75 g/day balsalazide.

Corticosteroids

Signs and symptoms of persistently active disease despite a history of at least one induction regimen that included a dose equivalent to prednisone ≥40 mg/day orally for at least 3 weeks or intravenously for 1 week, OR Unable to taper corticosteroids to below a dose equivalent to prednisone 10 mg daily orally without recurrent active disease, OR Signs and symptoms of persistently active disease during or after a course of at least 4 weeks of treatment with 9 mg/day budesonide or 5 mg/day beclomethasone, OR Unable to taper oral budesonide to at or below 6 mg/day without recurrent active disease, OR History of intolerance to corticosteroids (including, but not limited to Cushing's syndrome, osteopenia/osteoporosis, hyperglycemia, insomnia, infection).

Immunosuppressants

Signs and symptoms of persistently active disease despite a history of at least one 90 day regimen of oral azathioprine (≥1.5 mg/kg/day; for subjects in Japan, China, and Taiwan only: ≥1.0 mg/kg/day), 6-mercaptopurine (6-MP) (≥1 mg/kg/day; [for subjects in Japan, China, and Taiwan only: ≥0.6 mg/kg/day, rounded to the nearest available tablet of half tablet formulation] or a documented 6-thioguanine nucleotide (6-TGN) level of 230-450 pmol/8×$10^8$ RBC or higher on the current dosing regimen), injectable methotrexate (MTX) (≥15 mg/week subcutaneous [SC] or intramuscular), or tacrolimus (for subjects in Japan and Taiwan only: documented trough level of 5-10 ng/mL), OR History of intolerance to at least one immunosuppressant (including, but not limited to nausea/vomiting, abdominal pain, pancreatitis, liver enzyme abnormalities, lymphopenia, infection)

Biologic Agents for UC

Signs and symptoms of persistently active disease despite a history of any of the following:

at least one 6-week induction regimen of infliximab (≥5 mg/kg IV at 0, 2, and 6 weeks), at least one 4-week induction regimen of adalimumab (one 160 mg SC dose followed by one 80 mg SC dose [or one 80 mg SC dose in countries where this dosing regimen is allowed] followed by one 40 mg SC dose at least 2 weeks apart), at least one 2-week induction regimen of golimumab (one 200 mg SC dose followed by one 100 mg SC dose at least 2 weeks apart), at least one 6-week induction regimen of vedolizumab (300 mg IV at 0, 2, and 6 weeks), at least one induction regimen of ustekinumab, a single IV dose using weight-based dosing (260 mg for subjects with body ≤55 kg; 390 mg for subjects with body weight ≥55 kg to ≤85 kg; 520 mg for subjects with body weight ≥85 kg OR Recurrence of symptoms during scheduled maintenance dosing following prior clinical benefit (discontinuation despite clinical benefit does not qualify), OR History of intolerance to at least one biologic agent (including, but not limited to infusion-related reaction, demyelination, congestive heart failure, infection) Note: Non-bio-IR subjects who have received a prior biologic for up to 1 year may be enrolled, however, subjects must have discontinued the biologic for reasons other than inadequate response or intolerance (e.g., change of insurance, well controlled disease), and must meet the criteria for inadequate response, loss of response or intolerance to aminosalicylates, corticorsteroids and/or immunosuppressants as defined above.

Note: Oral MTX use is allowed during the study, however prior or current use of oral MTX is not sufficient for inclusion into the study unless these subjects were previously treated with aminosalicylates, corticosteroids or immunosuppressants (azathioprine or 6-MP) and have inadequate response to, loss of response to or intolerance to the therapy as defined above.

Main Exclusion:
1. Subject with current diagnosis of Crohn's disease (CD) or diagnosis of indeterminate colitis (IC).
2. Current diagnosis of fulminant colitis and/or toxic megacolon.
3. Subject with disease limited to the rectum (ulcerative proctitis) during the Screening endoscopy.
4. Received cyclosporine, tacrolimus, mycophenolate mofetil or thalidomide within 30 days prior to Baseline.
5. Subject who received azathioprine or 6-MP within 10 days of Baseline.
6. Received intravenous corticosteroids within 14 days prior to Screening or during the Screening Period.
7. Subject with previous exposure to JAK inhibitor (e.g., tofacitinib, baricitinib, filgotinib, upadacitinib).
8. Screening laboratory and other analyses show any of the following abnormal results:

Serum Aspartate Transaminase (AST) or Alanine Transaminase (ALT) >2.0×upper limit of the reference range (ULN);

Estimated glomerular filtration rate (eGFR) by simplified 4-variable Modification of Diet in Renal Disease (MDRD) formula <30 mL/min/1.73 $m^2$;

Total White Blood Cell (WBC) count <2500/µL;

Absolute neutrophil count (ANC)<1,200/µL;

Platelet count <100,000/µL;

Absolute lymphocytes count <750/µL;

Hemoglobin <9 g/dL.

Investigational Product: Upadacitinib (ABT-494)

Doses:

Part 1: Upadacitinib 45 mg QD (blinded)

Part 2: Upadacitinib 45 mg QD (open-label)

Mode of Administration: Oral

Reference Therapy: Part 1: Matching Placebo, Oral

DURATION OF TREATMENT: 8 weeks for subjects achieving clinical response at week 8; or 16 weeks for subjects who do not achieve clinical response at week 8.

Criteria for Evaluation:

Efficacy:

Primary Endpoint:

The primary endpoint for Study M14-675 is the proportion of subjects who achieve clinical remission per Adapted Mayo score (defined as stool frequency subscore [SFS]≤1 and not greater than baseline, RBS of 0, and endoscopic subscore ≤1) at Week 8. Note: evidence of friability during endoscopy in subjects with otherwise "mild" endoscopy activity will confer an endoscopic subscore of 2.

Ranked Secondary Endpoints:
1. Proportion of subjects with endoscopic improvement at Week 8
2. Proportion of subjects with endoscopic remission at Week 8
3. Proportion of subjects achieving clinical response per Adapted Mayo Score at Week 8
4. Proportion of subjects achieving clinical response per Partial Adapted Mayo score (defined as decrease from Baseline ≥1 points and ≥30% from Baseline, PLUS a decrease in RBS≥1 or an absolute RBS≤1) at Week 2
5. Proportion of subjects achieving histologic-endoscopic mucosal improvement at Week 8
6. Proportion of subjects who reported no bowel urgency at Week 8
7. Proportion of subjects who reported no abdominal pain at Week 8
8. Proportion of subjects who achieved histologic improvement at Week 8
9. Change from Baseline in IBDQ total score at Week 8
10. Proportion of subjects with mucosal healing at Week 8
11. Change from Baseline in FACIT-F score at Week 8.

Pharmacokinetic:
Blood samples will be collected for measurement of upadacitinib plasma concentration at Week 2, Week 6, and Week 8/PD in Part 1.

Safety:
Safety analyses will be performed on all subjects who receive at least one dose of study drug. Incidence of AEs, changes in vital signs, electrocardiogram, physical examination results, and clinical laboratory data will be assessed.

Exploratory Research Variables and Validation Studies (Optional):
Prognostic, predictive and pharmacodynamics biomarkers signatures may be investigated. Samples for different applications, including pharmacogenetic, epigenetic, transcriptomic, proteomic and targeted investigations will be collected at various time points. Assessments will include but may not be limited to nucleic acids, proteins, metabolites or lipids.

8-Week Induction Period—Part 1
This period will begin at the Baseline Visit (Week 0) and will end at the Week 8 Visit. At the Baseline Visit, subjects who meet all the inclusion criteria and none of the exclusion criteria described herein will be enrolled into the study and randomized to the double-blind induction period. During this period of the study, subjects will visit the study site at Weeks 2, 4, 6, and 8. A ±3-day window is permitted around scheduled study visits. The last dose of study drug during this period is recommended to be taken the day prior to the Week 8 Visit when possible.

8-Week Extended Treatment Period—Part 2
The period will begin after the Week 8 endoscopy in Part 1 and will end at the Week 16 Visit.
At Week 8, subjects in Part 1 who did not achieve clinical response (defined by Adapted Mayo Score) will be enrolled into Part 2 and receive open label upadacitinib 45 mg QD for an additional 8 weeks. Clinical response is defined as decrease from baseline in the Adapted Mayo score ≥2 points and ≥30% from baseline, PLUS a decrease in rectal bleeding score (RBS)≥1 or an absolute RBS≤1.
If the subject is a clinical responder at Week 8/16, the subject may enter Study M14-533 Cohort 1. If the subject is a clinical non-responder at Week 8, the subject may enter Part 2. If the subject is a clinical non-responder at Week 16 the subject will discontinue from the study. During this period of the study, subjects will visit the study site at Weeks 10, 12, 14, and 16. A ±3-day window is permitted around scheduled study visits. The last dose of study drug during this period is recommended to be taken the day prior to the Week 16 Visit when possible.

Re-Screen
Subjects that initially screen fail for the study will be permitted to re-screen following re-consent. For any subjects who screened and who were unable to enter the program during Study M14-234 Substudy 1 due to enrollment limits, these subjects may also be rescreened into Study M14-234 Substudy 2 or Study M14-675.
The subject must meet all the inclusion and none of the exclusion criteria at the time of re-screening in order to qualify for the study. There is no minimum period of time a subject must wait to re-screen for the study and there is no maximum number of re-screens allowed for a given subject. If the subject had a complete initial screening evaluation including the assessment of a purified protein derivative (PPD) test (or equivalent), or Interferon-Gamma Release Assay (IGRA; QuantiFERON-TB Gold Plus test or T-SPOT TB test), chest x-ray, hepatitis B virus (HBV), hepatitis C virus (HCV), HIV, Beta-D-glucan (Japan only) and electrocardiogram (ECG), these tests will not be required to be repeated for re-screening provided the conditions noted herein are met and no more than 90 calendar days have passed since the date of testing.
If a subject is being rescreened within 14 days (from the date of the previous screening testing), it is not required to repeat Screening testing for chemistry/hematology, urinalysis, serum pregnancy, and *Clostridium difficile* (*C. difficile*).
An endoscopy with biopsy will not be required to be repeated for re-screening provided the conditions noted herein are met and re-consent is no more than 30 calendar days after the initial screening endoscopy.
All other screening procedures will be repeated. As appropriate, sites are encouraged to contact the AbbVie TA MD to confirm if subjects should or should not be re-screened. Re-screened subjects will retain the same subject number assigned at the initial screening.

Efficacy Variables
The following endpoint definitions apply to the efficacy variables described below:

Clinical Remission:
Per Adapted Mayo: SFS≤1 and not greater than baseline, RBS of 0, and endoscopic subscore ≤1 (note: evidence of friability during endoscopy in subjects with otherwise "mild" endoscopic activity will confer an endoscopic subscore of 2).
Per Full Mayo: Full Mayo score of ≤2 with no subscore >1

Clinical Response:
Per Adapted Mayo: decrease from baseline in Adapted Mayo score ≥2 points and ≥30%, accompanied by a decrease in RBS of ≥1 or an absolute RBS of 0 or 1
Per Full Mayo: decrease from baseline in Full Mayo score ≥3 points and ≥30%, accompanied by a decrease in RBS of ≥1 or an absolute RBS of 0 or 1
Per Partial Adapted Mayo: decrease from Baseline ≥1 points and ≥30% from Baseline, PLUS a decrease in RBS≥1 or an absolute RBS≤1
Endoscopic remission: Endoscopic subscore of 0
Endoscopic improvement: Endoscopic subscore ≤1
Histologic improvement: Decrease from Baseline in Geboes score
Histologic-endoscopic mucosal improvement: Endoscopic subscore ≤1 and Geboes score ≤3.1

Mucosal healing: Endoscopic subscore=0 and Geboes score <2

Primary Variable

The primary endpoint is the proportion of subjects who achieve clinical remission per Adapted Mayo score (defined as SFS≤1 and not greater than baseline, RBS of 0, and endoscopic subscore ≤1) at Week 8. Note: Evidence of friability during endoscopy in subjects with otherwise "mild" endoscopic activity will confer an endoscopic subscore of 2.

Secondary Variables

Ranked secondary efficacy variables are as follows:
Proportion of subjects with endoscopic improvement at Week 8
Proportion of subjects with endoscopic remission at Week 8
Proportion of subjects achieving clinical response per Adapted Mayo Score at Week 8
Proportion of subjects achieving clinical response per Partial Adapted Mayo score (defined as decrease from Baseline ≥1 points and ≥30% from Baseline, PLUS a decrease in RBS≥1 or an absolute RBS≤1) at Week 2
Proportion of subjects achieving histologic-endoscopic mucosal improvement at Week 8
Proportion of subjects who reported no bowel urgency at Week 8
Proportion of subjects who reported no abdominal pain at Week 8
Proportion of subjects who achieved histologic improvement at Week 8
Change from Baseline in IBDQ total score at Week 8
Proportion of subjects with mucosal healing at Week 8
Change from Baseline in FACIT-F score at Week 8

Additional Variables

Additional efficacy variables are as follows and will be evaluated.
Proportion of subjects achieving response in IBDQ Bowel Symptom domain (increase of IBDQ bowel symptom domain score ≥6) at Week 8
Proportion of subjects with UC-related hospitalizations through Week 8
Proportion of subjects with UC-related surgeries through Week 8
Proportion of subjects achieving response in IBDQ fatigue item (increase of IBDQ fatigue item score ≥1) at Week 8
Proportion of subjects with SFS of 0, RBS of 0 and endoscopic subscore of 0 at Week 8
Proportion of subjects with SFS of 0, RBS of 0 and endoscopic subscore of ≤1 at Week 8
Proportion of subjects achieving clinical remission per Full Mayo Score (defined as a full Mayo score ≤2 with no sub-score >1) at Week 8
Change in Full Mayo Score from Baseline to Week 8
Proportion of subjects achieving clinical remission per Partial Mayo score over time.
Proportion of subject achieving clinical response per Partial Adapted Mayo score over time
Proportion of subjects achieving clinical response per Partial Mayo score over time.
Proportion of subjects with SFS≤1 over time.
Proportion of subjects with RBS=0 over time.
Proportion of subjects with SFS≤1 at Week 2.
Proportion of subjects with RBS of 0 at Week 2.
Proportion of subjects with fecal calprotectin below 150 mg/kg over time.
Change from Baseline in fecal calprotectin over time
Change from Baseline in hs-CRP over time.
Change from Baseline in Partial Adapted Mayo score, Partial Mayo score and SFS, RBS over time.
Change from Baseline in UCEIS score over time.
Change from Baseline in laboratory and nutritional parameters (e.g., hemoglobin, hematocrit, albumin, total protein concentration, and weight).
Change from Baseline in subject-reported stool frequency (absolute values).
Change from Baseline in IBDQ total and domain score over time.
Change from Baseline in individual IBDQ item under Bowel Symptom domain (for Q1, Q5, Q9, Q13, Q17, Q20, Q22, Q24, Q26, and Q29) over time.
Proportion of subjects with IBDQ response (increase of IBDQ≥16 from Baseline) over time.
Proportion of subjects with IBDQ remission (IBDQ total score ≥170) over time.
Change from Baseline in European Quality of Life—5 Dimensions 5 Levels (EQ-5D-5L) score over time.
Change from Baseline in WPAI scores over time.
Change from Baseline in SF-36 Physical Component Summary (PCS) and Mental Component Summary (MCS) components and domain scores over time.
Proportion of subjects by Patient Global Impression of Change (PGIC) category over time.
Proportion of subjects by Patient Global Impression of Severity (PGIS) category over time.
Change from Baseline in Functional Assessment of Chronic Illness Therapy-Fatigue (FACIT-F) score over time.
Change from Baseline in Ulcerative Colitis Symptoms Questionnaire (UC-SQ) score over time
Proportion of subjects with all cause hospitalization through Week 8
Proportion of subjects with all cause surgery through Week 8

Results

Figure 25:
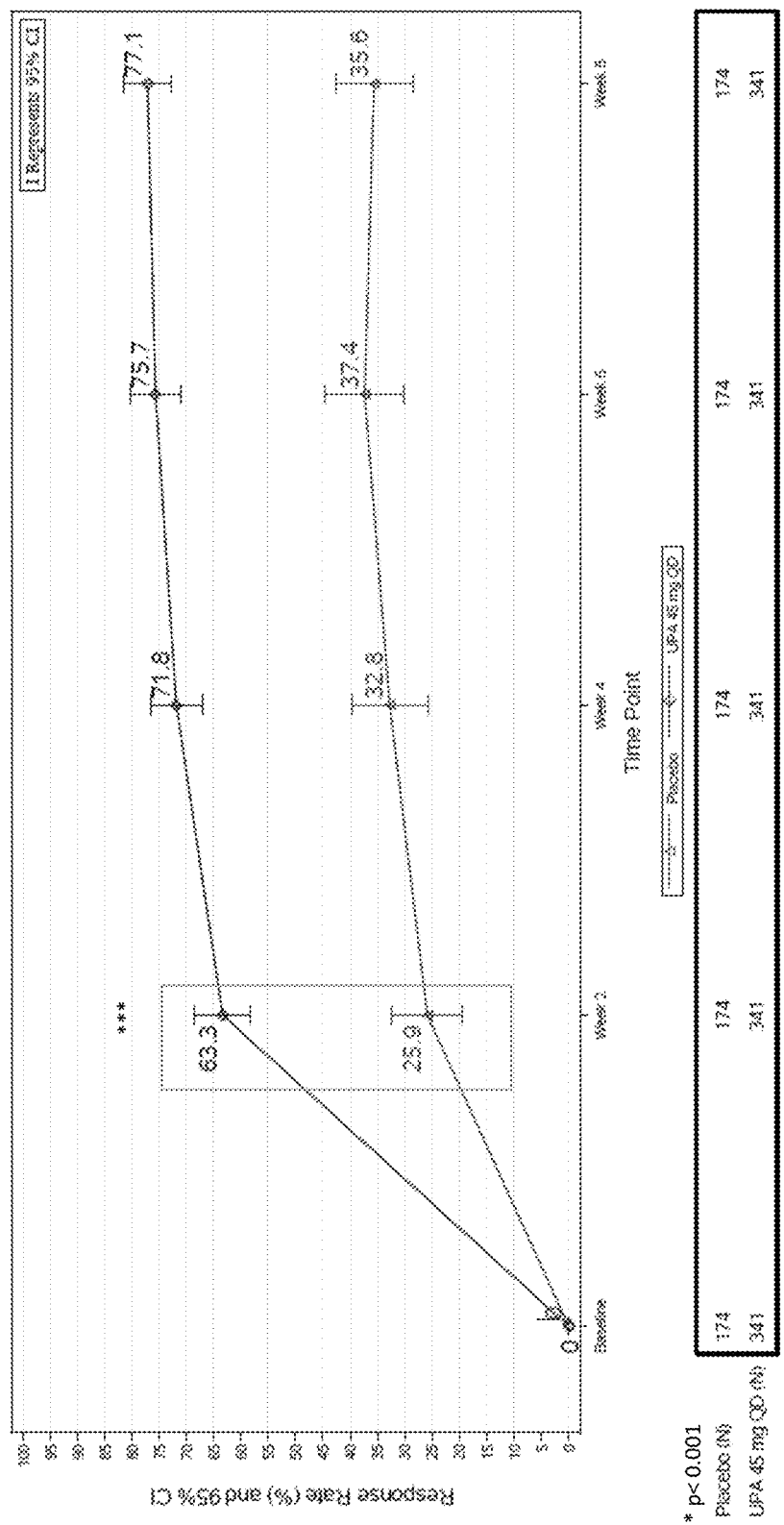
FIG. 25 shows the clinical response rate for weeks 2 to 8 in a patient population administered upadacitinib or placebo in the Example 19 ulcerative colitis clinical study, based on achieving a decrease in Partial Adapted Mayo score ≥1 point and ≥30% from Baseline, PLUS a decrease in RBS≥1 or an absolute RBS≤1.
Figure 27B:
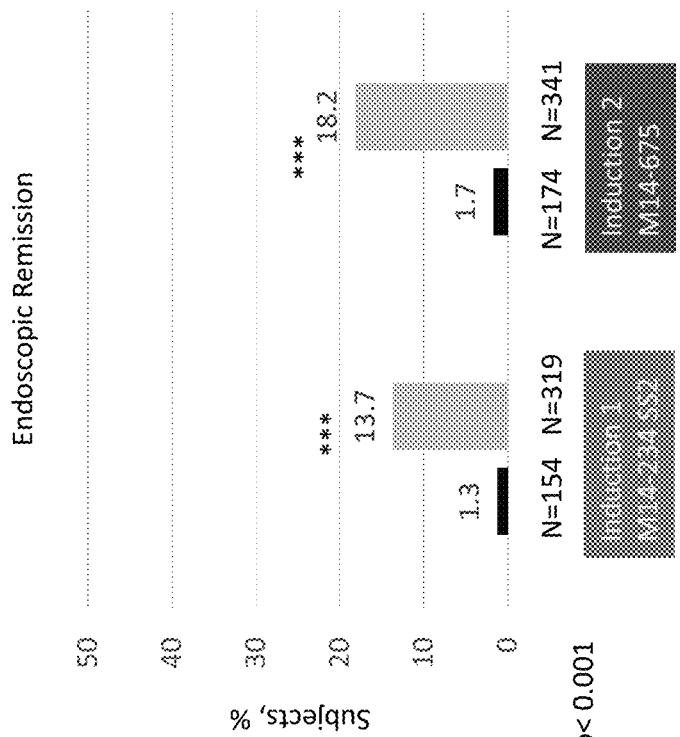
FIG. 27B shows the endoscopic remission rate at week 8 in a patient population administered upadacitinib or placebo in the Example 19 ulcerative colitis clinical study, based on achieving an endoscopic score of 0.
Figure 27A:
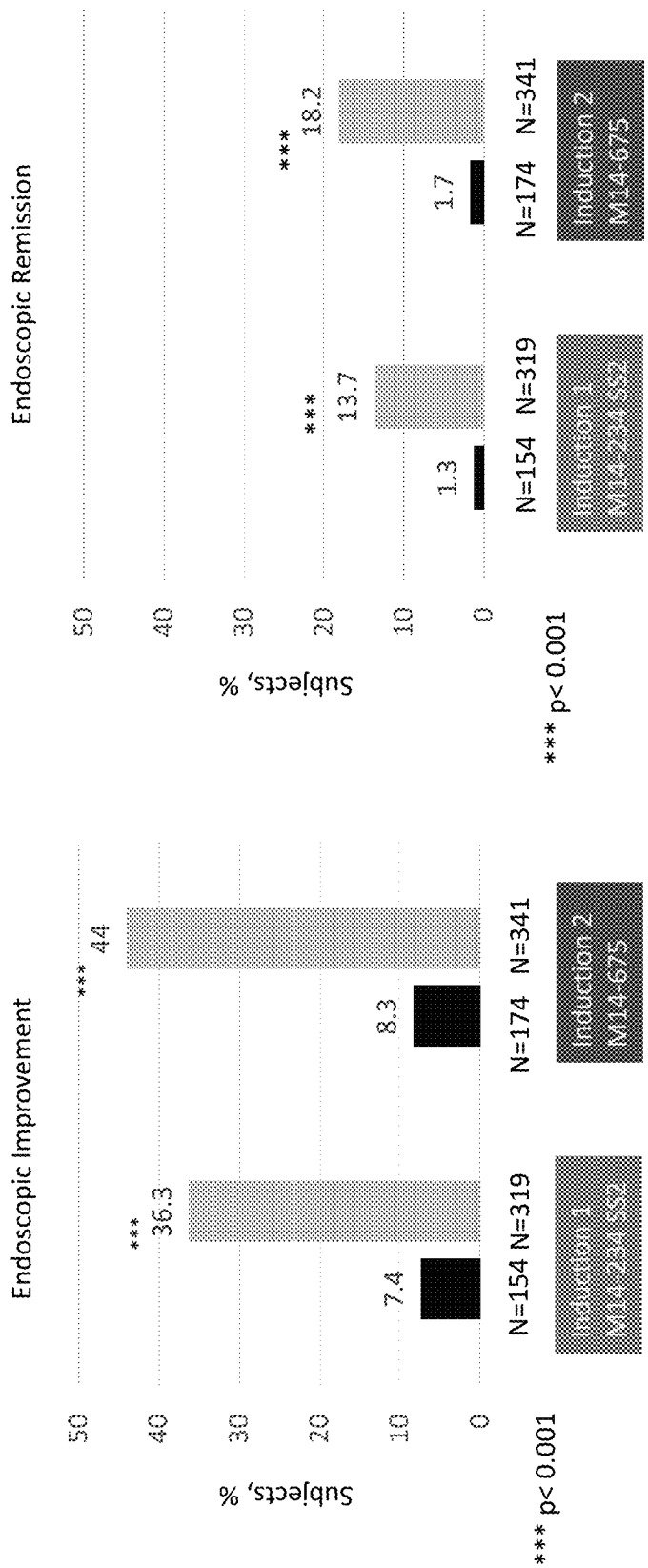
FIG. 27A shows the endoscopic improvement rate at week 8 in a patient population administered upadacitinib or placebo in the Example 19 ulcerative colitis clinical study, based on achieving an endoscopic score ≤1.

Results of this study are provided in FIGS. 24 to 28C. Generally, upadacitinib 45 mg QD met primary and all ranked secondary endpoints (all achieved p <0.001), demonstrating superiority vs placebo as an induction therapy. This efficacy was demonstrated across clinical, endoscopic and histologic endpoints. At week 8, approximately 75% of patients showed a clinical response (FIGS. 25 and 26B). Of the remaining 25% of non-responding patients, approximately 50% showed a clinical response by 16 weeks. Particularly surprising was the extent of mucosal healing observed after 8 weeks of induction, as defined by an endoscopic score of 0 and a Geboes score of less than 2. The proportion of subjects achieving the primary endpoint of clinical remission per Adapted Mayo score at Week 8 was significantly higher in the upadacitinib 45 mg QD group (33.5%) compared to the placebo group (4.1%) with p-value <0.001. Clinical response per Partial Adapted Mayo Score was seen as early as Week 2

Overall, the eight-week treatment with upadicitinib 45 mg QD as an induction therapy was well tolerated. No new safety risks were observed compared to the known safety profile of upadacitinib. The rates of severe adverse events (AE) and AEs leading to study drug discontinuation were lower with upadacitinib 45 mg as compared to placebo. No deaths were reported in the study. The rates of neutropenia, lymphopenia, hepatic disorder, and CPK elevation were higher with upadacitinib 45 mg QD as compared to placebo. The rate of anemia AEs was higher with upadacitinib 45 QD; however, Grade 3 hemoglobin decrease occurred more frequently on placebo. No reports of active TB, malignancy, adjudicated GI perforation, adjudicated VTE, or adjudicated MACE were made in the upadacitinib 45 mg QD group. One event each of adjudicated GI perforation and VTE (PE and DVT) was reported in the placebo group.

Example 20: Upadacitinib 15 mg or 30 mg as Maintenance Therapy for Ulcerative Colitis Approximately 750 subjects who achieved clinical response per Adapted Mayo Score after completion of induction treatment or Extended Treatment Period in Study M14-234 Substudy 1, Substudy 2, or Study M14-675, were eligible to enter this trial (Substudy 3) and treated with a blinded treatment assignment for up to 52 weeks. Subjects with missing Week 8 or/and Week 16 endoscopy during the period of COVID-19 pandemic were not eligible to enter Substudy 3. Subjects from Study M14-675 were required to have achieved clinical response at Week 8 or 16. The Baseline Visit of Substudy 3 was completed on the same day as the final visit in the Induction Phase (either at Week 8 or Week 16) for subjects who were eligible.

Clinical response was defined as a decrease from baseline in the Adapted Mayo score ≥2 points and ≥30% from baseline, PLUS a decrease in RBS≥1 or an absolute RBS≤1. The treatment assignment in Substudy 3 depended on the treatment received in Substudies 1 and 2, or Study M14-675, as detailed below. Substudy 3 included 4 cohorts:

Cohort 1:

The approximately 525 subjects who achieved clinical response in Study M14-234 Substudies 1 and 2, or Study M14-675, and received 1 of the following treatments, were re-randomized in a 1:1:1 ratio to one of the treatment groups in Cohort 1:

Upadacitinib 30 mg QD or 45 mg QD in Study M14-234 Substudy 1
  Upadacitinib 45 mg QD in Study M14-234 Substudy 2 Part 1
  Upadacitinib 45 mg QD in Study M14-675 Part 1
  Placebo QD in Study M14-234 Substudy 2 Part 1 followed by upadacitinib 45 mg QD in Study M14-234 Substudy 2 Part 2
  Placebo QD in Study M14-675 Part 1 followed by upadacitinib 45 mg QD in Part 2

Treatment groups in Cohort 1:
  Group 1: upadacitinib 15 mg QD
  Group 2: upadacitinib 30 mg QD
  Group 3: placebo QD Subjects who achieved clinical response and received upadacitinib 15 mg QD in Study M14-234 Substudy 1 were re-randomized 1:1 to only receive upadacitinib 15 mg QD or placebo QD (treatment Group 1 or 3).

Cohort 2:

Approximately 60 subjects who received double-blind placebo QD treatment for 8 weeks during Study M14-234 Substudy 1, Substudy 2 Part 1 or Study M14-675 Part 1 and achieved clinical response continued to receive blinded placebo QD in Substudy 3.

Cohort 3:

Approximately 150 subjects who received upadacitinib 45 mg QD in induction phase and did not achieve clinical response—and received upadacitinib 45 mg in Extended Treatment in Study M14-234 (Substudy 2, Part 2) or Study M14-675 (Part 2) and achieved clinical response at Week 16 were re-randomized 1:1 and received blinded upadacitinib 30 mg QD or upadacitinib 15 mg QD in Study M14-234 (Substudy 3).

Cohort 4:

Approximately 15 subjects who received double-blinded treatment of upadacitinib 7.5 mg for 8 weeks during Study M14-234 (Substudy 1) and achieved clinical response continued to receive blinded treatment of upadacitinib 7.5 mg QD in Substudy 3. The schematic of Substudy 3 is provided in Table 30.

TABLE 30

Substudy 3 schematic.

| Cohorts | Status | M14-234 Substudy 3 (Maintenance study; week 0-52) |
| --- | --- | --- |
| Cohort 1: Clinical responders to upadacitinib from: M14-234 SS1* (not including 7.5 mg QD) SS2 or M14-675 (week 8) Extended treatment clinical responders (week 16) who received placebo in induction | Re-randomized | Double blind (DB) upadacitinib 15 mg QD; n = 150 DB upadacitinib 30 mg QD; n = 150 DB placebo QD; n = 150 |
| Cohort 2: Placebo clinical responders (week 8) from M14-234 SS1, SS2, or M14-675 | Do not get re-randomized | DB placebo QD |
| Cohort 3: Clinical responders (week 16) to upadacitinib from the extended treatment period in M14-234 SS2 and M14-675 who received upadacitinib in induction | Re-randomized | DB upadacitinib 15 mg QD DB upadacitinib 30 mg QD |
| Cohort 4: Clinical responders (week 8) to upadacitinib 7.5 mg QD in M14-234 SS1 | Do not get re-randomized | DB upadacitinib 7.5 mg QD |

*Responders who received upadacitinib 15 mg QD in M14-234 SS1 will only be randomized to receive upadacitinib 15 mg QD or placebo QD The rationale for re-randomizing only induction responders who received upadacitinib 15, 30 or 45 mg QD from Substudy 1 is to ensure that no subject receives a dose during maintenance that is higher than what was received in the induction period.

During Substudy 3, subjects who met the criteria for initial loss of response after at least 2 weeks of treatment and had a second confirmed loss of response on a consecutive visit at least 14 days later had the option to enroll into Study M14-533 and receive open-label upadacitinib.

Loss of response is defined as follows: A subject who presents with an SFS and RBS score each at least 1 point greater than the end-of-induction value (Week 8 of Substudy 1, Substudy 2 Part 1, Study M14-675 Part 1 or Week 16 of Substudy 2 Part 2 or Study M14-675 Part 2) on two consecutive visits at least 14 days apart, associated with the presence of signs or symptoms of progression of UC.

For subjects with SFS or RBS≥2.1 at the end-of-induction, loss of response is defined as: An increase in either the SFS or RBS of at least 1 point greater than the end-of-induction value on two consecutive visits at least 14 days apart and associated with the presence of signs or symptoms of progression of UC disease.

Subjects who entered Substudy 3 from Study M14-234 Substudy 1 were only required to complete 44 weeks of maintenance therapy in Substudy 3. Subjects entering Substudy 3 from Study M14-234 Substudy 2 or from Study M14-675 were required to complete 52 weeks in Substudy 3 if they did not withdraw or have loss of response prior.

Screening

Subjects, who have been taking exclusionary medications prior to screening or Baseline were required to complete medication washout. The duration was based on the excluded medication. During Screening, biologic drug levels could be optionally assessed as an alternative to completing the required washout period as follows: (1) infliximab and natalizumab: may be tested approximately 4 weeks or later from the last dose; (2) adalimumab, certolizumab, golimumab, or vedolizumab: may be tested approximately 6 weeks or later from the last dose; (3) ustekinumab: may be tested approximately 8 weeks or later from the last dose. If the biologic drug was not detected, the subject was considered as eligible and the washout period was not required.

Concomitant UC-Related Medications (Oral Corticosteroids, Antibiotics, Aminosalicylates, and/or Methotrexate):

At Baseline of Substudy 3 (Week 8 or Week 16 of Study M14-234 Substudy 1, Substudy 2, and Study M14-675), subjects who were taking corticosteroid therapy will have their corticosteroid therapy tapered. Subjects taking corticosteroids who have worsening of disease after the steroid taper has been initiated may have had their corticosteroid dose increased. Use of inhaled or topical dermatologic corticosteroids was not restricted.

All subjects receiving UC-related antibiotics may discontinue treatment starting at Week 0 of Substudy 3 at the discretion of the investigator.

All subjects receiving stable dose of UC-related antibiotics (those subjects who did not discontinue), aminosalicylates, or MTX at Week 0 maintained their concomitant treatments and respective doses through the end of the study. Dose was allowed to be decreased or terminated in the event of moderate to severe treatment related toxicity (e.g., leukopenia or elevated liver enzymes. If the subject and investigator chose to receive/administer live vaccines, these vaccinations were completed (per local label) at least 30 days (8 weeks for subjects in Japan) before first dose of study drug. Live vaccinations were prohibited during study participation including at least 30 days (or longer if required locally) after the last dose of study drug.

Efficacy Assessment

The primary endpoint for Phase 3 maintenance (Substudy 3) is the proportion of subjects who achieve clinical remission per Adapted Mayo score at Week 52 (for subjects who enrolled under the protocol with 44-week maintenance period, these will apply at Week 44, as applicable).

Ranked secondary efficacy variables for Phase 3 Maintenance (Substudy 3) are as follows:

At Week 52 (for subjects who enrolled under the protocol with 44-week maintenance period, these will apply at Week 44, as applicable):
1. Proportion of subjects with endoscopic improvement
2. Proportion of subjects who maintain clinical remission per Adapted Mayo score among subjects who achieved clinical remission per Adapted Mayo score in Study M14-234 (Substudy 1 or 2) or Study M14-675
3. Proportion of subjects who achieved clinical remission at Week 52 per adapted Mayo score and were corticosteroid free for $\geq$ 90 days among subjects in clinical remission in the end of the induction treatment in Study M14-234 (Substudy 1 or 2) or Study M14-675.
4. Proportion of subjects with endoscopic improvement among subjects with endoscopic improvement in Study M14-234 (Substudy 1 or 2) or Study M14-675
5. Proportion of subjects with endoscopic remission
6. Proportion of subjects maintain clinical response per Adapted Mayo score
7. Proportion of subjects with histologic-endoscopic mucosal improvement
8. Change from Baseline in IBDQ total score
9. Proportion of subjects with mucosal healing
10. Proportion of subjects who reported no bowel urgency
11. Proportion of subjects who reported no abdominal pain
12. Change from Baseline in FACIT-F score Definitions of Mayo, Partial Mayo, and Adapted Mayo scores are provided in Table 31.

TABLE 31

Mayo, Partial Mayo, and Adapted Mayo Score Definitions

|  | Rectal Bleeding [RBS] (0-3) | Stool Frequency [SFS] (0-3) | Physician's Global Assessment [PGA] (0-3) | Endoscopy (0-3) | Score Range |
|---|---|---|---|---|---|
| Mayo Score | X | X | X | X | 0-12 |
| Partial Mayo Score | X | X | X |  | 0-9 |
| Adapted Mayo Score | X | X |  | X | 0-9 |
| Partial Adapted Mayo Score | X | X |  |  | 0-6 |

Additional efficacy variables are as follows and will be evaluated:

Proportion of subjects who discontinued corticosteroid use, remained corticosteroid free for $\geq$ 90 days immediately before Week 52 and achieved clinical remission per Adapted Mayo score in subjects taking steroids at Baseline (of induction)

Proportion of subjects achieving response in IBDQ Bowel Symptom domain at Week 52 (increase of IBDQ bowel symptom domain score $\geq$ 6)

Proportion of subjects achieving response in IBDQ fatigue item at Week 52 (increase of IBDQ fatigue item score ≥ 1)

Proportion of subjects who are taking corticosteroids at Baseline (of induction) and are steroid-free over time.

Proportion of subjects who are taking corticosteroid at Baseline (of induction) and are steroid free at Week 52

Proportion of subjects who discontinued corticosteroid use and achieved clinical remission per Adapted Mayo score at Week 52 in subjects taking steroids at Baseline (of induction)

Proportion of subjects achieving clinical remission per Full Mayo Score (defined as a full Mayo score ≤ 2 with no sub-score >1) at Week 52

Proportion of subjects who discontinued corticosteroid use and achieved clinical remission per Partial Mayo Score over time in subjects taking steroids at baseline (of induction)

Proportion of subjects who discontinued corticosteroid use of ≥ 90 days immediately before Week 52 and achieved clinical remission at Weeks 0 and Week 52 of Substudy 3, in subjects who were taking steroids at Baseline (of induction)

Proportion of subjects who discontinued corticosteroid use of ≥ 90 days immediately before Week 52 and achieved a SFS ≤ 1 (and not worse than Baseline of induction) and RBS=1 at Weeks 36 and 44 and clinical remission at Week 52, in subjects who were taking steroids at baseline (of induction)

Proportion of subjects achieving clinical remission per Partial Mayo score over time.

Proportion of subjects with SFS of 0, RBS of 0 and endoscopic subscore of 0 at Week 52

Proportion of subjects with SFS of 0, RBS of 0 and endoscopic subscore of ≤ 1 at Week 52

Proportion of subjects with SFS ≤ 1, RBS=0 at Week 28 and clinical remission per adapted Mayo score at Week 52

Proportion of subjects with SFS ≤ 1, RBS=0 at Week 28 and Week 52

Proportion of subjects with SFS of 0, RBS of 0, and endoscopic subscore of 0 over time.

Proportion of subjects achieving clinical response per Partial Mayo score over time.

Proportion of subjects with SFS≤1 over time.

Proportion of subjects with RBS of 0 over time.

Proportion of subjects with fecal calprotectin below 150 mg/kg over time.

Change from Baseline in hs-CRP over time.

Change from Baseline in fecal calprotectin over time

Change from Baseline in corticosteroid dose over time.

Change from Baseline in Adapted Mayo score, Partial Adapted Mayo score, Full Mayo score, Partial Mayo score and Mayo subscores over time.

Change from Baseline in UCEIS score over time.

Proportion of subjects with histologic improvement at Week 52

Proportion of subjects with histologic remission at Week 52

Proportion of subjects with histologic remission (defined as Geboes score ≤2) at Weeks 8, or Week 16, and Week 52.

Change from Baseline in histologic score over time.

Change from Baseline in laboratory and nutritional parameters (e.g., hemoglobin, hematocrit, albumin, total protein concentration, and weight).

Change from Baseline in subject-reported stool frequency (absolute values).

Change from Baseline in IBDQ total and domain score over time.

Change from Baseline in individual IBDQ item under Bowel Symptom domain (for Q1, Q5, Q9, Q13, Q17, Q20, Q22, Q24, Q26, and Q29) over time.

Proportion of subjects with IBDQ response (increase of IBDQ≥16 from Baseline) over time.

Proportion of subjects with IBDQ remission (IBDQ total score ≥170) over time.

Change from Baseline in EQ-5D-5L score over time.

Change from Baseline in WPAI scores over time.

Change from Baseline in SF-36 PCS, MCS components and domain scores over time.

Proportion of subjects by PGIC category over time.

Proportion of subjects by PGIS category over time.

Change from Baseline in UC-SQ score over time.

Health care resource utilization (all-cause and UC-related hospitalizations and surgeries) during the study.

Incidence rate of UC-related hospitalizations.

Incidence rate of UC-related surgeries.

In addition, change from Week 0 of Substudy 3 will be summarized for hs-CRP, fecal calprotectin, IBDQ total and domain score, EQ-5D-5L score, FACIT-F score, and other PRO endpoints, as applicable.

The following outcomes and questionnaires will be completed:

IBDQ—Inflammatory Bowel Disease Questionnaire. The IBDQ is a disease-specific instrument composed of 32 Likert-scaled items. The total score ranges from 32 to 224 using the 7-point response options, with higher scores indicating better health-related quality of life. The IBDQ scale contains 4 component subscales: bowel symptoms, systemic symptoms, emotional function, and social function. Each subscale can be computed with total scores ranging from 10 to 70, 5 to 35, 12 to 84, and 5 to 35, respectively. In some embodiment, patients treated according to the disclosed method exhibit a change (increase from baseline) in the IBDQ score.

SF-36—Short Form 36. The SF-36 questionnaire is a self-administered multi-domain scale with 36 items. Eight subscales cover a range of functioning: physical functioning, role-physical, bodily pain, general health, vitality, social functioning, role-emotional, and mental health. The scoring yields a physical component score, a mental component summary score, and subscale scores. Higher scores represent better outcomes. The concepts measured by the SF-36 are not specific to any age, disease, or treatment group, allowing comparison of relative burden of different diseases and the benefit of different treatments.

EQ-5D-5L—European Quality of Life 5 Dimensions 5 Levels. The EQ-5D-5L is a standardized non-disease specific instrument for describing and valuing health-related quality of life. The EQ-5D-5L consists of 5 dimensions: mobility, self-care, usual activity, pain/discomfort, and anxiety/depression. Each dimension has 5 levels: no problem, slight problem, moderate problem, severe problem or unable to do the activity. It also contains a Visual Analogue Scale (VAS). Subjects are asked to indicate the level that describes their current level of function or experience for each dimension. As a measure of health status, it provides a descriptive profile and can be used to generate a single index value for health status, where full health is equal to 1 and death is equal to 0. The VAS records the subject's assessment of his/her own health along a vertical 20 cm line, which has health state scores between 0 and 100.

FACIT-F—Functional Assessment of Chronic Illness Therapy-Fatigue. The FACIT system is a collection of quality of life (QOL) questionnaires targeted to the management of cancer and other chronic illnesses. The FACIT fatigue (FACIT-F) questionnaire was developed to assess fatigue associated with anemia. It consists of 13 fatigue-related questions. The responses to the 13 items on the FACIT fatigue questionnaire are each measured on a 4-point Likert scale. The responses to the answers are the following: (i) not at all: 0 points; (ii) a little bit: 1 point; (iii) somewhat: 2 points; (iv) quite a bit: 3 points; (v) very much: 4 points. Thus, the total score ranges from 0 to 52. High scores represent less fatigue. In some embodiment, patients treated according to the disclosed method exhibit a change (reduction from baseline) in the FACIT-F score.

WPAI—Work Productivity and Activity Impairment Questionnaire Ulcerative Colitis. The Work Productivity and Activity Index assesses the impact of the condition on work productivity losses and impairment in daily activity. WPAI has six items covering four domains: (1) Absenteeism (work time missed), measured as the number of hours missed from work in the past 7 days due to a condition related problems. Scores are expressed as impairment percentages, adjusting for hours actually worked according to the WPAI scoring algorithm; (2) Presenteeism (impairment at work/reduced on-the-job effectiveness), measured as the impact of the condition on productivity while at work (i.e., reduced amount or kind of work, or not as focused as usual). Responses are recorded on a 0-10 Likert scale (where, 0=no effect of UC on work and 10=severe impact of UC while at work); (3) Productivity loss (overall work impairment), measured as the sum of hours missed due to condition (i.e., absenteeism) and number of hours worked with impairment (i.e., product of number of hours worked and presenteeism); and (4) Activity impairment (i.e., activities other than paid work like work around house, cleaning, shopping, traveling, studying), recorded and scored in the same way as presenteeism. Higher numbers indicate greater impairment and less productivity.

PGIC—Patient Global Impression of Change. The PGIC is a self-administered instrument that assesses change in the overall symptoms due to UC. The PGIC is one item in which subjects are asked to rate overall improvement since start of the treatment. Subjects rate their change as "Very much improved," "Much improved," "Minimally improved," "No change," "Minimally worse," "Much worse" and Very much worse.

PGIS—Patient Global Impression of Severity. The PGIS is a self-administered instrument that assesses the severity of the overall symptoms due to ulcerative colitis. The PGIS is one item in which subjects are asked to rate overall severity of symptoms over the past week. Subjects rate their change as "Absent," "Minimal," "Mild," "Moderate," "Moderately severe," "Severe" and "Very severe."

UC-SQ—Ulcerative Colitis Symptoms Questionnaire. The Ulcerative Colitis Symptoms Questionnaire (UC-SQ) is a UC-specific instrument composed of 17 items. UC-SQ was developed to assess UC related gastrointestinal symptoms (e.g., frequent bowel movements, abdominal pain, cramping) and nongastrointestinal symptoms (e.g., joint pain and sleep difficulties). Each symptom item 1-9 can be responded on Likert-type of options such as (i) Not at all: 0 points; (ii) A little bit: 1 point; (iii) Somewhat: 2 points; (iv) Quite a bit: 3 points; (v) Very much: 4 points. Each symptom item 10-17 can be responded on Likert-type of options such as (i) Never: 0 points; (ii) Rarely: 1 point; (iii) Sometimes: 2 points; (iv) Often: 3 points; (v) Always: 4 points. Overall symptom scores are calculated by combining ratings of the individual items, with higher scores indicating greater severity.

HCRU—Health Care Resource Utilization. Health Care Resource Utilization data on number of all-cause and UC-related hospitalizations and surgeries will be collected Results Results of this study are provided in FIGS. 29 to 41E. Overall, the study met the primary and all ranked secondary endpoints, demonstrating superiority of upadacitinib at doses of 15 mg and 30 mg once daily, as maintenance therapy for 52 weeks versus placebo (PB 0, withdrawal from upadacitinib treatment; p<0.001) in subjects with moderately to severely active Ulcerative Colitis (UC) who responded to 8 weeks of upadacitinib 45 mg once daily induction treatment (FIG. 29). The primary endpoint of clinical remission per Adapted Mayo score at Week 52 was achieved by statistically significantly higher proportion of subjects in both upadacitinib treatment groups (42.3% for upadacitinib 15 mg, and 51.7% for upadacitinib 30 mg) than in the PB 0 group (withdrawal from upadacitinib treatment: 12.1%; p<0.001). Corticosteroid-free remission was achieved in 57% of patients in the 15 mg cohort and 68% of patients in the 30 mg cohort, and who were in remission at the completion of the 8-week induction studies. These rates were significantly higher for the 15 mg and 30 mg upadacitinib treated patients relative to the placebo group (22%; (p<0.001). The maintenance efficacy results are summarized in Table 32. An overview of primary and ranked secondary endpoints is provided in FIG. 29.

TABLE 32

Maintenance efficacy result summary
Phase 3 Maintenance Efficacy Results at Week 52*,[1]

|  | Upadacitinib 15 mg, once daily (n = 148) | Upadacitinib 30 mg, once daily (n = 154) | Placebo (n = 149) |
| --- | --- | --- | --- |
| Clinical remission[a] | 42% | 52% | 12% |
| Endoscopic improvement[b] | 49% | 62% | 14% |
| Histologic-endoscopic mucosal improvement[c] | 35% | 49% | 12% |

TABLE 32-continued

Maintenance efficacy result summary
Phase 3 Maintenance Efficacy Results at Week 52*,[1]

|  | Upadacitinib 15 mg, once daily (n = 148) | Upadacitinib 30 mg, once daily (n = 154) | Placebo (n = 149) |
|---|---|---|---|
| Corticosteroid-free clinical remission[d] | 57% | 68% | 22% |

*Primary endpoint was clinical remission (per Adapted Mayo Score) at week 52. Not all secondary endpoints are shown. All primary and secondary endpoints achieved p-values of <0.001 versus the placebo group.
[a]Clinical remission (per Adapted Mayo Score) is defined as stool frequency subscore (SFS) ≤ 1 and not greater than baseline, rectal bleeding subscore (RBS) of 0 and endoscopic subscore ≤ 1.
[b]Endoscopic improvement is defined as endoscopic subscore ≤ 1.
[c]Histologic-endoscopic mucosal improvement is defined as an endoscopic subscore of ≤ 1 and Geboes score ≤ 3.1.
[d]Corticosteroid-free remission is defined as clinical remission at week 52 and corticosteroid free for ≥90 days prior to week 52 among patients with clinical remission after 8 weeks of induction treatment. N = 47, 58 and 54 for upadacitinib 15 mg, upadacitinib 30 mg, and placebo group, respectively.

As shown in FIG. 30 and FIG. 31, the clinical response per Partial Adapted Mayo Score and clinical remission rate per Partial Mayo Score was maintained over time until Week 52 in both upadacitinib groups. Clear dose response was observed in the primary and most of the secondary endpoints. The remission rates at 30 mg were generally higher than at 15 mg across the primary and secondary endpoints, Endoscopic remission and mucosal healing remission rate were similar in the 15 mg and 30 mg groups.

Upadacitinib pharmacokinetics were consistent between the induction and maintenance periods in subjects with UC. Both upadacitinib doses were generally safe and well tolerated in subjects with UC. No new safety risks were identified in this UC study compared to the known safety profile of upadacitinib.

Statistical Analysis

The primary efficacy objective was assessed on the ITTA population, which was planned to comprise of the first 450 subjects enrolled under 52-week maintenance protocol in Cohort 1; subjects received 8-week UPA 45 mg QD induction treatment and at least 1 dose of study drug in the Maintenance Study. The 450 subjects were planned to be randomized in a 1:1:1 ratio to upadacitinib 15 mg QD, upadacitinib 30 mg QD or placebo. The randomization was stratified by Bio-IR status (Bio-IR; non-Bio-IR) at the Induction Baseline (referred to as Baseline hereafter), clinical remission status at Week 0 of the Maintenance Study (referred to as Week 0 hereafter) (yes; no), corticosteroid usage at Week 0 (yes; no), and induction dosage for subjects enrolled from the Phase 2b Induction Study.

The ITTA population included 451 subjects. Key demographics and baseline characteristics were generally balanced across treatment groups. A higher rate of discontinuation from study drug was observed in placebo group (65.8%) vs. upadacitinib treatment groups (upadacitinib 15 mg QD group 33.1%, and upadacitinib 30 mg QD group 21.4%), primarily due to lack of efficacy (Table 33).

TABLE 33

Subject disposition

| Subject Disposition[2] | Placebo (N = 149) n (%) | UPA 15 mg QD (N = 148) n (%) | UPA 30 mg QD (N = 154) n (%) |
|---|---|---|---|
| Completed the Study Drug | 51 (34.2) | 99 (66.9) | 121 (78.6) |
| Prematurely Discontinued from Study Drug | 98 (65.8) | 49 (33.1) | 33 (21.4) |

TABLE 33-continued

Subject disposition

| Subject Disposition[2] | Placebo (N = 149) n (%) | UPA 15 mg QD (N = 148) n (%) | UPA 30 mg QD (N = 154) n (%) |
|---|---|---|---|
| Adverse events | 14 (9.4) | 4 (2.7) | 8 (5.2) |
| Withdrew consent | 1 (0.7) | 1 (0.7) | 4 (2.6) |
| Lack of efficacy[3] | 74 (49.7) | 35 (23.6) | 12 (7.8) |
| Lost to follow-up | 0 | 0 | 1 (0.6) |
| COVID-19 infection | 0 | 0 | 1 (0.6) |
| COVID-19 logistical restrictions | 0 | 0 | 1 (0.6) |
| Other | 9 (6.0) | 9 (6.1) | 6 (3.9) |

[1]ITTA: the first 451 subjects enrolled under 52-week maintenance protocol in Cohort 1; subjects received 8-week UPA 45 mg QD induction treatment and at least 1 dose of study drug in the Maintenance Study.
[2]Primary reason.
[3]Include subjects who early escaped to extension study due to experiencing loss of response (in two consecutive visits at least 14 days apart) as defined in the protocol.

Response rate in clinical remission per Adapted Mayo Score at Week 52 was consistent across subgroups of Bio-IR and Non-Bio-IR (Table 34 and Forest plots (FIG. 32 and FIG. 33)). The 95% confidence intervals for the treatment difference between each UPA dose and placebo in all subgroups excluded zero favoring upadacitinib, except those with sample size <5.

TABLE 34

CLINICAL REMISSION PER ADAPTED MAYO SCORE AT WEEK 52 BY BIO-IR STATUS (BIO-IR, NON-BIO-IR) (ITTA[1]; NRI-C[2])

| Bio-IR Status | Placebo N % (n) | UPA 15 mg QD N % (n) | UPA 30 mg QD N % (n) | Treatment Difference vs. PBO (%) 95% CI[3] | |
|---|---|---|---|---|---|
|  |  |  |  | UPA 15 mg | UPA 30 mg |
| Bio-IR | N = 81 7.5% (6) | N = 71 40.5% (29) | N = 73 49.1% (36) | 33.0 [20.1, 45.9] | 41.6 [28.6, 54.7] |
| Non-Bio-IR | N = 68 71.6% (12) | N = 77 43.9% (34) | N = 81 54.0% (44) | 26.3 [11.9, 40.6] | 36.3 [22.1, 50.6] |

[1]ITTA: the first 451 subjects enrolled under 52-week Maintenance protocol in Cohort 1, and who received 8-week UPA 45 mg QD induction treatment, and at least 1 dose of study drug in the Maintenance Study.
[2]NRI-C: Non-Responder Imputation [NRI] incorporating Multiple Imputation [MI] for missing data due to COVID-19.
[3]95% CI for response rate difference (UPA − Placebo) was calculated based on normal approximation to the binomial distribution. The calculations were based on non-responder imputation incorporating multiple imputation to handle missing data due to COVID-19 or non-responder imputation if there were no missing data due to COVID-19.

Further graphical illustrations of study results with respect to various endpoints, as well as exposure-response relationships, are provided in FIGS. 34-41E. Notably, a trend was observed for increase in the % of subjects achieving each of the evaluated endpoints with increasing upadacitinib $C_{avg}$ (FIGS. 40A-40E), Specifically, an exposure-response trend was observed for Week 52 clinical remission, clinical remission & steroid free for ≥90 days (among all subjects in maintenance), endoscopic improvement, endoscopic remission, and HEMI within the 15 mg to 30 mg exposure range. The trend was less apparent for endoscopic remission than for the other efficacy endpoints. The efficacy exposure-response trends were more clearly observed in subjects who had not achieved clinical remission at the end of induction than in those had achieved remission at the end of induction. Based on preliminary exposure-response models, 30 mg is predicted to provide ~8% to 10% greater efficacy for clinical remission, clinical remission & steroid free for ≥90 days, endoscopic improvement, and HEMI compared to 15 mg QD exposures. Without wishing to be bound by theory, the data suggests that exposures from the 15 mg dose may be adequate in patients who achieved remission at end of 8-weeks of induction.

Example 21: Clinical Study for Crohn's Disease

This study (Study M14-431) was a Phase 3, randomized, double-blind, placebo-controlled induction study to evaluate the safety and efficacy of upadacitinib (UPA) compared to placebo (PBO) in adult subjects with moderately to severely active Crohn's disease (CD) who have inadequately responded to or are intolerant to biologic therapy (Bio-IR). This study was part of an overall induction and maintenance study program as illustrated in FIG. 42 and FIG. 43.

Study Population:

Males and females between 18 and 75 years of age (or minimum age of adult consent according to local regulations) with a confirmed diagnosis of CD for at least 3 months and moderately to severely active CD who have inadequately responded to or are intolerant to biologic therapy. Moderately to severely active CD was defined by: Average daily very soft or liquid stool frequency (SF)≥4 AND/OR average daily abdominal pain (AP) score ≥2 (values represent the unweighted daily averages of the corresponding subscores from the Crohn's Disease Activity Index [CDAI]); and Evidence of mucosal inflammation, defined as Simplified Endoscopic Score for CD (SES-CD)≥6 (≥4 for subjects with isolated ileal disease), excluding the presence of narrowing component. Subjects must have had an inadequate response or intolerance to one or more biologic agents for CD (adalimumab, certolizumab, infliximab, ustekinumab and/or vedolizumab). The study allowed enrollment of up to 35% of subjects who have demonstrated inadequate response or intolerance to 3 or more biologics.

Methodology:

Study M14-431 was a Phase 3, randomized, double-blind, placebo-controlled induction study to evaluate the efficacy and safety of upadacitinib, an orally administered Janus kinase 1 inhibitor, in adult subjects with moderately to severely active CD who have inadequately responded to or are intolerant to biologic therapy. Subjects who consent and meet all of the inclusion criteria and none of the exclusion criteria were enrolled into this study, which encompassed 3 parts: (Part 1) a randomized, double-blind, placebo controlled induction; (Part 2) an open-label, single-arm active induction; and (Part 3) an Extended Treatment Period for non-responders from Part 1 or Part 2.

Part 1

In Part 1, subjects (n=495) were randomized in a 2:1 ratio to upadacitinib 45 mg once daily (QD) or matching placebo for 12 weeks. The randomization was stratified by baseline corticosteroid use (yes or no), endoscopic disease severity (SES-CD<15 and ≥15), and number of prior biologic treatments (>1 and ≤1). The data collected from subjects from Part 1 was used for the primary efficacy analysis. Visits during the study were to occur at Baseline and Weeks 2, 4, 8, and 12/Premature Discontinuation (PD) to collect clinical, endoscopic, and laboratory assessments of disease activity. The last dose of study drug during this period was to be taken the day prior to the Week 12 visit.

At Week 12, subjects achieving clinical response, defined as ≥30% decrease in average daily very soft or liquid SF and/or ≥30% decrease in average daily AP score (both not worse than Baseline) were eligible to enter the 52-week, double-blind, maintenance portion of Study M14-430. All subjects who did not achieve clinical response at Week 12 were enrolled in Part 3 (Extended Treatment Period) and receive double-blind upadacitinib until Week 24/PD. Subjects were not eligible to enter Study M14-430 until the ileocolonoscopy procedure at Week 12 was completed. If the COVID-19 pandemic precluded a subject from undergoing an endoscopy, the subject was enrolled in Study M14-430 if clinical response was achieved at Week 12.

Part 2

Part 2 was an open-label portion (open-label cohort) of this study. Once enrollment in Part 1 was complete, 129 subjects were enrolled in Part 2 to receive open-label upadacitinib 45 mg QD for 12 weeks. The objective of Part 2 was to have a sufficient number of subjects with clinical response re-randomized in the double-blind, maintenance portion of Study M14-430, while minimizing unnecessary exposure to placebo. The data collected from subjects from Part 2 were not part of the primary efficacy analysis for this study, used descriptive statistics, and were reported separately in the clinical study report. Visits during the study occurred at Baseline and Weeks 2, 4, 8, and 12/PD to collect clinical, endoscopic, and laboratory assessments of disease activity. At Week 12, subjects achieving clinical response were eligible to enter Study M14-430. Subjects who did not achieve clinical response at Week 12 were eligible to participate in Part 3 (Extended Treatment Period) to receive open-label upadacitinib 30 mg QD until Week 24/PD.

Part 3

Part 3 was a 12-week Extended Treatment Period consisting of 3 cohorts of subjects who did not achieve clinical response at Week 12 in Part 1 or Part 2. Clinical response was defined as ≥30% decrease in average daily very soft or liquid SF and/or ≥30% decrease in average daily AP and both not greater than Baseline. The objectives of Part 3 were to offer blinded upadacitinib induction treatment to placebo non-responders from Part 1 and to evaluate delayed clinical response to upadacitinib in subjects who did not initially respond to upadacitinib during Part 1 or Part 2. Part 3 consisted of 3 cohorts, and the treatment assignment depended on the treatment received in Part 1 or Part 2, as follows:

Cohort 1: Subjects who received placebo in Part 1 and did not achieve clinical response at Week 12 are eligible to receive double-blind induction treatment with upadacitinib 45 mg QD for 12 weeks (until Week 24).

Cohort 2: Subjects who received double-blind upadacitinib in Part 1 and did not achieve clinical response at Week 12 were eligible to receive double-blind upadacitinib 30 mg QD for 12 weeks (until Week 24).

Cohort 3: Subjects who received open-label upadacitinib during Part 2 and did not achieve clinical response at Week 12 were eligible to receive open-label upadacitinib 30 mg QD for 12 weeks (until Week 24).

Subjects in Cohort 1 and 2 remained blinded to treatment to avoid unmasking the treatment received during Part 1. The data collected from subjects from Part 3 was not be part of the primary efficacy analysis for this study, used descriptive statistics, and were reported separately in the clinical study report. Subjects were not eligible to enter in Part 3 until the Week 12 endoscopy was completed. If the COVID-19 pandemic precluded a subject from undergoing an endoscopy, and the subject had not achieved clinical response, the subject entered Part 3 of Study M14-431. Visits occurred at Weeks 16, 20 and 24/PD to collect clinical, endoscopic, and laboratory assessments of disease activity. During Part 3, subjects with persistent symptoms or worsening of CD were discontinued.

At Week 24, subjects who achieved clinical response were eligible to enter Study M14-430. Subjects were not eligible to enter Study M14-430 until the ileocolonoscopy procedure at Week 24 for evaluation of mucosal inflammation was completed. If the COVID-19 pandemic precluded a subject from undergoing an endoscopy, the subject was enrolled in Study M14-430 if clinical response was achieved at Week 24. Subjects who do not achieve clinical response at Week 24 were discontinued from Study M14-431 and received standard of care treatment at the investigator's discretion. Subjects who do not achieve clinical response at Week 24 and all subjects who prematurely discontinued the study had a follow-up visit 30 days from the last dose of study drug to collect information on new or ongoing adverse events (AEs) and laboratory assessments. Subjects were discontinued from the study if they withdrew consent or if they were deemed unsuitable to continue for any reason by the investigator. The duration of the study was up to 33 weeks, including Screening Period (5 weeks), a 12-week double-blind or open-label cohort Induction Period (Part 1 and Part 2), a 12-week Extended Treatment Period (Part 3), and a 30-day follow-up for subjects who do not enroll into Study M14-430.

At the Screening Visit, all subjects were provided with an electronic diary. Subjects were instructed and trained on how to record CD-related symptoms (including total and very soft and liquid number of stools and abdominal pain), general well-being and use of antidiarrheals on a daily basis; and use of medications for endoscopy preparation throughout the study. The very soft and liquid stools were defined as consistency Type 6 or Type 7 based on the Bristol Stool Chart. The diary was reviewed by site personnel with the subject at each visit and for the assessment of the clinical endpoints. At each Study Visit, routine physical examination included evaluation of vital signs, extra intestinal manifestations, and presence or absence of fistulas; calculation of CDAI score, average daily very soft or liquid SF and average daily AP (SF and AP entries from the most recent 7-day period prior to each study visit were used); monitoring of AEs; reporting of concomitant medications and laboratory assessments was performed. The very soft or liquid SF and AP score values represented the unweighted daily averages of the corresponding subscores from the CDAI. Additionally, subjects completed quality of life (QoL), CD symptoms, symptoms impact on QoL, and work productivity questionnaires throughout the study. Subjects underwent a full colonoscopy (ileocolonoscopy) for evaluation of mucosal inflammation using the SES-CD. All endoscopies were centrally read to document eligibility at Screening and for Week 12 and 24/PD assessments. Intestinal biopsies during the endoscopic evaluation were collected for histologic assessment and exploratory research during endoscopy visits at Screening, Week 12, and Week 24/PD in approximately 200 subjects (intestinal biopsy substudy). Optional blood samples were collected for exploratory research at Baseline, Week 4, Week 12, and Week 24/PD. Optional stool collections were done at Baseline, Week 4 and Week 12 for exploratory evaluation of biomarkers in approximately 200 subjects (fecal biomarker substudy).

Investigational Product: Upadacitinib (ABT-494); film-coated tablet
Mode of Administration: Oral, taken at approximately the same time each day
Doses:
  Part 1: upadacitinib 45 mg QD
  Part 2: upadacitinib 45 mg QD
  Part 3: upadacitinib 45 mg QD or upadacitinib 30 mg QD
Reference Therapy: Part 1: placebo
Mode of Administration: Oral
Duration of Treatment: 12 weeks for subjects achieving clinical response at Week 12; or 24 weeks for subjects who did not achieve clinical response at Week 12.
Diagnosis and Main Criteria for Inclusion/Exclusion
  The main criteria for inclusion, and exclusion for the study were as follows.
Main Inclusion
1. Confirmed diagnosis of CD for at least 3 months prior to Baseline. Appropriate documentation of biopsy results consistent with the diagnosis of CD, as determined by the investigator, were available.
2. SES-CD (excluding the presence of narrowing component)≥6 (or ≥4 for subjects with isolated ileal disease), as confirmed by a central reader.
3. Average daily very soft or liquid SF≥4.0 AND/OR average daily AP score ≥2.0 at Baseline.
4. Demonstrated an inadequate response or intolerance to one or more of the following biologic agents:
    At least one 6-week induction regimen of infliximab (≥5 mg/kg intravenous [IV] at Baseline and Weeks 2, and 6),
    At least one 4-week induction regimen of adalimumab (one 160 mg subcutaneous [SC] dose at Baseline, followed by one 80 mg SC dose at Week 2 [or one 80 mg SC dose at Baseline, followed by one 40 mg SC dose at Week 2, in countries where this dosing regimen was approved])
    At least one 4-week induction regimen of certolizumab pegol (400 mg SC at Baseline and Weeks 2, and 4)
    At least one 6-week induction regimen of vedolizumab (300 mg IV at Baseline and Weeks 2, and 6)
    At least one 8-week induction regimen of ustekinumab [260 mg (≤55 kg) or 390 mg (≥55 to ≤85 kg) or 520 mg (≥85 kg) IV, followed by 90 mg SC at Week 8]
    Recurrence of symptoms during scheduled maintenance dosing following prior clinical benefit of the above biologics
    Intolerance to a biologic may include, but not limited to infusion-related reaction, rash, serum sickness, anaphylaxis, elevated liver enzymes, demyelination, congestive heart failure, infection. Demonstration of intolerance requires no minimum dose or duration of use.
Main Exclusion
1. Subject with a current diagnosis of ulcerative colitis or indeterminate colitis.
Concomitant Medications and Treatments
2. Subject on CD related antibiotics who:
    had not been on stable doses of these medications for at least 14 days prior to Baseline, or
    had discontinued these medications within 14 days of Baseline.
3. Subject on oral aminosalicylates who:
    had not been on stable doses of these medications for at least 14 days prior to Baseline, or
    had discontinued these medications within 14 days of Baseline.
4. Subject on corticosteroids who meet the following:
    prednisone or equivalent dose >30 mg/day; or
    budesonide >9 mg/day; or
    had not been on the current course for at least 14 days prior to Baseline and on a stable dose for at least 7 days prior to Baseline.

5. Subject on MTX who:
   had not been on the current course for ≥42 days prior to Baseline, and
   had not been on a stable dose for ≥28 days prior to Baseline
6. Infection(s) requiring treatment with intravenous (IV) anti-infectives within 30 days prior to the Baseline Visit or oral/intramuscular (IM) anti-infectives within 14 days prior to the Baseline Visit.
7. Subject requiring or receiving any parenteral nutrition and/or exclusive enteral nutrition.
8. Subject who received oral or parenteral traditional Chinese medicines within 30 days prior to Baseline.
9. Subject who received any live vaccination within 30 days (or longer if required locally [e.g., 8 weeks for Japan]) prior to Baseline, or who were expected to need live vaccination during study participation including at least 30 days (longer if required locally [e.g., 8 weeks for Japan]) after the last dose of study drug.
10. Subject who received cyclosporine, tacrolimus, mycophenolate mofetil, or thalidomide within 30 days prior to Baseline.
11. Subject who received azathioprine (AZA) or 6-mercaptopurine (6-MP) within 10 days of Baseline.
12. Subject who received fecal microbial transplantation within 30 days prior to Baseline.
13. Subject who received nonsteroidal anti-inflammatory drugs (NSAIDs) within 7 days prior to Baseline, except topical NSAIDs and low dose aspirin for cardiovascular protection.
14. Systemic use of known strong cytochrome P450 (CYP) 3A inhibitors or strong CYP3A inducers from Screening through the end of the study (refer to Table 1 for examples of commonly used strong CYP3A inhibitors and inducers.
15. Subject who received any of the following agents:
    adalimumab, certolizumab, golimumab, infliximab, natalizumab, vedolizumab within 8 weeks prior to Baseline; or
    ustekinumab within 12 weeks prior to Baseline.
      Note: If there was proper documentation of an undetectable drug level measured by a commercially available assay for any of the approved biologics above, there was no minimum washout prior to Baseline.
    any investigational agent within 30 days or 5 half-lives prior to Baseline, whichever was longer, or was currently enrolled in another interventional study.
16. Subject with previous exposure to a JAK inhibitor (e.g., tofacitinib, baricitinib, filgotinib) within 30 days from Baseline. Note: Subjects who received a JAK inhibitor prior to study entry may be enrolled if they have not had inadequate response or loss of response.
17. Subject was taking both oral budesonide (or oral beclomethasone) and oral prednisone (or equivalent) simultaneously, with the exception of topical or inhalers within 14 days prior to Screening or during the Screening Period.
18. Subject received IV corticosteroids within 14 days prior to Screening or during the Screening Period.
19. Subject received therapeutic enema or suppository (i.e., rectal aminosalicylates/corticosteroids), other than required for endoscopy, within 14 days prior to endoscopy used for Screening or during the Screening period.
20. Subject received apheresis (e.g., Adacolumn apheresis) within 60 days prior to Screening or during the Screening Period.
21. Subject used cannabis, either recreational or for medical reasons, within 14 days prior to Baseline or any history of clinically significant (per investigator's judgment) drug or alcohol abuse in the last 6 months.
22. Subject received stem cell transplantation (except for local stem cell therapy for complex perianal fistula).
23. Subject was a previous recipient of an organ transplant which requires continued immunosuppression. CD Related
24. Subject with the ongoing following known complications of CD:
    abscess (abdominal or peri-anal)
    symptomatic bowel strictures
    >2 entire missing segments of the following 5 segments: terminal ileum, right colon, transverse colon, sigmoid and left colon, and rectum
    fulminant colitis
    toxic megacolon
    or any other manifestation that might require surgery while enrolled in the study.
25. Subject with ostomy or ileoanal pouch
26. Subject diagnosed with conditions that could interfere with drug absorption including but not limited to short gut or short bowel syndrome.
27. Subject with surgical bowel resection within the past 3 months prior to Baseline, or a history of ≥3 bowel resections
Safety
28. Subject with positive *Clostridium difficile* (*C. difficile*) toxin stool assay during Screening.
29. Any active, chronic or recurrent infection that, based on the investigator's clinical assessment, made the subject an unsuitable candidate for the study, including hepatitis B virus (HBV) or hepatitis C virus (HCV), recurrent or disseminated (even a single episode) herpes zoster, disseminated (even a single episode) herpes simplex, or HIV infection. Active HBV, HCV and HIV are defined as:
    HBV: hepatitis B surface antigen (HBs Ag) positive (+) or detected sensitivity on the HBV-deoxyribonucleic acid (DNA) polymerase chain reaction (PCR) qualitative test for hepatitis B core antibody (HBc Ab) positive (+) subjects;
    HCV: HCV ribonucleic acid (RNA) detectable in any subject with anti-HCV antibody (HCV Ab);
    HIV: confirmed positive anti-HIV antibody (HIV Ab) test;
    Confirmed COVID-19: the Baseline visit must be at least 14 days from onset of signs/symptoms or positive SARS-CoV-2 test, symptomatic subjects must have recovered, defined as resolution of fever without use of anti-pyretics and improvement in symptoms;
    Suspected COVID-19: subjects with signs/symptoms suggestive of COVID-19, known exposure, or high risk behavior should undergo molecular (e.g., PCR) testing to rule out SARS-CoV-2 infection or must be asymptomatic for 14 days from a potential exposure.
30. Subject had active TB or meets TB exclusionary parameters
31. History of any malignancy except for successfully treated nonmelanoma skin cancer (NMSC) or localized carcinoma in situ of the cervix.
32. Prior or current gastrointestinal dysplasia, other than completely removed lowgrade dysplastic lesions in any biopsy performed during or before the Screening endoscopy.
33. History of gastrointestinal perforation (other than appendicitis or mechanical injury), diverticulitis or significantly increased risk for gastrointestinal perforation per investigator judgment.

34. Female who was pregnant, breastfeeding, or was considering becoming pregnant during the study or within 30 days after the last dose of study drug.
35. History of an allergic reaction or significant sensitivity to constituents of the study drug (and its excipients) and/or other products in the same.
36. Laboratory values meeting the following criteria within the Screening period prior to the first dose of study drug:
    Serum aspartate transaminase (AST) or alanine transaminase (ALT) >2.0× upper limit of the reference range (ULN)
    Total white blood cell count <2500/µL,
    Estimated glomerular filtration rate by simplified 4-variable Modification of Diet in Renal Disease (MDRD) formula <30 mL/min/1.73 m2
    Hemoglobin <9 g/dL;
    Platelet count <100,000/µL,
    Absolute neutrophil count <1200/µL,
    Absolute lymphocyte count <750/µL.
37. Any of the following cardiovascular conditions or thrombotic conditions within 6 months prior to the study)
    cerebrovascular accident, myocardial infarction, coronary stenting;
    current uncontrolled hypertension as defined by a confirmed systolic blood pressure (BP)≥160 mmHg or diastolic BP≥100 mmHg;
    prior history of thrombotic events including deep venous thrombosis and pulmonary embolism;
    known inherited conditions that predispose to hypercoagulability.
38. History of clinically significant medical conditions or any other reason that in the opinion of the investigator would have interfered with the subject's participation in this study or would have made the subject an unsuitable candidate to receive study drug or would have put the subject at risk by participating in the study.
39. For Japan subjects only: positive result of beta-D-glucan, or two consecutive indeterminate results of beta-D-glucan during the Screening Period.

Concomitant CD-Related Medications (Antibiotics, Aminosalicylates, and/or Methotrexate)

All subjects receiving a stable dose of CD-related antibiotics, aminosalicylates, or methotrexate (MTX) at Baseline maintained their concomitant treatments without dose changes through the end of the study. Initiating and/or changing doses of these medications was prohibited during the study. Doses of CD-related antibiotics, aminosalicylates, or MTX were decreased only in the event of moderate-to-severe treatment related toxicities. Setons were authorized as concomitant therapy in subjects with perianal fistulas and documented in the eCRF under concomitant medications.

Concomitant Corticosteroids

Subjects who entered the study on oral corticosteroids were not allowed to change the corticosteroid dose during the first 4 weeks of the induction treatment period. Doses of corticosteroids were decreased during the first 4 weeks only in the event of moderate-to-severe treatment related toxicities. At Week 4, subjects had their corticosteroid dose reduced according to a tapering schedule as described. At Week 4, subjects who were on prednisone (or oral equivalent) or oral budesonide had their corticosteroid dose tapered, according to the tapering schedule. Subjects who did not achieve clinical response at Week 12 in Part 1 or Part 2, and enter Part 3 without having completed the steroid taper resumed the corticosteroid taper at Week 16, according to the tapering schedule. Initiating locally acting (rectal or suppository) or systemic corticosteroids for any reason was prohibited during the induction treatment period and was considered a protocol deviation and was discussed with the TA MD. Use of inhaled or topical (except rectal or suppository) corticosteroids was not restricted. Subjects were not allowed to be on both budesonide (for CD disease) and prednisone (or equivalent) simultaneously.

Biologic Therapies

Subjects must have discontinued any biologic therapy prior to the first dose of study drug as specified in the washout procedures. Therapies including but not limited to the following biologic therapies were prohibited medications during the study:
    Adalimumab
    Etanercept
    Infliximab
    Abatacept
    Anakinra
    Rituximab
    Natalizumab
    Tocilizumab
    Golimumab
    Certolizumab
    Ustekinumab
    Belimumab
    Secukinumab
    Vedolizumab Strong CYP3A Inhibitors or Inducers Systemic use of known strong CYP3A inhibitors or strong CYP3A inducers was excluded from the Screening Visit through the end of the study.

Other Medications Prohibited During the Study
    JAK inhibitors (e.g., tofacitinib [Xeljanz®])
    Cyclosporine, tacrolimus, thalidomide, mycophenolate mofetil, AZA, or 6-MP.
    NSAIDs (except topical NSAIDs and the use of low dose aspirin for cardiovascular protection).
    Rectal therapy with any therapeutic enemas or suppositories, with the exception of those required for endoscopy.
    Any parenteral nutrition and exclusive enteral nutrition.
    Cytapheresis treatment (granulocytapheresis, etc.) (in Japan and China only).
    Cannabis Criteria for Evaluation Outcomes and Questionnaires The following outcomes and questionnaires were completed at the time points as indicated.
    Inflammatory Bowel Disease Questionnaire (IBDQ)
    Work Productivity and Activity Impairment Questionnaire (WPAI)-CD
    Crohn's Symptoms Severity Questionnaire (CSS)
    Short Form-36 (SF-36)
    European Quality of Life 5 Dimensions 5 Levels (EQ-5D-5L)
    Functional Assessment of Chronic Illness Therapy-Fatigue (FACIT-F)
    Patient Global Impression of Change (PGIC)
    Patient Global Impression of Severity (PGI-S)
    Bristol Stool Chart Primary/Secondary Efficacy Endpoints and the Overall Type-I Error Control The study had different sets of primary and secondary endpoints for EU/EMA (Table 35) or for US/FDA (Table 36) regulatory purposes. Endpoints and the corresponding overall type-I error control details are provided below and in FIG. 26.

Endpoint Definitions:
- Clinical remission per patient reported outcomes (PROs): Average daily very soft or liquid SF≤2.8 AND average daily AP score ≤1.0 and both not greater than baseline
- Clinical remission per CDAI: CDAI<150
- Steroid-Free Clinical Remission per CDAI/PRO: Discontinuation of corticosteroid use and clinical remission per CDAI/PRO at Week 12, among subjects taking corticosteroids at Baseline
- Clinical response 100 (CR-100): decrease of ≥100 points in CDAI from Baseline
- Enhanced Clinical Response: 60% decrease in average daily very soft or liquid SF and/or 35% decrease in average daily AP score and both not greater than baseline, or clinical remission
- Endoscopic remission: SES-CD≤4 and at least 2-point reduction from Baseline and no subscore >1 in any individual variable, as scored by central reviewer
- Endoscopic response: Decrease in SES-CD≥50% from Baseline of the induction study (or for subjects with an SES-CD of 4 at Baseline of the induction study, at least a 2-point reduction from Baseline), as scored by central reviewer.

TABLE 35

Primary and Key Secondary Endpoints for EU/EMA Regulatory Purposes

| Endpoint | Overall Type-I Error Control |
|---|---|
| Co-Primary Endpoints:<br>    Achievement of clinical remission per PROs at Week 12<br>    Achievement of endoscopic response at Week 12 | Co-primary endpoints must be achieved statistical significance simultaneously (alpha = 0.05). |
| Key Secondary Endpoint in Ranked Order:<br>  1. Achievement of clinical remission per CDAI at Week 12<br>  2. Achievement of clinical remission per PROs at Week 4<br>  3. Achievement of endoscopic remission at Week 12<br>  4. Achievement of steroid-free clinical remission per PROs at Week 12, among subjects taking corticosteroids for CD at Baseline<br>  5. Change from Baseline in Functional Assessment of Chronic Illness Therapy-Fatigue (FACIT-F) total score at Week 12<br>  6. Change from Baseline in Inflammatory Bowel Disease Questionnaire (IBDQ) total score at Week 12 | Fixed sequential testing procedure: a secondary endpoint was tested only if the co-primary endpoints and all higher-ranked secondary endpoints achieved statistical significance (alpha = 0.05). |
| Key Secondary Endpoints under Holm Procedure:<br>    Achievement of CR-100 at Week 2<br>    Achievement of CR-100 at Week 12<br>    Occurrence of hospitalizations due to CD during Part 1<br>    Achievement of resolution of extra-intestinal manifestations (EIMs) at Week 12, among subjects with EIMs at Baseline | Holm testing procedure: only if all co-primary endpoints and secondary endpoints 1-6 achieved statistical significance (alpha = 0.05). |

TABLE 36

Primary and Secondary Endpoints for US/FDA Regulatory Purposes

| Endpoint | Overall Type-I Error Control |
|---|---|
| Co-Primary Endpoints:<br>    Achievement of clinical remission per CDAI at Week 12<br>    Achievement of endoscopic response at Week 12 | Co-primary endpoints must be achieved statistical significance simultaneously (alpha = 0.05). |
| Key Secondary Endpoint in Ranked Order:<br>1. Achievement of clinical remission per PROs at Week 12<br>2. Achievement of endoscopic remission at Week 12<br>3. Achievement of steroid-free clinical remission per CDAI at Week 12, among subjects taking corticosteroids for CD at Baseline<br>4. Change from Baseline in FACIT-F total score at Week 12<br>5. Change from Baseline in IBDQ total score at Week 12 | Fixed sequential testing procedure: a secondary endpoint was tested only if the co-primary endpoints and all higher-ranked secondary endpoints achieved statistical significance (alpha = 0.05). |
| Key Secondary Endpoints under Holm Procedure:<br>    Achievement of CR-100 at Week 2<br>    Achievement of CR-100 at Week 12<br>    Achievement of clinical remission per CDAI at Week 4<br>    Occurrence of hospitalizations due to CD during Part 1<br>    Achievement of resolution of extra-intestinal manifestations (EIMs) at Week 12, among subjects with EIMs at Baseline | Holm testing procedure: only if all co-primary endpoints and secondary endpoints 1-5 achieved statistical significance (alpha = 0.05). |

Pharmacokinetic Variables

Upadacitinib plasma concentrations were determined from samples collected at each visit beginning at Week 2. Blood samples at the Week 4 visit were collected prior to dosing if possible. For all other visits, blood samples were collected at any time during the visit. A non-linear mixed effects modeling approach were used to estimate the population central values and the empirical Bayesian estimates of the individual values of upadacitinib oral clearance (CL/F) and volume of distribution (V/F). Additional parameters where estimated when useful in the interpretation of the data.

Safety Variables

Safety analyses were performed on the safety set, which included all subjects who receive at least one dose of study drug. The incidence of AEs, changes in vital signs, physical examination results, and clinical laboratory data were assessed throughout the study. Electrocardiograms were performed at screening, and at the end of each Part 1, 2, 3 of the study. AEs and laboratory data, when available, were graded as described in the National Cancer Institute Common Terminology Criteria for Adverse Events and summarized accordingly. An external, independent Data Monitoring Committee were responsible for monitoring unblended safety data and alerting AbbVie to possible safety concerns related to the conduct of the study.

Statistical Methods

Efficacy

The co-primary endpoints were the proportion of subjects with clinical remission per PROs (EU/EMA) or clinical remission per CDAI (US/FDA) at Week 12 and the proportion of subjects with endoscopic response at Week 12. This study evaluated one induction dose of upadacitinib 45 mg QD. Efficacy analysis was based on all intent-to-treat (ITT) subjects. The ITT analysis set included all randomized subjects who had taken at least one dose of study drug in the double-blind induction period from Part 1. The comparison between treatment groups on the co-primary efficacy endpoints was performed using the Cochran-Mantel-Haenszel (CMH) test and stratified by Baseline corticosteroid use (yes or no), endoscopic disease severity (SES-CD<15 and ≥15), and number of prior biologics used (>1 and ≤1). Both of the co-primary efficacy endpoints were tested at two-sided significance level of 0.05. A CMH-based, two-sided 95% confidence interval for the difference between treatment groups was calculated. If the average daily SF or average daily AP score (EU/EMA) or CDAI (US/FDA) data at Week 12 were missing, the non-responder imputation approach was applied for the clinical remission per PROs and clinical remission per CDAI endpoints, respectively. Subjects who discontinued prior to Week 12 for any reason were considered as "not-achieved" for clinical remission or endoscopic response endpoints. A multiple testing procedure was used to provide strong control of the type 1 error rate at alpha=0.05 (2-sided) across analyses with respect to the co-primary endpoints, and ranked secondary endpoints. Specifically, testing utilized a sequence of hypothesis testing for the co-primary endpoints followed by the ranked secondary endpoints, and began with testing co-primary endpoints using α of 0.05 (2-sided). If both co-primary endpoints achieved statistical significance, continued testing followed a pre-specified weight of α-allocation between individual hypotheses as well as between families of hypotheses. The details of the testing procedure are specified and documented in the statistical analysis plan (SAP). In general, continuous secondary efficacy variables with repeated measurements were analyzed using a Mixed Effect Repeated Measure (MMRM) model. Continuous secondary efficacy variables which were collected at only one post-baseline visit (such as SES-CD) were analyzed using an Analysis of Covariance (ANCOVA) model. Categorical secondary efficacy variables were analyzed using the CMH test controlling for stratification variables. NRI for missing data were used for categorical secondary endpoints.

Pharmacokinetics

A non-linear mixed-effects modeling approach were used to estimate the population central values and the empirical Bayesian estimates of the individual values for upadacitinib oral clearance and volume of distribution. Additional parameters were estimated when useful in the interpretation of the data.

Safety

AEs, laboratory data, and vital signs were the primary safety parameters in this study. All safety comparisons were performed between treatment groups using the safety set. Treatment-emergent AEs were defined as events that began or worsened either on or after the first dose of the study drug and within 30 days after the last dose of the study drug for subjects who did not participate in Study M14-430, or within 30 days after the last dose of study drug in Study M14-431 or first dose of study drug in Study M14-430 if the subject enrolled in Study M14-430, whichever came first. An overview of treatment-emergent AEs, including AEs of special interest, AEs leading to death, AEs leading to PD, AEs by Medical Dictionary for Drug Regulatory Activities preferred term and system organ class, AEs by maximum relationship to study drug, and AEs by maximum severity was summarized by number and percentage. Changes in laboratory data were described using statistical characteristics and comparison between treatment groups performed using a one-way Analysis of Variance. In addition, shift tables and listings were provided for abnormal values, whereby the normal range of the analyzing laboratory was used. Vital signs were analyzed similarly.

Primary Approach to Handle Missing Data

For categorical variables, the primary approach to handle missing data was Non-Responder Imputation (NRI) incorporating Multiple Imputation (MI) for missing data due to COVID-19 (NRI-C). For continuous variables, missing data were handled by Mixed-effect Model Repeat Measurement (MMRM).

Results

Study Summary

This study comprised a 12-week Induction Period (FIG. 45), an option of a 12-week Extended Treatment Period (FIG. 46), and a 30-day Follow-up Period for subjects who did not roll over to the Maintenance Study M14-430. Subjects which entered the study with background corticosteroid had their corticosteroid dose reduced according to the protocol-specified tapering schedule. The clinical response in FIG. 45 and FIG. 46 was defined as ≥30% decrease in average daily very soft or liquid SF and/or ≥30% decrease in average daily AP score, with both SF and AP not worse than Baseline. With reference to FIGS. 45 and 46, the Induction and Extended Treatment Periods were designed as follows:

Induction Period (Baseline to Week 12, (FIG. 27)):

At Baseline, eligible subjects were enrolled to a 12-week Induction Period (double-blinded, placebo (PBO)-controlled [Part 1] or single-arm, open-label [Part 2]). Part 1 was a randomized, double-blind, PBO-controlled part with 12-week induction treatment. Subjects in Part 1 were randomized to either UPA 45 mg QD or matching PBO in a 2:1 ratio. The randomization was stratified by corticosteroid use (yes or no), endoscopic disease severity as evaluated by the Simplified Endoscopic Score for Crohn's Disease (SES-CD; <15 or ≥15), and the number of prior biologic treatments (>1 or ≤1). All primary and secondary efficacy endpoints were analyzed in the ITT1 Population, which was defined as all randomized subjects with at least one dose of study drug in Part 1. To ensure sufficient sample size in the downstream Maintenance Study M14-430, additional subjects were enrolled to a single-arm, open-label arm to receive UPA 45 mg QD 12-week induction treatment (Part 2).

Extended Treatment Period (Week 12 to Week 24, (FIG. 28):

At Week 12, subjects who achieved the clinical response were rolled over to the Maintenance Study M14-430, whereas subjects who did not achieve the clinical response entered an Extended Treatment Period (Part 3). Specifically, subjects who received PBO in Part 1 received UPA 45 mg QD (Cohort 1), whereas subjects who received UPA 45 mg QD in Part 1 received UPA 30 mg QD (Cohort 2). Treatments in Cohort 1 and 2 were given in a blinded fashion. Subjects who received UPA 45 mg QD in Part 2 received open-label UPA 30 mg QD (Cohort 3).

Demographic, Baseline Characteristics, and Subject Disposition

A total of 495 subjects were randomized (171 in PBO and 324 in UPA 45 mg) in Part 1, and all were treated. There were 440 (88.9%) subjects who completed the 12-week induction period of study drug in Part 1 (Table 37). Demographics and baseline characteristics were generally balanced between treatment groups (Table 38). Subject disposition in Part 2 and 3 are presented in Table 39.

TABLE 37

Subject Disposition in Part 1

| Subject Disposition, n (%) | PBO (N = 171) | UPA 45 mg (N = 324) | Total (N = 495) |
| --- | --- | --- | --- |
| Randomized | 171 (100) | 324 (100) | 495 (100) |
| Treated | 171 (100) | 324 (100) | 495 (100) |
| Completed the Study Drug in Part 1 | 149 (87.1) | 291 (89.8) | 440 (88.9) |
| Discontinued Study Drug during Part 1 (Primary Reasons) | 22 (12.9) | 33 (10.2) | 55 (11.1) |
| Adverse event | 5 (2.9) | 16 (4.9) | 21 (4.2) |
| Withdrawal by subject | 8 (4.7) | 7 (2.2) | 15 (3.0) |
| Lost to follow-up | 0 | 1 (0.3) | 1 (0.2) |
| Lack of efficacy | 8 (4.7) | 5 (1.5) | 13 (2.6) |
| COVID-19 infection | 0 | 0 | 0 |
| COVID-19 logistical restrictions | 0 | 0 | 0 |
| Other | 1 (0.6) | 4 (1.2) | 5 (1.0) |
| Discontinued Study Drug during Part 1 (All Reasons) | 22 (12.9) | 33 (10.2) | 55 (11.1) |
| Adverse event | 7 (4.1) | 18 (5.6) | 25 (5.1) |
| Withdrawal by subject | 8 (4.7) | 7 (2.2) | 15 (3.0) |
| Lost to follow-up | 0 | 1 (0.3) | 1 (0.2) |
| Lack of efficacy | 8 (4.7) | 5 (1.5) | 13 (2.6) |
| COVID-19 infection | 0 | 0 | 0 |
| COVID-19 logistical restrictions | 0 | 0 | 0 |
| Other | 2 (1.2) | 6 (1.9) | 8 (1.6) |

TABLE 38

Demographics and Baseline Disease Characteristics

| Demographic and Baseline Characteristics, mean (SD) or n (%) | Part 1 Double-Blind | | Part 2 Open-Label |
| --- | --- | --- | --- |
| | PBO (N = 171) | UPA 45 mg (N = 324) | UPA 45 mg (N = 129) |
| Female | 75 (43.9) | 155 (47.8) | 60 (46.5) |
| Age (years) | 37.5 (12.12) | 38.4 (13.71) | 39.1 (12.05) |
| Weight (kg) | 69.8314 (19.3010) | 69.6181 (18.7540) | 74.3817 (18.6870) |
| Body Mass Index (kg/M^2) | 23.901 (6.1894) | 24.164 (5.9763) | 25.263 (5.9620) |
| Race | | | |
| White | 126 (73.7) | 230 (71.0) | 113 (87.6) |
| Black or African American | 6 (3.5) | 19 (5.9) | 5 (3.9) |
| Asian | 38 (22.2) | 69 (21.3) | 11 (8.5) |
| American Indian/Alaska Native | 1 (0.6) | 1 (0.3) | 0 |
| Multiple | 0 | 5 (1.5) | 0 |
| Disease Duration (years) | 10.9361 (7.9930) | 12.0521 (9.5409) | 11.4030 (8.2380) |
| CD-Related Corticosteroid Use | | | |
| Yes | 60 (35.1) | 108 (33.3) | 46 (35.7) |
| No | 111 (64.9) | 216 (66.7) | 83 (64.3) |
| Number of Prior Biologic Treatments | | | |
| ≤1 | 68 (39.8) | 126 (38.9) | 44 (34.1) |
| 2 | 55 (32.2) | 92 (28.4) | 30 (23.3) |
| ≥3 | 48 (28.1) | 106 (32.7) | 55 (42.6) |
| SES-CD Category | | | |
| <15 | 94 (55.0) | 181 (55.9) | 69 (53.5) |
| ≥15 | 77 (45.0) | 143 (44.1) | 60 (46.5) |
| SES-CD | 14.9 (7.75) | 15.2 (7.82) | 14.9 (6.78) |
| CDAI Score | 308.08 (84.267) | 306.64 (89.423) | 313.50 (99.237) |
| Average Very Soft/Liquid Stool Frequency | 6.0929 (3.3355) | 5.7299 (3.3603) | 5.9103 (3.4082) |
| Average Abdominal Pain | 1.7955 (0.6849) | 1.8508 (0.6913) | 1.9181 (0.7218) |

TABLE 38-continued

Demographics and Baseline Disease Characteristics

| Demographic and Baseline Characteristics, mean (SD) or n (%) | Part 1 Double-Blind | | Part 2 Open-Label |
|---|---|---|---|
| | PBO (N = 171) | UPA 45 mg (N = 324) | UPA 45 mg (N = 129) |
| Hs-CRP (mg/L) | | | |
| Mean (SD) | 18.983 (24.0176) | 20.860 (25.9725) | 17.994 (20.2435) |
| Median (range) | 9.470 (0.41, 126.00) | 10.500 (0.20, 144.00) | 12.600 (0.21, 122.00) |
| Fecal Calprotectin (μg/g) | | | |
| Mean (SD) | 2184.7 (3148.34) | 2286.6 (3880.36) | 2406.4 (3351.27) |
| Median (range) | 1115.0 (30, 19104) | 1041.0 (30, 28800) | 1486.0 (30, 28800) |

TABLE 39

Subject Disposition in Part 2 and Part 3

| | | | Part 3 | |
|---|---|---|---|---|
| Subject Disposition, n (%) | Part 2 OL UPA 45 mg (N = 129) | DB PBO/ UPA 45 mg (N = 78) | DB UPA 45 mg/ UPA 30 mg (N = 69) | OL UPA 45 mg/ UPA 30 mg (N = 14) |
| Treated | 129 (100) | 78 (100) | 69 (100) | 14 (100) |
| Completed the Study Drug | 122 (94.6) | 67 (85.9) | 51 (73.9) | 8 (57.1) |
| Discontinued Study Drug (Primary Reasons) | 7 (5.4) | 11 (14.1) | 18 (26.1) | 6 (42.9) |
| Adverse event | 2 (1.6) | 7 (9.0) | 5 (7.2) | 0 |
| Withdrew consent | 3 (2.3) | 0 | 5 (7.2) | 0 |
| Lost to follow-up | 0 | 0 | 0 | 1 (7.1) |
| Lack of efficacy | 1 (0.8) | 3 (3.8) | 6 (8.7) | 4 (28.6) |
| COVID-19 infection | 0 | 0 | 0 | 0 |
| COVID-19 logistical restrictions | 0 | 0 | 1 (1.4) | 0 |
| Other | 1 (0.8) | 1 (1.3) | 1 (1.4) | 1 (7.1) |
| Discontinued Study Drug (All Reasons) | 7 (5.4) | 11 (14.1) | 18 (26.1) | 6 (42.9) |
| Adverse event | 2 (1.6) | 8 (10.3) | 6 (8.7) | 1 (7.1) |
| Withdrew consent | 3 (2.3) | 0 | 6 (8.7) | 0 |
| Lost to follow-up | 0 | 0 | 0 | 2 (14.3) |
| Lack of efficacy | 2 (1.6) | 3 (3.8) | 7 (10.1) | 4 (28.6) |
| COVID-19 infection | 0 | 0 | 0 | 0 |
| COVID-19 logistical restrictions | 0 | 0 | 1 (1.4) | 0 |
| Other | 1 (0.8) | 2 (2.6) | 2 (2.9) | 1 (7.1) |

Clinical Results

In patients with moderately to severely active Crohn's disease who had failed one or more biologics, the study demonstrated the superiority of UPA 45 mg QD vs. placebo as induction treatment for 12 weeks in co-primary endpoints (clinical remission per CDAI, clinical remission per PRO and endoscopic response) for both EU/EMA and US/FDA regulatory purposes with p<0.0001 (FIG. 47). In addition, 8 out of 10 key secondary endpoints also achieved statistical significance. Efficacy was demonstrated across clinical, endoscopic, steroid-free, fatigue, and quality of life measures. Rapid onset of action was observed (achievement of clinical response and/or remission). Specifically, clinical remission per CDAI and PRO measures was observed as early as week 2 (FIG. 48 and FIG. 49, respectively). Endoscopic response and endoscopic remission were achieved at week 12 (FIG. 50). Steroid-free clinical remission with both CDAI and PRO measures was achieved at the end of induction treatment (week 12) with upadacitinib (FIG. 51). Efficacy results and associated statistical measures for primary and key secondary endpoints are shown in Table 40 (EU/EMA) and Table 41 (US/FDA). Consistent efficacy results of co-primary endpoints were observed in the sensitivity analyses, as shown in Table 42. Selected efficacy endpoints at the end of each study part are summarized in Table 43.

TABLE 40

Primary and Key Secondary Endpoints for EU/EMA Regulatory Purposes (ITT1 Population)

| Endpoint | PBO (N = 171) | UPA 45 mg (N = 324) | Adj. Duff [95% CI] | p-value[1] |
|---|---|---|---|---|
| Co-Primary Endpoints | | | | |
| Clinical remission per PROs at Week 12; n (%) | 24 (14.0) | 129 (39.8) | 25.9 [18.7, 33.1] | <.0001[S] |
| Endoscopic response at Week 12; n (%) | 6 (3.5) | 112 (34.6) | 31.2 [25.5, 37.0] | <.0001[S] |
| Key Secondary Endpoints | | | | |
| Clinical remission per CDAI at Week 12; n (%) | 36 (21.1) | 126 (38.9) | 17.9 [10.0, 25.8] | <.0001[S] |
| Clinical remission per PROs at Week 4; n (%) | 16 (9.4) | 105 (32.4) | 23.3 [16.6, 29.9] | <.0001[S] |
| Endoscopic remission at Week 12; n (%) | 4 (2.3) | 62 (19.1) | 16.8 [12.0, 21.6] | <.0001[S] |
| Steroid-free & clinical remission per PROs at Week 12, among patients with corticosteroids for CD at Baseline; n (%) | (N = 60) 4 (6.7) | (N = 108) 40 (37.0) | 30.2 [19.4, 41.0] | <.0001[S] |
| FACIT-F total score at Week 12; LS Mean Change (SE) | (N = 129) 3.9 (0.97) | (N = 278) 11.4 (0.69) | 7.5 [5.2, 9.8] | <.0001[S] |

TABLE 40-continued

Primary and Key Secondary Endpoints for EU/EMA Regulatory Purposes (ITT1 Population)

| Endpoint | PBO (N = 171) | UPA 45 mg (N = 324) | Adj. Duff [95% CI] | p-value[1] |
|---|---|---|---|---|
| IBDQ total score at Week 12; LS Mean Change (SE) | (N = 130) 21.6 (3.02) | (N = 280) 46.0 (2.14) | 24.3 [17.2, 31.5] | <.0001[S] |
| CR-100 at Week 2; n (%) | 21 (12.4) | 107 (33.2) | 20.7 [13.7, 27.8] | <.0001[S] |
| CR-100 at Week 12; n (%) | 47 (27.5) | 164 (50.5) | 22.8 [14.4, 31.2] | <.0001[S] |
| Occurrence of hospitalizations due to CD in Part 1; n (%) | 15 (8.8) | 20 (6.2) | −2.6 [−7.6, 2.4] | 0.2834[NS] |
| Resolution of EIMs at Week 12, among pts with EIMs at Baseline; n (%) | (N = 60) 13 (21.7) | (N = 131) 43 (32.8) | 11.5 [−1.5, 24.4] | 0.0833[NS] |

Among intent-to-treat population for Part 1 (ITT1), which includes all subjects who are randomized and received at least one dose of study drug in the 12-Week Induction Period. Missing data were imputed using Non-Responder Imputation (NRI) while incorporating Multiple Imputation to handle missing data due to COVID-19 (NRI-C) for categorical endpoints, and using Mixed-Effect Model Repeat Measurement (MMRM) for continuous endpoints.
[1]P-value for treatment difference between UPA 45 mg and PBO, using CMH test for categorical endpoints and using MMRM for continuous endpoints, controlling for stratification factors.
PBO: Placebo
UPA: Upadacitinib
CI: Confidence Interval
EIM: extra-intestinal manifestations
S/NS: Achieved/not achieved statistical significance according to the testing strategy for overall type-I error control as indicated.

TABLE 41

Primary and Key Secondary Endpoints for US/FDA Regulatory Purposes (ITT1 Population)

| Endpoint | PBO (N = 171) | UPA 45 mg (N = 324) | Adj. Duff [95% CI] | p-value[1] |
|---|---|---|---|---|
| Co-Primary Endpoints | | | | |
| Clinical remission per CDAI at Week 12; n (%) | 36 (21.1) | 126 (38.9) | 17.9 [10.0, 25.8] | <.0001[S] |
| Endoscopic response at Week 12; n (%) | 6 (3.5) | 112 (34.6) | 31.2 [25.5, 37.0] | <.0001[S] |
| Key Secondary Endpoints | | | | |
| Clinical remission per PROs at Week 12; n (%) | 24 (14.0) | 129 (39.8) | 25.9 [18.7, 33.1] | <.0001[S] |
| Endoscopic remission at Week 12; n (%) | 4 (2.3) | 62 (19.1) | 16.8 [12.0, 21.6] | <.0001[S] |
| Steroid-free & clinical remission per CDAI at Week 12, among pts with corticosteroids for CD at Baseline; n (%) | (N = 60) 7 (11.7) | (N = 108) 37 (34.3) | 22.5 [11.1, 34.0] | <.0001[S] |
| FACIT-F total score at Week 12; LS Mean Change (SE) | (N = 129) 3.9 (0.97) | (N = 278) 11.4 (0.69) | 7.5 [5.2, 9.8] | <.0001[S] |
| IBDQ total score at Week 12; LS Mean Change (SE) | (N = 130) 21.6 (3.02) | (N = 280) 46.0 (2.14) | 24.3 [17.2, 31.5] | <.0001[S] |
| CR-100 at Week 2; n (%) | 21 (12.4) | 107 (33.2) | 20.7 [13.7, 27.8] | <.0001[S] |
| CR-100 at Week 12; n (%) | 47 (27.5) | 164 (50.5) | 22.8 [14.4, 31.2] | <.0001[S] |
| Clinical remission per CDAI at Week 4; n (%) | 30 (17.7) | 96 (29.6) | 12.1 [4.7, 19.5] | <.0001[S] |
| Occurrence of hospitalizations due to CD in Part 1; n (%) | 15 (8.8) | 20 (6.2) | −2.6 [−7.6, 2.4] | 0.2834[NS] |
| Resolution of EIMs at Week 12, among pts with EIMs at Baseline; n (%) | (N = 60) 13 (21.7) | (N = 131) 43 (32.8) | 11.5 [−1.5, 24.4] | 0.0833[NS] |

Among intent-to-treat population for Part 1 (ITT1), which includes all subjects who are randomized and received at least one dose of study drug in the 12-Week Induction Period. Missing data were imputed using Non-Responder Imputation (NRI) while incorporating Multiple Imputation to handle missing data due to COVID-19 (NRI-C) for categorical endpoints, and using Mixed-Effect Model Repeat Measurement (MMRM) for continuous endpoints
[1]P-value for treatment difference between UPA 45 mg and PBO, using CMH test for categorical endpoints and using MMRM for continuous endpoints, controlling for stratification factors.
PBO: Placebo
UPA: Upadacitinib
CI: Confidence Interval
EIM: extra-intestinal manifestations
S/NS: Achieved/not achieved statistical significance according to the testing strategy for overall type-I error control as indicated.

TABLE 42

Results for Primary Efficacy Endpoints from Sensitivity Analyses

| Endpoint; n (%) | PBO (N = 171) | UPA 45 mg (N = 324) | Adj. Diff [95% CI] | p-value |
|---|---|---|---|---|
| Clinical remission per PROs at Week 12 | 24 (14.0) | 129 (39.8) | 25.9 [18.6, 33.3] | <.0001 |
| Clinical remission per CDAI at Week 12 | 34 (19.9) | 122 (37.6) | 18.0 [10.2, 25.8] | <.0001 |

Per regulatory feedback, sensitivity analyses were conducted using a total of 7-day collection period (i.e , 9 days prior to the visit, excluding the 2 days before and the day of endoscopy), instead of the originally planned 14-day collection period, for the PRO and CDAI calculation.

TABLE 43

Results for Selected Key Efficacy Endpoints at the End of Each Study Part (NRI-C)

| | Part 1 Week 12 | | Part 2 Week 12 | Part 3 Week 24 | | |
|---|---|---|---|---|---|---|
| Endpoint; n (%) | DB PBO (N = 171) | DB UPA 45 (N = 324) | OL UPA 45 (N = 129) | DB PBO/ UPA 45 (N = 78) | DP UPA 45/ UPA 30 (N = 69) | OL UPA 45/ UPA 30 (N = 14) |
| Clinical remission per PROs[1] | 24 (14.0) | 129 (39.8) | 65 (50.4) | 34 (43.6) | 16 (23.2) | 1 (7.1) |
| Clinical remission per CDAI[2] | 36 (21.1) | 126 (38.9) | 68 (52.7) | 27 (34.6) | 17 (24.6) | 5 (35.7) |
| Endoscopic response[3] | 6 (3.5) | 112 (34.6) | 46 (35.7) | 27 (34.6) | 8 (11.6) | 3 (21.4) |
| Clinical response[4] | 66 (38.6) | 211 (65.1) | 104 (80.6) | 54 (69.2) | 34 (49.3) | 6 (42.9) |

Note:
Results are summarized among the ITT population for each study part, defined as subjects who received at least one dose of study drug in the corresponding study part. DB: Double blind. OL: Open label. PBO: Placebo. UPA: Upadacitinib. NRI-C: Non-Responder Imputation (NRI) incorporating Multiple Imputation (MI) for missing data due to COVID-19.
[1]Result at Week 12 in Part 1 is one of the co-primary endpoints for EU/EMA regulatory purposes, as defined herein.
[2]Result at Week 12 in Part 1 is one of the co-primary endpoints for US/FDA regulatory purposes, as defined herein.
[3]Result at Week 12 in Part 1 is one of the co-primary endpoints for both EU/EMA and US/FDA regulatory purposes, as defined herein.
[4]Subjects who achieved the clinical response were to roll-over to the Maintenance Study M14-430. The clinical response is defined as the achievement of ≥30% decrease in average daily very soft or liquid stool frequency (SF) and/or ≥30% decrease in average daily abdominal pain (AP) score at Week 12, with both SF and AP not worse than Baseline.

The invention claimed is:

1. A method of treating ulcerative colitis in an adult patient having moderately to severely active ulcerative colitis to achieve clinical remission, the method comprising:
   (a) orally administering to the patient an induction dose of 45 mg of upadacitinib once daily for 8 weeks; and
   (b) orally administering to the patient, after the last induction dose of 45 mg of upadacitinib, a maintenance dose of 15 mg of upadacitinib once daily,
   wherein the method achieves clinical remission of the ulcerative colitis in the patient.

2. The method of claim 1, wherein the method achieves induction of clinical remission per Adapted Mayo Score at 8 weeks after the administration of the initial induction dose of 45 mg of upadacitinib.

3. The method of claim 1, wherein the method achieves maintenance of clinical remission per Adapted Mayo Score at 52 weeks after administration of the initial maintenance dose of 15 mg of upadacitinib.

4. The method of claim 1, wherein prior to receiving the initial induction dose the adult patient had an inadequate response or intolerance to a previous treatment with an anti-TNF agent.

* * * * *